United States Patent
Dou et al.

(10) Patent No.: US 12,125,561 B2
(45) Date of Patent: Oct. 22, 2024

(54) DETERMINATION OF JAK-STAT3 PATHWAY ACTIVITY USING UNIQUE COMBINATION OF TARGET GENES

(71) Applicant: InnoSIGN B.V., Eindhoven (NL)

(72) Inventors: Meng Dou, Eindhoven (NL); Wilhelmus Franciscus Johannes Verhaegh, Heusden gem. Asten (NL); Anja Van De Stolpe, Vught (NL); Rick Velter, Eindhoven (NL)

(73) Assignee: InnoSIGN B.V., Eindhoven (NL)

( * ) Notice: Subject to any disclaimer, the term of this patent is extended or adjusted under 35 U.S.C. 154(b) by 1368 days.

(21) Appl. No.: 16/143,708

(22) Filed: Sep. 27, 2018

(65) Prior Publication Data

US 2019/0102510 A1    Apr. 4, 2019

(30) Foreign Application Priority Data

Oct. 2, 2017  (EP) .................................... 17194293

(51) Int. Cl.
| | | |
|---|---|---|
| G16B 5/00 | (2019.01) |
| C12Q 1/6851 | (2018.01) |
| C12Q 1/6886 | (2018.01) |
| C40B 10/00 | (2006.01) |
| C40B 20/00 | (2006.01) |
| G01N 33/68 | (2006.01) |
| G16B 5/20 | (2019.01) |
| G16B 20/00 | (2019.01) |
| G16B 25/00 | (2019.01) |

(52) U.S. Cl.
CPC .............. *G16B 5/00* (2019.02); *C12Q 1/6851* (2013.01); *C12Q 1/6886* (2013.01); *C40B 10/00* (2013.01); *C40B 20/00* (2013.01); *G01N 33/6872* (2013.01); *G16B 5/20* (2019.02); *G16B 20/00* (2019.02); *G16B 25/00* (2019.02); *C12N 2501/42* (2013.01); *C12Q 2600/158* (2013.01); *G01N 2333/4703* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,436,134 A | 7/1995 | Haugland |
| 5,476,928 A | 12/1995 | Langer |
| 5,658,751 A | 8/1997 | Haugland |
| 5,874,219 A | 2/1999 | Fodor |
| 5,958,691 A | 9/1999 | Biesecker |
| 6,004,761 A | 12/1999 | Brown |
| 6,146,897 A | 11/2000 | Bhandare |
| 6,171,798 B1 | 1/2001 | Gish |
| 6,225,047 B1 | 5/2001 | Hutchens |
| 6,308,170 B1 | 10/2001 | Baid |
| 6,391,550 B1 | 5/2002 | Langer-Safer |
| 6,675,104 B2 | 1/2004 | Braginsky |
| 6,713,297 B2 | 3/2004 | Borkholder |
| 6,844,165 B2 | 1/2005 | Hutchens |
| 6,884,578 B2 | 4/2005 | Mahadevappa |
| 7,056,674 B2 | 6/2006 | Baker |
| 7,081,340 B2 | 7/2006 | Baker |
| 7,160,734 B2 | 1/2007 | Hutchens |
| 7,208,470 B2 | 4/2007 | Duan |
| 7,299,134 B2 | 11/2007 | Hutchens |
| 7,526,637 B2 | 4/2009 | Han |
| 7,569,345 B2 | 8/2009 | Baker |
| 7,695,913 B2 | 4/2010 | Baker |
| 7,723,033 B2 | 5/2010 | Baker |
| 7,754,431 B2 | 7/2010 | Beck |
| 7,754,861 B2 | 7/2010 | Boschetti |
| 7,816,084 B2 | 10/2010 | Beck |
| 7,838,224 B2 | 11/2010 | Baker |
| 7,858,304 B2 | 12/2010 | Baker |
| 7,888,019 B2 | 2/2011 | Baker |
| 7,919,261 B2 | 4/2011 | Fantin |
| 7,930,104 B2 | 4/2011 | Baker |

(Continued)

FOREIGN PATENT DOCUMENTS

| | | | |
|---|---|---|---|
| JP | 2005176804 A | 7/2005 | |
| WO | WO-2013011479 A2 * | 1/2013 | ............... C12Q 1/68 |

(Continued)

OTHER PUBLICATIONS

Gurbuz et al. (Oncology Letters 7: 755-763, 2014) (Year: 2014).*
Yu et al. (Nature Reviews Cancer, 2009, vol. 9, pp. 798-809) (Year: 2009).*
Bedard, Philippe L. et al Nature Insight: Tumor Heterogeneity, Sep. 19, 2013, vol. 501.
Zellmer, Victoria et al "Evolving concepts of tumor heterogeneity", Cell and Bioscience 2014, 4:69.
Liu, Bin et al ., "Inhibition of Stat1-mediated gene activation by PIAS1", Cell Biology, vol. 95, Sep. 1998, pp. 10626 to 10631.
Platanias, L.C., "Mechanisms of type-I- and type-II-interferon-mediated signaling", Nature Reviews Immunology, vol. 5, May 2015, pp. 375 to 386—Abstract Only.

(Continued)

*Primary Examiner* — Pablo S Whaley
(74) *Attorney, Agent, or Firm* — Bond, Schoeneck & King, PLLC

(57) ABSTRACT

A bioinformatics process which provides an improved means to detect a JAK-STAT3 cellular signaling pathway in a subject, such as a human, based on the expression levels of at least three unique target genes of the JAK-STAT3 cellular signaling pathway measured in a sample. The invention includes an apparatus comprising a digital processor configured to perform such a method, a non-transitory storage medium storing instructions that are executable by a digital processing device to perform such a method, and a computer program comprising program code means for causing a digital processing device to perform such a method. Kits are also provided for measuring expression levels of unique sets of JAK-STAT3 cellular signaling pathway target genes.

5 Claims, 19 Drawing Sheets

Specification includes a Sequence Listing.

(56) References Cited

U.S. PATENT DOCUMENTS

| | | |
|---|---|---|
| 7,939,261 B2 | 5/2011 | Baker |
| 8,008,003 B2 | 8/2011 | Baker |
| 8,021,894 B2 | 9/2011 | Hutchens |
| 8,026,060 B2 | 9/2011 | Baker |
| 8,029,995 B2 | 10/2011 | Baker |
| 8,029,997 B2 | 10/2011 | Kennedy |
| 8,034,565 B2 | 10/2011 | Baker |
| 8,067,178 B2 | 11/2011 | Baker |
| 8,071,286 B2 | 12/2011 | Baker |
| 8,148,076 B2 | 4/2012 | Baker |
| 8,153,378 B2 | 4/2012 | Baker |
| 8,153,379 B2 | 4/2012 | Baker |
| 8,153,380 B2 | 4/2012 | Baker |
| 8,198,024 B2 | 6/2012 | Baker |
| 8,206,919 B2 | 6/2012 | Baker |
| 8,273,537 B2 | 9/2012 | Baker |
| 8,367,345 B2 | 2/2013 | Baker |
| 8,451,450 B2 | 5/2013 | Heng |
| 8,518,639 B2 | 8/2013 | Rihet |
| 8,541,170 B2 | 9/2013 | Kennedy |
| 8,632,980 B2 | 1/2014 | Baker |
| 8,691,799 B2 * | 4/2014 | Sebti ............... A61P 35/00 514/177 |
| 8,703,736 B2 | 4/2014 | Han |
| 8,725,426 B2 | 5/2014 | Cherbavaz |
| 8,741,605 B2 | 6/2014 | Baker |
| 8,765,383 B2 | 7/2014 | Collin |
| 8,808,994 B2 | 8/2014 | Baker |
| 8,868,352 B2 | 10/2014 | Baker |
| 8,906,625 B2 | 12/2014 | Baker |
| 8,911,940 B2 | 12/2014 | Kim |
| 9,076,104 B2 | 7/2015 | Chang |
| 2012/0201824 A1 | 8/2012 | Wasik |
| 2013/0042333 A1 | 2/2013 | Cairo |
| 2014/0228414 A1 | 8/2014 | Priebe |
| 2014/0342924 A1 | 11/2014 | Harkin |
| 2015/0232926 A1 | 8/2015 | Wu |
| 2016/0117439 A1 | 4/2016 | Brussel |
| 2016/0296480 A1 | 10/2016 | Frank |

FOREIGN PATENT DOCUMENTS

| | | |
|---|---|---|
| WO | 2014102668 A2 | 7/2014 |
| WO | 2014174003 A1 | 10/2014 |
| WO | 2015101635 A1 | 7/2015 |
| WO | 2015193212 A1 | 12/2015 |
| WO | 2016062891 A1 | 4/2016 |

OTHER PUBLICATIONS

Verhaegh, W. et al., "Selection of personalized patient therapy through the use of knowledge-based computational models that identify tumor-driving signal transduction pathways", Cancer Research, vol. 74, No. 11, 2014, pp. 2936 to 2945.

Miklossy, Gabriella et al., "Therapeutic modulators of STAT signaling for human diseases", Nature Reviews Drug Discovery, vol. 12, No. 8, Aug. 2013, pp. 611 to 629.

Yue, Peibin et al."Targeting STAT3 in cancer: how successful are we?", Expert Opinion on Investigational Drugs, vol. 18, No. 1, pp. 45 to 56.

Yu, Hus et al , "STATs in cancer inflammation and immunity: a leading role for STAT3", Nature Reviews Cancer, vol. 9, No. 11, Nov. 2009, pp. 798 to 809.

* cited by examiner

DETERMINATION OF JAK-STAT3 PATHWAY ACTIVITY USING UNIQUE COMBINATION OF TARGET GENES

RELATED APPLICATIONS

This application claims the benefit of European Patent Application No. EP17194293.1, filed Oct. 2, 2017, the entirety of the specification and claims thereof is hereby incorporated by reference for all purposes.

INCORPORATION-BY-REFERENCE OF MATERIAL SUBMITTED ON AS A TEXT FILE VIA THE OFFICE ELECTRONIC FILING SYSTEM (EFS-WEB)

A Sequence Listing associated with this application is provided in text format in lieu of a paper copy, and is hereby incorporated by reference into the specification. The name of the text file containing the Sequence Listing is 2017PF02041_2018-09-25_sequencelisting_ST25.txt. The text file is 166 KB, was created on Sep. 25, 2018, and is being submitted electronically via EFS-Web.

FIELD OF THE INVENTION

The present invention is in the field of systems biology, bioinformatics, genomic mathematical processing and proteomic mathematical processing. In particular, the invention includes a systems-based mathematical process for determining the activity level of a JAK-STAT3 cellular signaling pathway in a subject based on expression levels of a unique set of selected target genes in a subject. The invention further provides an apparatus that includes a digital processor configured to perform such a method, a non-transitory storage medium storing instructions that are executable by a digital processing device to perform such a method, and a computer program comprising a program code means for causing a digital processing device to perform such a method. The present invention also includes kits for the determination of expression levels of the unique combinations of target genes.

BACKGROUND OF THE INVENTION

As knowledge of tumors including cancers evolve, it becomes more clear that they are extraordinarily heterogeneous and multifactorial. Tumors and cancers have a wide range of genotypes and phenotypes, they are influenced by their individualized cell receptors (or lack thereof), microenvironment, extracellular matrix, tumor vascularization, neighboring immune cells, and accumulations of mutations, with differing capacities for proliferation, migration, stem cell properties and invasion. This scope of heterogeneity exists even among same classes of tumors. See generally: Nature Insight: Tumor Heterogeneity (entire issue of articles), 19 Sep. 2013 (Vol. 501, Issue 7467); Zellmer and Zhang, "Evolving concepts of tumor heterogeneity", *Cell and Bioscience* 2014, 4:69.

Traditionally, physicians have treated tumors, including cancers, as the same within class type (including within receptor type) without taking into account the enormous fundamental individualized nature of the diseased tissue. Patients have been treated with available chemotherapeutic agents based on class and receptor type, and if they do not respond, they are treated with an alternative therapeutic, if it exists. This is an empirical approach to medicine.

There has been a growing trend toward taking into account the heterogeneity of tumors at a more fundamental level as a means to create individualized therapies, however, this trend is still in its formative stages. What is desperately needed are approaches to obtain more metadata about the tumor to inform therapeutic treatment in a manner that allows the prescription of approaches more closely tailored to the individual tumor, and perhaps more importantly, avoiding therapies destined to fail and waste valuable time, which can be life-determinative.

A number of companies and institutions are active in the area of classical, and some more advanced, genetic testing, diagnostics, and predictions for the development of human diseases, including, for example: Affymetrix, Inc.; Bio-Rad, Inc; Roche Diagnostics; Genomic Health, Inc.; Regents of the University of California; Illumina; Fluidigm Corporation; Sequenom, Inc.; High Throughput Genomics; NanoString Technologies; Thermo Fisher; Danaher; Becton, Dickinson and Company; bioMerieux; Johnson & Johnson; Myriad Genetics, and Hologic.

Several companies have developed technology or products directed to gene expression profiling and disease classification. For example, Genomic Health, Inc. is the assignee of numerous patents pertaining to gene expression profiling, for example: U.S. Pat. Nos. 7,081,340; 8,808,994; 8,034,565; 8,206,919; 7,858,304; 8,741,605; 8,765,383; 7,838,224; 8,071,286; 8,148,076; 8,008,003; 8,725,426; 7,888,019; 8,906,625; 8,703,736; 7,695,913; 7,569,345; 8,067,178; 7,056,674; 8,153,379; 8,153,380; 8,153,378; 8,026,060; 8,029,995; 8,198,024; 8,273,537; 8,632,980; 7,723,033; 8,367,345; 8,911,940; 7,939,261; 7,526,637; 8,868,352; 7,930,104; 7,816,084; 7,754,431 and 7,208,470, and their foreign counterparts.

U.S. Pat. No. 9,076,104 to the Regents of the University of California titled "Systems and Methods for Identifying Drug Targets using Biological Networks" claims a method with computer executable instructions by a processor for predicting gene expression profile changes on inhibition of proteins or genes of drug targets on treating a disease, that includes constructing a genetic network using a dynamic Bayesian network based at least in part on knowledge of drug inhibiting effects on a disease, associating a set of parameters with the constructed dynamic Bayesian network, determining the values of a joint probability distribution via an automatic procedure, deriving a mean dynamic Bayesian network with averaged parameters and calculating a quantitative prediction based at least in part on the mean dynamic Bayesian network, wherein the method searches for an optimal combination of drug targets whose perturbed gene expression profiles are most similar to healthy cells.

Affymetrix has developed a number of products related to gene expression profiling. Non-limiting examples of U.S. patents to Affymetrix include: U.S. Pat. Nos. 6,884,578; 8,029,997; 6,308,170; 6,720,149; 5,874,219; 6,171,798; and 6,391,550.

Likewise, Bio-Rad has a number of products directed to gene expression profiling. Illustrative examples of U.S. patents to Bio-Rad include: U.S. Pat. Nos. 8,021,894; 8,451,450; 8,518,639; 6,004,761; 6,146,897; 7,299,134; 7,160,734; 6,675,104; 6,844,165; 6,225,047; 7,754,861 and 6,004,761.

Koninklijke Philips N. V. (NL) has filed a number of patent applications in the general area of assessment of cellular signaling pathway activity using various mathematical models, including U.S. Ser. No. 14/233,546 (WO 2013/011479), titled "Assessment of Cellular Signaling Pathway Using Probabilistic Modeling of Target Gene Expression";

U.S. Ser. No. 14/652,805 (WO 2014/102668) titled "Assessment of Cellular Signaling Pathway Activity Using Linear Combinations of Target Gene Expressions"; WO 2014/174003 titled "Medical Prognosis and Prediction of Treatment Response Using Multiple Cellular Signaling Pathway Activities"; and WO 2015/101635 titled "Assessment of the PI3K Cellular Signaling Pathway Activity Using Mathematical Modeling of Target Gene Expression".

Despite this progress, more work is needed to definitively characterize tumor cellular behavior. In particular, there is a critical need to determine which pathways have become pathogenic to the cell. However, it is difficult to identify and separate abnormal cellular signaling from normal cellular pathway activity.

STAT3 is an inducible transcription factor that regulates the expression of many genes involved in the immune response and in cancer. Biological processes that are crucial for cancer progression are mediated by the JAK signal transducer and activator of STAT3 signaling. In the nucleus, STAT3 binds to the promoters of genes and induces a genetic program that promotes various cellular processes that are required for cancer progression (see also FIG. 1, which is based on Yu H. et al., "STATs in cancer inflammation and immunity: a leading role for STAT3", Nature Reviews Cancer, Vol. 9, No. 11, November 2009, pages 798 to 809).

With respect to the JAK-STAT3 signaling in e.g. cancer, it is important to be able to detect abnormal JAK-STAT3 signaling activity in order to enable the right choice of targeted drug treatment. Currently anti-JAK-STAT3 therapies are being developed (see Yue P. and Turkson J., "Targeting STAT3 in cancer: how successful are we?", Expert Opinion on Investigational Drugs, Vol. 18, No. 1, pages 45 to 56). However, today there is no clinical assay available to assess the functional state resp. activity of the JAK-STAT3 cellular signaling pathway, which in its active state indicates that it is, for instance, more likely to be tumor-promoting compared to its passive state. It is therefore desirable to be able to improve the possibilities of characterizing patients that have a disease, such as a cancer, e.g., a breast, cervical, endometrial, ovarian, pancreatic or prostate cancer, or an immune disorder, which is at least partially driven by an abnormal activity of the JAK-STAT3 cellular signaling pathway, and that are therefore likely to respond to inhibitors of the JAK-STAT3 cellular signaling pathway.

It is therefore an object of the invention to provide a more accurate process to determine the tumorigenic propensity of the JAK-STAT3 cellular signaling pathway in a cell, as well as associated methods of therapeutic treatment, kits, systems, etc.

SUMMARY OF THE INVENTION

The present invention includes methods and apparatuses for determining the activity level of a JAK-STAT3 cellular signaling pathway in a subject, typically a human with diseased tissue such as a tumor or cancer, wherein the activity level of the JAK-STAT3 cellular signaling pathway is determined by calculating an activity level of a JAK-STAT3 transcription factor element in a sample of the involved tissue isolated from the subject, wherein the activity level of the JAK-STAT3 transcription factor element in the sample is associated with JAK-STAT3 cellular signaling, wherein the activity level of the JAK-STAT3 transcription factor element in the sample is determined by measuring the expression levels of a unique set of target genes controlled by the JAK-STAT3 transcription factor element using a calibrated pathway model that compares the expression levels of the target genes in the sample with expression levels of the target genes in the calibrated pathway model.

In particular, the unique set of target genes whose expression level is analyzed in the calibrated pathway model includes at least three target genes, at least four target genes, at least five target genes, at least six target genes, at least seven target genes, at least eight target genes, at least nine target genes, at least ten target genes or more selected from AKT1, BCL2, BCL2L1, BIRC5, CCND1, CD274, CDKN1A, CRP, FGF2, FOS, FSCN1, FSCN2, FSCN3, HIF1A, HSP90AA1, HSP90AB1, HSP90B1, HSPA1A, HSPA1B, ICAM1, IFNG, IL10, JunB, MCL1, MMP1, MMP3, MMP9, MUC1, MYC, NOS2, POU2F1, PTGS2, SAA1, STAT1, TIMP1, TNFRSF1B, TWIST1, VIM, and ZEB1. In one embodiment, the unique set of target genes whose expression level is analyzed in the calibrated pathway model comprises at least three target genes, at least four target genes, at least five target genes, at least six target genes, at least seven target genes, at least eight target genes, at least nine target genes or more selected from BCL2L1, BIRC5, CCND1, CD274, FOS, HIF1A, HSP90AA1, HSP90AB1, MMP1, and MYC. In one embodiment, the unique set of target genes whose expression level is analyzed in the calibrated pathway model comprises at least three target genes, at least four target genes, at least five target genes, at least six target genes, at least seven target genes, at least eight target genes, at least nine target genes or more selected from BCL2L1, CD274, FOS, HSP90B1, HSPA1B, ICAM1, IFNG, JunB, PTGS2, STAT1, TNFRSF1B, and ZEB1.

Using this invention, health care providers will be able to more accurately assess the functional state of the JAK-STAT3 cellular signaling pathway at specific points in disease progression. Without being bound by any particular theory, it is believed that the identified target genes of the present invention in combination with the analytical methods described herein reduces the noise associated with the use of large subsets of target genes as previously described in the literature. Furthermore, as described and exemplified below, the use of specific combinations of select target genes allows for the precise determination of cellular signaling activity, and allows for an increased accuracy in the determination of disease state and prognosis. Accordingly, such cellular signaling pathway status can be used to, for example but not limited to, identify the presence or absence of disease and/or particular disease state or advancement, identify the presence or absence of a disorder or disease state, identify a particular subtype within a disease or disorder based one the activity level of the JAK-STAT3 cellular signaling pathway, derive a course of treatment based on the presence or absence of JAK-STAT3 signaling activity for example by administering a JAK-STAT3 inhibitor, and/or monitor disease progression in order to, for example, adjust therapeutic protocols based on a predicted drug efficacy in light of the determined activity level of the JAK-STAT3 cellular signaling pathway in the sample.

The term "JAK-STAT3 transcriptional factor element" or "JAK-STAT3 TF element" or "TF element" refers to a protein complex containing at least a STAT3 homodimer, which is capable of binding to specific DNA sequences, preferably the response elements with binding motif CTGG-GAA, thereby controlling transcription of target genes. Preferably, the term refers to either a protein or protein complex transcriptional factor triggered by the binding of STAT3 inducing ligands such as interleukin-6 (IL-6) and IL-6 family cytokines to its receptor or an intermediate downstream signaling agent between the binding the ligand to its receptor and the final transcriptional factor protein or protein complex.

The present invention is based on the realization of the inventors that a suitable way of identifying effects occurring in the JAK-STAT3 cellular signaling pathway can be based on a measurement of the signaling output of the JAK-STAT3 cellular signaling pathway, which is—amongst others—the transcription of the unique target genes described herein by a JAK-STAT3 transcription factor (TF) element controlled by the JAK-STAT3 cellular signaling pathway. This realization by the inventors assumes that the TF level is at a quasi-steady state in the sample which can be detected by means of—amongst others—the expression values of the target genes. The JAK-STAT3 cellular signaling pathway targeted herein is known to control many functions in many cell types in humans, such as proliferation, differentiation and wound healing. Regarding pathological disorders, such as cancer (e.g., breast, cervical, endometrial, ovarian, pancreatic or prostate cancer), the abnormal JAK-STAT3 cellular signaling activity plays an important role, which is detectable in the expression profiles of the target genes and thus exploited by means of a calibrated mathematical pathway model.

The present invention makes it possible to determine the activity level of the JAK-STAT3 cellular signaling pathway in a subject by (i) determining an activity level of a JAK-STAT3 TF element in a sample isolated from the subject, wherein the determining is based at least in part on evaluating a calibrated pathway model relating expression levels of at least three target genes of the JAK-STAT3 cellular signaling pathway, the transcription of which is controlled by the JAK-STAT3 TF element, to the activity level of the JAK-STAT3 TF element, and by (ii) calculating the activity level of the JAK-STAT3 cellular signaling pathway in the sample based on the calculated activity level of the JAK-STAT3 TF element in the sample. This preferably allows improving the possibilities of characterizing patients that have a disease, such as cancer, e.g., a breast, cervical, endometrial, ovarian, pancreatic or prostate cancer, which is at least partially driven by an abnormal activity of the JAK-STAT3 cellular signaling pathway, and that are therefore likely to respond to inhibitors of the JAK-STAT3 cellular signaling pathway. In particular embodiments, treatment determination can be based on specific JAK-STAT3 activity. In a particular embodiment the JAK-STAT3 cellular signaling status can be set at a cutoff value of odds of the JAK-STAT3 cellular signaling pathway being activate of, for example, 10:1, 5:1, 4:1, 2:1, 1:1, 1:2, 1:4, 1:5, or 1:10.

In one aspect of the invention, provided herein is a computer implemented method for determining the activity level of a JAK-STAT3 cellular signaling pathway in a subject performed by computerized device having a processor comprising:
   a. calculating an activity level of a JAK-STAT3 transcription factor element in a sample isolated from the subject, wherein the activity level of the JAK-STAT3 transcription factor element in the sample is associated with JAK-STAT3 cellular signaling, and wherein the activity level of the JAK-STAT3 transcription factor element in the sample is calculated by:
      i. receiving data on the expression levels of at least three, for example, at least four, at least five, at least six, at least seven, at least eight, at least nine, at least ten or more target genes derived from the sample, wherein the JAK-STAT3 transcription factor element controls transcription of the at least three target genes, and wherein the at least three target genes are selected from AKT1, BCL2, BCL2L1, BIRC5, CCND1, CD274, CDKN1A, CRP, FGF2, FOS, FSCN1, FSCN2, FSCN3, HIF1A, HSP90AA1, HSP90AB1, HSP90B1, HSPA1A, HSPA1B, ICAM1, IFNG, IL10, JunB, MCL1, MMP1, MMP3, MMP9, MUC1, MYC, NOS2, POU2F1, PTGS2, SAA1, STAT1, TIMP1, TNFRSF1B, TWIST1, VIM, and ZEB1;
      ii. calculating the activity level of the JAK-STAT3 transcription factor element in the sample using a calibrated pathway model, wherein the calibrated pathway model compares the expression levels of the at least three target genes in the sample with expression levels of the at least three target genes in the calibrated pathway model which define an activity level of the JAK-STAT3 transcription factor element; and,
   b. calculating the activity level of the JAK-STAT3 cellular signaling pathway in the sample based on the calculated activity level of the JAK-STAT3 transcription factor element in the sample.

In one embodiment, the at least three, for example, at least four, at least five, at least six, at least seven, at least eight, at least nine or more target genes are selected from BCL2L1, BIRC5, CCND1, CD274, FOS, HIF1A, HSP90AA1, HSP90AB1, MMP1, and MYC. In one embodiment, the at least three, for example, at least four, at least five, at least six, at least seven, at least eight, at least nine or more target genes are selected from BCL2L1, CD274, FOS, HSP90B1, HSPA1B, ICAM1, IFNG, JunB, PTGS2, STAT1, TNFRSF1B, and ZEB1. In one embodiment, the method further comprises assigning a JAK-STAT3 cellular signaling pathway activity status to the calculated activity level of the JAK-STAT3 cellular signaling pathway in the sample wherein the activity status is indicative of either an active JAK-STAT3 cellular signaling pathway or a passive JAK-STAT3 cellular signaling pathway. In one embodiment, the activity status of the JAK-STAT3 cellular signaling pathway is established by establishing a specific threshold for activity as described further below. In one embodiment, the threshold is set as a probability that the cellular signaling pathway is active, for example, a 10:1, 5:1, 4:1, 3:1, 2:1, 1:1, 1:2, 1:4, 1:5, or 1:10. In one embodiment, the activity status is based, for example, on a minimum calculated activity. In one embodiment, the method further comprises assigning to the calculated JAK-STAT3 cellular signaling in the sample a probability that the JAK-STAT3 cellular signaling pathway is active.

As contemplated herein, the activity level of the JAK-STAT3 transcription factor element is determined using a calibrated pathway model executed by one or more computer processors, as further described below. The calibrated pathway model compares the expression levels of the at least three target genes in the sample with expression levels of the at least three target genes in the calibrated pathway model which define an activity level of the JAK-STAT3 transcription factor element. In one embodiment, the calibrated pathway model is a probabilistic model incorporating conditional probabilistic relationships that compare the expression levels of the at least three target genes in the sample with expression levels of the at least three target genes in the calibrated pathway model which define a level of a JAK-STAT3 transcription factor element to determine the activity level of the JAK-STAT3 transcription factor element in the sample. In one embodiment, the probabilistic model is a Bayesian network model. In an alternative embodiment, the calibrated pathway model can be a linear or pseudo-linear model. In an embodiment, the linear or pseudo-linear model is a linear or pseudo-linear combination model.

As contemplated herein, the expression levels of the unique set of target genes can be determined using standard methods known in the art. For example, the expression levels of the target genes can be determined by measuring the level of mRNA of the target genes, through quantitative reverse transcriptase-polymerase chain reaction techniques, using probes associated with a mRNA sequence of the target genes, using a DNA or RNA microarray, and/or by measuring the protein level of the protein encoded by the target genes. Once the expression level of the target genes is determined, the expression levels of the target genes within the sample can be utilized in the calibrated pathway model in a raw state or, alternatively, following normalization of the expression level data. For example, expression level data can be normalized by transforming it into continuous data, z-score data, discrete data, or fuzzy data.

As contemplated herein, the calculation of JAK-STAT3 signaling in the sample is performed on a computerized device having a processor capable of executing a readable program code for calculating the JAK-STAT3 signaling in the sample according to the methods described above. Accordingly, the computerized device can include means for receiving expression level data, wherein the data is expression levels of at least three target genes derived from the sample, a means for calculating the activity level of a JAK-STAT3 transcription factor element in the sample using a calibrated pathway model, wherein the calibrated pathway model compares the expression levels of the at least three target genes in the sample with expression levels of the at least three target genes in the calibrated pathway model which define an activity level of the JAK-STAT3 transcription factor element; a means for calculating the JAK-STAT3 cellular signaling in the sample based on the calculated activity level of a JAK-STAT3 transcription factor element in the sample; and a means for assigning a JAK-STAT3 cellular signaling pathway activity probability or status to the calculated JAK-STAT3 cellular signaling in the sample, and, optionally, a means for displaying the JAK-STAT3 signaling pathway activity probability or status.

In accordance with another disclosed aspect, further provided herein is a non-transitory storage medium capable of storing instructions that are executable by a digital processing device to perform the method according to the present invention as described herein. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

Further contemplated herein are methods of treating a subject having a disease or disorder associated with an activated JAK-STAT3 cellular signaling pathway, or a disorder whose advancement or progression is exacerbated or caused by, whether partially or wholly, an activated JAK-STAT3 cellular signaling pathway, wherein the determination of the JAK-STAT3 cellular signaling pathway activity is based on the methods described above, and administering to the subject a JAK-STAT3 inhibitor if the information regarding the activity level of JAK-STAT3 cellular signaling pathway is indicative of an active JAK-STAT3 cellular signaling pathway. In one embodiment, the subject is suffering from a cancer, for example, a breast cancer, a cervical cancer, an endometrial cancer, an ovarian cancer, a pancreatic cancer, or a prostate cancer, or an immune disorder.

Also contemplated herein is a kit for measuring the expression levels of at least six, for example, at least seven, at least eight, at least nine, at least ten or more JAK-STAT3 cellular signaling pathway target genes, as described herein. In one embodiment, the kit includes one or more components, for example probes, for example labeled probes, and/or PCR primers, for measuring the expression levels of at least six, for example, at least seven, at least eight, at least nine, at least ten or more target genes selected from AKT1, BCL2, BCL2L1, BIRC5, CCND1, CD274, CDKN1A, CRP, FGF2, FOS, FSCN1, FSCN2, FSCN3, HIF1A, HSP90AA1, HSP90AB1, HSP90B1, HSPA1A, HSPA1B, ICAM1, IFNG, IL10, JunB, MCL1, MMP1, MMP3, MMP9, MUC1, MYC, NOS2, POU2F1, PTGS2, SAA1, STAT1, TIMP1, TNFRSF1B, TWIST1, VIM, and ZEB1. In one embodiment, the kit includes one or more components for measuring the expression levels of at least six, for example, at least seven, at least eight, at least nine or more target genes selected from BCL2L1, BIRC5, CCND1, CD274, FOS, HIF1A, HSP90AA1, HSP90AB1, MMP1, and MYC. In one embodiment, the kit includes one or more components for measuring the expression levels of at least six, for example, at least seven, at least eight, at least nine or more target genes selected from BCL2L1, CD274, FOS, HSP90B1, HSPA1B, ICAM1, IFNG, JunB, PTGS2, STAT1, TNFRSF1B, and ZEB1.

As contemplated herein, the one or more components or means for measuring the expression levels of the particular target genes can be selected from the group consisting of: an DNA array chip, an oligonucleotide array chip, a protein array chip, an antibody, a plurality of probes, for example, labeled probes, a set of RNA reverser-transcriptase sequencing components, and/or RNA or DNA, including cDNA, amplification primers. In one embodiment, the kit includes a set of labeled probes directed to a portion of an mRNA or cDNA sequence of the targeted genes as described herein. In one embodiment, the kit includes a set of primers and probes directed to a portion of an mRNA or cDNA sequence of the targeted genes as described herein. In one embodiment, the labeled probes are contained in a standardized 96-well plate. In one embodiment, the kit further includes primers or probes directed to a set of reference genes. Such reference genes can be, for example, constitutively expressed genes useful in normalizing or standardizing expression levels of the target gene expression levels described herein.

In one embodiment, the kit further includes a non-transitory storage medium containing instructions that are executable by a digital processing device to perform a method according to the present invention as described herein. In one embodiment, the kit includes an identification code that provides access to a server or computer network for analyzing the activity level of the JAK-STAT3 cellular signaling pathway based on the expression levels of the target genes and the methods described herein.

DETAILED DESCRIPTION OF THE INVENTION

Figure 1:
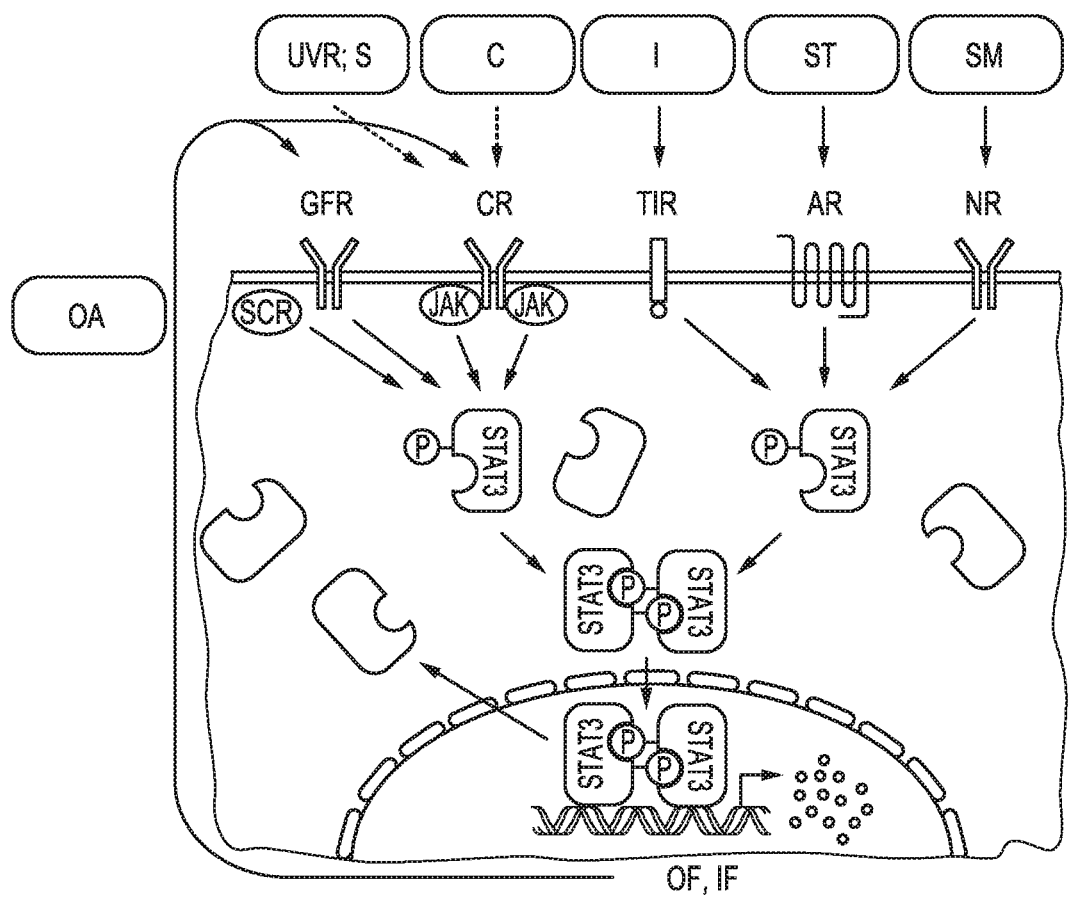
FIG. 1 shows schematically and exemplarily the JAK-STAT3 cellular signaling pathway. In the nucleus, STAT3 binds to the promoters of genes and induces a genetic program that promotes various cellular processes that are required for cancer progression (see also FIG. 1, which is based on Yu H. et al., "STATs in cancer inflammation and immunity: a leading role for STAT3", Nature Reviews Cancer, Vol. 9, No. 11, November 2009, pages 798 to 809; "UVR; S"=UV radiation or sunlight; "C"=carcinogen; "I"=infection; "ST"=stress; "SM"=smoke; "OA"=oncogene activation; "GFR"=growth factor receptor; "CR"=cytokine receptor; "TlR"=toll-like receptor; "AR"=adrenergic receptor; "NR"=nicotinic receptor; "OF, IF"=oncogenic and inflammatory factors).

Provided herein are methods and apparatuses, and in particular computer implemented methods and apparatuses, for determining the activity level of a JAK-STAT3 cellular signaling pathway in a subject, wherein the activity level of the JAK-STAT3 cellular signaling pathway is calculated by a) calculating an activity level of a JAK-STAT3 transcription factor element in a sample isolated from a subject, wherein the activity level of the JAK-STAT3 transcription factor element in the sample is associated with JAK-STAT3 cellular signaling, and wherein the activity level of the JAK-STAT3 transcription factor element in the sample is calculated by measuring the expression levels of a unique set of target genes, wherein the JAK-STAT3 transcription factor element controls transcription of the target genes, calculating the activity level of the JAK-STAT3 transcription factor element in the sample using a calibrated pathway model, wherein the calibrated pathway model compares the expression levels of the target genes in the sample with expression levels of the target genes in the calibrated pathway model which define an activity level of the JAK-STAT3 transcription factor element; and calculating the activity level of the JAK-STAT3 cellular signaling pathway in the sample based on the calculated activity level of the JAK-STAT3 transcription factor element in the sample.

In particular, the unique set of target genes whose expression levels is analyzed in the calibrated pathway model includes at least three, for example, at least four, at least five, at least six, at least seven, at least eight, at least nine, at least ten or more target genes selected from AKT1, BCL2, BCL2L1, BIRC5, CCND1, CD274, CDKN1A, CRP, FGF2, FOS, FSCN1, FSCN2, FSCN3, HIF1A, HSP90AA1, HSP90AB1, HSP90B1, HSPA1A, HSPA1B, ICAM1, IFNG, IL10, JunB, MCL1, MMP1, MMP3, MMP9, MUC1, MYC, NOS2, POU2F1, PTGS2, SAA1, STAT1, TIMP1, TNFRSF1B, TWIST1, VIM, and ZEB1. It has been discovered that analyzing a specific set of target genes as described herein in the disclosed pathway model provides for an advantageously accurate JAK-STAT3 cellular signaling pathway activity determination. Accordingly, such status can be used to, for example but not limited to, identify the presence or absence of disease and/or particular disease state or advancement, diagnose a specific disease or disease state, or diagnose the presence or absence of a particular disease, derive a course of treatment based on the presence or absence of JAK-STAT3 signaling activity, monitor disease progression in order to, for example, adjust therapeutic protocols based on a predicted drug efficacy in light of the determined activity of the JAK-STAT3 signaling pathway in the sample, or develop JAK-STAT3 targeted therapeutics.

DEFINITIONS

All terms used herein are intended to have their plain and ordinary meaning as normally ascribed in the art unless otherwise specifically indicated herein.

Herein, the "level" of a TF element denotes the level of activity of the TF element regarding transcription of its target genes.

The term "subject" or "host", as used herein, refers to any living being. In some embodiments, the subject is an animal, for example a mammal, including a human. In a particular embodiment, the subject is a human. In one embodiment, the human is suspected of having a disorder mediated or exacerbated by an active JAK-STAT3 cellular signaling pathway, for example, a cancer. In one embodiment, the human has or is suspected of having a breast cancer.

The term "sample", as used herein, means any biological specimen isolated from a subject. Accordingly, "sample" as used herein is contemplated to encompasses the case where e.g. a tissue and/or cells and/or a body fluid of the subject have been isolated from the subject. Performing the claimed method may include where a portion of this sample is extracted, e.g., by means of Laser Capture Microdissection (LCM), or by scraping off the cells of interest from the slide, or by fluorescence-activated cell sorting techniques. In addition, the term "sample", as used herein, also encompasses the case where e.g. a tissue and/or cells and/or a body fluid of the subject has been taken from the subject and has been put on a microscope slide, and the claimed method is performed on the slide. In addition, the term "samples," as used herein, may also encompass circulating tumor cells or CTCs.

The term "JAK-STAT3 transcriptional factor element" or "JAK-STAT3 TF element" or "TF element" refers to a protein complex containing at least a STAT3 homodimer, which is capable of binding to specific DNA sequences, preferably the response elements with binding motif CTGGGAA, thereby controlling transcription of target genes. Preferably, the term refers to either a protein or protein complex transcriptional factor triggered by the binding of STAT3 inducing ligands such as interleukin-6 (IL-6) and IL-6 family cytokines to its receptor or an intermediate downstream signaling agent between the binding the ligand to its receptor and the final transcriptional factor protein or protein complex.

The term "target gene" as used herein, means a gene whose transcription is directly or indirectly controlled by a JAK-STAT3 transcription factor element. The "target gene" may be a "direct target gene" and/or an "indirect target gene" (as described herein).

As contemplated herein, target genes include at least AKT1, BCL2, BCL2L1, BIRC5, CCND1, CD274, CDKN1A, CRP, FGF2, FOS, FSCN1, FSCN2, FSCN3, HIF1A, HSP90AA1, HSP90AB1, HSP90B1, HSPA1A, HSPA1B, ICAM1, IFNG, IL10, JunB, MCL1, MMP1, MMP3, MMP9, MUC1, MYC, NOS2, POU2F1, PTGS2, SAA1, STAT1, TIMP1, TNFRSF1B, TWIST1, VIM, and ZEB1.

As contemplated herein, the present invention includes:
A) A computer implemented method for determining the activity level of a JAK-STAT3 cellular signaling pathway in a subject performed by a computerized device having a processor comprising:

a. calculating an activity level of a JAK-STAT3 transcription factor element in a sample isolated from the subject, wherein the activity level of the JAK-STAT3 transcription factor element in the sample is associated with JAK-STAT3 cellular signaling, and wherein the activity level of the JAK-STAT3 transcription factor element in the sample is calculated by:
  i. receiving data on the expression levels of at least three, for example, at least five, at least six, at least seven, at least eight, at least nine, at least ten or more target genes derived from the sample, wherein the JAK-STAT3 transcription factor element controls transcription of the at least three target genes, and wherein the at least three target genes are selected from AKT1, BCL2, BCL2L1, BIRC5, CCND1, CD274, CDKN1A, CRP, FGF2, FOS, FSCN1, FSCN2, FSCN3, HIF1A, HSP90AA1, HSP90AB1, HSP90B1, HSPA1A, HSPA1B, ICAM1, IFNG, IL10, JunB, MCL1, MMP1, MMP3, MMP9, MUC1, MYC, NOS2, POU2F1, PTGS2, SAA1, STAT1, TIMP1, TNFRSF1B, TWIST1, VIM, and ZEB1;
  ii. calculating the activity level of the JAK-STAT3 transcription factor element in the sample using a calibrated pathway model, wherein the calibrated pathway model compares the expression levels of the at least three target genes in the sample with expression levels of the at least three target genes in the calibrated pathway model which define an activity level of the JAK-STAT3 transcription factor element; and,
b. calculating the activity level of the JAK-STAT3 cellular signaling pathway in the sample based on the calculated activity level of the JAK-STAT3 transcription factor element in the sample.

In one embodiment, the at least three, for example, at least four, at least five, at least six, at least seven, at least eight, at least nine or more target genes are selected from BCL2L1, BIRC5, CCND1, CD274, FOS, HIF1A, HSP90AA1, HSP90AB1, MMP1, and MYC. In one embodiment, the at least three, for example, at least four, at least five, at least six, at least seven, at least eight, at least nine or more target genes are selected from BCL2L1, CD274, FOS, HSP90B1, HSPA1B, ICAM1, IFNG, JunB, PTGS2, STAT1, TNFRSF1B, and ZEB1. In one embodiment, the method further comprises assigning a JAK-STAT3 cellular signaling pathway activity status to the calculated activity level of the JAK-STAT3 cellular signaling in the sample, wherein the activity status is indicative of either an active JAK-STAT3 cellular signaling pathway or a passive JAK-STAT3 cellular signaling pathway. In one embodiment, the method further comprises displaying the JAK-STAT3 cellular signaling pathway activity status. In one embodiment, the calibrated pathway model is a probabilistic model incorporating conditional probabilistic relationships that compare the expression levels of the at least three target genes in the sample with expression levels of the at least three target genes in the calibrated pathway model which define a level of the JAK-STAT3 transcription factor element to determine the activity level of the JAK-STAT3 transcription factor element in the sample. In one embodiment, the probabilistic model is a Bayesian network model. In one embodiment, the calibrated pathway model is a linear model incorporating relationships that compare the expression levels of the at least three target genes in the sample with expression levels of the at least three target genes in the calibrated pathway model which define a level of JAK-STAT3 transcription factor element to determine the activity level of the JAK-STAT3 transcription factor element in the sample.

B) A computer program product for determining the activity level of a JAK-STAT3 cellular signaling pathway in a subject comprising:
  a. a non-transitory computer readable storage medium having computer readable program code embodied therewith, the computer readable program code executable by at least one processor to:
    i. calculate an activity level of a JAK-STAT3 transcription factor element in a sample isolated from a subject, wherein the activity level of the JAK-STAT3 transcription factor element in the sample is associated with JAK-STAT3 cellular signaling, and wherein the activity level of the JAK-STAT3 transcription factor element in the sample is calculated by:
      1. receiving data on the expression levels of at least three, for example, at least four, at least five, at least six, at least seven, at least eight, at least nine, at least ten or more target genes derived from the sample, wherein the at least three target genes are selected from AKT1, BCL2, BCL2L1, BIRC5, CCND1, CD274, CDKN1A, CRP, FGF2, FOS, FSCN1, FSCN2, FSCN3, HIF1A, HSP90AA1, HSP90AB1, HSP90B1, HSPA1A, HSPA1B, ICAM1, IFNG, IL10, JunB, MCL1, MMP1, MMP3, MMP9, MUC1, MYC, NOS2, POU2F1, PTGS2, SAA1, STAT1, TIMP1, TNFRSF1B, TWIST1, VIM, and ZEB1;
      2. calculating the activity level of the JAK-STAT3 transcription factor element in the sample using a calibrated pathway model, wherein the calibrated pathway model compares the expression levels of the at least three target genes in the sample with expression levels of the at least three target genes in the calibrated pathway model which define an activity level of JAK-STAT3 transcription factor element; and,
  b. calculate the activity level of the JAK-STAT3 cellular signaling pathway in the sample based on the calculated activity level of the JAK-STAT3 transcription factor element in the sample.

In one embodiment, the at least three, for example, at least four, at least five, at least six, at least seven, at least eight, at least nine or more target genes are selected from BCL2L1, BIRC5, CCND1, CD274, FOS, HIF1A, HSP90AA1, HSP90AB1, MMP1, and MYC. In one embodiment, the at least three, for example, at least four, at least five, at least six, at least seven, at least eight, at least nine or more target genes are selected from BCL2L1, CD274, FOS, HSP90B1, HSPA1B, ICAM1, IFNG, JunB, PTGS2, STAT1, TNFRSF1B, and ZEB1. In one embodiment, the computer readable program code is executable by at least one processor to assign a JAK-STAT3 cellular signaling pathway activity status to the calculated activity level of the JAK-STAT3 cellular signaling in the sample, wherein the activity status is indicative of either an active JAK-STAT3 cellular signaling pathway or a passive JAK-STAT3 cellular signaling pathway. In one embodiment, the computer readable program code is executable by at least one processor to display the JAK-STAT signaling pathway activity status. In one embodiment, the calibrated pathway model is a probabilistic model incorporating conditional probabilistic relationships that compare the expression levels of the at least three target genes in the sample with expression levels of the at least three target genes in the calibrated pathway model which define a level of JAK-STAT3 transcription factor element to determine the activity level of JAK-STAT3 transcription factor element in the sample. In one embodiment, the probabilistic model is a Bayesian network model. In one embodiment, the calibrated pathway model is a linear model incorporating relationships that compare the expression levels of the at least three target genes in the sample with expression levels of the at least three target genes in the calibrated pathway model which define a level of a JAK-STAT3 transcription factor element to determine the activity level of the JAK-STAT3 transcription factor element in the sample.

C) A method of treating a subject suffering from a disease associated with an activated JAK-STAT3 cellular signaling pathway comprising:
  a. receiving information regarding the activity level of a JAK-STAT3 cellular signaling pathway derived from a sample isolated from the subject, wherein the activity level of the JAK-STAT3 cellular signaling pathway is determined by:
    i. calculating an activity level of a JAK-STAT3 transcription factor element in a sample isolated from the subject, wherein the activity level of the JAK-STAT3 transcription factor element in the sample is associated with JAK-STAT3 cellular signaling, and wherein the level of the JAK-STAT3 transcription factor element in the sample is calculated by:
      1. receiving data on the expression levels of at least three, for example, at least four, at least five, at least six, at least seven, at least eight, at least nine, at least ten or more target genes derived from the sample, wherein the JAK-STAT3 transcription factor element controls transcription of the at least three target genes, and wherein the at least three target genes are selected from AKT1, BCL2, BCL2L1, BIRC5, CCND1, CD274, CDKN1A, CRP, FGF2, FOS, FSCN1, FSCN2, FSCN3, HIF1A, HSP90AA1, HSP90AB1, HSP90B1, HSPA1A, HSPA1B, ICAM1, IFNG, IL10, JunB, MCL1, MMP1, MMP3, MMP9, MUC1, MYC, NOS2, POU2F1, PTGS2, SAA1, STAT1, TIMP1, TNFRSF1B, TWIST1, VIM, and ZEB1;
      2. calculating the activity level of the JAK-STAT3 transcription factor element in the sample using a calibrated pathway model, wherein the calibrated pathway model compares the expression levels of the at least three target genes in the sample with expression levels of the at least three target genes in the calibrated pathway model which define an activity level of the JAK-STAT3 transcription factor element; and,
    ii. calculating the activity level of the JAK-STAT3 cellular signaling pathway in the sample based on the calculated activity level of the JAK-STAT3 transcription factor element in the sample; and,
  b. administering to the subject a JAK-STAT3 inhibitor if the information regarding the activity level of the JAK-STAT3 cellular signaling pathway is indicative of a pathogenically active JAK-STAT3 cellular signaling pathway.

In one embodiment, the at least three, for example, at least four, at least five, at least six, at least seven, at least eight, at least nine or more target genes are selected from BCL2L1, BIRC5, CCND1, CD274, FOS, HIF1A, HSP90AA1, HSP90AB1, MMP1, and MYC. In one embodiment, the at least three, for example, at least four, at least five, at least six, at least seven, at least eight, at least nine or more target genes are selected from BCL2L1, CD274, FOS, HSP90B1, HSPA1B, ICAM1, IFNG, JunB, PTGS2, STAT1, TNFRSF1B, and ZEB1. In one embodiment, the calibrated pathway model is a probabilistic model incorporating conditional probabilistic relationships that compare the expression levels of the at least three target genes in the sample with expression levels of the at least three target genes in the calibrated pathway model which define a level of the JAK-STAT3 transcription factor element to determine the activity level of the JAK-STAT3 transcription factor element in the sample. In one embodiment, the probabilistic model is a Bayesian network model. In one embodiment, the calibrated pathway model is a linear model incorporating relationships that compare the expression levels of the at least three target genes in the sample with expression levels of the at least three target genes in the calibrated pathway model which define a level of JAK-STAT3 transcription factor element to determine the activity level of the JAK-STAT3 transcription factor element in the sample. In an illustrative embodiment, the JAK-STAT3 inhibitor is STA-21, LLL-3, curcumin, or AZD9150. In one embodiment, the cancer is a breast cancer, a cervical cancer, an endometrial cancer, an ovarian cancer, a pancreatic cancer, or a prostate cancer. In one embodiment, the cancer is a breast cancer.

D) A kit for measuring expression levels of JAK-STAT3 cellular signaling pathway target genes comprising:
  a. a set of polymerase chain reaction primers directed to at least six, for example, at least seven, at least eight, at least nine, at least ten or more JAK-STAT3 cellular signaling pathway target genes derived from a sample isolated from a subject; and
  b. a set of probes directed to the at least six JAK-STAT3 cellular signaling pathway target genes;
    wherein the at least six target genes are selected from AKT1, BCL2, BCL2L1, BIRC5, CCND1, CD274, CDKN1A, CRP, FGF2, FOS, FSCN1, FSCN2, FSCN3, HIF1A, HSP90AA1, HSP90AB1, HSP90B1, HSPA1A, HSPA1B, ICAM1, IFNG, IL10, JunB, MCL1, MMP1, MMP3, MMP9, MUC1, MYC, NOS2, POU2F1, PTGS2, SAA1, STAT1, TIMP1, TNFRSF1B, TWIST1, VIM, and ZEB1.

In one embodiment, the at least six, for example, at least seven, at least eight, at least nine or more target genes are selected from BCL2L1, BIRC5, CCND1, CD274, FOS, HIF1A, HSP90AA1, HSP90AB1, MMP1, and MYC. In one embodiment, the at least six, for example, at least seven, at least eight, at least nine or more target genes are selected from BCL2L1, CD274, FOS, HSP90B1, HSPA1B, ICAM1, IFNG, JunB, PTGS2, STAT1, TNFRSF1B, and ZEB1. In one embodiment, the kit further comprises a computer program product for determining the activity level of a JAK-STAT3 cellular signaling pathway in the subject comprising: a. a non-transitory computer readable storage medium having computer readable program code embodied therewith, the computer readable program code executable by at least one processor to: i. calculate an activity level of a JAK-STAT3 transcription factor element in the sample, wherein the activity level of the JAK-STAT3 transcription factor element in the sample is associated with JAK-STAT3 cellular signaling, and wherein the activity level of the JAK-STAT3 transcription factor element in the sample is calculated by: 1. receiving data on the expression levels of the at least six target genes derived from the sample; 2. calculating the activity level of the JAK-STAT3 transcription factor element in the sample using a calibrated pathway model, wherein the calibrated pathway model compares the expression levels of the at least six target genes in the sample with expression levels of the at least six target genes in the calibrated pathway model which define an activity level of the JAK-STAT3 transcription factor element; and, ii. calculate the activity level of the JAK-STAT3 cellular signaling pathway in the sample based on the calculated activity level of the JAK-STAT3 transcription factor element in the sample.

E) A kit for determining the activity level of a JAK-STAT3 cellular signaling pathway in a subject comprising:
  a. one or more components capable of identifying expression levels of at least three, for example, at least four, at least five, at least six, at least seven, at least eight, at least nine, at least ten or more JAK-STAT3 cellular signaling pathway target genes derived from a sample of the subject, wherein the at least three target genes are selected from AKT1, BCL2, BCL2L1, BIRC5, CCND1, CD274, CDKN1A, CRP, FGF2, FOS, FSCN1, FSCN2, FSCN3, HIF1A, HSP90AA1, HSP90AB1, HSP90B1, HSPA1A, HSPA1B, ICAM1, IFNG, IL10, JunB, MCL1, MMP1, MMP3, MMP9, MUC1, MYC, NOS2, POU2F1, PTGS2, SAA1, STAT1, TIMP1, TNFRSF1B, TWIST1, VIM, and ZEB1; and,
  b. optionally, a non-transitory computer readable storage medium having computer readable program code embodied therewith, the computer readable program code executable by at least one processor to:
    i. calculate an activity level of a JAK-STAT3 transcription factor element in the sample, wherein the activity level of the JAK-STAT3 transcription factor element in the sample is associated with JAK-STAT3 cellular signaling, and wherein the activity level of the JAK-STAT3 transcription factor element in the sample is calculated by:
      1. receiving data on the expression levels of the at least three target genes derived from the sample;
      2. calculating the activity level of the JAK-STAT3 transcription factor element in the sample using a calibrated pathway model, wherein the calibrated pathway model compares the expression levels of the at least three target genes in the sample with expression levels of the at least three target genes in the calibrated pathway model which define an activity level of the JAK-STAT3 transcription factor element; and,
    ii. calculate the activity level of the JAK-STAT3 cellular signaling pathway in the sample based on the calculated activity level of the JAK-STAT3 transcription factor element in the sample.

Determining the Activity Level of the JAK-STAT3 Cellular Signaling Pathway

The present invention provides new and improved methods and apparatuses, and in particular computer implemented methods and apparatuses, as disclosed herein, to assess the functional state or activity of the JAK-STAT3 cellular signaling pathway.

In one aspect of the invention, provided herein is a method of determining JAK-STAT3 cellular signaling in a subject comprising the steps of:
  a. calculating an activity level of a JAK-STAT3 transcription factor element in a sample isolated from a subject, wherein the activity level of the JAK-STAT3 transcription factor element in the sample is associated with JAK-STAT3 cellular signaling, and wherein the activity level of the JAK-STAT3 transcription factor element in the sample is calculated by:

i. receiving data on the expression levels of at least three, for example, at least four, at least five, at least six, at least seven, at least eight, at least nine, at least ten or more target genes derived from the sample, wherein the JAK-STAT3 transcription factor element controls transcription of the at least three target genes, and wherein the at least three target genes are selected from AKT1, BCL2, BCL2L1, BIRC5, CCND1, CD274, CDKN1A, CRP, FGF2, FOS, FSCN1, FSCN2, FSCN3, HIF1A, HSP90AA1, HSP90AB1, HSP90B1, HSPA1A, HSPA1B, ICAM1, IFNG, IL10, JunB, MCL1, MMP1, MMP3, MMP9, MUC1, MYC, NOS2, POU2F1, PTGS2, SAA1, STAT1, TIMP1, TNFRSF1B, TWIST1, VIM, and ZEB1, ii. calculating the activity level of the JAK-STAT3 transcription factor element in the sample using a calibrated pathway model, wherein the calibrated pathway model compares the expression levels of the at least three target genes in the sample with expression levels of the at least three more target genes in the calibrated pathway model which define an activity level of the JAK-STAT3 transcription factor element; and, b. calculating the activity level of the JAK-STAT3 cellular signaling pathway in the sample based on the calculated activity level of the JAK-STAT3 transcription factor element in the sample.

As contemplated herein, the method of calculating the activity level of the JAK-STAT3 cellular signaling pathway is performed by a computer processor.

Figure 2:
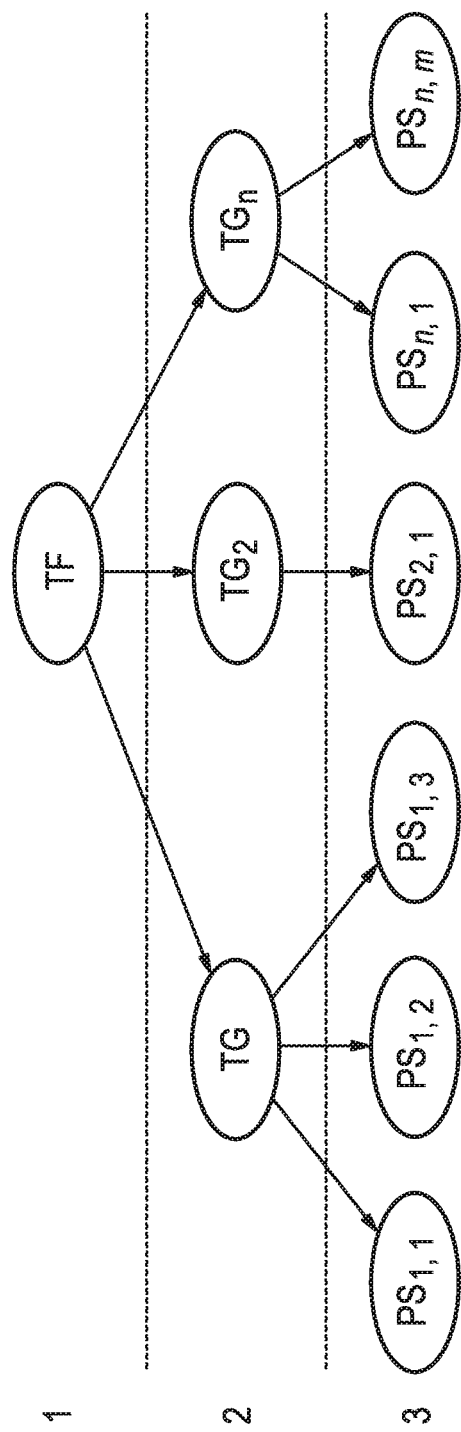
FIG. 2 shows schematically and exemplarily a mathematical model, herein, a Bayesian network model, useful in modelling the transcriptional program of the JAK-STAT3 cellular signaling pathway.

As a non-limiting generalized example, FIG. 2 provides an exemplary flow diagram used to determine the activity level of the JAK-STAT3 cellular signaling pathway based on a computer implemented mathematical model constructed of three nodes: (a) a transcription factor (TF) element (for example, but not limited to being, discretized into the states "absent" and "present" or as a continuous observable) in a first layer 1; (b) target genes $TG_1$, $TG_2$, $TG_n$ (for example, but not limited to being, discretized into the states "down" and "up" or as a continuous observable) in a second layer 2, and; (c) measurement nodes linked to the expression levels of the target genes in a third layer 3. The expression levels of the target genes can be determined by, for example, but not limited to, microarray probesets $PS_{1,1}$, $PS_{1,2}$, $PS_{1,3}$, $PS_{2,1}$, $PS_{n,1}$, $PS_{n,m}$ (for example, but limited to being, discretized into the states "low" and "high" or as a continuous observable), but could also be any other gene expression measurements such as, for example, RNAseq or RT-qPCR. The expression of the target genes depends on the activation of the respective transcription factor element, and the measured intensities of the selected probesets depend in turn on the expression of the respective target genes. The model is used to calculate JAK-STAT3 pathway activity by first determining probeset intensities, i.e., the expression level of the target genes, and calculating backwards in the calibrated pathway model what the probability is that the transcription factor element must be present.

The present invention makes it possible to determine the activity level of the JAK-STAT3 cellular signaling pathway in a subject by (i) determining an activity level of a JAK-STAT3 TF element in a sample of the subject, wherein the determining is based at least in part on evaluating a mathematical model relating expression levels of at least three, for example, at least four, at least five, at least six, at least seven, at least eight, at least nine, at least ten or more target genes of the JAK-STAT3 cellular signaling pathway, the transcription of which is controlled by the JAK-STAT3 TF element, to the activity level of the JAK-STAT3 TF element, and by (ii) calculating the activity level of the JAK-STAT3 cellular signaling pathway in the samplebased on the determined activity level of the JAK-STAT3 TF element in the sample. This preferably allows improving the possibilities of characterizing patients that have a disease, such as cancer, e.g., a breast, cervical, endometrial, ovarian, pancreatic or prostate cancer, which is at least partially driven by an abnormal activity of the JAK-STAT3 cellular signaling pathway, and that are therefore likely to respond to inhibitors of the JAK-STAT3 cellular signaling pathway. An important advantage of the present invention is that it makes it possible to determine the activity of the JAK-STAT3 cellular signaling pathway using a single sample, rather than requiring a plurality of samples extracted at different points in time.

Figure 3:
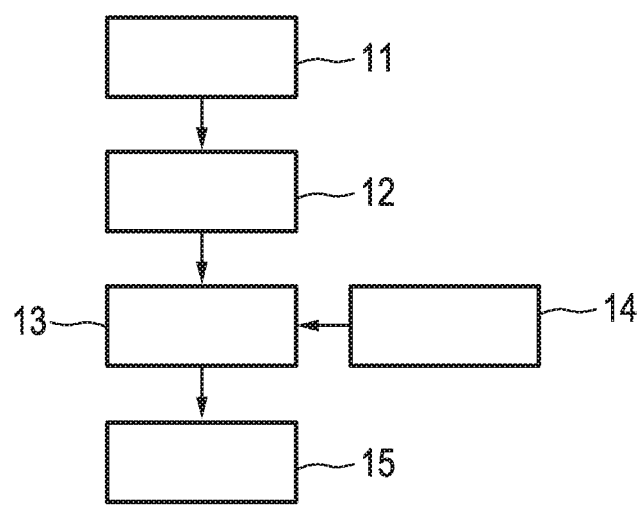
FIG. 3 shows an exemplary flow chart for calculating the activity level of the JAK-STAT3 cellular signaling pathway based on expression levels of target genes derived from a sample.

Generalized Workflow for Determining the Activity Level of JAK-STAT3 Cellular Signaling An example flow chart illustrating an exemplary calculation of the activity level of JAK-STAT3 cellular signaling from a sample isolated from a subject is provided in FIG. 3. First, the mRNA from a sample is isolated (11). Second, the mRNA expression levels of a unique set of at least three or more JAK-STAT3 target genes, as described herein, are measured (12) using methods for measuring gene expression that are known in the art. Next, the calculation of transcription factor element (13) is calculated using a calibrated pathway model (14), wherein the calibrated pathway model compares the expression levels of the at least three target genes in the sample with expression levels of the at least three target genes in the calibrated pathway model which have been correlated with a level of a JAK-STAT3 transcription factor element. Finally, the activity level of the JAK-STAT3 cellular signaling pathway is calculated in the sample based on the calculated levels of JAK-STAT3 transcription factor element in the sample (15). For example, the JAK-STAT3 signaling pathway is determined to be active if the activity is above a certain threshold, and can be categorized as passive if the activity falls below a certain threshold.

Target Genes

The present invention utilizes the analyses of the expression levels of unique sets of target genes. Particularly suitable target genes are described in the following text passages as well as the examples below (see, e.g., Tables 1 to 3 below).

Thus, according to an embodiment the target genes are selected from the group consisting of the target genes listed in Table 1 or Table 2 or Table 3 below.

In particular, the unique set of target genes whose expression is analyzed in the calibrated pathway model includes at least three or more target genes, for example, three, four, five, six, seven, eight, nine, ten or more, selected from AKT1, BCL2, BCL2L1, BIRC5, CCND1, CD274, CDKN1A, CRP, FGF2, FOS, FSCN1, FSCN2, FSCN3, HIF1A, HSP90AA1, HSP90AB1, HSP90B1, HSPA1A, HSPA1B, ICAM1, IFNG, IL10, JunB, MCL1, MMP1, MMP3, MMP9, MUC1, MYC, NOS2, POU2F1, PTGS2, SAA1, STAT1, TIMP1, TNFRSF1B, TWIST1, VIM, and ZEB1.

In one embodiment, the at least three or more target genes, for example, three, four, five, six, seven, eight, nine or more, are selected from BCL2L1, BIRC5, CCND1, CD274, FOS, HIF1A, HSP90AA1, HSP90AB1, MMP1, and MYC.

In one embodiment, the at least three or more target genes, for example, three, four, five, six, seven, eight, nine or more, are selected from BCL2L1, CD274, FOS, HSP90B1, HSPA1B, ICAM1, IFNG, JunB, PTGS2, STAT1, TNFRSF1B, and ZEB1.

It has been found by the present inventors that the target genes in the shorter lists are probative for determining the activity of the JAK-STAT3 cellular signaling pathway.

Measuring Levels of Gene Expression

Data derived from the unique set of target genes described herein is further utilized to determine the activity level of the JAK-STAT3 cellular signaling pathway using the methods described herein.

Methods for analyzing gene expression levels in isolated samples are generally known. For example, methods such as Northern blotting, the use of PCR, nested PCR, quantitative real-time PCR (qPCR), RNA-seq, or microarrays can all be used to derive gene expression level data. All methods known in the art for analyzing gene expression of the target genes are contemplated herein.

Methods of determining the expression product of a gene using PCR based methods may be of particular use. In order to quantify the level of gene expression using PCR, the amount of each PCR product of interest is typically estimated using conventional quantitative real-time PCR (qPCR) to measure the accumulation of PCR products in real time after each cycle of amplification. This typically utilizes a detectible reporter such as an intercalating dye, minor groove binding dye, or fluorogenic probe whereby the application of light excites the reporter to fluoresce and the resulting fluorescence is typically detected using a CCD camera or photomultiplier detection system, such as that disclosed in U.S. Pat. No. 6,713,297 which is hereby incorporated by reference.

In some embodiments, the probes used in the detection of PCR products in the quantitative real-time PCR (qPCR) assay can include a fluorescent marker. Numerous fluorescent markers are commercially available. For example, Molecular Probes, Inc. (Eugene, Oreg.) sells a wide variety of fluorescent dyes. Non-limiting examples include Cy5, Cy3, TAMRA, R6G, R110, ROX, JOE, FAM, Texas Red™, and Oregon Green™. Additional fluorescent markers can include IDT ZEN Double-Quenched Probes with traditional 5' hydrolysis probes in qPCR assays. These probes can contain, for example, a 5' FAM dye with either a 3' TAMRA Quencher, a 3' Black Hole Quencher (BHQ, Biosearch Technologies), or an internal ZEN Quencher and 3' Iowa Black Fluorescent Quencher (IBFQ).

Fluorescent dyes useful according to the invention can be attached to oligonucleotide primers using methods well known in the art. For example, one common way to add a fluorescent label to an oligonucleotide is to react an N-Hydroxysuccinimide (NHS) ester of the dye with a reactive amino group on the target. Nucleotides can be modified to carry a reactive amino group by, for example, inclusion of an allyl amine group on the nucleobase. Labeling via allyl amine is described, for example, in U.S. Pat. Nos. 5,476,928 and 5,958,691, which are incorporated herein by reference. Other means of fluorescently labeling nucleotides, oligonucleotides and polynucleotides are well known to those of skill in the art.

Other fluorogenic approaches include the use of generic detection systems such as SYBR-green dye, which fluoresces when intercalated with the amplified DNA from any gene expression product as disclosed in U.S. Pat. Nos. 5,436,134 and 5,658,751 which are hereby incorporated by reference.

Another useful method for determining target gene expression levels includes RNA-seq, a powerful analytical tool used for transcriptome analyses, including gene expression level difference between different physiological conditions, or changes that occur during development or over the course of disease progression.

Another approach to determine gene expression levels includes the use of microarrays for example RNA and DNA microarray, which are well known in the art. Microarrays can be used to quantify the expression of a large number of genes simultaneously.

Calibrated Pathway Model

As contemplated herein, the expression levels of the unique set of target genes described herein are used to calculate the activity level of the JAK-STAT3 transcription factor element using a calibrated pathway model as further described below. The calibrated pathway model compares the expression levels of the at least three target genes in the sample with expression levels of the at least three target genes in the calibrated pathway model which define an activity level of the JAK-STAT3 transcription factor element.

As contemplated herein, the calibrated pathway model is based on the application of a mathematical model. For example, the calibrated model can be based on a probabilistic model, for example a Bayesian network, or a linear or pseudo-linear model.

In one embodiment, the calibrated pathway model is a probabilistic model incorporating conditional probabilistic relationships that compare the expression levels of the at least three target genes in the sample with expression levels of the at least three target genes in the calibrated pathway model which define a level of a JAK-STAT3 transcription factor element to determine the activity level of the JAK-STAT3 transcription factor element in the sample. In one embodiment, the probabilistic model is a Bayesian network model.

In an alternative embodiment, the calibrated pathway model can be a linear or pseudo-linear model. In an embodiment, the linear or pseudo-linear model is a linear or pseudo-linear combination model.

Figure 4:
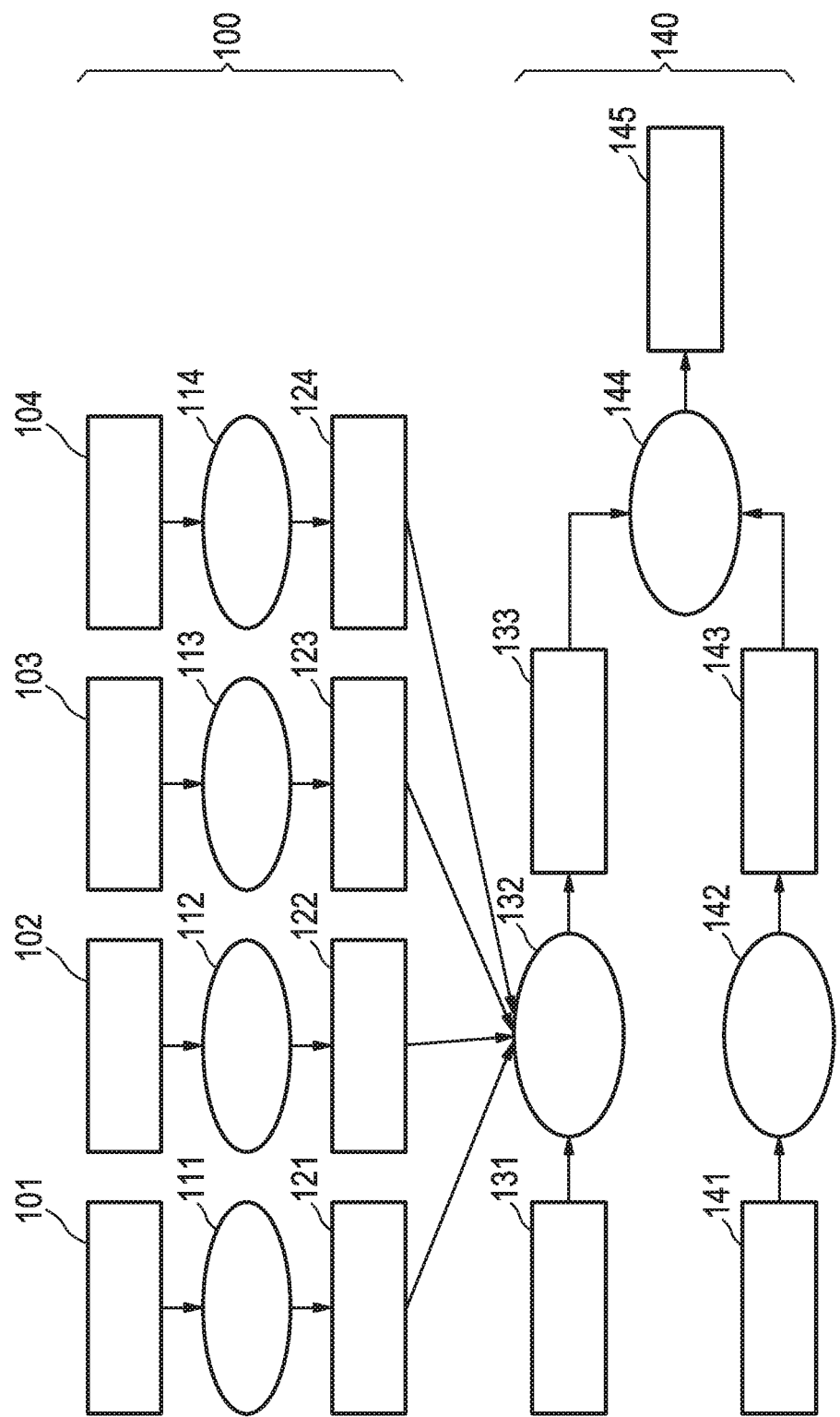
FIG. 4 shows an exemplary flow chart for obtaining a calibrated pathway model as described herein.

A non-limiting exemplary flow chart for a calibrated pathway model is shown in FIG. 4. As an initial step, the training data for the mRNA expression levels is collected and normalized. The data can be collected using, for example microarray probeset intensities (101), real-time PCR Cq values (102), raw RNAseq reads (103), or alternative measurement modalities (104) known in the art. The raw expression level data can then be normalized for each method, respectively, by normalization using a normalization algorithm, for example, frozen robust military analysis (fRMA) or MAS5.0 (111), normalization to average Cq of reference genes (112), normalization of reads into reads/fragments per kilobase of transcript per million mapped reads (RPKM/FPKM) (113), or normalization to w.r.t. reference genes/proteins (114). This normalization procedure leads to a normalized probeset intensity (121), normalized Cq values (122), normalized RPKM/FPKM (123), or normalized measurement (124) for each method, respectively, which indicate target gene expression levels within the training samples.

Once the training data has been normalized, a training sample ID or IDs (131) is obtained and the training data of these specific samples is obtained from one of the methods for determining gene expression (132). The final gene expression results from the training sample are output as training data (133). All of the data from various training samples are incorporated to calibrate the model (including for example, thresholds, CPTs, for example in the case of the probabilistic or Bayesian network, weights, for example, in the case of the linear or pseudo-linear model, etc) (144). In addition, the pathway's target genes and measurement nodes (141) are used to generate the model structure for example, as described in FIG. 2 (142). The resulting model structure (143) of the pathway is then incorporated with the training data (133) to calibrate the model (144), wherein the gene expression levels of the target genes is indicative of the transcription factor element activity. As a result of the transcription factor element calculations in the training samples, a calibrated pathway model (145) is calculated which assigns the JAK-STAT3 cellular signaling pathway activity level for a subsequently examined sample of interest, for example from a subject with a cancer, based on the target gene expression levels in the training samples.

Transcription Factor Element Calculation

Figure 5:
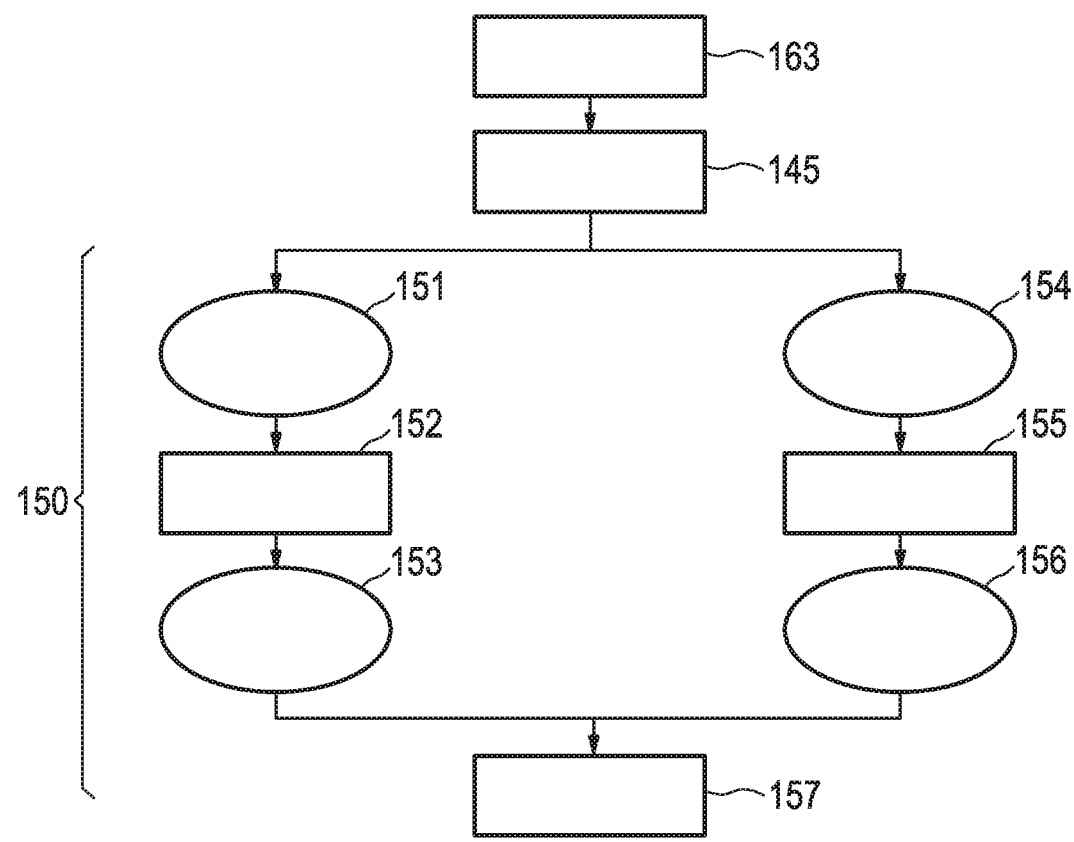
FIG. 5 shows an exemplary flow chart for calculating the Transcription Factor (TF) Element as described herein.

A non-limiting exemplary flow chart for calculating the Transcription Factor Element activity level is provided in FIG. 5. The expression level data (test data) (163) from a sample isolated from a subject is input into the calibrated pathway model (145). The mathematical model may be a probabilistic model, for example a Bayesian network model, a linear model, or pseudo-linear model.

The mathematical model may be a probabilistic model, for example a Bayesian network model, based at least in part on conditional probabilities relating the JAK-STAT3 TF element and expression levels of the at least three target genes of the JAK-STAT3 cellular signaling pathway measured in the sample of the subject, or the mathematical model may be based at least in part on one or more linear combination(s) of expression levels of the at least three target genes of the JAK-STAT3 cellular signaling pathway measured in the sample of the subject. In particular, the determining of the activity of the JAK-STAT3 cellular signaling pathway may be performed as disclosed in the published international patent application WO 2013/011479 A2 ("Assessment of cellular signaling pathway activity using probabilistic modeling of target gene expression"), and incorporated herein by reference. Briefly, the data is entered into a Bayesian network (BN) inference engine call (for example, a BNT toolbox) (154). This leads to a set of values for the calculated marginal BN probabilities of all the nodes in the BN (155). From these probabilities, the transcription factor (TF) node's probability (156) is determined and establishes the TF's element activity level (157).

Alternatively, the mathematical model may be a linear model. For example, a linear model can be used as described in the published international patent application WO 2014/102668 A2 ("Assessment of cellular signaling pathway activity using linear combination(s) of target gene expressions"), the contents of which are herewith incorporated in their entirety. Further details regarding the calculating/determining of cellular signaling pathway activity using mathematical modeling of target gene expression can also be found in Verhaegh W. et al., "Selection of personalized patient therapy through the use of knowledge-based computational models that identify tumor-driving signal transduction pathways", Cancer Research, Vol. 74, No. 11, 2014, pages 2936 to 2945. Briefly, the data is entered into a calculated weighted linear combination score (w/c) (151). This leads to a set of values for the calculated weighted linear combination score (152). From these weighted linear combination scores, the transcription factor (TF) node's weighted linear combination score (153) is determined and establishes the TF's element activity level (157).

Procedure for Discretized Observables

Figure 6:
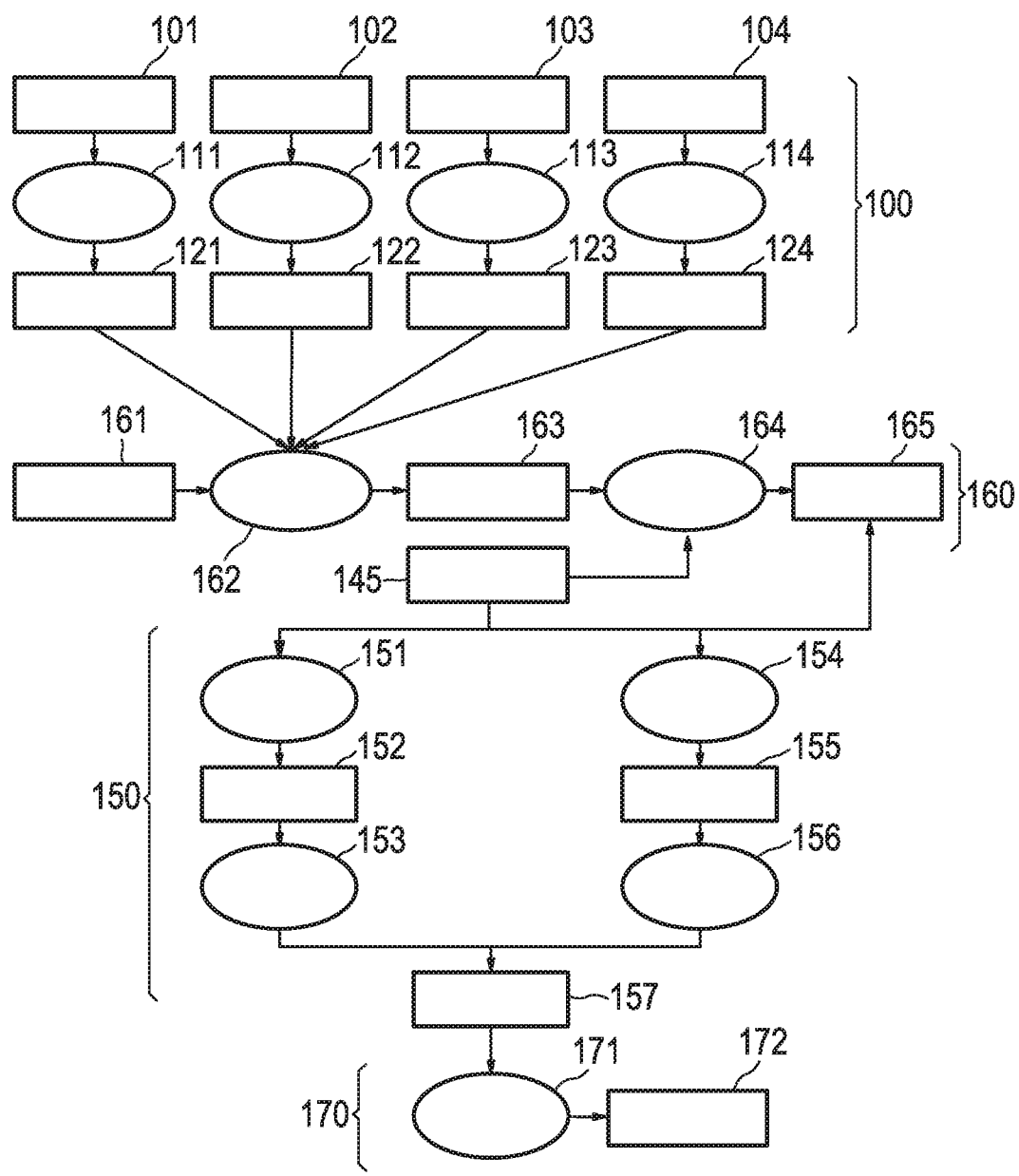
FIG. 6 shows an exemplary flow chart for calculating the JAK-STAT3 cellular signaling pathway activity level using discretized observables.

A non-limiting exemplary flow chart for calculating the activity level of a JAK-STAT3 cellular signaling pathway as a discretized observable is shown in FIG. 6. First, the test sample is isolated and given a test sample ID (161). Next, the test data for the mRNA expression levels is collected and normalized (162). The test data can be collected using the same methods as discussed for the training samples in FIG. 5, using microarray probeset intensities (101), real-time PCR Cq values (102), raw RNAseq reads (103), or an alternative measurement modalities (104). The raw expression level data can then be normalized for each method, respectively, by normalization using an algorithm, for example fRMA or MAS5.0 (111), normalization to average Cq of reference genes (112), normalization of reads into RPKM/FPKM (113), and normalization to w.r.t. reference genes/proteins (114). This normalization procedure leads to a normalized probeset intensity (121), normalized Cq values (122), normalized RPKM/FPKM (123), or normalized measurement (124) for each method, respectively.

Once the test data has been normalized, the resulting test data (163) is analyzed in a thresholding step (164) based on the calibrated pathway model (145), resulting in the thresholded test data (165). In using discrete observables, in one non-limiting example, every expression above a certain threshold is, for example, given a value of 1 and values below the threshold are given a value of 0, or in an alternative embodiment, the probability mass above the threshold as described herein is used as a thresholded value. Based on the calibrated pathway model, this value represents the TF's element activity level (157), which is then used to calculate the pathway's activity level (171). The final output gives the pathway's activity level (172) in the test sample being examined from the subject.

Procedure for Continuous Observables

Figure 7:
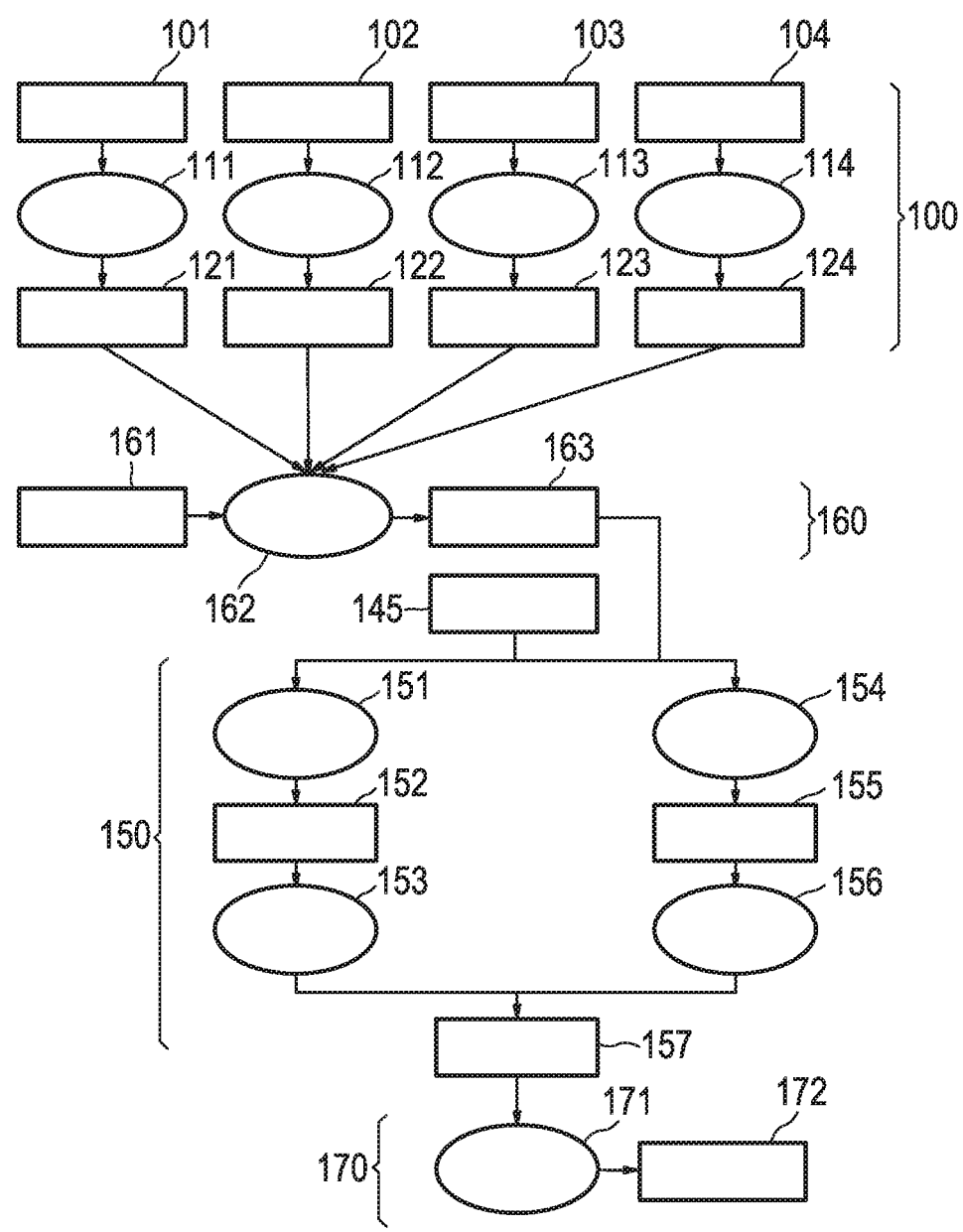
FIG. 7 shows an exemplary flow chart for calculating the JAK-STAT3 cellular signaling pathway activity level using continuous observables.

A non-limiting exemplary flow chart for calculating the activity level of a JAK-STAT3 cellular signaling pathway as a continuous observable is shown in FIG. 7. First, the test sample is isolated and given a test sample ID (161). Next, the test data for the mRNA expression levels is collected and normalized (162). The test data can be collected using the same methods as discussed for the training samples in FIG. 5, using microarray probeset intensities (101), real-time PCR Cq values (102), raw RNAseq reads (103), or an alternative measurement modalities (104). The raw expression level data can then be normalized for each method, respectively, by normalization using an algorithm, for example fRMA (111), normalization to average Cq of reference genes (112), normalization of reads into RPKM/FPKM (113), and normalization to w.r.t. reference genes/proteins (114). This normalization procedure leads to a a normalized probeset intensity (121), normalized Cq values (122), normalized RPKM/FPKM (123), or normalized measurement (124) for each method, respectively.

Once the test data has been normalized, the resulting test data (163) is analyzed in the calibrated pathway model (145). In using continuous observables, as one non-limiting example, the expression levels are converted to values between 0 and 1 using a sigmoid function as described in further detail below. The transcription factor element calculation as described herein is used to interpret the test data in combination with the calibrated pathway model, the resulting value represents the TF's element activity level (157), which is then used to calculate the pathway's activity level (171). The final output then gives the pathway's activity level (172) in the test sample.

Target Gene Expression Level Determination Procedure

Figure 8:
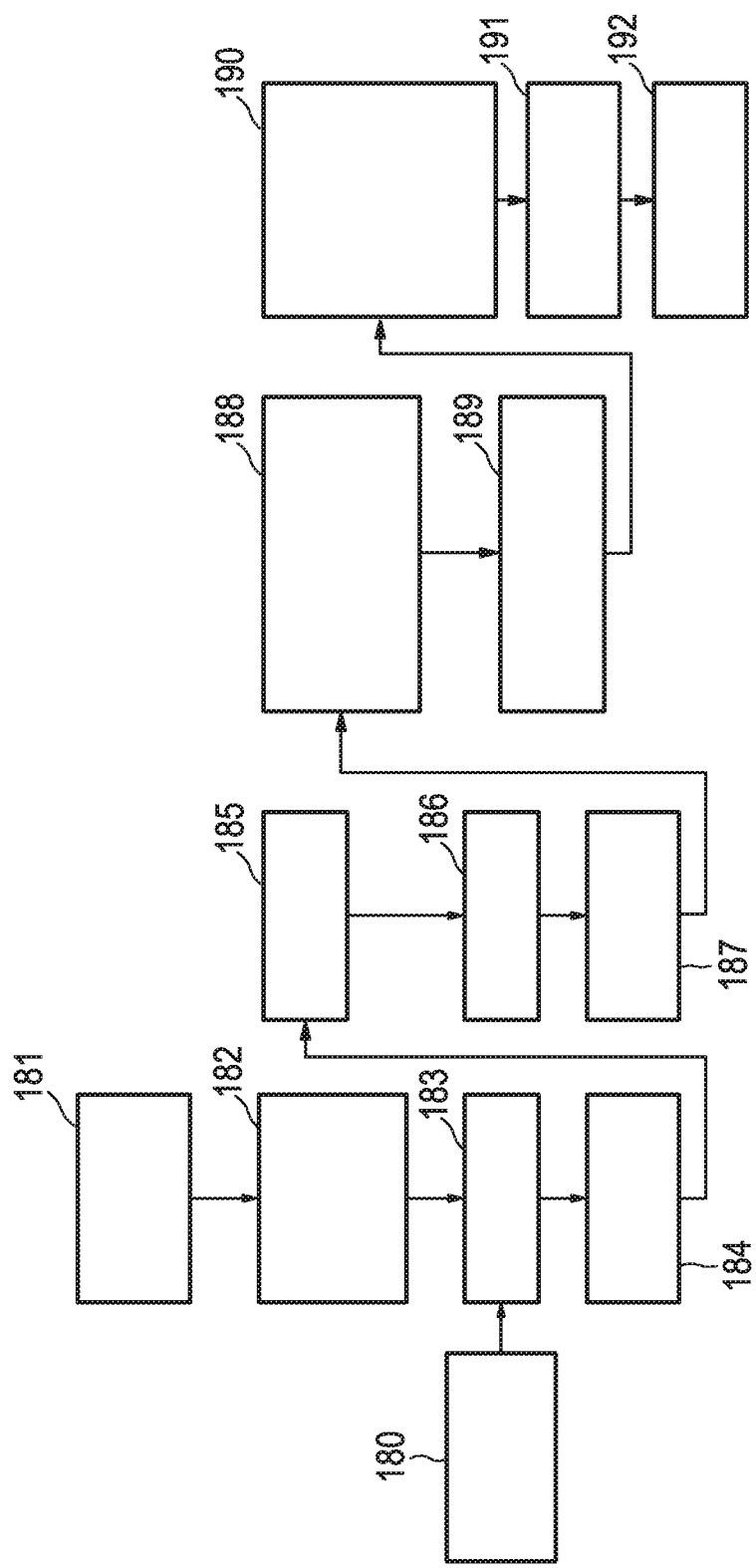
FIG. 8 shows an exemplary flow chart for determining Cq values from RT-qPCR analysis of the target genes of the JAK-STAT3 cellular signaling pathway.

A non-limiting exemplary flow chart for deriving target gene expression levels from a sample isolated from a subject is shown in FIG. 8. In one exemplary embodiment, samples are received and registered in a laboratory. Samples can include, for example, Formalin-Fixed, Paraffin-Embedded (FFPE) samples (181) or fresh frozen (FF) samples (180). FF samples can be directly lysed (183 . For FFPE samples, the paraffin can be removed with a heated incubation step upon addition of Proteinase K (182). Cells are then lysed (183), which destroys the cell and nuclear membranes which makes the nucleic acid (NA) available for further processing. The nucleic acid is bound to a solid phase (184) which could for example, be beads or a filter. The nucleic acid is then washed with washing buffers to remove all the cell debris which is present after lysis (185). The clean nucleic acid is then detached from the solid phase with an elution buffer (186). The DNA is removed by DNAse treatment to ensure that only RNA is present in the sample (187). The nucleic acid sample can then be directly used in the RT-qPCR sample mix (187). The RT-qPCR sample mixes contains the RNA sample, the RT enzyme to prepare cDNA from the RNA sample and a PCR enzyme to amplify the cDNA, a buffer solution to ensure functioning of the enzymes and can potentially contain molecular grade water to set a fixed volume of concentration. The sample mix can then be added to a multiwell plate (i.e., 96 well or 384 well plate) which contains dried RT-qPCR assays (189). The RT-qPCR can then be run in a PCR machine according to a specified protocol (190). An example PCR protocol includes i) 30 minutes at 50° C.; ii) 5 minutes at 95° C.; iii) 15 seconds at 95° C.; iv) 45 seconds at 60° C.; v) 50 cycles repeating steps iii and iv. The Cq values are then determined with the raw data by using the second derivative method (191). The Cq values are exported for analysis (192).

Computer Programs and Computer Implemented Methods

As contemplated herein, the calculation of JAK-STAT3 signaling in the sample is performed on a computerized device having a processor capable of executing a readable program code for calculating the JAK-STAT3 cellular signaling pathway activity in the sample according to the methods described above. Accordingly, the computerized device can include means for receiving expression level data, wherein the data is expression levels of at least three, for example, at least four, at least five, at least six, at least seven, at least eight, at least nine, at least ten or more target genes derived from the sample, a means for calculating the activity level of a JAK-STAT3 transcription factor element in the sample using a calibrated pathway model, wherein the calibrated pathway model compares the expression levels of the at least three target genes in the sample with expression levels of the at least three target genes in the calibrated pathway model which have been correlated with a level of the JAK-STAT3 transcription factor element; a means for calculating the activity level of the JAK-STAT3 cellular signaling pathway in the sample based on the calculated activity level of JAK-STAT3 transcription factor element in the sample; and a means for assigning a JAK-STAT3 cellular signaling pathway activity probability or status to the calculated activity level of the JAK-STAT3 cellular signaling pathway in the sample, and a means for displaying the JAK-STAT3 signaling pathway activity probability or status.

In accordance with another disclosed aspect, a non-transitory storage medium stores instructions that are executable by a digital processing device to perform a method according to the present invention as described herein. The non-transitory storage medium may be a computer-readable storage medium, such as a hard drive or other magnetic storage medium, an optical disk or other optical storage medium, a random access memory (RAM), read only memory (ROM), flash memory, or other electronic storage medium, a network server, or so forth. The digital processing device may be a handheld device (e.g., a personal data assistant or smartphone), a notebook computer, a desktop computer, a tablet computer or device, a remote network server, or so forth.

In accordance with another disclosed aspect, an apparatus comprises a digital processor configured to perform a method according to the present invention as described herein.

In accordance with another disclosed aspect, a computer program comprises program code means for causing a digital processing device to perform a method according to the present invention as described herein. The digital processing device may be a handheld device (e.g., a personal data assistant or smartphone), a notebook computer, a desktop computer, a tablet computer or device, a remote network server, or so forth.

In one embodiment, a computer program or system is provided for predicting the activity status of a JAK-STAT3 transcription factor element in a human cancer sample that includes a means for receiving data corresponding to the expression level of at least three JAK-STAT3 target genes in a sample from a host. In some embodiments, a means for receiving data can include, for example, a processor, a central processing unit, a circuit, a computer, or the data can be received through a website.

In one embodiment, a computer program or system is provided for predicting the activity status of a JAK-STAT3 transcription factor element in a human cancer sample that includes a means for displaying the JAK-STAT3 pathway signaling status in a sample from a host. In some embodiments, a means for displaying can include a computer monitor, a visual display, a paper print out, a liquid crystal display (LCD), a cathode ray tube (CRT), a graphical keyboard, a character recognizer, a plasma display, an organic light-emitting diode (OLED) display, or a light emitting diode (LED) display, or a physical print out.

In accordance with another disclosed aspect, a signal represents a determined activity of a JAK-STAT3 cellular signaling pathway in a subject, wherein the determined activity results from performing a method according to the present invention as described herein. The signal can be a digital signal or it can be an analog signal.

In one aspect of the present invention, a computer implemented method is provided for predicting the activity status of a JAK-STAT3 signaling pathway in a human cancer sample performed by a computerized device having a processor comprising: a) calculating an activity level of a JAK-STAT3 transcription factor element in a human cancer sample, wherein the activity level of the JAK-STAT3 transcription factor element in the human cancer sample is associated with JAK-STAT3 cellular signaling, and wherein the activity level of the JAK-STAT3 transcription factor element in the human cancer sample is calculated by i) receiving data on the expression levels of at least three, for example, at least four, at least five, at least six, at least seven, at least eight, at least nine, at least ten or more target genes derived from the human cancer sample, wherein the JAK-STAT3 transcription factor controls transcription of the at least three target genes, and wherein the at least three target genes are selected from AKT1, BCL2, BCL2L1, BIRC5, CCND1, CD274, CDKN1A, CRP, FGF2, FOS, FSCN1, FSCN2, FSCN3, HIF1A, HSP90AA1, HSP90AB1, HSP90B1, HSPA1A, HSPA1B, ICAM1, IFNG, IL10, JunB, MCL1, MMP1, MMP3, MMP9, MUC1, MYC, NOS2, POU2F1, PTGS2, SAA1, STAT1, TIMP1, TNFRSF1B, TWIST1, VIM, and ZEB1; ii) calculating the activity level of the JAK-STAT3 transcription factor element in the human cancer sample using a calibrated pathway model, wherein the calibrated pathway model compares the expression levels of the at least three target genes in the human cancer sample with expression levels of the at least three target genes in the calibrated pathway model which have been correlated with an activity level of the JAK-STAT3 transcription factor element; b) calculating the activity level of the JAK-STAT3 cellular signaling pathway in the human cancer sample based on the calculated activity level of the JAK-STAT3 transcription factor element in the human cancer sample; c) assigning a JAK-STAT3 cellular signaling pathway activity status to the calculated activity level of the JAK-STAT3 cellular signaling pathway in the human cancer sample, wherein the activity status is indicative of either an active JAK-STAT3 cellular signaling pathway or a passive JAK-STAT3 cellular signaling pathway; and d) displaying the JAK-STAT3 signaling pathway activity status.

In one aspect of the invention, a system is provided for determining the activity level of a JAK-STAT3 cellular signaling pathway in a subject comprising a) a processor capable of calculating an activity level of a JAK-STAT3 transcription factor element in a sample derived from the subject; b) a means for receiving data, wherein the data is an expression level of at least three, for example, at least four, at least five, at least six, at least seven, at least eight, at least nine, at least 10 or more target genes derived from the sample; c) a means for calculating the activity level of the JAK-STAT3 transcription factor element in the sample using a calibrated pathway model, wherein the calibrated pathway model compares the expression levels of the at least three target genes in the sample with expression levels of the at least three target genes in the calibrated pathway model which define an activity level of the JAK-STAT3 transcription factor element; d) a means for calculating the activity level of the JAK-STAT3 cellular signaling pathway in the sample based on the calculated activity level of JAK-STAT3 transcription factor element in the sample; a means for assigning a JAK-STAT3 cellular signaling pathway activity status to the calculated activity level of the JAK-STAT3 cellular signaling pathway in the sample, wherein the activity status is indicative of either an active JAK-STAT3 cellular signaling pathway or a passive JAK-STAT3 cellular signaling pathway; and f) a means for displaying the JAK-STAT3 signaling pathway activity status.

JAK-STAT3 Mediated Diseases and Disorders and Methods of Treatment

As contemplated herein, the methods and apparatuses of the present invention can be utilized to assess JAK-STAT3 cellular signaling pathway activity in a subject, for example a subject suspected of having, or having, a disease or disorder wherein the status of the JAK-STAT3 signaling pathway is probabtive, either wholly or partially, of disease presence or progression. In one embodiment, provided herein is a method of treating a subject comprising receiving information regarding the activity status of a JAK-STAT3 cellular signaling pathway derived from a sample isolated from the subject using the methods described herein and administering to the subject a JAK-STAT3 inhibitor if the information regarding the level of JAK-STAT3 cellular signaling pathway is indicative of an active JAK-STAT3 signaling pathway. In a particular embodiment, the JAK-STAT3 cellular signaling pathway activity indication is set at a cutoff value of odds of the JAK-STAT3 cellular signaling pathway being active of 10:1, 5:1, 4:1, 2:1, 1:1, 1:2, 1:4, 1:5, 1:10. JAK-STAT3 inhibitors are known and include, but are not limited to, STA-21, LLL-3, curcumin, or AZD9150.

The JAK-STAT3 pathway plays a role in a large number of diseases, such as in various cancer types like, for example, pancreatic cancer, colon cancer, breast cancer, head and neck cancer, osteosarcoma, multiple myeloma, follicular lymphoma, prostate cancer, cervical dysplasia, laryngeal papilloma, Peritoneal cavity carcinoma, ovarian cancer, cervical cancer, non-small cell lung cancer, bladder cancer, melanoma, oesophageal cancer, thyroid cancer, gastric cancer; lymphomas, prostate cancer, rhabdomyosarcoma, gastric cancer, melanoma, low-grade gliomas, Hodgkin's lymphoma; Hepatocellular carcinoma, head and neck squamous cell carcinoma, kidney cancer, liver cancer, glioblastoma multiforme Neuroendocrine carcinoma, multiple myeloma, Chronic lymphocytic leukaemia, squamous cell lung cancer, and other cancer types and cancer subtypes that have an active STAT3 signaling pathway as a cancer driving pathway, in immune system-mediated diseases like inflammatory bowel disease, rheumatoid arthritis, psoriasis, SLE, multiple sclerosis, et cetera, and in inflammatory diseases like asthma, atherosclerosis, diabetes, psychiatric diseases like depression and schizophrenia, acne, endometriosis, et cetera. With such diseases, measuring the JAK-STAT3 pathway activity profile in immune cell types in tissue and blood is expected to be helpful to diagnose, subtype, and predict and/or monitor response to immunomodulatory, especially immunosuppressive and targeted immunosuppressive, therapy and monitoring immune response status. For example, especially for rheumatoid arthritis and psoriasis. Prediction of response to drugs can be used to match an anti-STAT3 pathway drug to a patient, like for example STA-21 for treatment of psoriasis, curcumin for treatment of Pancreatic cancer (Phase II/III clinical trial), colon cancer (Phase I/II/III), breast cancer (Phase II), head and neck cancer (Phase 0), osteosarcoma (Phase I/II), multiple myeloma (Phase II), atopic asthma (phase not provided), dermatitis (Phase II/III), type 2 diabetes (Phase IV), schizophrenia (Phase I/II), Alzheimer's disease (Phase I/II), multiple sclerosis (Phase II), rheumatoid arthritis (Phase 0), AZD for treatment of Hepatocellular carcinoma, lung carcinoma and gastric cancer (Phase I), essential thrombocythaemia myelofibrosis and post-polycythaemia vera (Phase I), Oligodeoxy-nucleotide decoy for treatment of head and neck cancer (Phase O), Tofacitinib for treatment of Rheumatoid arthritis (Phase I/II/III), juvenile idiopathic arthritis (Phase I/II/III), psoriasis (Phase I/II/III), ankylosing spondylitis (Phase II), keratoconjunctivitis sicca (Phase II), ulcerative colitis (Phase III), capsaicin for treatment of Chronic obstructive pulmonary disease (Phase 0/I/II), psoriasis (Phase IV), chronic neck pain (Phase II), rhinitis (Phase I/II/IV), pulmonary hypertension (Phase II), HIV infections (Phase II/III), peripheral nervous system diseases (Phase II/III), migraine (Phase I), burning mouth syndrome (Phase 0), curcumin for treatment of Pancreatic cancer (Phase II/III), colon cancer (Phase I/II/III), breast cancer (Phase II), head and neck cancer (Phase 0), osteosarcoma (Phase I/II), multiple myeloma (Phase II), atopic asthma (phase not provided), dermatitis (Phase II/III), type 2 diabetes (Phase IV), schizophrenia (Phase I/II), Alzheimer's disease (Phase I/II), multiple sclerosis (Phase II), rheumatoid arthritis (Phase 0), resveratrol for treatment of Colorectal cancer (Phase I), follicular lymphoma (Phase II), cardiovascular diseases (Phase I/II), type 2 diabetes (Phase I/II/III), obesity (Phase II), Alzheimer's disease (Phase II/III), memory impairment (phase not provided), WithaferinA for treatment of schizophrenia, 3,3"-diindolyl-methane for treatment of Breast cancer (Phase I/II/III), prostate cancer (Phase I/II), cervical dysplasia (Phase III), laryngeal papilloma (Phase II), thyroid disease (Phase 0), Emodin for treatment of polycysitic kidney disease, paclitaxel for treatment of Peritoneal cavity carcinoma (Phase I/II/III), breast cancer (Phase I/II/III/IV), ovarian cancer (Phase I/II/III/IV), cervical cancer (Phase I/II/III), non-small cell lung cancer (Phase I/II/III/IV), bladder cancer (Phase I/II/III), melanoma (Phase I/II/III), oesophageal cancer (Phase I/II/III), thyroid cancer (Phase I/II/III), gastric cancer (Phase I/II/III), Oleanolic acid/CDDO-Me for treatment of Solid tumours and lymphomas (Phase I), chronic kidney disease and type 2 diabetes (Phase I/II/III), diabetic nephropathy (Phase II), hepatic dysfunction (Phase I/II), vinorelbine for treatment of Non-small cell lung cancer (Phase I/II/III/IV), breast cancer (Phase I/II/III/IV), prostate cancer (Phase I/II), rhabdomyosarcoma (Phase I/II/III), gastric cancer (Phase II), melanoma (Phase II), low-grade gliomas (Phase II), Hodgkin's lymphoma (Phase I/II/III), Cryptotanshinone for treatment of Polycystic ovary syndrome, cinnamon bark for treatment of Polycystic ovary syndrome (Phase I), hypercholesterolaemia and type 2 diabetes (Phase II), sorafenib for treatment of Hepatocellular carcinoma (Phase I/II/III/IV), head and neck squamous cell carcinoma (Phase I/II), gastric cancer (Phase I/II), breast cancer (Phase I/II/III), prostate cancer (Phase I/II), thyroid cancer (Phase II/III), non-small cell lung cancer (Phase I/II/III), pancreatic cancer (Phase I/II/III), bladder cancer (Phase I/II), colorectal cancer (Phase I/II), kidney cancer (Phase I/II/III/IV), liver cancer (Phase I/II/III), glioblastoma multiforme (Phase I/II), leukaemia (Phase I/II/III), melanoma (Phase I/II/III), Atiprimod for treatment of Neuroendocrine carcinoma (Phase II), multiple myeloma (Phase I/II), Auranofin for treatment of Chronic lymphocytic leukaemia (Phase II), squamous cell lung cancer (Phase II), ovarian cancer (phase not provided), and Oligodeoxy-nucleotide decoy to treat head and neck cancer (Phase O) (see also Miklossy G. et al., "Therapeutic modulators of STAT signaling for human diseases", Nature Reviews Drug Discovery, Vol. 12, No. 8, August 2013, pages 611 to 629).

The sample(s) to be used in accordance with the present invention can be an extracted sample, that is, a sample that has been extracted from the subject. Examples of the sample include, but are not limited to, a tissue, cells, blood and/or a body fluid of a subject. It can be, e.g., a sample obtained from a cancer lesion, or from a lesion suspected for cancer, or from a metastatic tumor, or from a body cavity in which fluid is present which is contaminated with cancer cells (e.g., pleural or abdominal cavity or bladder cavity), or from other body fluids containing cancer cells, and so forth, for example, via a biopsy procedure or other sample extraction procedure. The cells of which a sample is extracted may also be tumorous cells from hematologic malignancies (such as leukemia or lymphoma). In some cases, the cell sample may also be circulating tumor cells, that is, tumor cells that have entered the bloodstream and may be extracted using suitable isolation techniques, e.g., apheresis or conventional venous blood withdrawal. Aside from blood, a body fluid of which a sample is extracted may be urine, gastrointestinal contents, or an extravasate.

In one aspect of the present invention, the methods and apparatuses described herein are used to identify an active JAK-STAT3 cellular signaling pathway in a subject suffering from a cancer, and administering to the subject an anti-cancer agent, for example a JAK-STAT3 inhibitor, selected from, but not limited to, STA-21, LLL-3, curcumin, or AZD9150.

Another aspect of the present invention relates to a method (as described herein), further comprising:
determining whether the JAK-STAT3 cellular signaling pathway is operating abnormally in the subject based on the calculated activity of the JAK-STAT3 cellular signaling pathway in the subject.

Here, the term "abnormally" denotes disease-promoting activity of the JAK-STAT3 cellular signaling pathway, for example, a tumor-promoting activity.

The present invention also relates to a method (as described herein) further comprising:
recommending prescribing a drug, for example, a JAK-STAT3 inhibitor, for the subject that corrects for abnormal operation of the JAK-STAT3 cellular signaling pathway,
wherein the recommending is performed if the JAK-STAT3 cellular signaling pathway is determined to be operating abnormally in the subject based on the calculated/determined activity of the JAK-STAT3 cellular signaling pathway.

The present invention also relates to a method (as described herein), wherein the calculating/determining comprises:
calculating the activity of the JAK-STAT3 cellular signaling pathway in the subject based at least on expression levels of two, three or more target genes of a set of target genes of the JAK-STAT3 cellular signaling pathway measured in the sample of the subject.

The present invention as described herein can, e.g., also advantageously be used in connection with:
diagnosis based on the determined activity of the JAK-STAT3 cellular signaling pathway in the subject;
prognosis based on the determined activity of the JAK-STAT3 cellular signaling pathway in the subject;
drug prescription based on the determined activity of the JAK-STAT3 cellular signaling pathway in the subject;
prediction of drug efficacy based on the determined activity of the JAK-STAT3 cellular signaling pathway in the subject;
prediction of adverse effects based on the determined activity of the JAK-STAT3 cellular signaling pathway in the subject;
monitoring of drug efficacy;
drug development;
assay development;
pathway research;
cancer staging;
enrollment of the subject in a clinical trial based on the determined activity of the JAK-STAT3 cellular signaling pathway in the subject;
selection of subsequent test to be performed; and
selection of companion diagnostics tests.

Further advantages will be apparent to those of ordinary skill in the art upon reading and understanding the attached figures, the following description and, in particular, upon reading the detailed examples provided herein below.

It shall be understood that an embodiment of the present invention can also be any combination of the dependent claims or above embodiments with the respective independent claim.

These and other aspects of the invention will be apparent from and elucidated with reference to the embodiments described hereinafter.

EXAMPLES

The following examples merely illustrate exemplary methods and selected aspects in connection therewith. The teaching provided therein may be used for constructing several tests and/or kits, e.g., to detect, predict and/or diagnose the abnormal activity of the JAK-STAT3 cellular signaling pathway. Furthermore, upon using methods as described herein drug prescription can advantageously be guided, drug response prediction and monitoring of drug efficacy (and/or adverse effects) can be made, drug resistance can be predicted and monitored, e.g., to select subsequent test(s) to be performed (like a companion diagnostic test). The following examples are not to be construed as limiting the scope of the present invention.

Example 1: Mathematical Model Construction

As described in detail in the published international patent application WO 2013/011479 A2 ("Assessment of cellular signaling pathway activity using probabilistic modeling of target gene expression"), by constructing a probabilistic model, e.g., a Bayesian network model, and incorporating conditional probabilistic relationships between expression levels of at least three, for example, at least four, at least five, at least six, at least seven, at least nine, at least ten or more target genes of a cellular signaling pathway, herein, the JAK-STAT3 cellular signaling pathway, and the level of a transcription factor (TF) element, herein, the JAK-STAT3 TF element, the TF element controlling transcription of the at least three target genes of the cellular signaling pathway, such a model may be used to determine the activity of the cellular signaling pathway with a high degree of accuracy. Moreover, the probabilistic model can be readily updated to incorporate additional knowledge obtained by later clinical studies, by adjusting the conditional probabilities and/or adding new nodes to the model to represent additional information sources. In this way, the probabilistic model can be updated as appropriate to embody the most recent medical knowledge.

In another easy to comprehend and interpret approach described in detail in the published international patent application WO 2014/102668 A2 ("Assessment of cellular signaling pathway activity using linear combination(s) of target gene expressions"), the activity of a cellular signaling pathway, herein, the JAK-STAT3 cellular signaling pathway, may be determined by constructing and evaluating a linear or (pseudo-)linear model incorporating relationships between expression levels of at least three, for example, at least four, at least five, at least six, at least seven, at least nine, at least ten or more target genes of the cellular signaling pathway and the level of a transcription factor (TF) element, herein, the JAK-STAT3 TF element, the TF element controlling transcription of the at least three target genes of the cellular signaling pathway, the model being based at least in part on one or more linear combination(s) of expression levels of the at least three target genes.

In both approaches, the expression levels of the at least three target genes may, for example, be measurements of the level of mRNA, which can be the result of, e.g., (RT)-PCR and microarray techniques using probes associated with the target genes mRNA sequences, and of RNA-sequencing. In another embodiment, the expression levels of the at least three target genes can be measured by protein levels, e.g., the concentrations and/or activity of the protein(s) encoded by the target genes.

The aforementioned expression levels may optionally be converted in many ways that might or might not suit the application better. For example, four different transformations of the expression levels, e.g., microarray-based mRNA levels, may be:

"continuous data", i.e., expression levels as obtained after preprocessing of microarrays using well known algorithms such as MAS5.0 and fRMA, "z-score", i.e., continuous expression levels scaled such that the average across all samples is 0 and the standard deviation is 1, "discrete", i.e., every expression above a certain threshold is set to 1 and below it to 0 (e.g., the threshold for a probeset may be chosen as the (weighted) median of its value in a set of a number of positive and the same number of negative clinical samples), "fuzzy", i.e., the continuous expression levels are converted to values between 0 and 1 using a sigmoid function of the following format: $1/(1+\exp((thr-expr)/se))$, with expr being the continuous expression levels, thr being the threshold as mentioned before and se being a softening parameter influencing the difference between 0 and 1.

One of the simplest linear models that can be constructed is a model having a node representing the transcription factor (TF) element, herein, the JAK-STAT3 TF element, in a first layer and weighted nodes representing direct measurements of the target genes expression levels, e.g., by one probeset that is particularly highly correlated with the particular target gene, e.g., in microarray or (q)PCR experiments, in a second layer. The weights can be based either on calculations from a training data set or based on expert knowledge. This approach of using, in the case where possibly multiple expression levels are measured per target gene (e.g., in the case of microarray experiments, where one target gene can be measured with multiple probesets), only one expression level per target gene is particularly simple. A specific way of selecting the one expression level that is used for a particular target gene is to use the expression level from the probeset that is able to separate active and passive samples of a training data set the best. One method to determine this probeset is to perform a statistical test, e.g., the t-test, and select the probeset with the lowest p-value. The training data set's expression levels of the probeset with the lowest p-value is by definition the probeset with the least likely probability that the expression levels of the (known) active and passive samples overlap. Another selection method is based on odds-ratios. In such a model, one or more expression level(s) are provided for each of the at least three target genes and the one or more linear combination(s) comprise a linear combination including for each of the at least three target genes a weighted term, each weighted term being based on only one expression level of the one or more expression level(s) provided for the respective target gene. If the only one expression level is chosen per target gene as described above, the model may be called a "most discriminant probesets" model.

In an alternative to the "most discriminant probesets" model, it is possible, in the case where possibly multiple expression levels are measured per target gene, to make use of all the expression levels that are provided per target gene. In such a model, one or more expression level(s) are provided for each of the at least three target genes and the one or more linear combination(s) comprise a linear combination of all expression levels of the one or more expression level(s) provided for the at least three target genes. In other words, for each of the at least three target genes, each of the one or more expression level(s) provided for the respective target gene may be weighted in the linear combination by its own (individual) weight. This variant may be called an "all probesets" model. It has an advantage of being relatively simple while making use of all the provided expression levels.

Both models as described above have in common that they are what may be regarded as "single-layer" models, in which the level of the TF element is calculated based on a linear combination of expression levels of the one or more probeset of the one or more target genes.

After the level of the TF element, herein, the JAK-STAT3 TF element, has been determined by evaluating the respective model, the determined TF element level can be thresholded in order to infer the activity of the cellular signaling pathway, herein, the JAK-STAT3 cellular signaling pathway. An exemplary method to calculate such an appropriate threshold is by comparing the determined TF element levels w/c of training samples known to have a passive cellular signaling pathway and training samples with an active cellular signaling pathway. A method that does so and also takes into account the variance in these groups is given by using a threshold $$thr = \frac{\sigma_{wlc_{pas}} \mu_{wlc_{act}} + \sigma_{wlc_{act}} \mu_{wlc_{pas}}}{\sigma_{wlc_{pas}} + \sigma_{wlc_{act}}} \quad (1)$$

where $\sigma$ and $\mu$ are the standard deviation and the mean of the determined TF element levels w/c for the training samples. In case only a small number of samples are available in the active and/or passive training samples, a pseudocount may be added to the calculated variances based on the average of the variances of the two groups:

$$\bar{v}_{wlc_{pas}} = \frac{x\bar{v} + (n_{pas} - 1)v_{wlc_{pas}}}{x + n_{pas} - 1} \quad (2)$$

$$\bar{v} = \frac{v_{wlc_{act}} + v_{wlc_{pas}}}{2}$$

where v is the variance of the determined TF element levels w/c of the groups, x is a positive pseudocount, e.g., 1 or 10, and nact and npas are the number of active and passive samples, respectively. The standard deviation $\sigma$ can next be obtained by taking the square root of the variance v.

The threshold can be subtracted from the determined TF element levels w/c for ease of interpretation, resulting in a cellular signaling pathway's activity score in which negative values correspond to a passive cellular signaling pathway and positive values correspond to an active cellular signaling pathway.

As an alternative to the above-described "single-layer" models, a "two-layer" may also be used in an example. In such a model, a summary value is calculated for every target gene using a linear combination based on the measured intensities of its associated probesets ("first (bottom) layer"). The calculated summary value is subsequently combined with the summary values of the other target genes of the cellular signaling pathway using a further linear combination ("second (upper) layer"). Again, the weights can be either learned from a training data set or based on expert knowledge or a combination thereof. Phrased differently, in the "two-layer" model, one or more expression level(s) are provided for each of the at least three target genes and the one or more linear combination(s) comprise for each of the at least three target genes a first linear combination of all expression levels of the one or more expression level(s) provided for the respective target gene ("first (bottom) layer"). The model is further based at least in part on a further linear combination including for each of the at least three target genes a weighted term, each weighted term being based on the first linear combination for the respective target gene ("second (upper) layer").

The calculation of the summary values can, in an exemplary version of the "two-layer" model, include defining a threshold for each target gene using the training data and subtracting the threshold from the calculated linear combination, yielding the target gene summary. Here the threshold may be chosen such that a negative target gene summary value corresponds to a down-regulated target gene and that a positive target gene summary value corresponds to an up-regulated target gene. Also, it is possible that the target gene summary values are transformed using, e.g., one of the above-described transformations (fuzzy, discrete, etc.), before they are combined in the "second (upper) layer".

After the level of the TF element has been determined by evaluating the "two-layer" model, the determined TF element level can be thresholded in order to infer the activity of the cellular signaling pathway, as described above.

In the following, the models described above are collectively denoted as "(pseudo-) linear" models. A more detailed description of the training and use of probabilistic models, e.g., a Bayesian network model, is provided in Example 3 below.

Example 2: Selection of Target Genes

A transcription factor (TF) is a protein complex (i.e., a combination of proteins bound together in a specific structure) or a protein that is able to regulate transcription from target genes by binding to specific DNA sequences, thereby controlling the transcription of genetic information from DNA to mRNA. The mRNA directly produced due to this action of the TF complex is herein referred to as a "direct target gene" (of the transcription factor). Cellular signaling pathway activation may also result in more secondary gene transcription, referred to as "indirect target genes". In the following, (pseudo-)linear models or Bayesian network models (as exemplary mathematical models) comprising or consisting of direct target genes as direct links between cellular signaling pathway activity and mRNA level, are exemplified, however the distinction between direct and indirect target genes is not always evident. Herein, a method to select direct target genes using a scoring function based on available scientific literature data is presented. Nonetheless, an accidental selection of indirect target genes cannot be ruled out due to limited information as well as biological variations and uncertainties. In order to select the target genes, the MEDLINE database of the National Institute of Health accessible at "www.ncbi.nlm.nih.gov/pubmed" and herein further referred to as "Pubmed" was employed to generate a lists of target genes. Furthermore, three additional lists of target genes were selected based on the probative nature of their expression.

Publications containing putative JAK-STAT3 target genes were searched for by using queries such as ("JAK-STAT3" AND "target gene") in the period of the first and second quarter of 2017. The resulting publications were further analyzed manually following the methodology described in more detail below.

Specific cellular signaling pathway mRNA target genes were selected from the scientific literature, by using a ranking system in which scientific evidence for a specific target gene was given a rating, depending on the type of scientific experiments in which the evidence was accumulated. While some experimental evidence is merely suggestive of a gene being a direct target gene, like for example an mRNA increasing as detected by means of an increasing intensity of a probeset on a microarray of a cell line in which it is known that the JAK-STAT3 cellular signaling pathway is active, other evidence can be very strong, like the combination of an identified JAK-STAT3 cellular signaling pathway TF binding site and retrieval of this site in a chromatin immunoprecipitation (ChIP) assay after stimulation of the specific cellular signaling pathway in the cell and increase in mRNA after specific stimulation of the cellular signaling pathway in a cell line.

Several types of experiments to find specific cellular signaling pathway target genes can be identified in the scientific literature:

1. ChIP experiments in which direct binding of a TF of the cellular signaling pathway of interest to its binding site on the genome is shown. Example: By using chromatin immunoprecipitation (ChIP) technology subsequently putative functional JAK-STAT3 TF binding sites in the DNA of cell lines with and without active induction of the JAK-STAT3 cellular signaling pathway, e.g., by stimulation with JAK-STAT3, were identified, as a subset of the binding sites recognized purely based on nucleotide sequence. Putative functionality was identified as ChIP-derived evidence that the TF was found to bind to the DNA binding site.
2. Electrophoretic Mobility Shift (EMSA) assays which show in vitro binding of a TF to a fragment of DNA containing the binding sequence. Compared to ChIP-based evidence EMSA-based evidence is less strong, since it cannot be translated to the in vivo situation.
3. Stimulation of the cellular signaling pathway and measuring mRNA expression using a microarray, RNA sequencing, quantitative PCR or other techniques, using JAK-STAT3 cellular signaling pathway-inducible cell lines and measuring mRNA profiles measured at least one, but preferably several time points after induction—in the presence of cycloheximide, which inhibits translation to protein, thus the induced mRNAs are assumed to be direct target genes.
4. Similar to 3, but alternatively measure the mRNAs expression further downstream with protein abundance measurements, such as western blot.
5. Identification of TF binding sites in the genome using a bioinformatics approach. Example for the JAK-STAT3 TF element: Using the binding motif CTGGGAA, the potential binding sites were identified in gene promoter regions.
6. Similar as 3, only in the absence of cycloheximide.
7. Similar to 4, only in the absence of cycloheximide.

In the simplest form one can give every potential gene 1 point for each of these experimental approaches in which the gene was identified as being a target gene of the JAK-STAT3 family of transcription factors. Using this relative ranking strategy, one can make a list of most reliable target genes.

Alternatively, ranking in another way can be used to identify the target genes that are most likely to be direct target genes, by giving a higher number of points to the technology that provides most evidence for an in vivo direct target gene. In the list above, this would mean 7 points for experimental approach 1), 6 for 2), and going down to 1 point for experimental approach 7). Such a list may be called a "general list of target genes".

Despite the biological variations and uncertainties, the inventors assumed that the direct target genes are the most likely to be induced in a tissue-independent manner. A list of these target genes may be called an "evidence curated list of target genes". Such an evidence curated list of target genes has been used to construct computational models of the JAK-STAT3 cellular signaling pathway that can be applied to samples coming from different tissue sources.

The following will illustrate exemplary how the selection of an evidence curated target gene list specifically was constructed for the JAK-STAT3 cellular signaling pathway.

A scoring function was introduced that gave a point for each type of experimental evidence, such as ChIP, EMSA, differential expression, knock down/out, luciferase gene reporter assay, sequence analysis, that was reported in a publication. The same experimental evidence is sometimes mentioned in multiple publications resulting in a corresponding number of points, e.g., two publications mentioning a ChIP finding results in twice the score that is given for a single ChIP finding. Further analysis was performed to allow only for genes that had diverse types of experimental evidence and not only one type of experimental evidence, e.g., differential expression. Those genes that had more than one type of experimental evidence available were selected (as shown in Table 1).

A further selection of the evidence curated list of target genes (listed in Table 2) was made by the inventors. The target genes of the evidence curated list that were proven to be more probative in determining the activity of the JAK-STAT3 signaling pathway from the training samples were selected. Herein, available expression data sets of EGFR mutant cells of lung cancer from data set GSE57156 were used. The cells that were treated with Erlotinib were JAK-STAT3 inactive and cells that were treated with DMSO were JAK-STAT3 active. The gene expression values for the "evidence curated list of target genes" (39 target genes list) from Table 1 were compared between STAT3 active and inactive samples from the GSE57156 data set. If the expression level of a target gene was obviously differentiated between the pathway active and inactive groups, which signifies that the target gene can be used to distinguish between the pathway active and inactive groups, then the target gene was selected. This resulted in the "10 target genes shortlist for the JAK-STAT3 lung model" shown in Table 2. Regarding the JAK-STAT3 blood model, a Sez-4 cell line, which was derived from a cutaneous T-cell lymphoma in data set GSE8687, was adopted to select the target genes shortlist. The cells starved of IL-2 were JAK-STAT3 inactive and the cells cultured with IL-2 were JAK-STAT3 active. The gene expression values for the "evidence curated list of target genes" (39 target genes list) from Table 1 were compared between STAT3 active and inactive samples from the GSE8687 data set. If the expression level of a target gene was obviously differentiated between the pathway active and inactive groups, which signifies that the target gene can be used to distinguish between the pathway active and inactive groups, then the target gene was selected. This resulted in the "12 target genes shortlist for the JAK-STAT3 blood model" shown in Table 3.

TABLE 1

"Evidence curated list of target genes" (39 target genes list) of the JAK-STAT3 cellular signaling pathway used in the JAK-STAT3 cellular signaling pathway models and associated probesets used to measure the mRNA expression level of the target genes.

| Target gene | Probeset | Target gene | Probeset |
|---|---|---|---|
| AKT1 | 207163_s_at | HSPA1B | 202581_at |
| BCL2 | 203685_at | ICAM1 | 202637_s_at |

TABLE 1-continued

"Evidence curated list of target genes" (39 target genes list) of the JAK-STAT3 cellular signaling pathway used in the JAK-STAT3 cellular signaling pathway models and associated probesets used to measure the mRNA expression level of the target genes.

| Target gene | Probeset | Target gene | Probeset |
|---|---|---|---|
| | 203684_s_at | | 202638_s_at |
| | 232614_at | | 215485_s_at |
| | 232210_at | IFNG | 210354_at |
| | 244035_at | JunB | 201473_at |
| | 207004_at | MCL1 | 200796_s_at |
| | 207005_s_at | | 200797_s_at |
| BCL2L1 | 212312_at | | 200798_x_at |
| | 206665_s_at | | 227175_at |
| | 215037_s_at | MMP1 | 204475_at |
| BIRC5 | 202094_at | MMP3 | 205828_at |
| | 202095_s_at | MMP9 | 203936_s_at |
| | 210334_x_at | MUC1 | 207847_s_at |
| CCND1 | 214019_at | | 213693_s_at |
| | 208711_s_at | | 211695_x_at |
| | 208712_at | MYC | 238381_x_at |
| CD274 | 223834_at | | 202431_s_at |
| | 227458_at | | 239931_at |
| CDKN1A | 202284_s_at | NOS2 | 210037_s_at |
| CRP | 37020_at | POU2F1 | 206789_s_at |
| | 205753_at | | 234649_at |
| FGF2 | 204422_s_at | | 1562280_at |
| | 204421_s_at | | 1564351_at |
| FOS | 209189_at | PTGS2 | 204748_at |
| FSCN1 | 201564_s_at | | 1554997_a_at |
| FSCN2 | 207204_at | SAA1 | 214456_x_at |
| FSCN3 | 220379_at | STAT1 | 200887_s_at |
| HIF1A | 200989_at | | 232375_at |
| | 238869_at | | 209969_s_at |
| HSP90AA1 | 211968_s_at | TIMP1 | 201666_at |
| | 211969_at | TNFRSF1B | 203508_at |
| | 210211_s_at | TWIST1 | 213943_at |
| HSP90AB1 | 200064_at | VIM | 201426_s_at |
| | 214359_s_at | | 1555938_x_at |
| HSP90B1 | 200598_s_at | ZEB1 | 210875_s_at |
| | 200599_s_at | | 208078_s_at |
| | 239451_at | | 212758_s_at |
| HSPA1A | 200799_at | | 212764_at |
| | 200800_s_at | | 239952_at |
| IL10 | 207433_at | | |

TABLE 2

"10 target genes shortlist for the JAK-STAT3 lung model" of JAK-STAT3 target genes based on the evidence curated list of JAK-STAT3 target genes. (The associated probesets are the same as in Table 1.)
Target gene

BCL2L1
BIRC5
CCND1
CD274
FOS
HIF1A
HSP90AA1
HSP90AB1
MMP1
MYC

TABLE 3

"12 target genes shortlist for the JAK-STAT3 blood model" of JAK-STAT3 target genes based on the evidence curated list of JAK-STAT3 target genes. (The associated probesets are the same as in Table 1.)
Target gene BCL2L1
CD274
FOS
HSP90B1
HSPA1B
ICAM1
IFNG
JunB
PTGS2
STAT1
TNFRSF1B
ZEB1

Example 3: Training and Using the Mathematical Model

Before the mathematical model can be used to infer the activity of the cellular signaling pathway, herein, the JAK-STAT3 cellular signaling pathway, in a subject, the model must be appropriately trained.

If the mathematical model is a probabilistic model, e.g., a Bayesian network model, based at least in part on conditional probabilities relating the JAK-STAT3 TF element and expression levels of the at least three target genes of the JAK-STAT3 cellular signaling pathway measured in a sample, the training may preferably be performed as described in detail in the published international patent application WO 2013/011479 A2 ("Assessment of cellular signaling pathway activity using probabilistic modeling of target gene expression").

If the mathematical model is based at least in part on one or more linear combination(s) of expression levels of the at least three target genes of the JAK-STAT3 cellular signaling pathway measured in the sample, the training may preferably be performed as described in detail in the published international patent application WO 2014/102668 A2 ("Assessment of cellular signaling pathway activity using linear combination(s) of target gene expressions").

Herein, an exemplary Bayesian network model as shown in FIG. 2 was used to model the transcriptional program of the JAK-STAT3 cellular signaling pathway in a simple manner. The model consists of three types of nodes: (a) a transcription factor (TF) element (with states "absent" and "present") in a first layer 1; (b) target genes $TG_1$, $TG_2$, $TG_n$ (with states "down" and "up") in a second layer 2, and; (c) measurement nodes linked to the expression levels of the target genes in a third layer 3. These can be microarray probesets $PS_{1,1}$, $PS_{1,2}$, $PS_{1,3}$, $PS_{2,1}$, $PS_{n,1}$, $PS_{n,m}$ (with states "low" and "high"), as preferably used herein, but could also be other gene expression measurements such as RNAseq or RT-qPCR.

A suitable implementation of the mathematical model, herein, the exemplary Bayesian network model, is based on microarray data. The model describes (i) how the expression levels of the target genes depend on the activation of the TF element, and (ii) how probeset intensities, in turn, depend on the expression levels of the respective target genes. For the latter, probeset intensities may be taken from fRMA pre-processed Affymetrix HG-U133Plus2.0 microarrays, which are widely available from the Gene Expression Omnibus (GEO, www.ncbi.nlm.nih.gov/geo) and ArrayExpress (www.ebi.ac.uk/arrayexpress).

As the exemplary Bayesian network model is a simplification of the biology of a cellular signaling pathway, herein, the JAK-STAT3 cellular signaling pathway, and as biological measurements are typically noisy, a probabilistic approach was opted for, i.e., the relationships between (i) the TF element and the target genes, and (ii) the target genes and their respective probesets, are described in probabilistic terms. Furthermore, it was assumed that the activity of the oncogenic cellular signaling pathway which drives tumor growth is not transiently and dynamically altered, but long term or even irreversibly altered. Therefore the exemplary Bayesian network model was developed for interpretation of a static cellular condition. For this reason complex dynamic cellular signaling pathway features were not incorporated into the model.

Once the exemplary Bayesian network model is built and calibrated (see below), the model can be used on microarray data of a new sample by entering the probeset measurements as observations in the third layer 3, and inferring backwards in the calibrated pathway model what the probability must have been for the TF element to be "present". Here, "present" is considered to be the phenomenon that the TF element is bound to the DNA and is controlling transcription of the cellular signaling pathway's target genes, and "absent" the case that the TF element is not controlling transcription. This probability is hence the primary read-out that may be used to indicate activity of the cellular signaling pathway, herein, the JAK-STAT3 cellular signaling pathway, which can next be translated into the odds of the cellular signaling pathway being active by taking the ratio of the probability of it being active vs. it being passive (i.e., the odds are given by $p/(1-p)$, where p is the predicted probability of the cellular signaling pathway being active).

In the exemplary Bayesian network model, the probabilistic relations have been made quantitative to allow for a quantitative probabilistic reasoning. In order to improve the generalization behavior across tissue types, the parameters describing the probabilistic relationships between (i) the TF element and the target genes have been carefully hand-picked. If the TF element is "absent", it is most likely that the target gene is "down", hence a probability of 0.95 is chosen for this, and a probability of 0.05 is chosen for the target gene being "up". The latter (non-zero) probability is to account for the (rare) possibility that the target gene is regulated by other factors or that it is accidentally observed as being "up" (e.g. because of measurement noise). If the TF element is "present", then with a probability of 0.70 the target gene is considered "up", and with a probability of 0.30 the target gene is considered "down". The latter values are chosen this way, because there can be several causes why a target gene is not highly expressed even though the TF element is present, e.g., because the gene's promoter region is methylated. In the case that a target gene is not up-regulated by the TF element, but down-regulated, the probabilities are chosen in a similar way, but reflecting the down-regulation upon presence of the TF element. The parameters describing the relationships between (ii) the target genes and their respective probesets have been calibrated on experimental data. For the latter, in this example, microarray data was used from patients samples which are known to have an active JAK-STAT3 cellular signaling pathway whereas normal, healthy samples from the same dataset were used as passive JAK-STAT3 cellular signaling pathway samples, but this could also be performed using cell line experiments or other patient samples with known cellular signaling pathway activity status. The resulting conditional probability tables are given by:

A: For Upregulated Target Genes

|  | $PS_{i,j}$ = low | $PS_{i,j}$ = high |
|---|---|---|
| $TG_i$ = down | $\dfrac{AL_{i,j}+1}{AL_{i,j}+AH_{i,j}+2}$ | $\dfrac{AH_{i,j}+1}{AL_{i,j}+AH_{i,j}+2}$ |
| $TG_i$ = up | $\dfrac{PL_{i,j}+1}{PL_{i,j}+PH_{i,j}+2}$ | $\dfrac{PH_{i,j}+1}{PL_{i,j}+PH_{i,j}+2}$ |

B: For Downregulated Target Genes

|  | $PS_{i,j}$ = low | $PS_{i,j}$ = high |
|---|---|---|
| $TG_i$ = down | $\dfrac{PL_{i,j}+1}{PL_{i,j}+PH_{i,j}+2}$ | $\dfrac{PH_{i,j}+1}{PL_{i,j}+PH_{i,j}+2}$ |
| $TG_i$ = up | $\dfrac{AL_{i,j}+1}{AL_{i,j}+AH_{i,j}+2}$ | $\dfrac{AH_{i,j}+1}{AL_{i,j}+AH_{i,j}+2}$ |

In these tables, the variables $AL_{i,j}$, $AH_{i,j}$, $PL_{i,j}$, and $PH_{i,j}$ indicate the number of calibration samples with an "absent" (A) or "present" (P) transcription complex that have a "low" (L) or "high" (H) probeset intensity, respectively. Dummy counts have been added to avoid extreme probabilities of 0 and 1.

To discretize the observed probeset intensities, for each probeset $PS_{i,j}$ a threshold $t_{i,j}$ was used, below which the observation is called "low", and above which it is called "high". This threshold has been chosen to be the (weighted) median intensity of the probeset in the used calibration dataset. Due to the noisiness of microarray data, a fuzzy method was used when comparing an observed probeset intensity to its threshold, by assuming a normal distribution with a standard deviation of 0.25 (on a log 2 scale) around the reported intensity, and determining the probability mass below and above the threshold.

If instead of the exemplary Bayesian network described above, a (pseudo-)linear model as described in Example 1 above is employed, the weights indicating the sign and magnitude of the correlation between the nodes and a threshold to call whether a node is either "absent" or "present" would need to be determined before the model could be used to infer cellular signaling pathway activity in a test sample. One could use expert knowledge to fill in the weights and the threshold a priori, but typically the model would be trained using a representative set of training samples, of which preferably the ground truth is known, e.g., expression data of probesets in samples with a known "present" transcription factor complex (=active cellular signaling pathway) or "absent" transcription factor complex (=passive cellular signaling pathway).

Known in the field are a multitude of training algorithms (e.g., regression) that take into account the model topology and changes the model parameters, here, the weights and the threshold, such that the model output, here, a weighted linear score, is optimized. Alternatively, it is also possible to calculate the weights directly from the expression observed levels without the need of an optimization algorithm.

A first method, named "black and white"-method herein, boils down to a ternary system, in which each weight is an element of the set $\{-1, 0, 1\}$. If this is put in a biological context, the −1 and 1 correspond to target genes or probesets that are down- and up-regulated in case of cellular signaling pathway activity, respectively. In case a probeset or target gene cannot be statistically proven to be either up- or down-regulated, it receives a weight of 0. In one example, a left-sided and right-sided, two sample t-test of the expression levels of the active cellular signaling pathway samples versus the expression levels of the samples with a passive cellular signaling pathway can be used to determine whether a probe or gene is up- or down-regulated given the used training data. In cases where the average of the active samples is statistically larger than the passive samples, i.e., the p-value is below a certain threshold, e.g., 0.3, the target gene or probeset is determined to be up-regulated. Conversely, in cases where the average of the active samples is statistically lower than the passive samples, the target gene or probeset is determined to be down-regulated upon activation of the cellular signaling pathway. In case the lowest p-value (left- or right-sided) exceeds the aforementioned threshold, the weight of the target gene or probeset can be defined to be 0.

A second method, named "log odds"-weights herein, is based on the logarithm (e.g., base e) of the odds ratio. The odds ratio for each target gene or probeset is calculated based on the number of positive and negative training samples for which the probeset/target gene level is above and below a corresponding threshold, e.g., the (weighted) median of all training samples. A pseudo-count can be added to circumvent divisions by zero. A further refinement is to count the samples above/below the threshold in a somewhat more probabilistic manner, by assuming that the probeset/target gene levels are e.g. normally distributed around its observed value with a certain specified standard deviation (e.g., 0.25 on a 2-log scale), and counting the probability mass above and below the threshold. Herein, an odds ratio calculated in combination with a pseudo-count and using probability masses instead of deterministic measurement values is called a "soft" odds ratio.

Further details regarding the determining of cellular signaling pathway activity using mathematical modeling of target gene expression can be found in Verhaegh W. et al., "Selection of personalized patient therapy through the use of knowledge-based computational models that identify tumor-driving signal transduction pathways", Cancer Research, Vol. 74, No. 11, 2014, pages 2936 to 2945.

Herein, we have used publically available mRNA expression data from Affymetrix U133Plus2.0 on two data sets from the GEO database. Because the STAT3 pathway activation of solid cancer cells and blood cells has slightly different effects on the target gene expression levels, two different calibration data sets were used, representative for STAT3 activation in solid cancer cell and blood cell. One data set has EGFR mutant cells from non-small cell lung cancers. EGFR mutant cells treated with Erlotinib formed the JAK-STAT3 inactive group, and EGFR mutant cells treated with DMSO were taken as JAK-STAT3 active calibration samples. Another data set had a Sez-4 cell line which was derived from a cutaneous T-cell lymphoma. Cells that were starved of IL-2 were taken as the JAK-STAT3 inactive group, and cells cultured with IL-2 were taken as JAK-STAT3 active calibration samples. Hence, two different models were calibrated separately on calibration samples with lung cancer cells and blood cells, respectively, using the same target gene list (see Table 1).

Figure 9:
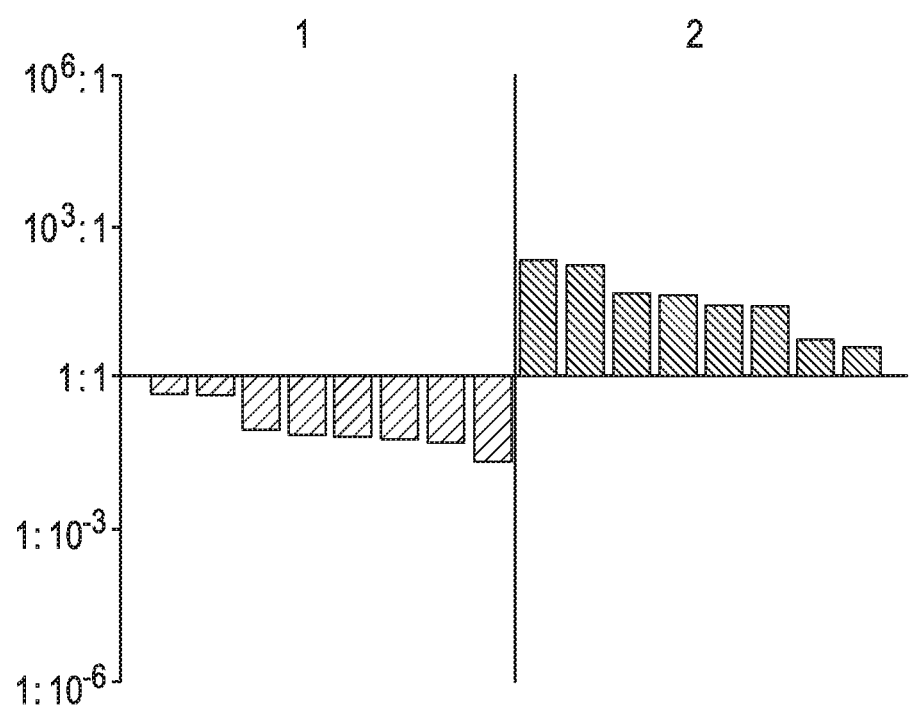
FIG. 9 shows calibration results of the Bayesian network model based on the evidence curated list of target genes (39 target genes list) from Table 1 and the methods as described herein using EGFR mutant cells of lung cancer from data set GSE57156.
Figure 10:
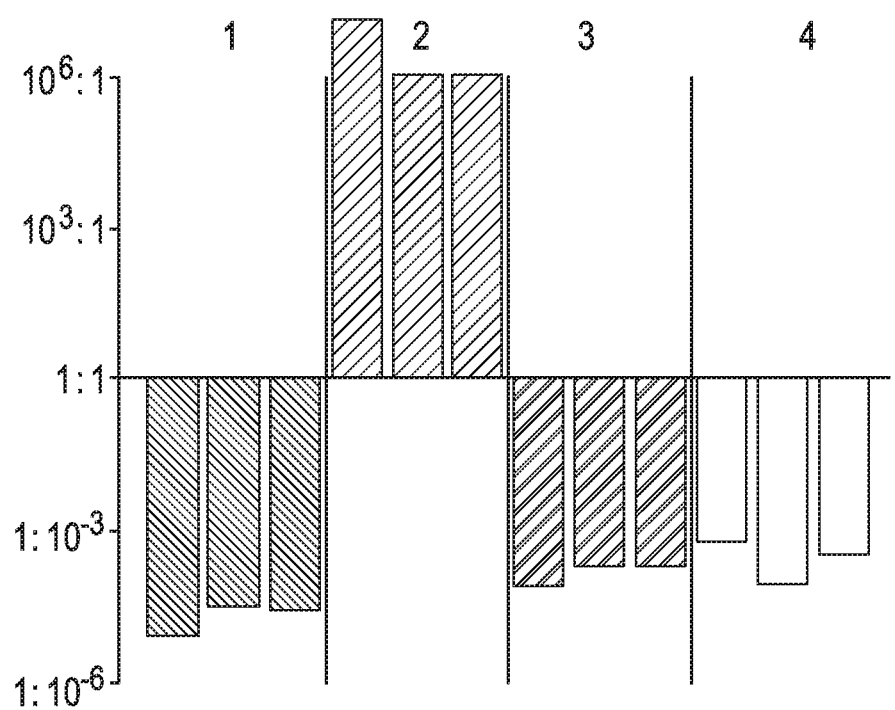
FIG. 10 shows calibration results of the Bayesian network model based on the evidence curated list of target genes (39 target genes list) from Table 1 and the methods as described using a Sez-4 cell line which was derived from a cutaneous T-cell lymphoma from data set GSE8687.

In the following, calibration results of the Bayesian network model on data sets with lung cancer cells and blood cells, respectively, are shown in FIGS. 9 and 10.

FIG. 9 shows calibration results of the Bayesian network model based on the evidence curated list of target genes (39 target genes list) from Table 1 and the methods as described herein using EGFR mutant cells of lung cancer from data set GSE57156. The cells that were treated with Erlotinib (group 1) were JAK-STAT3 inactive and the cells treated with DMSO (group 2) were considered JAK-STAT3 active. In the diagram, the vertical axis indicates the odds that the TF element is "present" resp. "absent", which corresponds to the JAK-STAT3 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT3 model (lung model) was able to separate clearly the inactive from the active calibration samples.

FIG. 10 shows calibration results of the Bayesian network model based on the evidence curated list of target genes (39 target genes list) from Table 1 and the methods as described using a Sez-4 cell line which was derived from a cutaneous T-cell lymphoma from data set GSE8687. The cells starved of IL-2 (group 1) were JAK-STAT3 inactive and have been used as control group. The training group included 3 samples with cells cultured with IL-2, which were STAT3 active. The model was tested on other samples treated with pan-Jak inhibitor (group 3) and Jak3 inhibitor (group 4). In the diagram, the vertical axis indicates the odds that the TF element is "present" resp. "absent", which corresponds to the JAK-STAT3 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT3 model (blood model) was able to separate clearly the inactive from the active calibration samples.

In the following, validation results of the trained exemplary lung Bayesian network model using the evidence curated list of target genes (39 target genes list) are shown in FIGS. 11 to 15.

Figure 11:
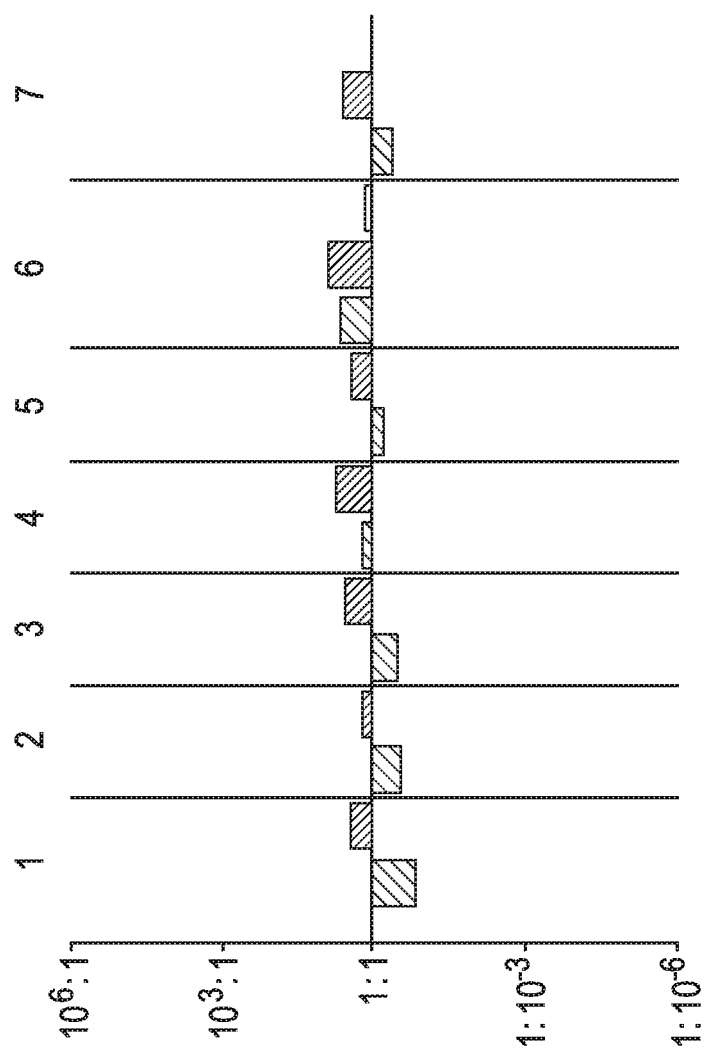
FIG. 11 shows JAK-STAT3 cellular signaling pathway activity predictions of the trained exemplary lung Bayesian network model using the evidence curated list of target genes (39 target genes list) from Table 1 (data set GSE32975).

FIG. 11 shows JAK-STAT3 cellular signaling pathway activity predictions of the trained exemplary lung Bayesian network model using the evidence curated list of target genes (39 target genes list) from Table 1. Epithelial cells from HaCaT cell lines were stimulated with epidermal growth factor (EGF) in data set GSE32975. Each group represents one replica from the cell line. In the diagram, the vertical axis indicates the odds that the TF element is "present" resp. "absent", which corresponds to the JAK-STAT3 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT3 lung model correctly predicts higher STAT3 activity in the samples which were stimulated with EGF (second bar of each group), and inactive STAT3 in the unstimulated control group (first of each group). In group 6 and group 7, the samples were treated with gefitinib, and JAK-STAT3 lung model can predict the decreased STAT3 pathway activity (third bar of group 6 and group 7).

Figure 12:
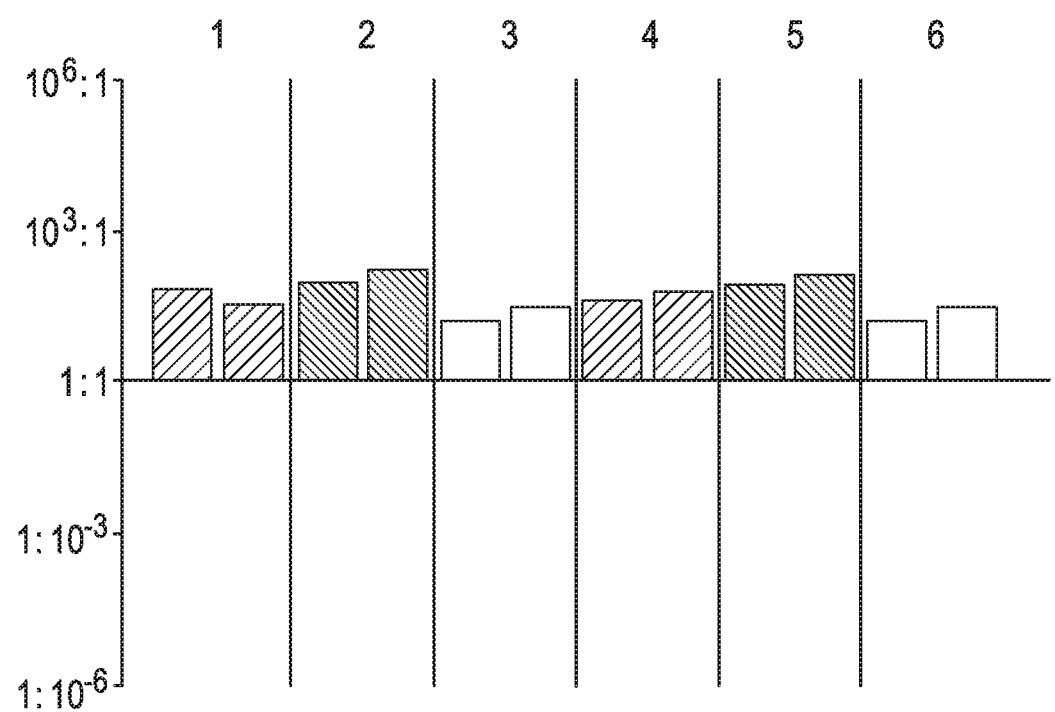
FIG. 12 shows JAK-STAT3 cellular signaling pathway activity predictions of the trained exemplary lung Bayesian network model using the evidence curated list of target genes (39 target genes list) from Table 1 (data set GSE20854).

FIG. 12 shows JAK-STAT3 cellular signaling pathway activity predictions of the trained exemplary lung Bayesian network model using the evidence curated list of target genes (39 target genes list) from Table 1. Ishikawa H cells (derived endometrial carcinomas) were dosed with either EGF (epidermal growth factor) or Iressa (gefitinib) for 12 or 24 hours in data set GSE20854. In the diagram, the vertical axis indicates the odds that the TF element is "present" resp. "absent", which corresponds to the JAK-STAT3 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT3 lung model correctly predicts higher STAT3 activity in the samples which were stimulated with EGF for 12 hours (group 2) and 24 hours (group 5), compared to undosed samples and harvested at 12 hours (group 1) and at 24 hours (group 4). Group 3 and group 6 were dosed with iressa for 12 hours and 24 hours, respectively, and the JAK-STAT3 lung model predicts decreased STAT3 pathway activity.

Figure 13:
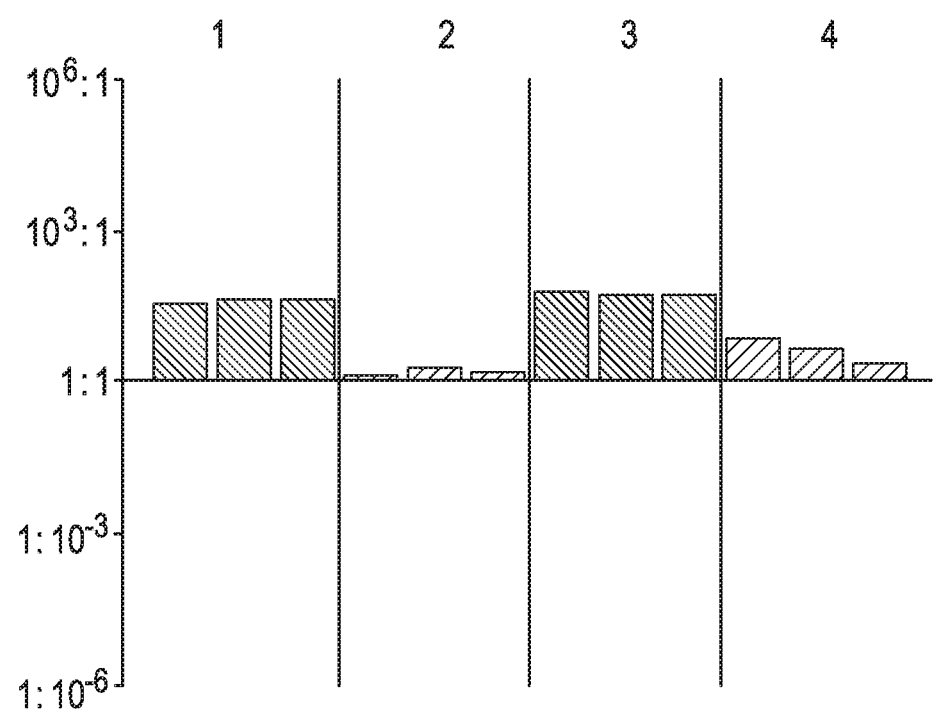
FIG. 13 shows JAK-STAT3 cellular signaling pathway activity predictions of the trained exemplary lung Bayesian network model using the evidence curated list of target genes (39 target genes list) from Table 1 (data set GSE67051).

FIG. 13 shows JAK-STAT3 cellular signaling pathway activity predictions of the trained exemplary lung Bayesian network model using the evidence curated list of target genes (39 target genes list) from Table 1. PC9 or HCC827 cells are GFR-mutant NSCLC (Non-small cell lung cancer) cells, and they were treated with erlotinib or DMSO for 8 days (data set GSE67051). In the diagram, the vertical axis indicates the odds that the TF element is "present" resp. "absent", which corresponds to the JAK-STAT3 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT3 lung model correctly predicts higher STAT3 activity in the PC 9 (group 1) and HCC827 (group 3) cells that were treated with DMSO, compared to PC 9 (group 2) and HCC827 (group 4) cells that were treated with erlotinib.

Figure 14:
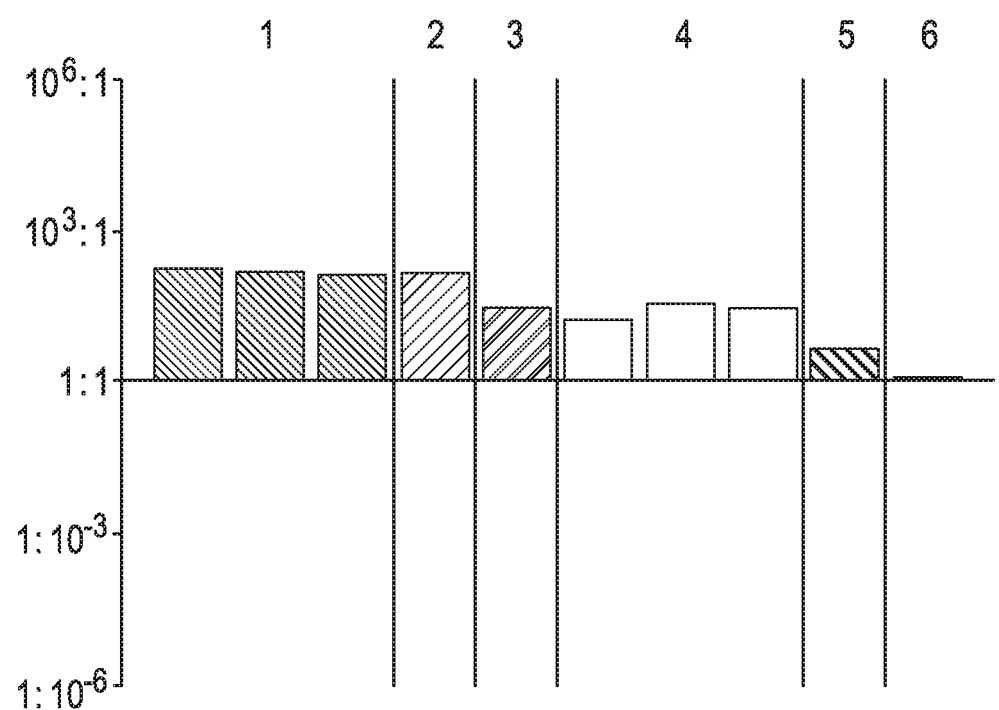
FIG. 14 shows JAK-STAT3 cellular signaling pathway activity predictions of the trained exemplary lung Bayesian network model using the evidence curated list of target genes (39 target genes list) from Table 1 (data set GSE52212).

FIG. 14 shows JAK-STAT3 cellular signaling pathway activity predictions of the trained exemplary lung Bayesian network model using the evidence curated list of target genes (39 target genes list) from Table 1. EGFR-mutant lung cancer cells HCC827 were treated with 1 uM erlotinib (EGFR inhibitor) and DMSO in data set GSE51212. In the diagram, the vertical axis indicates the odds that the TF element is "present" resp. "absent", which corresponds to the JAK-STAT3 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT3 lung model correctly predicts higher STAT3 activity in the cells that were treated with DMSO for 6 hours (group 1) and 24 hours (group 2), compared to cells that were treated with erlotinib for 3 hours (group 3), 6 hours (group 4), 12 hours (group 5) and 24 hours (group 6).

Figure 15:
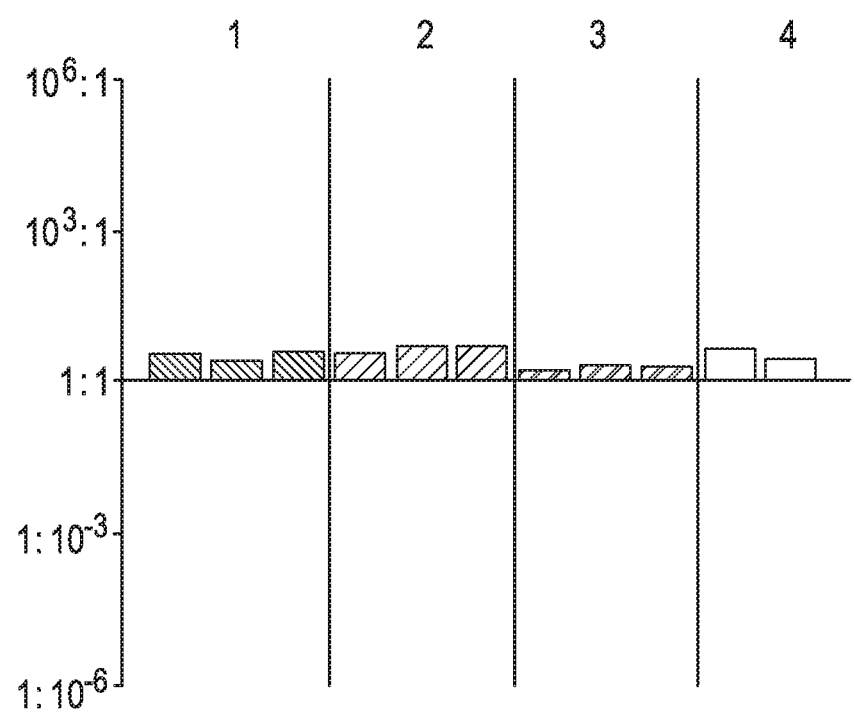
FIG. 15 shows JAK-STAT3 cellular signaling pathway activity predictions of the trained exemplary lung Bayesian network model using the evidence curated list of target genes (39 target genes list) from Table 1 (data set GS64536).

FIG. 15 shows JAK-STAT3 cellular signaling pathway activity predictions of the trained exemplary lung Bayesian network model using the evidence curated list of target genes (39 target genes list) from Table 1. siSTAT3 knockdown of a tamoxifen initiated, transformation inducible, breast cancer model system (data set GSE64536) with associated controls of ethanol (EtOH) and siNEG treatments. In the diagram, the vertical axis indicates the odds that the TF element is "present" resp. "absent", which corresponds to the JAK-STAT3 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT3 lung model correctly predicts higher JAK-STAT3 activity in the cells that were treated with EtOH for 4 hours (group 1) and 24 hours (group 2), compared to cells that were initiated with tamoxifen for 4 hours (group 3) and 24 hours (group 4).

Figure 16:
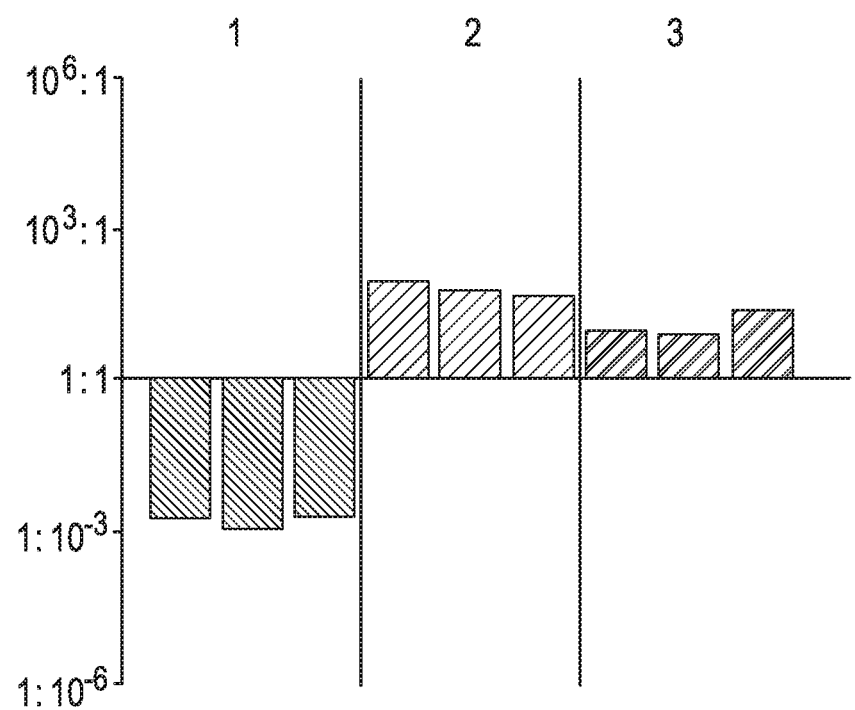
FIG. 16 shows JAK-STAT3 cellular signaling pathway activity predictions of the trained exemplary lung Bayesian network model using the evidence curated list of target genes (39 target genes list) from Table 1 (data set GS8685).
Figure 17:
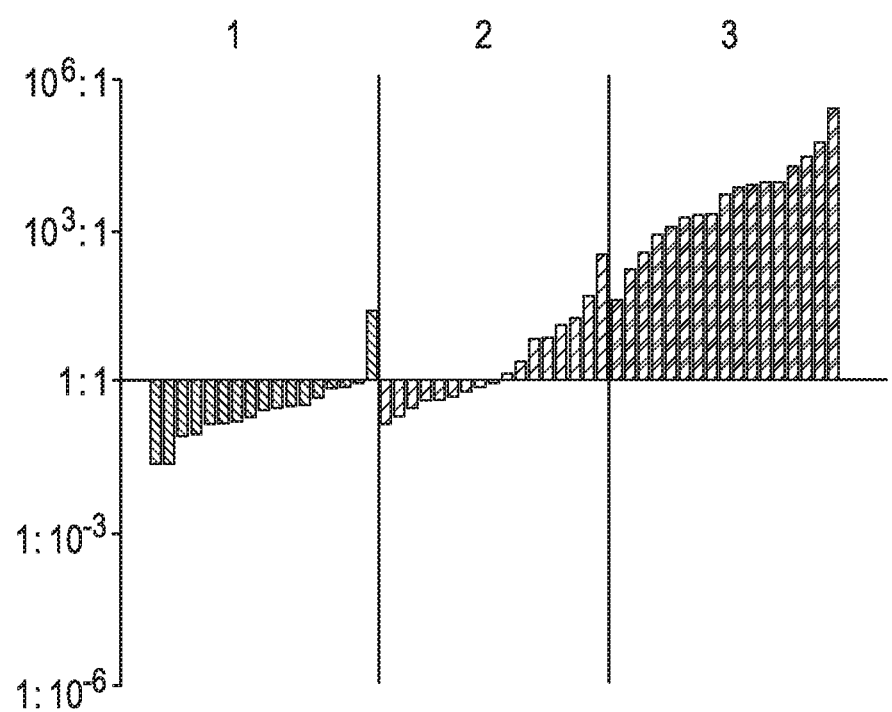
FIG. 17 shows JAK-STAT3 cellular signaling pathway activity predictions of the trained exemplary lung Bayesian network model using the evidence curated list of target genes (39 target genes list) from Table 1 (data set GS8507).

In the following, validation results of the trained exemplary blood Bayesian network model using the evidence curated list of target genes (39 target genes list) are shown in FIGS. 16 and 17.

FIG. 16 shows JAK-STAT3 cellular signaling pathway activity predictions of the trained exemplary blood Bayesian network model using the evidence curated list of target genes (39 target genes list) from Table 1. A Sez-4 cell line which was derived from a cutaneous T-cell lymphoma (data set GSE8685). The cells starved of IL-2 for 16 hours (group 1), followed by addition of IL-2 (200 U) resp. IL-15 (20 ng/mL). In the diagram, the vertical axis indicates the odds that the TF element is "present" resp. "absent", which corresponds to the JAK-STAT3 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT3 blood model correctly predicts that JAK-STAT3 is active in the cells that were treated with IL-2 (group 2) and IL-15 (group 3) compared to the control group (group 1).

FIG. 17 shows JAK-STAT3 cellular signaling pathway activity predictions of the trained exemplary blood Bayesian network model using the evidence curated list of target genes (39 target genes list) from Table 1. Peripheral blood mononuclear cells (PBMC) were isolated from whole blood from patients, who had JAK-STAT3 mutations and a resulting immune disease (hyper-IgE syndrome), and healthy control subjects (data set GSE8507). In the diagram, the vertical axis indicates the odds that the TF element is "present" resp. "absent", which corresponds to the JAK-STAT3 cellular signaling pathway being active resp. passive, wherein values above the horizontal axis correspond to the TF element being more likely "present"/active and values below the horizontal axis indicate that the odds that the TF element is "absent"/passive are larger than the odds that it is "present"/active. The JAK-STAT3 blood model correctly predicts that JAK-STAT3 is inactive in healthy control groups (group 1), that JAK-STAT3 activity is increased for the control group (no latex beads) after 180 minutes (group 2), and that STAT3 is highly active in cells treated with IgG-coated latex beads for 180 minutes.

Figure 18:
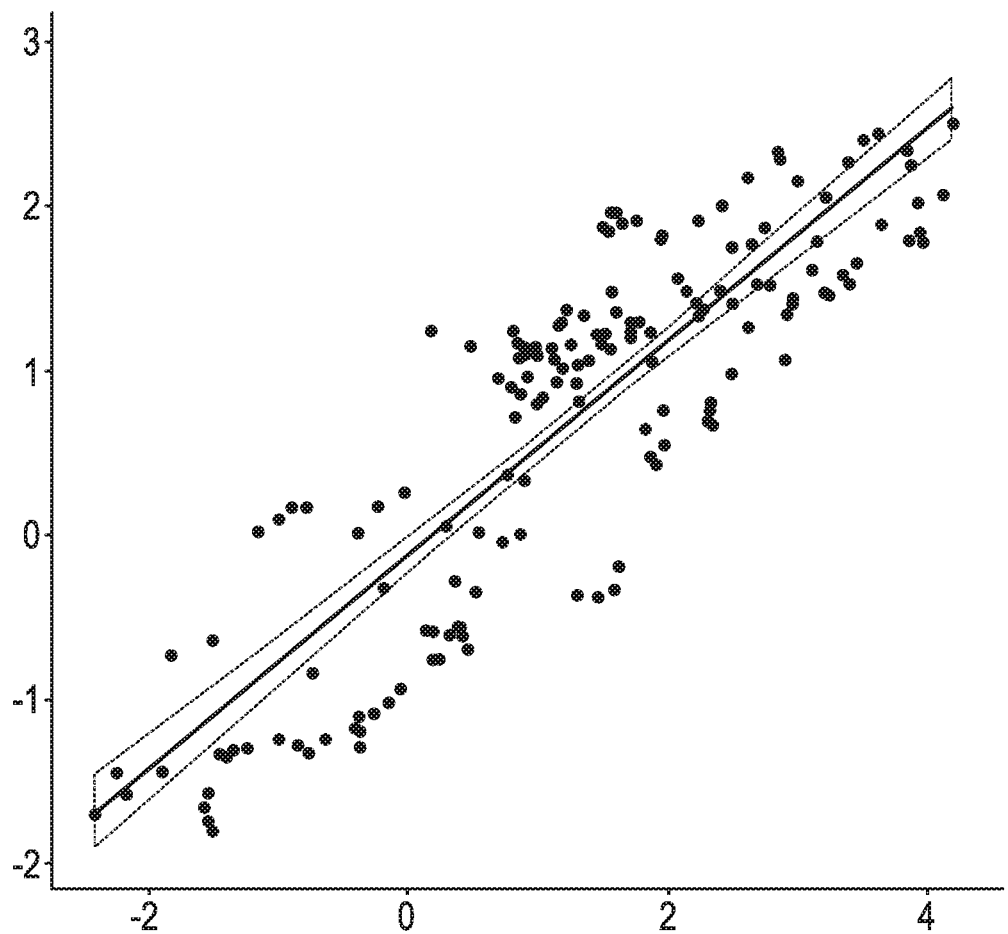
FIG. 18 shows the correlation between the trained exemplary lung Bayesian network model using the evidence curated list of target genes (39 target genes list) from Table 1 and the 10 target gene shortlist for the JAK-STAT3 lung model from Table 2, respectively.

Further validation results of the trained exemplary lung Bayesian network model using the evidence curated list of target genes (39 target genes list) from Table 1 and the 10 target gene shortlist for the JAK-STAT3 lung model from Table 2 are shown in FIG. 18. Here, the evidence curated list of target genes (39 target genes list) of Table 1 is compared with the 10 target gene shortlist for the JAK-STAT3 lung model for the same data sets for the JAK-STAT3 lung model.

FIG. 18 shows the correlation between the trained exemplary lung Bayesian network model using the evidence curated list of target genes (39 target genes list) from Table 1 and the 10 target gene shortlist for the JAK-STAT3 lung model from Table 2, respectively. In the diagram, the horizontal axis indicates the odds (on a log 2 scale) that the TF element is "present" resp. "absent", which corresponds to the JAK-STAT3 cellular signaling pathway being active resp. passive, as predicted by the trained exemplary lung Bayesian network model using the evidence curated list of target genes (39 target genes list) from Table 1. The vertical axis indicates the same information, as predicted by the trained exemplary lung Bayesian network model using the 10 target gene shortlist for the JAK-STAT3 lung model (data sets GSE57156, GSE32975, GSE20854, GSE67051, GSE51212, GSE64536). The two models are significantly correlated with a p-value of 2.2e-16 and a correlation coefficient of 0.866.

Figure 19:
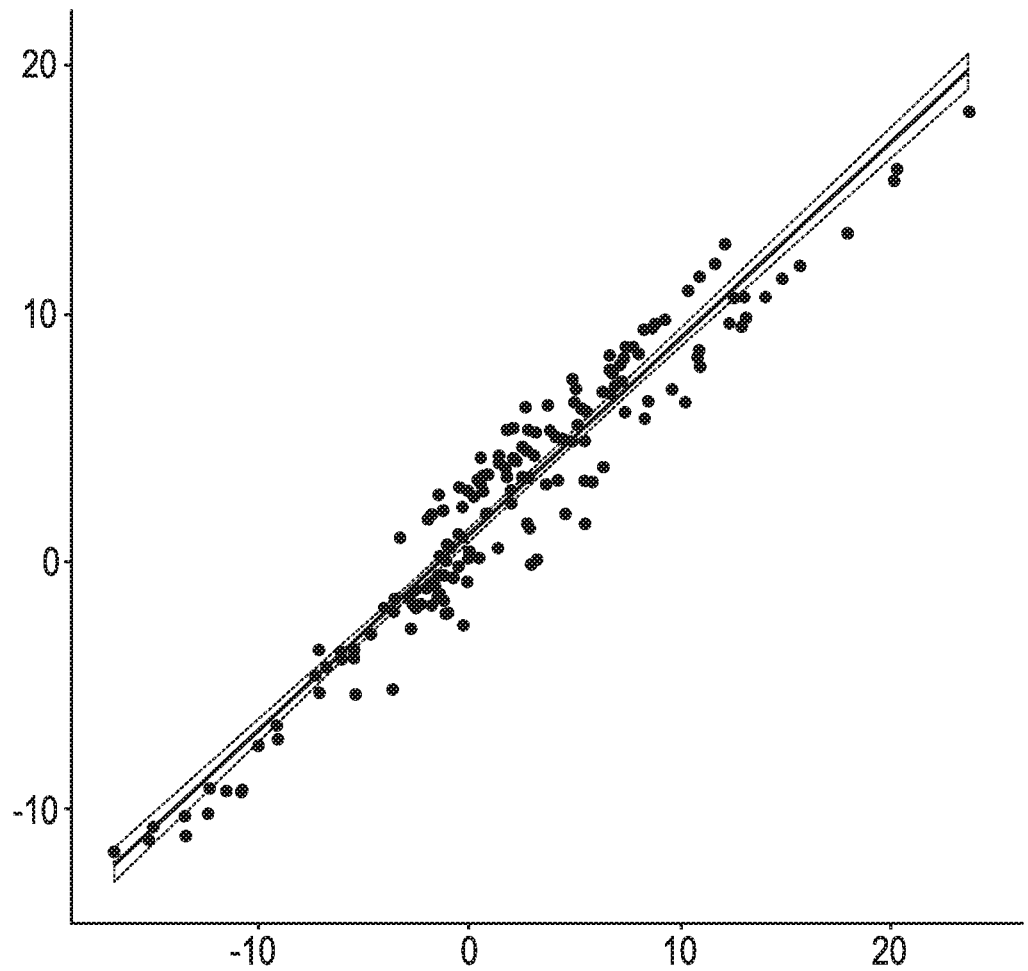
FIG. 19 shows the correlation between the trained exemplary blood Bayesian network model using the evidence curated list of target genes (39 target genes list) from Table 1 and the 12 target gene shortlist for the JAK-STAT3 blood model from Table 3, respectively.

Further validation results of the trained exemplary lung Bayesian network model using the evidence curated list of target genes (39 target genes list) from Table 1 and the 12 target gene shortlist for the JAK-STAT3 blood model from Table 3 are shown in FIG. 19. Here, the evidence curated list of target genes (39 target genes list) of Table 1 is compared with the 12 target gene shortlist for the JAK-STAT3 blood model for the same data sets for the JAK-STAT3 blood model.

FIG. 19 shows the correlation between the trained exemplary blood Bayesian network model using the evidence curated list of target genes (39 target genes list) from Table 1 and the 12 target gene shortlist for the JAK-STAT3 blood model from Table 3, respectively. In the diagram, the horizontal axis indicates the odds (on a log 2 scale) that the TF element is "present" resp. "absent", which corresponds to the JAK-STAT3 cellular signaling pathway being active resp. passive, as predicted by the trained exemplary blood Bayesian network model using the evidence curated list of target genes (39 target genes list) from Table 1. The vertical axis indicates the same information, as predicted by the trained exemplary blood Bayesian network model using the 10 target gene shortlist for the JAK-STAT3 blood model (data sets GSE8687, GSE8685, GSE8507). The two models are significantly correlated with a p-value of 2.2e-16 and a correlation coefficient of 0.963.

Further experiments with respect to the predictability of diseases, e.g. rheumatoid arthritis, and/or therapy response, e.g., to JAK-STAT inhibitors based on JAK-STAT3 activity are described. In a public data set GSE65010 memory and naïve T effector (i.e., mature and, unlike activated or memory T cells, in a state where its cognate antigen has not encountered within the periphery) and T-Reg (CD4+- CD25+) cells were isolated from peripheral blood from healthy individuals and patients with rheumatoid arthritis (RA). RNA was isolated and an Affymetrix HG-U133Plus2.0 microarray was performed. The JAK-STAT3 blood-based pathway model was used to analyze the Affymetrix data, and the JAK-STAT3 pathway activity was determined on a log 2odds scale for each individual sample. The results clearly indicated that in samples from patients with rheumatoid arthritis the JAK-STAT3 pathway is more active in activated memory and T-Reg cells, compared to healthy individuals (Wilcox test p-value 0.04 between activated memory cells from healthy controls vs. RA patients; Wilcox test p-value 0.065 between T-Reg cells from healthy controls vs. RA patients; combined Wilcox test p-value 0.0045 between activated memory plus T-Reg cells from healthy controls vs. RA patients). Measuring JAK-STAT3 pathway activity using the JAK-STAT3 pathway model can therefore enable diagnosis of rheumatoid arthritis and prediction of response to anti-STAT therapy, and monitoring of therapy response, correct dosing of the drug and compliance checking.

Instead of applying the mathematical model, e.g., the exemplary Bayesian network model, on mRNA input data coming from microarrays or RNA sequencing, it may be beneficial in clinical applications to develop dedicated assays to perform the sample measurements, for instance on an integrated platform using qPCR to determine mRNA levels of target genes. The RNA/DNA sequences of the disclosed target genes can then be used to determine which primers and probes to select on such a platform.

Validation of such a dedicated assay can be done by using the microarray-based mathematical model as a reference model, and verifying whether the developed assay gives similar results on a set of validation samples. Next to a dedicated assay, this can also be done to build and calibrate similar mathematical models using RNA sequencing data as input measurements.

The set of target genes which are found to best indicate specific cellular signaling pathway activity, e.g., Tables 1 to 3, based on microarray/RNA sequencing based investigation using the calibrated mathematical model, e.g., the exemplary Bayesian network model, can be translated into a multiplex quantitative PCR assay to be performed on a sample of the subject and/or a computer to interpret the expression measurements and/or to infer the activity of the JAK-STAT3 cellular signaling pathway. To develop such a test (e.g., FDA-approved or a CLIA waived test in a central service lab or a laboratory developed test for research use only) for cellular signaling pathway activity, development of a standardized test kit is required, which needs to be clinically validated in clinical trials to obtain regulatory approval.

The present invention relates to a method comprising determining an activity level of a JAK-STAT3 cellular signaling pathway in a subject based at least on expression levels of at least three, for example, at least four, at least five, at least six, at least seven, at least eight, at least nine, at least ten or more target genes of the JAK-STAT3 cellular signaling pathway measured in a sample. The present invention further relates to an apparatus comprising a digital processor configured to perform such a method, a non-transitory storage medium storing instructions that are executable by a digital processing device to perform such a method, and a computer program comprising program code means for causing a digital processing device to perform such a method.

The method may be used, for instance, in diagnosing an (abnormal) activity of the JAK-STAT3 cellular signaling pathway, in prognosis based on the determined activity level of the JAK-STAT3 cellular signaling pathway, in the enrollment in a clinical trial based on the determined activity level of the JAK-STAT3 cellular signaling pathway, in the selection of subsequent test(s) to be performed, in the selection of companion diagnostics tests, in clinical decision support systems, or the like. In this regard, reference is made to the published international patent application WO 2013/011479 A2 ("Assessment of cellular signaling pathway activity using probabilistic modeling of target gene expression"), to the published international patent application WO 2014/ 102668 A2 ("Assessment of cellular signaling pathway activity using linear combination(s) of target gene expressions"), and to Verhaegh W. et al., "Selection of personalized patient therapy through the use of knowledge-based computational models that identify tumor-driving signal transduction pathways", Cancer Research, Vol. 74, No. 11, 2014, pages 2936-2945, which describe these applications in more detail.

This specification has been described with reference to embodiments, which are illustrated by the accompanying Examples. The invention can, however, be embodied in different forms and should not be construed as limited to the embodiments set forth herein. Given the teaching herein, one of ordinary skill in the art will be able to modify the invention for a desired purpose and such variations are considered within the scope of the disclosure.

| Sequence Listing: | |
|---|---|
| Seq. No. | Gene: |
| Seq. 1 | AKT1 |
| Seq. 2 | BCL2 |
| Seq. 3 | BCL2L1 |
| Seq. 4 | BIRC5 |
| Seq. 5 | CCND1 |
| Seq. 6 | CD274 |
| Seq. 7 | CDKN1A |
| Seq. 8 | CRP |
| Seq. 9 | FGF2 |
| Seq. 10 | FOS |
| Seq. 11 | FSCN1 |
| Seq. 12 | FSCN2 |
| Seq. 13 | FSCN3 |
| Seq. 14 | HIF1A |
| Seq. 15 | HSP90AA1 |
| Seq. 16 | HSP90AB1 |
| Seq. 17 | HSP90B1 |
| Seq. 18 | HSPA1A |
| Seq. 19 | HSPA1B |

| Sequence Listing: | |
|---|---|
| Seq. No. | Gene: |
| Seq. 20 | ICAM1 |
| Seq. 21 | IFNG |
| Seq. 22 | IL10 |
| Seq. 23 | JunB |
| Seq. 24 | MCL1 |
| Seq. 25 | MMP1 |
| Seq. 26 | MMP3 |
| Seq. 27 | MMP9 |
| Seq. 28 | MUC1 |
| Seq. 29 | MYC |
| Seq. 30 | NOS2 |
| Seq. 31 | POU2F1 |
| Seq. 32 | PTGS2 |
| Seq. 33 | SAA1 |
| Seq. 34 | STAT1 |
| Seq. 35 | TIMP1 |
| Seq. 36 | TNFRSF1B |
| Seq. 37 | TWIST1 |
| Seq. 38 | VIM |
| Seq. 39 | ZEB1 |

The invention claimed is:

1. A method of treating a subject suffering from a disease associated with an activated JAK-STAT3 cellular signaling pathway, comprising:

receiving data on expression levels of at least six target genes derived from a sample obtained from the subject, wherein a JAK-STAT3 transcription factor element controls transcription of the at least six target genes, and wherein the at least six target genes are selected from BCL2L1, BIRC5, CCND1, CD274, FOS, HIF1A, HSP90AA1, HSP90AB1, MMP1, and MYC, or from BCL2L1, CD274, FOS, HSP90B1, HSPA1B, ICAM1, IFNG, JunB, PTGS2, STAT1, TNFRSF1B, and ZEB1;

calculating an activity level of the JAK-STAT3 transcription factor element in the sample using a calibrated pathway model, wherein the calibrated pathway model compares the expression levels of the at least six target genes in the sample with expression levels of the at least six target genes in the calibrated pathway model which define an activity level of JAK-STAT3 transcription factor element;

calculating an activity level of the JAK-STAT3 cellular signaling pathway in the sample based on the calculated activity level of the JAK-STAT3 transcription factor element in the sample, wherein the calculated activity level of the JAK-STAT3 cellular signaling pathway indicates that the JAK-STAT3 cellular signaling pathway in the sample is active, wherein the calculated activity level of the JAK-STAT3 cellular signaling pathway indicates that the JAK-STAT3 cellular signaling pathway in the sample is active when the calculated activity level of the JAK-STAT3 cellular signaling pathway is above a log-odds ratio of 1:1; and, administering to the subject a JAK-STAT3 inhibitor in response to receiving the indication that the activity level of the JAK-STAT3 cellular signaling pathway is active.

2. The method of claim 1, wherein the at least six target genes comprise at least six target genes selected from BCL2L1, BIRC5, CCND1, CD274, FOS, HIF1A, HSP90AA1, HSP90AB1, MMP1, and MYC, or from BCL2L1, CD274, FOS, HSP90B1, HSPA1B, ICAM1, IFNG, JunB, PTGS2, STAT1, TNFRSF1B, and ZEB1.

3. The method of claim 1, wherein the at least six target genes selected from BCL2L1, BIRC5, CCND1, CD274, FOS, HIF1A, HSP90AA1, HSP90AB1, MMP1, and MYC, are selected based on their ability to differentiate between solid tumor, preferably epithelial samples of which the activity of the JAK-STAT3 cellular signaling pathway is active vs. inactive and/or are used in a calibrated pathway model which is calibrated on solid tumor, preferably lung samples, or wherein the at least six target genes selected from BCL2L1, CD274, FOS, HSP90B1, HSPA1B, ICAM1, IFNG, JunB, PTGS2, STAT1, TNFRSF1B, and ZEB1, are selected based on their ability to differentiate between hematological samples of which the activity of the JAK-STAT3 cellular signaling pathway is active vs. inactive and/or are used in a calibrated pathway model which is calibrated on hematological samples.

4. The method of claim 1, wherein the JAK-STAT3 inhibitor is STA-21, LLL-3, curcumin, or AZD9150.

5. The method of claim 1, wherein the disease is a cancer or an immune disorder.

* * * * *

SEQUENCE LISTING

<160> NUMBER OF SEQ ID NOS: 39

<210> SEQ ID NO 1
<211> LENGTH: 3008
<212> TYPE: DNA
<213> ORGANISM: Homo sapiens

<400> SEQUENCE: 1

```
taattatggg tctgtaacca ccctggactg ggtgctcctc actgacggac ttgtctgaac      60
ctctctttgt ctccagcgcc cagcactggg cctggcaaaa cctgagacgc ccggtacatg     120
ttggccaaat gaatgaacca gattcagacc ggcaggggcg ctgtggttta ggaggggcct     180
ggggtttctc ccaggaggtt tttgggcttg cgctggaggg ctctggactc ccgtttgcgc     240
cagtggcctg catcctggtc ctgtcttcct catgtttgaa tttctttgct ttcctagtct     300
ggggagcagg gaggagccct gtgccctgtc ccaggatcca tgggtaggaa caccatggac     360
agggagagca acgggggcca tctgtcacca ggggcttagg gaaggccgag ccagcctggg     420
tcaaagaagt caaaggggct gcctggagga ggcagcctgt cagctggtgc atcagaggct     480
gtggccaggc cagctgggct cggggagcgc cagcctgaga ggagcgcgtg agcgtcgcgg     540
gagcctcggg caccatgagc gacgtggcta ttgtgaagga gggttggctg cacaaacgag     600
gggagtacat caagacctgg cggccacgct acttcctcct caagaatgat ggcaccttca     660
ttggctacaa ggagcggccg caggatgtgg accaacgtga ggctcccctc aacaacttct     720
ctgtggcgca gtgccagctg atgaagacgg agcggccccg gcccaacacc ttcatcatcc     780
gctgcctgca gtggaccact gtcatcgaac gcaccttcca tgtggagact cctgaggagc     840
gggaggagtg gacaaccgcc atccagactg tggctgacgg cctcaagaag caggaggagg     900
aggagatgga cttccggtcg ggctcaccca gtgacaactc aggggctgaa gagatggagg     960
tgtccctggc caagcccaag caccgcgtga ccatgaacga gtttgagtac ctgaagctgc    1020
tgggcaaggg cacttcggc aaggtgatcc tggtgaagga gaaggccaca ggccgctact    1080
acgccatgaa gatcctcaag aaggaagtca tcgtggccaa ggacgaggtg gcccacacac    1140
tcaccgagaa ccgcgtcctg cagaactcca ggcacccctt cctcacagcc ctgaagtact    1200
```

-continued

| | |
|---|---|
| ctttccagac ccacgaccgc ctctgctttg tcatggagta cgccaacggg ggcgagctgt | 1260 |
| tcttccacct gtcccgggag cgtgtgttct ccgaggaccg ggcccgcttc tatggcgctg | 1320 |
| agattgtgtc agccctggac tacctgcact cggagaagaa cgtggtgtac cgggacctca | 1380 |
| agctggagaa cctcatgctg acaaggacg ggcacattaa gatcacagac ttcgggctgt | 1440 |
| gcaaggaggg gatcaaggac ggtgccacca tgaagacctt tgcggcaca cctgagtacc | 1500 |
| tggcccccga ggtgctggag acaatgact acggccgtgc agtggactgg tggggctgg | 1560 |
| gcgtggtcat gtacgagatg atgtgcggtc gcctgccctt ctacaaccag gaccatgaga | 1620 |
| agcttttga gctcatcctc atggaggaga tccgcttccc gcgcacgctt ggtcccgagg | 1680 |
| ccaagtcctt gctttcaggg ctgctcaaga aggaccccaa gcagaggctt ggcggggct | 1740 |
| ccgaggacgc caaggagatc atgcagcatc gcttctttgc cggtatcgtg tggcagcacg | 1800 |
| tgtacgagaa gaagctcagc ccaccccttca agccccaggt cacgtcggag actgacacca | 1860 |
| ggtattttga tgaggagttc acggcccaga tgatcaccat cacaccacct gaccaagatg | 1920 |
| acagcatgga gtgtgtggac agcgagcgca ggccccactt cccccagttc tcctactcgg | 1980 |
| ccagcggcac ggcctgaggc ggcggtggac tgcgctggac gatagcttgg agggatggag | 2040 |
| aggcggcctc gtgccatgat ctgtatttaa tggttttat ttctcgggtg catttgagag | 2100 |
| aagccacgct gtcctctcga gcccagatgg aaagacgttt ttgtgctgtg ggcagcaccc | 2160 |
| tcccccgcag cggggtaggg aagaaaacta tcctgcgggt tttaatttat ttcatccagt | 2220 |
| ttgttctccg ggtgtggcct cagccctcag aacaatccga ttcacgtagg gaaatgttaa | 2280 |
| ggacttctgc agctatgcgc aatgtggcat tggggggccg ggcaggtcct gcccatgtgt | 2340 |
| cccctcactc tgtcagccag ccgccctggg ctgtctgtca ccagctatct gtcatctctc | 2400 |
| tggggccctg ggcctcagtt caacctggtg gcaccagatg caacctcact atggtatgct | 2460 |
| ggccagcacc ctctcctggg ggtggcaggc acacagcagc ccccagcac taaggccgtg | 2520 |
| tctctgagga cgtcatcgga ggctgggccc ctgggatggg accagggatg ggggatgggc | 2580 |
| cagggtttac ccagtgggac agaggagcaa ggtttaaatt tgttattgtg tattatgttg | 2640 |
| ttcaaatgca ttttgggggt ttttaatctt tgtgacagga aagccctccc ccttcccctt | 2700 |
| ctgtgtcaca gttcttggtg actgtcccac cgggagcctc cccctcagat gatctctcca | 2760 |
| cggtagcact tgaccttttc gacgcttaac cttccgctg tcgccccagg ccctccctga | 2820 |
| ctccctgtgg gggtggccat ccctgggccc ctccacgcct cctggccaga cgctgccgct | 2880 |
| gccgctgcac cacggcgttt ttttacaaca ttcaacttta gtattttac tattataata | 2940 |
| taatatggaa ccttccctcc aaattcttca ataaagttg cttttcaaaa aaaaaaaaa | 3000 |
| aaaaaaaa | 3008 |

<210> SEQ ID NO 2
<211> LENGTH: 6492
<212> TYPE: DNA
<213> ORGANISM: Homo sapiens

<400> SEQUENCE: 2

| | |
|---|---|
| tttctgtgaa gcagaagtct gggaatcgat ctggaaatcc tcctaatttt tactccctct | 60 |
| ccccgcgact cctgattcat tgggaagttt caaatcagct ataactggag agtgctgaag | 120 |
| attgatggga tcgttgcctt atgcatttgt tttggtttta caaaaggaa acttgacaga | 180 |
| ggatcatgct gtacttaaaa aatacaacat cacagaggaa gtagactgat attaacaata | 240 |

```
cttactaata ataacgtgcc tcatgaaata aagatccgaa aggaattgga ataaaaattt    300
cctgcatctc atgccaaggg ggaaacacca gaatcaagtg ttccgcgtga ttgaagacac    360
cccctcgtcc aagaatgcaa agcacatcca ataaaatagc tggattataa ctcctcttct    420
ttctctgggg gccgtggggt gggagctggg gcgagaggtg ccgttggccc ccgttgcttt    480
tcctctggga aggatggcgc acgctgggag aacagggtac gataaccggg agatagtgat    540
gaagtacatc cattataagc tgtcgcagag gggctacgag tgggatgcgg gagatgtggg    600
cgccgcgccc ccggggggccg cccccgcacc gggcatcttc tcctcccagc ccgggcacac    660
gccccatcca gccgcatccc gggacccggt cgccaggacc tcgccgctgc agaccccggc    720 tgccccccggc gccgccgcgg ggcctgcgct cagcccggtg ccacctgtgg tccacctgac    780
cctccgccag gccggcgacg acttctcccg ccgctaccgc cgcgacttcg ccgagatgtc    840
cagccagctg cacctgacgc ccttcaccgc gcggggacgc tttgccacgg tggtggagga    900
gctcttcagg gacggggtga actggggggag gattgtggcc ttctttgagt tcggtggggt    960
catgtgtgtg gagagcgtca accgggagat gtcgcccctg gtggacaaca tcgccctgtg    1020
gatgactgag tacctgaacc ggcacctgca cacctggatc caggataacg gaggctggga    1080
tgcctttgtg gaactgtacg gccccagcat gcggcctctg tttgatttct cctggctgtc    1140
tctgaagact ctgctcagtt tggccctggt gggagcttgc atcaccctgg gtgcctatct    1200
gggccacaag tgaagtcaac atgcctgccc caaacaaata tgcaaaaggt tcactaaagc    1260
agtagaaata atatgcattg tcagtgatgt accatgaaac aaagctgcag gctgtttaag    1320
aaaaaataac acacatataa acatcacaca cacagacaga cacacacaca caacaatt     1380 aacagtcttc aggcaaaacg tcgaatcagc tatttactgc caaagggaaa tatcatttat    1440 ttttacatt attaagaaaa aaagatttat ttatttaaga cagtcccatc aaaactcctg    1500
tctttggaaa tccgaccact aattgccaag caccgcttcg tgtggctcca cctggatgtt    1560
ctgtgcctgt aaacatagat tcgctttcca tgttgttggc cggatcacca tctgaagagc    1620
agacggatgg aaaaaggacc tgatcattgg ggaagctggc tttctggctg ctggaggctg    1680
gggagaaggt gttcattcac ttgcatttct ttgccctggg ggctgtgata ttaacagagg    1740
gagggttcct gtgggggggaa gtccatgcct ccctggcctg aagaagagac tctttgcata    1800
tgactcacat gatgcatacc tggtgggagg aaaagagttg ggaacttcag atggacctag    1860
tacccactga gatttccacg ccgaaggaca gcgatgggaa aaatgcccctt aaatcatagg    1920 aaagtatttt tttaagctac caattgtgcc gagaaaagca ttttagcaat ttatacaata    1980
tcatccagta ccttaagccc tgattgtgta tattcatata ttttggatac gcacccccca    2040
actcccaata ctggctctgt ctgagtaaga aacagaatcc tctggaactt gaggaagtga    2100
acatttcggt gacttccgca tcaggaaggc tagagttacc cagagcatca ggccgccaca    2160
agtgcctgct tttaggagac cgaagtccgc agaacctgcc tgtgtcccag cttggaggcc    2220
tggtcctgga actgagccgg ggccctcact ggcctcctcc agggatgatc aacagggcag    2280
tgtggtctcc gaatgtctgg aagctgatgg agctcagaat tccactgtca gaaagagca    2340 gtagaggggt gtggctgggc ctgtcaccct ggggccctcc aggtaggccc gttttcacgt    2400
ggagcatggg agccacgacc cttcttaaga catgtatcac tgtagaggga aggaacagag    2460
gccctgggcc cttcctatca gaaggacatg gtgaaggctg ggaacgtgag gagaggcaat    2520
ggccacggcc cattttggct gtagcacatg gcacgttggc tgtgtggcct ggcccacct     2580 gtgagtttaa agcaaggctt taaatgactt tggagagggt cacaaatcct aaaagaagca    2640
```

-continued

```
ttgaagtgag gtgtcatgga ttaattgacc cctgtctatg gaattacatg taaaacatta    2700
tcttgtcact gtagtttggt tttatttgaa aacctgacaa aaaaaaagtt ccaggtgtgg    2760
aatatggggg ttatctgtac atcctggggc attaaaaaaa aaatcaatgg tggggaacta    2820
taaagaagta acaaaagaag tgacatcttc agcaaataaa ctaggaaatt ttttttttctt   2880 ccagtttaga atcagccttg aaacattgat ggaataactc tgtggcatta ttgcattata    2940
taccatttat ctgtattaac tttggaatgt actctgttca atgtttaatg ctgtggttga    3000
tatttcgaaa gctgctttaa aaaaatacat gcatctcagc gttttttttgt ttttaattgt   3060 atttagttat ggcctataca ctatttgtga gcaaaggtga tcgttttctg tttgagattt    3120
ttatctcttg attcttcaaa agcattctga gaaggtgaga taagccctga gtctcagcta   3180
cctaagaaaa acctggatgt cactggccac tgaggagctt tgtttcaacc aagtcatgtg    3240
catttccacg tcaacagaat tgtttattgt gacagttata tctgttgtcc ctttgacctt    3300
gtttcttgaa ggtttcctcg tccctgggca attccgcatt taattcatgg tattcaggat    3360
tacatgcatg tttggttaaa cccatgagat tcattcagtt aaaaatccag atggcaaatg    3420
accagcagat tcaaatctat ggtggtttga cctttagaga gttgctttac gtggcctgtt   3480
tcaacacaga cccacccaga gccctcctgc cctccttccg cgggggcttt ctcatggctg    3540
tccttcaggg tcttcctgaa atgcagtggt gcttacgctc caccaagaaa gcaggaaacc    3600
tgtggtatga agccagacct ccccggcggg cctcagggaa cagaatgatc agacctttga   3660
atgattctaa ttttttaagca aaatattatt ttatgaaagg tttacattgt caaagtgatg    3720
aatatggaat atccaatcct gtgctgctat cctgccaaaa tcattttaat ggagtcagtt   3780
tgcagtatgc tccacgtggt aagatcctcc aagctgcttt agaagtaaca atgaagaacg    3840
tggacgtttt taatataaag cctgtttttgt cttttgttgt tgttcaaacg ggattcacag    3900
agtatttgaa aaatgtatat atattaagag gtcacggggg ctaattgctg gctggctgcc    3960
ttttgctgtg gggttttgtt acctggtttt aataacagta aatgtgccca gcctcttggc    4020
cccagaactg tacagtattg tggctgcact tgctctaaga gtagttgatg ttgcattttc    4080
cttattgtta aaaacatgtt agaagcaatg aatgtatata aaagcctcaa ctagtcattt   4140
ttttctcctc ttctttttttt tcattatatc taattatttt gcagttgggc aacagagaac   4200
catccctatt ttgtattgaa gagggattca catctgcatc ttaactgctc tttatgaatg   4260
aaaaaacagt cctctgtatg tactcctctt tacactggcc agggtcagag ttaaatagag    4320
tatatgcact ttccaaattg gggacaaggg ctctaaaaaa agccccaaaa ggagaagaac    4380
atctgagaac ctcctcggcc ctcccagtcc ctcgctgcac aaatactccg caagagaggc    4440
cagaatgaca gctgacaggg tctatggcca tcgggtcgtc tccgaagatt tggcaggggc    4500
agaaaactct ggcaggctta agatttggaa taaagtcaca gaattaagga agcacctcaa    4560
tttagttcaa acaagacgcc aacattctct ccacagctca cttacctctc tgtgttcaga   4620
tgtggccttc catttatatg tgatctttgt tttattagta aatgcttatc atctaaagat    4680
gtagctctgg cccagtggga aaaattagga agtgattata atcgagagg agttataata    4740 atcaagatta aatgtaaata atcagggcaa tcccaacaca tgtctagctt tcacctccag   4800
gatctattga gtgaacagaa ttgcaaatag tctctatttg taattgaact tatcctaaaa    4860
caaatagttt ataaatgtga acttaaactc taattaattc caactgtact tttaaggcag    4920
tggctgtttt tagactttct tatcacttat agttagtaat gtacacctac tctatcagag    4980
```

| | |
|---|---:|
| aaaaacagga aaggctcgaa atacaagcca ttctaaggaa attagggagt cagttgaaat | 5040 |
| tctattctga tcttattctg tggtgtcttt tgcagcccag acaaatgtgg ttacacactt | 5100 |
| tttaagaaat acaattctac attgtcaagc ttatgaaggt tccaatcaga tctttattgt | 5160 |
| tattcaattt ggatctttca gggattttt ttttaaatta ttatgggaca aaggacattt | 5220 |
| gttggagggg tgggagggag gaagaatttt taaatgtaaa acattcccaa gtttggatca | 5280 |
| gggagttgga agttttcaga ataaccagaa ctaagggtat gaaggacctg tattggggtc | 5340 |
| gatgtgatgc ctctgcgaag aaccttgtgt gacaaatgag aaacattttg aagtttgtgg | 5400 |
| tacgaccttt agattccaga gacatcagca tggctcaaag tgcagctccg tttggcagtg | 5460 |
| caatggtata aatttcaagc tggatatgtc taatgggtat ttaaacaata aatgtgcagt | 5520 |
| tttaactaac aggatattta atgacaacct tctggttggt agggacatct gtttctaaat | 5580 |
| gtttattatg tacaatacag aaaaaaattt tataaaatta agcaatgtga aactgaattg | 5640 |
| gagagtgata atacaagtcc tttagtctta cccagtgaat cattctgttc catgtctttg | 5700 |
| gacaaccatg accttggaca atcatgaaat atgcatctca ctggatgcaa agaaaatcag | 5760 |
| atggagcatg aatggtactg taccggttca tctggactgc cccagaaaaa taacttcaag | 5820 |
| caaacatcct atcaacaaca aggttgttct gcataccaag ctgagcacag aagatgggaa | 5880 |
| cactggtgga ggatggaaag gctcgctcaa tcaagaaaat tctgagacta ttaataaata | 5940 |
| agactgtagt gtagatactg agtaaatcca tgcacctaaa cctttggaa atctgccgt | 6000 |
| gggccctcca gatagctcat tcattaagt ttttccctcc aaggtagaat ttgcaagagt | 6060 |
| gacagtggat tgcatttctt ttggggaagc tttcttttgg tggttttgtt tattataccct | 6120 |
| tcttaagttt tcaaccaagg tttgcttttg ttttgagtta ctggggttat ttttgtttta | 6180 |
| aataaaaata agtgtacaat aagtgttttt gtattgaaag cttttgttat caagattttc | 6240 |
| atacttttac cttccatggc tctttttaag attgatactt ttaagaggtg gctgatattc | 6300 |
| tgcaacactg tacacataaa aaatacggta aggatacttt acatggttaa ggtaaagtaa | 6360 |
| gtctccagtt ggccaccatt agctataatg gcactttgtt tgtgttgttg gaaaaagtca | 6420 |
| cattgccatt aaactttcct tgtctgtcta gttaatattg tgaagaaaaa taaagtacag | 6480 |
| tgtgagatac tg | 6492 |

<210> SEQ ID NO 3
<211> LENGTH: 2820
<212> TYPE: DNA
<213> ORGANISM: Homo sapiens

<400> SEQUENCE: 3

| | |
|---|---:|
| gaaaccttga accccattga gaagtcccctt tagggtttcg gacgcctcca cctcaccctg | 60 |
| ggctggtgct taaatagaaa aagaaaaac aaaaccaac taaatccata ccagccacct | 120 |
| ccgggagagt actcctggct cccagtagga ggcggagagc caagggcgt gcaagagaga | 180 |
| ggggctggg ctcccgggtg gcaggaggcc gcggctgcgg agcggccgcc ctcgatccgg | 240 |
| gcgatggagg aggaagcaag cgagggggct ggttcctgag cttcgcaatt cctgtgtcgc | 300 |
| cttctgggct cccagcctgc cgggtcgcat gatccctccg gccggagctg gttttttgc | 360 |
| cagccaccgc gaggccggct gagttaccgg catccccgca gccacctcct ctcccgacct | 420 |
| gtgatacaaa agatcttccg ggggctgcac ctgcctgcct ttgcctaagg cggatttgaa | 480 |
| tctctttctc tcccttcaga atcttatctt ggctttggat cttagaagag aatcactaac | 540 |
| cagagacgag actcagtgag tgagcaggtg ttttggacaa tggactggtt gagcccatcc | 600 |

-continued

```
ctattataaa aatgtctcag agcaaccggg agctggtggt tgactttctc tcctacaagc    660
tttcccagaa aggatacagc tggagtcagt ttagtgatgt ggaagagaac aggactgagg    720
ccccagaagg gactgaatcg gagatggaga cccccagtgc catcaatggc aacccatcct    780
ggcacctggc agacagcccc gcggtgaatg gagccactgg ccacagcagc agtttggatg    840
cccgggaggt gatccccatg gcagcagtaa agcaagcgct gagggaggca ggcgacgagt    900
ttgaactgcg gtaccggcgg gcattcagtg acctgacatc ccagctccac atcccccag    960 ggacagcata tcagagcttt gaacaggtag tgaatgaact cttccgggat ggggtaaact   1020
ggggtcgcat tgtggccttt ttctccttcg gcggggcact gtgcgtggaa agcgtagaca   1080
aggagatgca ggtattggtg agtcggatcg cagcttggat ggccacttac ctgaatgacc   1140
acctagagcc ttggatccag gagaacggcg gctgggatac ttttgtggaa ctctatggga   1200
acaatgcagc agccgagagc cgaaagggcc aggaacgctt caaccgctgg ttcctgacgg   1260
gcatgactgt ggccggcgtg gttctgctgg gctcactctt cagtcggaaa tgaccagaca   1320
ctgaccatcc actctaccct cccacccccct tctctgctcc accacatcct ccgtccagcc   1380
gccattgcca ccaggagaac cactacatgc agcccatgcc cacctgccca tcacagggtt   1440
gggcccagat ctggtccctt gcagctagtt ttctagaatt tatcacactt ctgtgagacc   1500
cccacacctc agttcccttg gcctcagaat tcacaaaatt tccacaaaat ctgtccaaag   1560
gaggctggca ggtatggaag ggtttgtggc tgggggcagg agggccctac ctgattggtg   1620
caacccttac cccttagcct ccctgaaaat gttttttctgc cagggagctt gaaagttttc   1680
agaacctctt ccccagaaag gagactagat tgcctttgtt ttgatgtttg tggcctcaga   1740
attgatcatt ttccccccac tctccccaca ctaacctggg ttccctttcc ttccatccct   1800 acccccctaag agccatttag gggccacttt tgactaggga ttcaggctgc ttgggataaa   1860
gatgcaagga ccaggactcc ctcctcacct ctggactggc tagagtcctc actcccagtc   1920
caaatgtcct ccagaagcct ctggctagag gccagcccca ccaggaggg aggggggctat   1980 agctacagga agcacccat gccaaagcta gggtggccct tgcagttcag caccacccta   2040
gtcccttccc ctccctggct cccatgacca tactgaggga ccaactgggc caagacaga   2100 tgccccagag ctgtttatgg cctcagctgc ctcacttcct acaagagcag cctgtggcat   2160 cttttgccttg ggctgctcct catggtgggt tcagggggact cagccctgag gtgaaaggga   2220
gctatcagga acagctatgg gagcccagg gtcttcccta cctcaggcag gaagggcagg   2280
aaggagagcc tgctgcatgg ggtgggggtag ggctgactag aagggccagt cctgcctggc   2340
caggcagatc tgtgccccat gcctgtccag cctgggcagc caggctgcca aggccagagt   2400
ggcctggcca ggagctcttc aggcctccct ctctcttctg ctccacccctt ggcctgtctc   2460 atccccaggg gtcccagcca ccccgggctc tctgctgtac atatttgaga ctagttttta   2520
ttccttgtga agatgatata ctatttttgt taagcgtgtc tgtatttatg tgtgaggagc   2580
tgctggcttg cagtgcgcgt gcacgtggag agctggtgcc cggagattgg acggcctgat   2640
gctccctccc ctgccctggt ccagggaagc tggccgaggg tcctggctcc tgaggggcat   2700
ctgcccctcc cccaacccccc accccacact tgttccagct ctttgaaata gtctgtgtga   2760
aggtgaaagt gcagttcagt aataaactgt gtttactcag tgaaaaaaaa aaaaaaaaa    2820
```

<210> SEQ ID NO 4
<211> LENGTH: 2655
<212> TYPE: DNA

<213> ORGANISM: Homo sapiens

<400> SEQUENCE: 4

| | | | | | |
|---|---|---|---|---|---|
| cccagaaggc | cgcgggggt | ggaccgccta | agagggcgtg | cgctcccgac | atgccccgcg | 60 |
| gcgcgccatt | aaccgccaga | tttgaatcgc | gggacccgtt | ggcagaggtg | gcggcggcgg | 120 |
| catgggtgcc | ccgacgttgc | ccctgcctg | gcagccctt | ctcaaggacc | accgcatctc | 180 |
| tacattcaag | aactggccct | tcttggaggg | ctgcgcctgc | accccggagc | ggatggccga | 240 |
| ggctggcttc | atccactgcc | ccactgagaa | cgagccagac | ttggcccagt | gtttcttctg | 300 |
| cttcaaggag | ctggaaggct | gggagccaga | tgacgacccc | atagaggaac | ataaaaagca | 360 |
| ttcgtccggt | tgcgctttcc | tttctgtcaa | gaagcagttt | gaagaattaa | cccttggtga | 420 |
| attttgaaa | ctggacagag | aaagagccaa | gaacaaaatt | gcaaggaaa | ccaacaataa | 480 |
| gaagaaagaa | tttgaggaaa | ctgcggagaa | agtgcgccgt | gccatcgagc | agctggctgc | 540 |
| catggattga | ggcctctggc | cggagctgcc | tggtcccaga | gtggctgcac | cacttccagg | 600 |
| gtttattccc | tggtgccacc | agccttcctg | tgggccccct | agcaatgtct | taggaaagga | 660 |
| gatcaacatt | ttcaaattag | atgtttcaac | tgtgctcttg | ttttgtcttg | aaagtggcac | 720 |
| cagaggtgct | tctgcctgtg | cagcgggtgc | tgctggtaac | agtggctgct | ctctctctc | 780 |
| tctctctttt | tgggggctc | atttttgctg | ttttgattcc | cgggcttacc | aggtgagaag | 840 |
| tgagggagga | agaaggcagt | gtcccttttg | ctagagctga | cagcttttgtt | cgcgtgggca | 900 |
| gagccttcca | cagtgaatgt | gtctggacct | catgttgttg | aggctgtcac | agtcctgagt | 960 |
| gtggacttgg | caggtgcctg | ttgaatctga | gctgcaggtt | ccttatctgt | cacacctgtg | 1020 |
| cctcctcaga | ggacagtttt | tttgttgttg | tgtttttttg | ttttttttt | tttggtagat | 1080 |
| gcatgacttg | tgtgtgatga | gagaatggag | acagagtccc | tggctcctct | actgtttaac | 1140 |
| aacatggctt | tcttatttg | tttgaattgt | taattcacag | aatagcacaa | actacaatta | 1200 |
| aaactaagca | caaagccatt | ctaagtcatt | ggggaaacgg | ggtgaacttc | aggtggatga | 1260 |
| ggagacagaa | tagagtgata | ggaagcgtct | ggcagatact | ccttttgcca | ctgctgtgtg | 1320 |
| attagacagg | cccagtgagc | cgcggggcac | atgctggccg | ctcctccctc | agaaaaaggc | 1380 |
| agtggcctaa | atccttttta | aatgacttgg | ctcgatgctg | tggggactg | gctgggctgc | 1440 |
| tgcaggccgt | gtgtctgtca | gcccaacctt | cacatctgtc | acgttctcca | cacggggag | 1500 |
| agacgcagtc | cgcccaggtc | cccgctttct | ttggaggcag | cagctcccgc | agggctgaag | 1560 |
| tctggcgtaa | gatgatggat | ttgattcgcc | ctcctccctg | tcatagagct | gcagggtgga | 1620 |
| ttgttacagc | ttcgctggaa | acctctggag | gtcatctcgg | ctgttcctga | gaaataaaaa | 1680 |
| gcctgtcatt | tcaaacactg | ctgtggaccc | tactgggttt | ttaaaatatt | gtcagttttt | 1740 |
| catcgtcgtc | cctagcctgc | caacagccat | ctgcccagac | agccgcagtg | aggatgagcg | 1800 |
| tcctggcaga | gacgcagttg | tctctgggcg | cttgccagag | ccacgaaccc | cagacctgtt | 1860 |
| tgtatcatcc | gggctccttc | cgggcagaaa | caactgaaaa | tgcacttcag | acccacttat | 1920 |
| ttctgccaca | tctgagtcgg | cctgagatag | acttttccct | ctaaactggg | agaatatcac | 1980 |
| agtggttttt | gttagcagaa | aatgcactcc | agcctctgta | ctcatctaag | ctgcttattt | 2040 |
| ttgatatttg | tgtcagtctg | taaatggata | cttcacttta | ataactgttg | cttagtaatt | 2100 |
| ggctttgtag | agaagctgga | aaaaaatggt | tttgtcttca | actcctttgc | atgccaggcg | 2160 |
| gtgatgtgga | tctcggcttc | tgtgagcctg | tgctgtgggc | agggctgagc | tggagccgcc | 2220 |
| cctctcagcc | cgcctgccac | ggcctttcct | taaaggccat | ccttaaaacc | agaccctcat | 2280 |

```
ggctaccagc acctgaaagc ttcctcgaca tctgttaata aagccgtagg cccttgtcta    2340
agtgcaaccg cctagacttt ctttcagata catgtccaca tgtccatttt tcaggttctc    2400
taagttggag tggagtctgg aagggttgt gaatgaggct tctgggctat gggtgaggtt    2460
ccaatggcag gttagagccc ctcgggccaa ctgccatcct ggaaagtaga dacagcagtg    2520
cccgctgccc agaagagacc agcaagccaa actggagccc ccattgcagg ctgtcgccat    2580
gtggaaagag taactcacaa ttgccaataa agtctcatgt ggttttatct aaaaaaaaaa    2640
aaaaaaaaaa aaaaa                                                     2655

<210> SEQ ID NO 5
<211> LENGTH: 4304
<212> TYPE: DNA
<213> ORGANISM: Homo sapiens

<400> SEQUENCE: 5
cacacggact acaggggagt tttgttgaag ttgcaaagtc ctggagcctc cagagggctg     60
tcggcgcagt agcagcgagc agcagagtcc gcacgctccg gcgaggggca aagagcgcg    120 agggagcgcg gggcagcaga agcgagagcc gagcgcggac ccagccagga cccacagccc    180
tccccagctg cccaggaaga gccccagcca tggaacacca gctcctgtgc tgcgaagtgg    240
aaaccatccg ccgcgcgtac cccgatgcca acctcctcaa cgaccgggtg ctgcgggcca    300
tgctgaaggc ggaggagacc tgcgcgccct cggtgtccta cttcaaatgt gtgcagaagg    360
aggtcctgcc gtccatgcgg aagatcgtcg ccacctggat gctggaggtc tgcgaggaac    420
agaagtgcga ggaggaggtc ttcccgctgg ccatgaacta cctggaccgc ttcctgtcgc    480
tggagcccgt gaaaaagagc cgcctgcagc tgctgggggc cacttgcatg ttcgtggcct    540
ctaagatgaa ggagaccatc cccctgacgg ccagaagct gtgcatctac accgacaact    600
ccatccggcc cgaggagctg ctgcaaatgg agctgctcct ggtgaacaag ctcaagtgga    660
acctggccgc aatgacccca cacgatttca ttgaacactt cctctccaaa atgccagagg    720
cggaggagaa caaacagatc atccgcaaac acgcgcagac cttcgttgcc ctctgtgcca    780
cagatgtgaa gttcatttcc aatccgccct ccatggtggc agcggggagc gtggtggccg    840
cagtgcaagg cctgaacctg aggagcccca caacttcct gtcctactac cgcctcacac    900
gcttcctctc cagagtgatc aagtgtgacc cggactgcct ccgggcctgc caggagcaga    960
tcgaagccct gctggagtca agcctgcgcc aggcccagca gaacatggac cccaaggccg   1020
ccgaggagga ggaagaggag gaggaggagg tggacctggc ttgcacaccc accgacgtgc   1080
gggacgtgga catctgaggg cgccaggcag gcgggcgcca ccgccacccg cagcgagggc   1140
ggagccggcc ccaggtgctc ccctgacagt ccctcctctc cggagcattt tgataccaga   1200
agggaaagct tcattctcct tgttgttggt tgttttttcc tttgctcttt cccccttcca   1260
tctctgactt aagcaaaaga aaagattac ccaaaaactg tctttaaaag agagagagag   1320
aaaaaaaaaa tagtatttgc ataaccctga gcggtggggg aggagggttg tgctacagat   1380
gatagaggat tttataccccc aataatcaac tcgtttttat attaatgtac ttgtttctct   1440
gttgtaagaa taggcattaa cacaaaggag gcgtctcggg agaggattag gttccatcct   1500
ttacgtgttt aaaaaaaagc ataaaaacat tttaaaaaca tagaaaaatt cagcaaacca   1560
tttttaaagt agaagagggt tttaggtaga aaaacatatt cttgtgcttt tcctgataaa   1620
gcacagctgt agtggggttc taggcatctc tgtactttgc ttgctcatat gcatgtagtc   1680
```

-continued

```
actttataag tcattgtatg ttattatatt ccgtaggtag atgtgtaacc tcttcacctt    1740
attcatggct gaagtcacct cttggttaca gtagcgtagc gtgcccgtgt gcatgtcctt    1800
tgcgcctgtg accaccaccc aacaaaacca tccagtgaca aaccatccag tggaggtttg    1860
tcgggcacca gccagcgtag cagggtcggg aaaggccacc tgtcccactc ctacgatacg    1920
ctactataaa gagaagacga aatagtgaca taatatattc tatttttata ctcttcctat    1980
ttttgtagtg acctgtttat gagatgctgg ttttctaccc aacggccctg cagccagctc    2040
acgtccaggt tcaacccaca gctacttggt ttgtgttctt cttcatattc taaaaccatt    2100
ccatttccaa gcactttcag tccaataggt gtaggaaata gcgctgtttt tgttgtgtgt    2160
gcagggaggg cagttttcta atggaatggt ttgggaatat ccatgtactt gtttgcaagc    2220
aggactttga ggcaagtgtg ggccactgtg gtggcagtgg aggtggggtg tttgggaggc    2280
tgcgtgccag tcaagaagaa aaaggtttgc attctcacat tgccaggatg ataagttcct    2340 ttcctttttct ttaaagaagt tgaagtttag gaatcctttg gtgccaactg gtgtttgaaa    2400
gtagggacct cagaggttta cctagagaac aggtggtttt taagggttat cttagatgtt    2460
tcacaccgga aggttttttaa acactaaaat atataattta tagttaaggc taaaaagtat    2520
atttattgca gaggatgttc ataaggccag tatgattat aaatgcaatc tccccttgat    2580
ttaaacacac agatacacac acacacacac acacacacaa accttctgcc tttgatgtta    2640
cagatttaat acagtttatt tttaaagata gatccttta taggtgagaa aaaacaatc    2700 tggaagaaaa aaaccacaca aagacattga ttcagcctgt ttggcgtttc ccagagtcat    2760
ctgattggac aggcatgggt gcaaggaaaa ttagggtact caacctaagt tcggttccga    2820
tgaattctta tccctgccc cttccttttaa aaaacttagt gacaaaatag acaatttgca    2880
catcttggct atgtaattct tgtaatttt atttaggaag tgttgaaggg aggtggcaag    2940
agtgtggagg ctgacgtgtg agggaggaca ggcgggagga ggtgtgagga ggaggctccc    3000
gaggggaagg ggcggtgccc acaccgggga caggccgcag ctccatttc ttattgcgct    3060 gctaccgttg acttccaggc acggtttgga aatattcaca tcgcttctgt gtatctcttt    3120
cacattgttt gctgctattg gaggatcagt tttttgtttt acaatgtcat atactgccat    3180
gtactagttt tagttttctc ttagaacatt gtattacaga tgccttttt gtagttttt    3240 tttttttat gtgatcaatt ttgacttaat gtgattactg ctctattcca aaaaggttgc    3300
tgtttcacaa tacctcatgc ttcacttagc catggtggac ccagcgggca ggttctgcct    3360
gctttggcgg gcagacacgc gggcgcgatc ccacacaggc tggcggggc cggcccgag     3420 gccgcgtgcg tgagaaccgc gccggtgtcc ccagagacca ggctgtgtcc ctcttctctt    3480
ccctgcgcct gtgatgctgg gcacttcatc tgatcggggg cgtagcatca tagtagtttt    3540
tacagctgtg ttattctttg cgtgtagcta tggaagttgc ataattatta ttattattat    3600
tataacaagt gtgtcttacg tgccaccacg gcgttgtacc tgtaggactc tcattcggga    3660
tgattggaat agcttctgga atttgttcaa gttttgggta tgtttaatct gttatgtact    3720
agtgttctgt ttgttattgt tttgttaatt acaccataat gctaatttaa agagactcca    3780
aatctcaatg aagccagctc acagtgctgt gtgcccgggt cacctagcaa gctgccgaac    3840
caaaagaatt tgcaccccgc tgcgggccca cgtggttggg gccctgccct ggcagggtca    3900
tcctgtgctc ggaggccatc tcgggcacag gcccacccg cccaccccct ccagaacacg    3960
gctcacgctt acctcaacca tcctggctgc ggcgtctgtc tgaaccacgc ggggccttg    4020 agggacgctt tgtctgtcgt gatggggcaa gggcacaagt cctggatgtt gtgtgtatcg    4080
```

-continued

| | |
|---|---|
| agaggccaaa ggctggtggc aagtgcacgg ggcacagcgg agtctgtcct gtgacgcgca | 4140 |
| agtctgaggg tctgggcggc gggcggctgg gtctgtgcat ttctggttgc accgcggcgc | 4200 |
| ttcccagcac caacatgtaa ccggcatgtt tccagcagaa gacaaaaaga caaacatgaa | 4260 |
| agtctagaaa taaaactggt aaaaccccaa aaaaaaaaa aaaa | 4304 |

<210> SEQ ID NO 6
<211> LENGTH: 3691
<212> TYPE: DNA
<213> ORGANISM: Homo sapiens

<400> SEQUENCE: 6

| | |
|---|---|
| ggcgcaacgc tgagcagctg gcgcgtcccg cgcggcccca gttctgcgca gcttcccgag | 60 |
| gctccgcacc agccgcgctt ctgtccgcct gcagggcatt ccagaaagat gaggatattt | 120 |
| gctgtctta tattcatgac ctactggcat ttgctgaacg catttactgt cacggttccc | 180 |
| aaggacctat atgtggtaga gtatggtagc aatatgacaa ttgaatgcaa attcccagta | 240 |
| gaaaaacaat tagacctggc tgcactaatt gtctattggg aaatggagga taagaacatt | 300 |
| attcaatttg tgcatggaga ggaagacctg aaggttcagc atagtagcta cagacagagg | 360 |
| gcccggctgt tgaaggacca gctctccctg ggaaatgctg cacttcagat cacagatgtg | 420 |
| aaattgcagg atgcagggt gtaccgctgc atgatcagct atggtggtgc cgactacaag | 480 |
| cgaattactg tgaaagtcaa tgccccatac aacaaaatca ccaaagaat tttggttgtg | 540 |
| gatccagtca cctctgaaca tgaactgaca tgtcaggctg agggctaccc caaggccgaa | 600 |
| gtcatctgga caagcagtga ccatcaagtc ctgagtggta gaccaccac caccaattcc | 660 |
| aagagagagg agaagctttt caatgtgacc agcacactga gaatcaacac aacaactaat | 720 |
| gagatttct actgcacttt taggagatta gatcctgagg aaaaccatac agctgaattg | 780 |
| gtcatcccag aactacctct ggcacatcct ccaaatgaaa ggactcactt ggtaattctg | 840 |
| ggagccatct tattatgcct tggtgtagca ctgacattca tcttccgttt aagaaaaggg | 900 |
| agaatgatgg atgtgaaaaa atgtggcatc caagatacaa actcaaagaa gcaaagtgat | 960 |
| acacatttgg aggagacgta atccagcatt ggaacttctg atcttcaagc agggattctc | 1020 |
| aacctgtggt ttaggggttc atcggggctg agcgtgacaa gaggaaggaa tgggcccgtg | 1080 |
| ggatgcaggc aatgtgggac ttaaaaggcc caagcactga aaatgaaacc tggcgaaagc | 1140 |
| agaggaggag aatgaagaaa gatggagtca acagggagc ctggagggag accttgatac | 1200 |
| tttcaaatgc ctgagggct catcgacgcc tgtgacaggg agaaaggata cttctgaaca | 1260 |
| aggagcctcc aagcaaatca tccattgctc atcctaggaa gacgggttga gaatccctaa | 1320 |
| tttgagggtc agttcctgca gaagtgccct ttgcctccac tcaatgcctc aatttgtttt | 1380 |
| ctgcatgact gagagtctca gtgttggaac gggacagtat ttatgtatga gttttcccta | 1440 |
| tttatttga gtctgtgagg tcttcttgtc atgtgagtgt ggttgtgaat gatttctttt | 1500 |
| gaagatatat tgtagtagat gttacaattt tgtcgccaaa ctaaacttgc tgcttaatga | 1560 |
| tttgctcaca tctagtaaaa catggagtat ttgtaaggtg cttggtctcc tctataacta | 1620 |
| caagtataca ttggaagcat aaagatcaaa ccgttggttg cataggatgt caccttttatt | 1680 |
| taacccatta atactctggt tgacctaatc ttattctcag acctcaagtg tctgtgcagt | 1740 |
| atctgttcca tttaaatatc agcttttacaa ttatgtggta gcctacacac ataatctcat | 1800 |
| ttcatcgctg taaccaccct gttgtgataa ccactattat tttacccatc gtacagctga | 1860 |

| | |
|---|---|
| ggaagcaaac agattaagta acttgcccaa accagtaaat agcagacctc agactgccac | 1920 |
| ccactgtcct tttataatac aatttacagc tatattttac tttaagcaat tcttttattc | 1980 |
| aaaaaccatt tattaagtgc ccttgcaata tcaatcgctg tgccaggcat tgaatctaca | 2040 |
| gatgtgagca agacaaagta cctgtcctca aggagctcat agtataatga ggagattaac | 2100 |
| aagaaaatgt attattacaa tttagtccag tgtcatagca taaggatgat gcgagggaa | 2160 |
| aacccgagca gtgttgccaa gaggaggaaa taggccaatg tggtctggga cggttggata | 2220 |
| tacttaaaca tcttaataat cagagtaatt ttcatttaca aagagaggtc ggtacttaaa | 2280 |
| ataaccctga aaataacac tggaattcct tttctagcat tatatttatt cctgatttgc | 2340 |
| ctttgccata taatctaatg cttgtttata tagtgtctgg tattgtttaa cagttctgtc | 2400 |
| ttttctattt aaatgccact aaattttaaa ttcatacctt tccatgattc aaaattcaaa | 2460 |
| agatcccatg ggagatggtt ggaaaatctc cacttcatcc tccaagccat tcaagtttcc | 2520 |
| tttccagaag caactgctac tgcctttcat tcatatgttc ttctaaagat agtctacatt | 2580 |
| tggaaatgta tgttaaaagc acgtattttt aaaattttt tcctaaatag taacacattg | 2640 |
| tatgtctgct gtgtactttg ctattttat ttattttagt gtttcttata tagcagatgg | 2700 |
| aatgaatttg aagttcccag ggctgaggat ccatgccttc tttgtttcta agttatcttt | 2760 |
| cccatagctt tcattatct ttcatatgat ccagtatatg ttaaatatgt cctacatata | 2820 |
| catttagaca accaccattt gttaagtatt tgctctagga cagagtttgg atttgtttat | 2880 |
| gtttgctcaa aaggagaccc atgggctctc cagggtgcac tgagtcaatc tagtcctaaa | 2940 |
| aagcaatctt attattaact ctgtatgaca gaatcatgtc tggaactttt gttttctgct | 3000 |
| ttctgtcaag tataaacttc actttgatgc tgtacttgca aaatcacatt tctttctgg | 3060 |
| aaattccggc agtgtacctt gactgctagc taccctgtgc cagaaaagcc tcattcgttg | 3120 |
| tgcttgaacc cttgaatgcc accagctgtc atcactacac agccctccta agaggcttcc | 3180 |
| tggaggtttc gagattcaga tgccctggga gatcccagag tttcctttcc ctcttggcca | 3240 |
| tattctggtg tcaatgacaa ggagtacctt ggctttgcca catgtcaagg ctgaagaaac | 3300 |
| agtgtctcca acagagctcc ttgtgttatc tgtttgtaca tgtgcatttg tacagtaatt | 3360 |
| ggtgtgacag tgttctttgt gtgaattaca ggcaagaatt gtggctgagc aaggcacata | 3420 |
| gtctactcag tctattccta agtcctaact cctccttgtg gtgttggatt tgtaaggcac | 3480 |
| tttatcccctt tgtctcatg tttcatcgta aatggcatag gcagagatga tacctaattc | 3540 |
| tgcatttgat tgtcactttt tgtacctgca ttaatttaat aaaatattct tatttatttt | 3600 |
| gttacttggt acaccagcat gtccattttc ttgtttattt tgtgtttaat aaaatgttca | 3660 |
| gtttaacatc ccagtggaga aagttaaaaa a | 3691 |

<210> SEQ ID NO 7
<211> LENGTH: 2122
<212> TYPE: DNA
<213> ORGANISM: Homo sapiens

<400> SEQUENCE: 7

| | |
|---|---|
| ggtggctatt ttgtccttgg gctgcctgtt ttcagctgct gcaaccacag ggatttcttc | 60 |
| tgttcaggcg ccatgtcaga accggctggg gatgtccgtc agaacccatg cggcagcaag | 120 |
| gcctgccgcc gcctcttcgg cccagtggac agcgagcagc tgagccgcga ctgtgatgcg | 180 |
| ctaatgcgcg gctgcatcca ggaggcccgt gagcgatgga acttcgactt tgtcaccgag | 240 |
| acaccactgg agggtgactt cgcctgggag cgtgtgcggg gccttggcct gcccaagctc | 300 |

```
taccttccca cggggcccog gcgaggccgg gatgagttgg gaggaggcag gcggcctggc    360
acctcacctg ctctgctgca ggggacagca gaggaagacc atgtggacct gtcactgtct    420
tgtacccttg tgcctcgctc aggggagcag gctgaagggt ccccaggtgg acctggagac    480
tctcagggtc gaaaacggcg gcagaccagc atgacagatt ctaccactc caaacgccgg     540
ctgatcttct ccaagaggaa gccctaatcc gcccacagga agcctgcagt cctggaagcg    600
cgagggcctc aaaggcccgc tctacatctt ctgccttagt ctcagtttgt gtgtcttaat    660
tattatttgt gttttaattt aaacacctcc tcatgtacat accctggccg cccctgccc    720
cccagcctct ggcattagaa ttatttaaac aaaaactagg cggttgaatg agaggttcct    780
aagagtgctg gcatttttta ttttatgaaa tactatttaa agcctcctca tcccgtgttc    840
tcctttcct ctctcccgga ggttgggtgg gccggcttca tgccagctac ttcctcctcc    900
ccacttgtcc gctgggtggt accctctgga ggggtgtggc tccttcccat cgctgtcaca    960
ggcggttatg aaattcaccc cctttcctgg acactcagac ctgaattctt tttcatttga   1020
gaagtaaaca gatggcactt tgaaggggcc tcaccgagtg ggggcatcat caaaaacttt   1080
ggagtcccct cacctcctct aaggttgggc agggtgaccc tgaagtgagc acagcctagg   1140
gctgagctgg ggacctggta ccctcctggc tcttgatacc ccctctgtc ttgtgaaggc    1200
aggggggaagg tggggtcctg gagcagacca ccccgcctgc cctcatggcc cctctgacct   1260
gcactgggga gcccgtctca gtgttgagcc ttttccctct ttggctcccc tgtaccttt    1320
gaggagcccc agctacccct tcttctccagc tgggctctgc aattcccctc tgctgctgtc   1380
cctcccccct gtcctttccc ttcagtaccc tctcagctcc aggtggctct gaggtgcctg   1440
tcccacccc accccccagct caatggactg gaaggggaag ggacacacaa gaagaagggc   1500
accctagttc tacctcaggc agctcaagca gcgaccgccc cctcctctag ctgtggggt    1560
gagggtccca tgtggtggca caggcccccct tgagtgggt tatctctgtg ttaggggtat   1620
atgatggggg agtagatctt tctaggaggg agacactggc ccctcaaatc gtccagcgac   1680
cttcctcatc cacccatcc ctccccagtt cattgcactt tgattagcag cggaacaagg    1740
agtcagacat tttaagatgg tggcagtaga ggctatggac agggcatgcc acgtgggctc   1800
atatggggct gggagtagtt gtcttttcctg gcactaacgt tgagcccctg gaggcactga   1860
agtgcttagt gtacttggag tattgggggtc tgaccccaaa caccttccag ctcctgtaac   1920
atactggcct ggactgtttt ctctcggctc cccatgtgtc ctggttcccg tttctccacc   1980
tagactgtaa acctctcgag ggcagggacc acaccctgta ctgttctgtg tcttcacag    2040
ctcctcccac aatgctgaat atacagcagg tgctcaataa atgattctta gtgactttac   2100
ttgtaaaaaa aaaaaaaaaa aa                                            2122
```

<210> SEQ ID NO 8
<211> LENGTH: 2024
<212> TYPE: DNA
<213> ORGANISM: Homo sapiens
<400> SEQUENCE: 8

```
aaggcaagag atctaggact tctagccccct gaactttcag ccgaatacat cttttccaaa     60
ggagtgaatt caggcccttg tatcactggc agcaggacgt gaccatggag aagctgttgt    120
gtttcttggt cttgaccagc ctctctcatg cttttggcca gacagacatg tcgaggaagg    180
cttttgtgtt tcccaaagag tcggatactt cctatgtatc cctcaaagca ccgttaacga    240
```

| | |
|---|---|
| agcctctcaa agccttcact gtgtgcctcc acttctacac ggaactgtcc tcgacccgtg | 300 |
| ggtacagtat tttctcgtat gccaccaaga gacaagacaa tgagattctc atattttggt | 360 |
| ctaaggatat aggatacagt tttacagtgg gtgggtctga aatattattc gaggttcctg | 420 |
| aagtcacagt agctccagta cacatttgta caagctggga gtccgcctca gggatcgtgg | 480 |
| agttctgggt agatgggaag cccagggtga ggaagagtct gaagaaggga tacactgtgg | 540 |
| gggcagaagc aagcatcatc ttggggcagg agcaggattc cttcggtggg aactttgaag | 600 |
| gaagccagtc cctggtggga gacattggaa atgtgaacat gtgggacttt gtgctgtcac | 660 |
| cagatgagat taacaccatc tatcttggcg ggcccttcag tcctaatgtc ctgaactggc | 720 |
| gggcactgaa gtatgaagtg caaggcgaag tgttcaccaa accccagctg tggccctgag | 780 |
| gcccagctgt gggtcctgaa ggtacctccc ggttttttac accgcatggg ccccacgtct | 840 |
| ctgtctctgg tacctcccgc tttttacac tgcatggttc ccacgtctct gtctctgggc | 900 |
| ctttgttccc ctatatgcat tgcaggcctg ctccaccctc ctcagcgcct gagaatggag | 960 |
| gtaaagtgtc tggtctggga gctcgttaac tatgctggga aacggtccaa aagaatcaga | 1020 |
| atttgaggtg ttttgttttc attttttattt caagttggac agatcttgga gataatttct | 1080 |
| tacctcacat agatgagaaa actaacaccc agaaaggaga aatgatgtta taaaaaactc | 1140 |
| ataaggcaag agctgagaag gaagcgctga tcttctattt aattcccac ccatgacccc | 1200 |
| cagaaagcag gagggcattg cccacattca cagggctctt cagtctcaga atcaggacac | 1260 |
| tggccaggtg tctggtttgg gtccagagtg ctcatcatca tgtcatagaa ctgctgggcc | 1320 |
| caggtctcct gaaatgggaa gcccagcaat accacgcagt ccctccactt tctcaaagca | 1380 |
| cactggaaag gccattagaa ttgccccagc agagcagatc tgcttttttt ccagagcaaa | 1440 |
| atgaagcact aggtataaat atgttgttac tgccaagaac ttaaatgact ggttttttgtt | 1500 |
| tgcttgcagt gctttcttaa ttttatggct cttctgggaa actcctcccc ttttccacac | 1560 |
| gaaccttgtg gggctgtgaa ttctttcttc atccccgcat tcccaatata cccaggccac | 1620 |
| aagagtggac gtgaaccaca gggtgtcctg tcagaggagc ccatctccca tctccccagc | 1680 |
| tccctatctg gaggatagtt ggatagttac gtgttcctag caggaccaac tacagtcttc | 1740 |
| ccaaggattg agttatggac tttgggagtg agacatcttc ttgctgctgg atttccaagc | 1800 |
| tgagaggacg tgaacctggg accaccagta gccatcttgt ttgccacatg gagagagact | 1860 |
| gtgaggacag aagccaaact ggaagtggag gagccaaggg attgacaaac aacagagcct | 1920 |
| tgaccacgtg gagtctctga atcagccttg tctggaacca gatctacacc tggactgccc | 1980 |
| aggtctataa gccaataaag cccctgttta cttgaaaaaa aaaa | 2024 |

<210> SEQ ID NO 9
<211> LENGTH: 6774
<212> TYPE: DNA
<213> ORGANISM: Homo sapiens

<400> SEQUENCE: 9

| | |
|---|---|
| cggccccaga aacccgagc gagtaggggg cggcgcgcag gagggaggag aactgggggc | 60 |
| gcggaggct ggtgggtgtg gggggtggag atgtagaaga tgtgacgccg cggcccggcg | 120 |
| ggtgccagat tagcggacgc ggtgcccgcg gttgcaacgg gatcccgggc gctgcagctt | 180 |
| gggaggcggc tctccccagg cggcgtccgc ggagacaccc atccgtgaac cccaggtccc | 240 |
| gggccgccgc ctcgccgcgc accaggggcc ggcggacaga gagcggccg agcggctcga | 300 |
| ggctggggga ccgcgggcgc ggccgcgcgc tgccgggcgg gaggctgggg ggccggggcc | 360 |

```
ggggccgtgc cccggagcgg gtcggaggcc ggggccgggg ccggggacg gcggctcccc    420 gcgcggctcc agcggctcgg ggatcccggc cgggccccgc agggaccatg gcagccggga    480
gcatcaccac gctgcccgcc ttgcccgagg atggcggcag cggcgccttc ccgcccggcc    540
acttcaagga ccccaagcgg ctgtactgca aaaacggggg cttcttcctg cgcatccacc    600
ccgacggccg agttgacggg gtccgggaga agagcgaccc tcacatcaag ctacaacttc    660
aagcagaaga gagaggagtt gtgtctatca aggagtgtg tgctaaccgt tacctggcta    720
tgaaggaaga tggaagatta ctggcttcta aatgtgttac ggatgagtgt ttcttttttg    780
aacgattgga atctaataac tacaatactt accggtcaag gaaatacacc agttggtatg    840
tggcactgaa acgaactggg cagtataaac ttggatccaa acaggacct gggcagaaag     900 ctatactttt tcttccaatg tctgctaaga gctgatttta atggccacat ctaatctcat    960
ttcacatgaa agaagaagta tattttagaa atttgttaat gagagtaaaa gaaaataaat   1020
gtgtatagct cagtttggat aattggtcaa acaattttt atccagtagt aaaatatgta    1080
accattgtcc cagtaaagaa aaataacaaa agttgtaaaa tgtatattct ccctttata    1140 ttgcatctgc tgttacccag tgaagcttac ctagagcaat gatcttttc acgcatttgc    1200 tttattcgaa aagaggcttt taaaatgtgc atgtttagaa acaaaatttc ttcatggaaa    1260
tcatatacat tagaaaatca cagtcagatg tttaatcaat ccaaaatgtc cactatttct    1320
tatgtcattc gttagtctac atgtttctaa acatataaat gtgaatttaa tcaattcctt    1380
tcatagtttt ataattctct ggcagttcct tatgatagag tttataaaac agtcctgtgt    1440
aaactgctgg aagttcttcc acagtcaggt caattttgtc aaacccttct ctgtacccat    1500
acagcagcag cctagcaact ctgctggtga tgggagttgt attttcagtc ttcgccaggt    1560
cattgagatc catccactca catcttaagc attcttcctg gcaaaattt atggtgaatg    1620 aatatggctt taggcggcag atgatataca tatctgactt cccaaaagct ccaggatttg    1680
tgtgctgttg ccgaatactc aggacggacc tgaattctga ttttatacca gtctcttcaa    1740
aaacttctcg aaccgctgtg tctcctacgt aaaaaaagag atgtacaaat caataataat    1800
tacactttta gaaactgtat catcaaagat tttcagttaa agtagcatta tgtaaaggct    1860
caaaacatta ccctaacaaa gtaaagtttt caatacaaat tctttgcctt gtggatatca    1920
agaaatccca aaatatttc ttaccactgt aaattcaaga agcttttgaa atgctgaata     1980
tttctttggc tgctacttgg aggcttatct acctgtacat ttttggggtc agctcttttt    2040
aacttcttgc tgctctttt cccaaaaggt aaaaatatag attgaaaagt taaacatttt     2100
tgcatggctg cagttccttt gtttcttgag ataagattcc aaagaactta gattcatttc    2160
ttcaacaccg aaatgctgga ggtgtttgat cagttttcaa gaaacttgga atataaataa    2220
ttttataatt caacaaaggt tttcacattt tataaggttg atttttcaat taaatgcaaa    2280
tttgtgtggc aggattttta ttgccattaa catattttg tggctgcttt ttctacacat     2340
ccagatggtc cctctaactg gctttctct aattttgtga tgttctgtca ttgtctccca     2400
aagtatttag gagaagccct ttaaaaagct gccttcctct accactttgc tggaaagctt    2460
cacaattgtc acagacaaag attttgttc caatactcgt tttgcctcta tttttcttgt    2520
ttgtcaaata gtaaatgata tttgcccttg cagtaattct actggtgaaa aacatgcaaa    2580
gaagaggaag tcagaaaac atgtctcaat tcccatgtgc tgtgactgta gactgtctta    2640
ccatagactg tcttacccat cccctggata tgctcttgtt ttttccctct aatagctatg    2700
```

```
gaaagatgca tagaaagagt ataatgtttt aaaacataag gcattcgtct gccattttc    2760 aattacatgc tgacttccct tacaattgag atttgcccat aggttaaaca tggttagaaa    2820
caactgaaag cataaaagaa aaatctaggc cgggtgcagt ggctcatgcc tatattccct    2880
gcactttggg aggccaaagc aggaggatcg cttgagccca ggagttcaag accaacctgg    2940
tgaaaccccg tctctacaaa aaaacacaaa aaatagccag gcatggtggc gtgtacatgt    3000
ggtctcagat acttgggagg ctgaggtggg agggttgatc acttgaggct gagaggtcaa    3060
ggttgcagtg agccataatc gtgccactgc agtccagcct aggcaacaga gtgagacttt    3120
gtctcaaaaa aagagaaatt ttccttaata agaaaagtaa tttttactct gatgtgcaat    3180
acatttgtta ttaaatttat tatttaagat ggtagcacta gtcttaaatt gtataaaata    3240
tcccctaaca tgtttaaatg tccatttta ttcattatgc tttgaaaaat aattatgggg     3300
aaatacatgt ttgttattaa atttattatt aaagatagta gcactagtct taaatttgat    3360
ataacatctc ctaacttgtt taaatgtcca tttttattct ttatgtttga aaataaatta    3420
tggggatcct atttagctct tagtaccact aatcaaaagt tcggcatgta gctcatgatc    3480
tatgctgttt ctatgtcgtg aagcaccgg atggggtag tgagcaaatc tgccctgctc      3540
agcagtcacc atagcagctg actgaaaatc agcactgcct gagtagtttt gatcagttta    3600
acttgaatca ctaactgact gaaaattgaa tgggcaaata agtgcttttg tctccagagt    3660
atgcgggaga cccttccacc tcaagatgga tatttcttcc ccaaggattt caagatgaat    3720 tgaattttt aatcaagata gtgtgcttta ttctgttgta ttttttatta tttaatata     3780 ctgtaagcca aactgaaata acatttgctg ttttataggt ttgaagaaca taggaaaaac    3840
taagaggttt tgttttttatt tttgctgatg aagagatatg tttaaatatg ttgtattgtt    3900
ttgtttagtt acaggacaat aatgaaatgg agtttatatt tgttatttct attttgttat    3960
atttaataat agaattagat tgaaataaaa tataatggga aataatctgc agaatgtggg    4020
ttttcctggt gtttccctct gactctagtg cactgatgat ctctgataag gctcagctgc    4080
tttatagttc tctggctaat gcagcagata ctcttcctgc cagtggtaat acgattttt     4140 aagaaggcag tttgtcaatt ttaatcttgt ggatacctt atactcttag ggtattattt      4200
tatacaaaag ccttgaggat tgcattctat tttctatatg accctcttga tatttaaaaa    4260
acactatgga taacaattct tcattacct agtattatga agaatgaag gagttcaaac      4320 aaatgtgttt cccagttaac tagggtttac tgtttgagcc aatataaatg tttaactgtt    4380
tgtgatggca gtattcctaa agtacattgc atgttttcct aaatacagag tttaaataat    4440
ttcagtaatt cttagatgat tcagcttcat cattaagaat atcttttgtt ttatgttgag    4500
ttagaaatgc cttcatatag acatagtctt tcagacctct actgtcagtt tcatttcta    4560 gctgctttca gggttttatg aattttcagg caaagcttta atttatacta agcttaggaa    4620
gtatggctaa tgccaacggc agtttttttc ttcttaattc cacatgactg aggcatatat    4680
gatctctggg taggtgagtt gttgtgacaa ccacaagcac ttttttttt tttaaagaaa     4740 aaaaggtagt gaattttta tcatctggac tttaagaagg attctggagt atacttaggc     4800
ctgaaattat atatatttgg cttggaaatg tgttttctt caattacatc tacaagtaag     4860
tacagctgaa attcagagga cccataagag ttcacatgaa aaaaatcaat ttatttgaaa    4920
aggcaagatg caggagagag gaagccttgc aaacctgcag actgcttttt gcccaatata    4980
gattgggtaa ggctgcaaaa cataagctta attagctcac atgctctgct ctcacgtggc    5040
accagtggat agtgtgagag aattaggctg tagaacaaat ggccttctct ttcagcattc    5100
```

-continued

```
acaccactac aaaatcatct tttatatcaa cagaagaata agcataaaact aagcaaaagg    5160 tcaataagta cctgaaacca agattggcta gagatatatc ttaatgcaat ccattttctg    5220
atggattgtt acgagttggc tatataatgt atgtatggta ttttgatttg tgtaaaagtt    5280
ttaaaaatca agctttaagt acatggacat ttttaaataa aatatttaaa gacaatttag    5340
aaaattgcct taatatcatt gttggctaaa tagaataggg gacatgcata ttaaggaaaa    5400
ggtcatggag aaataatatt ggtatcaaac aaatacattg atttgtcatg atacacattg    5460
aatttgatcc aatagtttaa ggaataggta ggaaaatttg gtttctattt ttcgatttcc    5520
tgtaaatcag tgacataaat aattcttagc ttattttata tttccttgtc ttaaatactg    5580
agctcagtaa gttgtgttag gggattattt ctcagttgag actttcttat atgacatttt    5640
actatgtttt gacttcctga ctattaaaaa taaatagtag atacaatttt cataaagtga    5700
agaattatat aatcactgct ttataactga ctttattata tttatttcaa agttcattta    5760
aaggctacta ttcatcctct gtgatggaat ggtcaggaat ttgttttctc atagtttaat    5820
tccaacaaca atattagtcg tatccaaaat aacctttaat gctaaacttt actgatgtat    5880
atccaaagct tctcattttc agacagatta atccagaagc agtcataaac agaagaatag    5940
gtggtatgtt cctaatgata ttatttctac taatggaata aactgtaata ttagaaatta    6000
tgctgctaat tatatcagct ctgaggtaat ttctgaaatg ttcagactca gtcggaacaa    6060
attggaaaat ttaaattttt attcttagct ataaagcaag aaagtaaaca cattaatttc    6120
ctcaacattt ttaagccaat taaaaatata aagatacac accatatct tcttcaggct    6180 ctgacaggcc tcctggaaac ttccacatat ttttcaactg cagtataaag tcagaaaata    6240
aagttaacat aactttcact aacacacaca tatgtagatt tcacaaaatc cacctataat    6300
tggtcaaagt ggttgagaat atattttta gtaattgcat gcaaaatttt tctagcttcc    6360
atcctttctc cctcgtttct tcttttttg ggggagctgg taactgatga atctttttcc    6420
caccttttct cttcaggaaa tataagtggt tttgtttggt taacgtgata cattctgtat    6480
gaatgaaaca ttggagggaa acatctactg aatttctgta atttaaaata ttttgctgct    6540
agttaactat gaacagatag aagaatctta cagatgctgc tataaataag tagaaaatat    6600
aaatttcatc actaaaatat gctattttaa aatctatttc ctatattgta tttctaatca    6660
gatgtattac tcttattatt tctattgtat gtgttaatga ttttatgtaa aaatgtaatt    6720
gcttttcatg agtagtatga ataaaattga ttagtttgtg ttttcttgtc tccc          6774
```

<210> SEQ ID NO 10
<211> LENGTH: 2158
<212> TYPE: DNA
<213> ORGANISM: Homo sapiens

<400> SEQUENCE: 10

```
attcataaaa cgcttgttat aaaagcagtg gctgcggcgc ctcgtactcc aaccgcatct     60
gcagcgagca tctgagaagc caagactgag ccggcggccg cggcgcagcg aacgagcagt    120
gaccgtgctc ctacccagct ctgctccaca gcgcccacct gtctccgccc ctcggcccct    180
cgcccggctt tgcctaaccg ccacgatgat gttctcgggc ttcaacgcag actacgaggc    240
gtcatcctcc cgctgcagca gcgcgtcccc ggccggggat agcctctctt actaccactc    300
acccgcagac tccttctcca gcatgggctc gcctgtcaac gcgcaggact ctgcacggga    360
cctggccgtc tccagtgcca acttcattcc cacggtcact gccatctcga ccagtccgga    420
```

| | |
|---|---|
| cctgcagtgg ctggtgcagc ccgccctcgt ctcctccgtg gccccatcgc agaccagagc | 480 |
| ccctcaccct ttcggagtcc ccgcccccte cgctggggct tactccaggg ctggcgttgt | 540 |
| gaagaccatg acaggaggcc gagcgcagag cattggcagg aggggcaagg tggaacagtt | 600 |
| atctccagaa gaagaagaga aaaggagaat ccgaagggaa aggaataaga tggctgcagc | 660 |
| caaatgccgc aaccggagga gggagctgac tgatacactc caagcggaga cagaccaact | 720 |
| agaagatgag aagtctgctt tgcagaccga gattgccaac ctgctgaagg agaaggaaaa | 780 |
| actagagttc atcctggcag ctcaccgacc tgcctgcaag atccctgatg acctgggctt | 840 |
| cccagaagag atgtctgtgg cttcccttga tctgactggg ggcctgccag aggttgccac | 900 |
| cccggagtct gaggaggcct tcaccctgcc tctcctcaat gaccctgagc ccaagccctc | 960 |
| agtggaacct gtcaagagca tcagcagcat ggagctgaag accgagccct ttgatgactt | 1020 |
| cctgttccca gcatcatcca ggcccagtgg ctctgagaca gcccgctccg tgccagacat | 1080 |
| ggacctatct gggtccttct atgcagcaga ctgggagcct ctgcacagtg gctccctggg | 1140 |
| gatgggccc atggccacag agctggagcc cctgtgcact ccggtggtca cctgtactcc | 1200 |
| cagctgcact gcttacacgt cttccttcgt cttcacctac cccgaggctg actccttccc | 1260 |
| cagctgtgca gctgcccacc gcaagggcag cagcagcaat gagccttcct ctgactcgct | 1320 |
| cagctcaccc acgctgctgg ccctgtgagg gggcagggaa ggggaggcag ccggcaccca | 1380 |
| caagtgccac tgcccgagct ggtgcattac agagaggaga acacatcttt ccctagaggg | 1440 |
| ttcctgtaga cctagggagg accttatctg tgcgtgaaac acaccaggct gtgggcctca | 1500 |
| aggacttgaa agcatccatg tgtggactca agtccttacc tcttccggag atgtagcaaa | 1560 |
| acgcatggag tgtgtattgt tcccagtgac acttcagaga ctggtagtt agtagcatgt | 1620 |
| tgagccaggc ctgggtctgt gtctcttttc tctttctcct tagtcttctc atagcattaa | 1680 |
| ctaatctatt gggttcatta ttggaattaa cctggtgctg atatttttca aattgtatct | 1740 |
| agtgcagctg atttttaacaa taactactgt gttcctggca atagtgtgtt ctgattagaa | 1800 |
| atgaccaata ttatactaag aaaagatacg actttatttt ctggtagata gaaataaata | 1860 |
| gctatatcca tgtactgtag ttttttcttca acatcaatgt tcattgtaat gttactgatc | 1920 |
| atgcattgtt gaggtggtct gaatgttctg acattaacag ttttccatga aaacgtttta | 1980 |
| ttgtgttttt aatttattta ttaagatgga ttctcagata tttatatttt tattttattt | 2040 |
| ttttctacct tgaggtcttt tgacatgtgg aaagtgaatt tgaatgaaaa atttaagcat | 2100 |
| tgtttgctta ttgttccaag acattgtcaa taaaagcatt taagttgaat gcgaccaa | 2158 |

<210> SEQ ID NO 11
<211> LENGTH: 2812
<212> TYPE: DNA
<213> ORGANISM: Homo sapiens

<400> SEQUENCE: 11

| | |
|---|---|
| agctgggctt tgtggagcgc tgcggagggt gcgtgcgggc cgcggcagcc gaacaaagga | 60 |
| gcagggcgc cgccgcaggg acccgccacc cacctcccgg ggccgcgcag cggcctctcg | 120 |
| tctactgcca ccatgaccgc caacggcaca gccgaggcgc tgcagatcca gttcggcctc | 180 |
| atcaactgcg gcaacaagta cctgacggcc gaggcgttcg ggttcaaggt gaacgcgtcc | 240 |
| gccagcagcc tgaagaagaa gcagatctgg acgctggagc agccccctga cgaggcgggc | 300 |
| agcgcggccg tgtgcctgcg cagccaccTg ggccgctacc tggcggcgga caaggacggc | 360 |
| aacgtgacct gcgagcgcga ggtgcccggt cccgactgcc gtttcctcat cgtggcgcac | 420 |

```
gacgacggtc gctggtcgct gcagtccgag gcgcaccggc gctacttcgg cggcaccgag    480
gaccgcctgt cctgcttcgc gcagacggtg tcccccgccg agaagtggag cgtgcacatc    540
gccatgcacc ctcaggtcaa catctacagc gtcacccgta agcgctacgc gcacctgagc    600
gcgcggccgg ccgacgagat cgccgtggac cgcgacgtgc cctggggcgt cgactcgctc    660
atcaccctcg ccttccagga ccagcgctac agcgtgcaga ccgccgacca ccgcttcctg    720
cgccacgacg ggcgcctggt ggcgcgcccc gagccggcca ctggctacac gctggagttc    780
cgctccggca aggtggcctt ccgcgactgc gagggccgtt acctggcgcc gtcggggccc    840
agcggcacgc tcaaggcggg caaggccacc aaggtgggca aggacgagct ctttgctctg    900
gagcagagct gcgcccaggt cgtgctgcag gcggccaacg agaggaacgt gtccacgcgc    960
cagggtatgg acctgtctgc caatcaggac gaggagaccg accaggagac cttccagctg   1020
gagatcgacc gcgacaccaa aaagtgtgcc ttccgtaccc acacgggcaa gtactggacg   1080
ctgacggcca ccggggggcgt gcagtccacc gcctccagca agaatgccag ctgctacttt   1140
gacatcgagt ggcgtgaccg gcgcatcaca ctgagggcgt ccaatggcaa gtttgtgacc   1200
tccaagaaga atgggcagct ggccgcctcg gtggagacag caggggactc agagctcttc   1260
ctcatgaagc tcatcaaccg ccccatcatc gtgttccgcg gggagcatgg cttcatcggc   1320
tgccgcaagg tcacgggcac cctggacgcc aaccgctcca gctatgacgt cttccagctg   1380
gagttcaacg atggcgccta caacatcaaa gactccacag gcaaatactg gacggtgggc   1440
agtgactccg cggtcaccag cagcggcgac actcctgtgg acttcttctt cgagttctgc   1500
gactataaca aggtggccat caaggtgggc gggcgctacc tgaagggcga ccacgcaggc   1560
gtcctgaagg cctcggcgga aaccgtggac cccgcctcgc tctgggagta ctagggccgg   1620
cccgtccttc cccgcccctg cccacatggc ggctcctgcc aaccctccct gctaacccct   1680
tctccgccag gtgggctcca gggcgggagg caagccccct tgcctttcaa actggaaacc   1740
ccagagaaaa cggtgccccc acctgtcgcc cctatggact ccccactctc ccctccgccc   1800
gggttcccta ctcccctcgg gtcagcggct gcggcctggc cctgggaggg atttcagatg   1860
cccctgccct cttgtctgcc acggggcgag tctggcacct cttcttctg acctcagacg   1920 gctctgagcc ttatttctct ggaagcggct aagggacggt tgggggctgg gagccctggg   1980
cgtgtagtgt aactggaatc ttttgcctct cccagccacc tcctcccagc cccccaggag   2040
agctgggcac atgtcccaag cctgtcagtg gccctccctg gtgcactgtc cccgaaaccc   2100
ctgcttggga agggaagctg tcgggtgggc taggactgac ccttgtggtg ttttttttggg   2160 tggtggctgg aaacagcccc tctcccacgt ggcagaggct cagcctggct cccttccctg   2220
gagcggcagg gcgtgacggc cacagggtct gcccgctgca cgttctgcca aggtggtggt   2280
ggcgggcggg tagggtgtg ggggccgtct tcctcctgtc tctttccttt caccctagcc   2340
tgactggaag cagaaaatga ccaaatcagt attttttta atgaaatatt attgctggag   2400
gcgtcccagg caagcctggc tgtagtagcg agtgatctgg cgggggggcgt ctcagcaccc   2460 tccccagggg gtgcatctca gcccctctt tccgtccttc ccgtccagcc ccagccctgg   2520
gcctgggctg ccgacacctg gccagagcc ctgctgtga ttggtgctcc ctgggcctcc    2580
cgggtggatg aagccaggcg tcgcccctc cgggagccct gggtgagcc gccggggccc    2640 ccctgctgcc agcctccccc gtccccaaca tgcatctcac tctgggtgtc ttggtctttt   2700 atttttgta agtgtcattt gtataactct aaacgcccat gatagtagct tcaaactgga    2760
```
aatagcgaaa taaaataact cagtctgcag ccccagaaaa aaaaaaaaaa aa        2812

<210> SEQ ID NO 12
<211> LENGTH: 1690
<212> TYPE: DNA
<213> ORGANISM: Homo sapiens

<400> SEQUENCE: 12
gcaggcaggg ggttcgtgac gccggctggg tctgggggct gtgggccagc cgagccgacc    60
cgggcttctg ggggaccgcg ggggccgtga gcactcagag ggcgcatccc aggcccctcc   120
ggggacccgg ccagcctgaa gatgccgacg aacggcctgc accaggtgct gaagatccag   180
tttggcctcg tcaacgacac tgaccgctac ctgacagctg agagcttcgg cttcaaggtc   240
aatgcctcgg cacccagcct caagaggaag cagacctggg tgctggaacc cgacccagga   300
caaggcacgg ctgtgctgct ccgcagcagc cacctgggcc gctacctgtc ggcagaagag   360
gacgggcgcg tggcctgtga ggcagagcag ccgggccgtg actgccgctt cctggtcctg   420
ccgcagccag atgggcgctg ggtgctgcgg tccgagccgc acgccgcttc ttcggaggc   480
accgaggacc agctgtcctg cttcgccaca gccgtttccc cggccgagct gtggaccgtg   540
cacctggcca tccacccgca ggcccacctg ctgagcgtga gccggcggcg ctacgtgcac   600
ctgtgcccgc gggaggacga gatggccgca gacggagaca gccctgggg cgtggacgcc   660
ctcctcaccc tcatcttccg gagccgacgg tactgcctca gtcctgtga cagccgctac   720
ctgcgcagcg acggccgtct ggtctgggag cctgagcccc gtgcctgcta cacgctggag   780
ttcaaggcgg gcaagctggc cttcaaggac tgcgacggcc actacctggc acccgtgggg   840
cccgcaggca ccctcaaggc cggccgaaac acgcgacctg gcaaggatga gctctttgat   900
ctggaggaga gtcacccaca ggtggtgctg gtggctgcca accaccgcta cgtctctgtg   960
cggcaagggg tcaacgtctc agccaatcag gatgatgaac tagaccacga gaccttcctg  1020
atgcaaattg accaggagac aaagaagtgc accttctatt ccagcactgg gggctactgg  1080
accctggtca cccatggggg cattcacgcc acagccacac aagtttctgc caacaccatg  1140
tttgagatgg agtggcgtgg ccggcgggta gcactcaaag ccagcaacgg gcgctacgtg  1200
tgcatgaaga agaatgggca gctggcggct atcagcgatt ttgtcggcaa ggacgaagag  1260
ttcacccctca agctcatcaa ccggcccatc ctggtgctgc gcggcctgga cggcttcgtc  1320
tgccaccacc gcggctccaa ccagctggac accaaccgct ccgtctacga cgtcttccac  1380
ctgagcttca gcgacggcgc ctaccggatc cgaggccgcg acggagggtt ctggtacacg  1440
ggcagccacg gcagcgtgtg cagcgacggc gaacgcgccg aggacttcgt cttcgagttc  1500
cgtgagcgcg gccgcctggc catccgcgcc cggagcggca agtacctgcg cggcggcgcc  1560
tcgggcctgc tgcgggccga tgccgacgcc ccggccggga ccgcgctttg ggagtactga  1620
ggccgcgccc agaccagcct gtcgcgcatt aaaaccgtgt ctctcccgca aaaaaaaaa   1680
aaaaaaaaaa                                                         1690

<210> SEQ ID NO 13
<211> LENGTH: 1911
<212> TYPE: DNA
<213> ORGANISM: Homo sapiens

<400> SEQUENCE: 13 cccctttcccc actgtggtgt gataagaggc tgccctcaca gtcacaatgc tcccgggtca    60
cagaggtgct gggccccagg ccagcctctg cctgggaagt tctctctggg aacatctggt   120

```
gggtactaca ggccctattc caggccctat ggcctgtgga acctcaccac ggggggagg       180 gctgggccag acggagacat cacctgtggt gtcagcccca tggatgagac agagtggata       240
cacagacatc ccaaggctga ggacctaagg gttgggctca tcagctgggc aggaacctac       300
ctcacctttg aggcatgcaa gaatacagtc actgcaactg cgaagagttt gggcaggaga       360
cagacctggg agatcttggt gagcaatgag catgagacac aggccgtggt gcgactaaag       420
agcgtgcagg gcctctacct gctgtgtgag tgtgatggca ccgtgtgtta tggccgccca       480
aggaccagcc accatgggtg ctttctactg cgtttccacc ggaacagcaa gtggaccctc       540
cagtgcctaa tctctggtcg ttatttggag tccaatggca aggacgtgtt ttgcacttcc       600
cacgtcctct cagcttacca catgtggacc ccccgaccag ccctccatgt ccacgtgatc       660
ctctacagcc ccatccaccg ctgctatgcc cgggctgacc ccactatggg ccgcatctgg       720
gtggacgcag cagttccctg cctggaggag tgtggcttcc tgttgcattt ccgagatgga       780
tgctaccacc tggagacctc tacacaccac ttcttgtccc atgtagaccg gctgttctcc       840
caaccctcat cacagacagc ttttcacatg caagtgcggc ctggagggct tgtggcactg       900
tgtgatggag aaggaggcat gttatatcca cagggcacgc atctgctctt gggcatgggc       960
tgcaacccca tgaggggtga ggagtggttc atcctacagc actgcccaac ctgggtcagc      1020
ctcaggtcaa agactgggcg gttcatctca gtcatctacg atggtgaggt gcgtgctgct      1080
tctgagcgct taaaccgaat gtccttgttc cagtttgaat gtgacagtga gagcccact       1140 gtgcagcttc gttcagccaa tggctactac ctatcccaga ggcgccacag ggcagtaatg      1200
gctgatgggc accccctgga gtctgacacg ttcttccgaa tgcactggaa ctgtggcagg      1260
atcatcctgc agtcctgcag ggggcgcttc ctgggcattg cacccaacag cctgctgatg      1320
gccaatgtca tccttccagg cccaaatgag gaatttggga tttttatttgc caatcgctcc      1380 ttccttgtat tgcgaggtcg ttatggctat gtgggctcct catcgggcca tgacctcata      1440
cagtgcaacc aggatcagcc cgaccgcatt catctactac cctgccgacc gggtatctac      1500
cacttccagg cacaggggg atccttctgg tcaataacat cctttggcac ctttcgccct      1560
tggggcaagt ttgccctcaa cttctgtatc gagcttcagg ggagcaactt actcactgta      1620
ctggccccca atggcttcta catgcgagcc gaccaaagtg gcaccctgtt ggcagacagt      1680
gaagacatta ccagagagtg tatctgggaa ttttaggtca atgggatgtc acctaccaaa      1740
atccaaatcc tccaggaaaa actactacac taaatggacc aggaacctca gagtcaagat      1800
ccaagagaag aacatctgtt acaacttttc ctacccagtt tagcaaaaca cctgtttat       1860 gcaacaatac atcacaacag gccacccca aaaaaaaaaa aaaaaaaaa a                 1911

<210> SEQ ID NO 14
<211> LENGTH: 4082
<212> TYPE: DNA
<213> ORGANISM: Homo sapiens

<400> SEQUENCE: 14
gcgcgcgccg gcctgggcag gcgagcgggc gcgctcccgc ccctctcccc ctcccgcgc        60 gcccgagcgc gcctccgccc ttgcccgccc cctgacgctg cctcagctcc tcagtgcaca      120
gtgctgcctc gtctgagggg acaggaggat caccctcttc gtcgcttcgg ccagtgtgtc      180
gggctgggcc ctgacaagcc acctgaggag aggctcggag ccgggcccgg acccggcga       240 ttgccgcccg cttctctcta gtctcacgag gggtttcccg cctcgcaccc ccacctctgg      300
```

-continued

```
acttgccttt ccttctcttc tccgcgtgtg gagggagcca gcgcttaggc cggagcgagc    360 ctggggccg cccgccgtga agacatcgcg gggaccgatt caccatggag ggcgccggcg     420
gcgcgaacga caagaaaaag ataagttctg aacgtcgaaa agaaaagtct cgagatgcag    480
ccagatctcg gcgaagtaaa gaatctgaag ttttttatga gcttgctcat cagttgccac    540
ttccacataa tgtgagttcg catcttgata aggcctctgt gatgaggctt accatcagct    600
atttgcgtgt gaggaaactt ctggatgctg gtgatttgga tattgaagat gacatgaaag    660
cacagatgaa ttgcttttat ttgaaagcct tggatggttt tgttatggtt ctcacagatg    720
atggtgacat gatttacatt tctgataatg tgaacaaata catgggatta actcagtttg    780
aactaactgg acacagtgtg tttgatttta ctcatccatg tgaccatgag gaaatgagag    840
aaatgcttac acacagaaat ggccttgtga aaagggtaa agaacaaaac acacagcgaa     900
gcttttttct cagaatgaag tgtaccctaa ctagccgagg aagaactatg aacataaagt    960
ctgcaacatg gaaggtattg cactgcacag gccacattca cgtatatgat accaacagta    1020
accaacctca gtgtgggtat aagaaaccac ctatgacctg cttggtgctg atttgtgaac    1080
ccattcctca cccatcaaat attgaaattc ctttagatag caagactttc ctcagtcgac    1140
acagcctgga tatgaaattt tcttattgtg atgaaagaat taccgaattg atgggatatg    1200
agccagaaga acttttaggc cgctcaattt atgaatatta tcatgctttg gactctgatc    1260
atctgaccaa aactcatcat gatatgttta ctaaaggaca agtcaccaca ggacagtaca    1320
ggatgcttgc caaagaggt ggatatgtct gggttgaaac tcaagcaact gtcatatata     1380
acaccaagaa ttctcaacca cagtgcattg tatgtgtgaa ttacgttgtg agtggtatta    1440
ttcagcacga cttgattttc tcccttcaac aaacagaatg tgtccttaaa ccggttgaat    1500
cttcagatat gaaaatgact cagctattca ccaaagttga atcagaagat acaagtagcc    1560
tctttgacaa acttaagaag gaacctgatg ctttaacttt gctggcccca gccgctggag    1620
acacaatcat atctttagat tttggcagca acgacacaga aactgatgac cagcaacttg    1680
aggaagtacc attatataat gatgtaatgc tcccctcacc caacgaaaaa ttacagaata    1740
taaatttggc aatgtctcca ttacccaccg ctgaaacgcc aaagccactt cgaagtagtg    1800
ctgaccctgc actcaatcaa gaagttgcat taaaattaga accaaatcca gagtcactgg    1860
aactttcttt taccatgccc cagattcagg atcagacacc tagtccttcc gatgaaagca    1920
ctagacaaag ttcacctgag cctaatagtc ccagtgaata ttgttttat gtggatagtg     1980 atatggtcaa tgaattcaag ttggaattgg tagaaaaact ttttgctgaa gacacagaag    2040
caaagaaccc attttctact caggacacag atttagactt ggagatgtta gctccctata    2100
tcccaatgga tgatgacttc cagttacgtt ccttcgatca gttgtcacca ttagaaagca    2160
gttccgcaag ccctgaaagc gcaagtcctc aaagcacagt tacagtattc cagcagactc    2220
aaatacaaga acctactgct aatgccacca ctaccactgc caccactgat gaattaaaaa    2280
cagtgacaaa agaccgtatg gaagacatta aatattgat tgcatctcca tctcctaccc     2340
acatacataa agaaactact agtgccacat catcaccata tagagatact caaagtcgga    2400
cagcctcacc aaacagagca ggaaaaggag tcatagaaca gacagaaaaa tctcatccaa    2460
gaagccctaa cgtgttatct gtcgctttga gtcaaagaac tacagttcct gaggaagaac    2520
taaatccaaa gatactagct ttgcagaatg ctcagagaaa gcgaaaaatg gaacatgatg    2580
gttcactttt tcaagcagta ggaattggaa cattattaca gcagccagac gatcatgcag    2640
ctactacatc actttcttgg aaacgtgtaa aaggatgcaa atctagtgaa cagaatggaa    2700
```

```
tggagcaaaa gacaattatt ttaatacact ctgatttagc atgtagactg ctggggcaat    2760
caatggatga aagtggatta ccacagctga ccagttatga ttgtgaagtt aatgctccta    2820
tacaaggcag cagaaaccta ctgcagggtg aagaattact cagagctttg gatcaagtta   2880
actgagcttt ttcttaattt cattccttt tttggacact ggtggctcat tacctaaagc    2940
agtctattta tattttctac atctaatttt agaagcctgg ctacaatact gcacaaactt   3000
ggttagttca attttgatcc cctttctact taatttacat taatgctctt ttttagtatg   3060
ttctttaatg ctggatcaca gacagctcat tttctcagtt ttttggtatt taaaccattg   3120
cattgcagta gcatcatttt aaaaaatgca ccttttatt tatttatttt tggctaggga   3180
gtttatccct ttttcgaatt attttttaaga agatgccaat ataattttg taagaaggca    3240
gtaacctttc atcatgatca taggcagttg aaaaatttt acaccttttt tttcacattt    3300
tacataaata ataatgcttt gccagcagta cgtggtagcc acaattgcac aatatatttt   3360
cttaaaaaat accagcagtt actcatggaa tatattctgc gtttataaaa ctagttttta   3420
agaagaaatt tttttggcc tatgaaattg ttaaacctgg aacatgacat tgttaatcat    3480
ataaataatga ttcttaaatg ctgtatggtt tattatttaa atgggtaaag ccatttacat   3540
aatatagaaa gatatgcata tatctagaag gtatgtggca tttatttgga taaaattctc   3600
aattcagaga atcatctga tgtttctata gtcacttgc cagctcaaaa gaaaacaata    3660
ccctatgtag ttgtggaagt ttatgctaat attgtgtaac tgatattaaa cctaaatgtt   3720
ctgcctaccc tgttggtata aagatatttt gagcagactg taaacaagaa aaaaaaaatc   3780
atgcattctt agcaaaattg cctagtatgt taatttgctc aaaatacaat gtttgatttt   3840
atgcactttg tcgctattaa catccttttt ttcatgtaga tttcaataat tgagtaattt   3900
tagaagcatt attttaggaa tatatagttg tcacagtaaa tatcttgttt tttctatgta   3960
cattgtacaa attttttcatt cctttttgctc tttgtggttg gatctaacac taactgtatt   4020
gttttgttac atcaaataaa catcttctgt ggaccaggca aaaaaaaaaa aaaaaaaaa    4080
aa                                                                   4082

<210> SEQ ID NO 15
<211> LENGTH: 3366
<212> TYPE: DNA
<213> ORGANISM: Homo sapiens

<400> SEQUENCE: 15
gcatgcgtag gcgcgcggcc gcggcggcgg ctggggaggg ttcttccgga aggttcggga      60
ggcttctgga aaaagcgccg cgcgctgggc gggcccgtcg ctatataagg caggcgcggg     120
ggtggcgcgt cagttgcttc agcgtccggg tgtggctgtg ccgttggtcc tgtgcggtca     180
cttagccaag atgcctgagg aaacccagac ccaagaccaa ccgatggagg aggaggaggt     240
tgagacgttc gcctttcagg cagaaattgc ccagttgatg tcattgatca tcaatacttt     300
ctactcgaac aaagagatct ttctgagaga gctcatttca aattcatcag atgcattgga     360
caaaatccgg tatgaaagct tgacagatcc cagtaaatta gactctggga aagagctgca     420
tattaacctt ataccgaaca acaagatcg aactctcact attgtggata ctggaattgg     480
aatgaccaag gctgacttga tcaataacct tggtactatc gccaagtctg ggaccaaagc     540
gttcatggaa gctttgcagg ctggtgcaga tatctctatg attggccagt tcggtgttgg     600
ttttattct gcttatttgg ttgctgagaa agtaactgtg atcaccaaac ataacgatga     660
```

```
tgagcagtac gcttgggagt cctcagcagg gggatcattc acagtgagga cagacacagg    720
tgaacctatg ggtcgtggaa caaaagttat cctacacctg aaagaagacc aaactgagta    780
cttggaggaa cgaagaataa aggagattgt gaagaaacat tctcagttta ttggatatcc    840
cattactctt tttgtggaga aggaacgtga taaagaagta agcgatgatg aggctgaaga    900
aaaggaagac aaagaagaag aaaagaaaa agaagagaaa gagtcggaag acaaacctga    960
aattgaagat gttggttctg atgaggaaga agaaaagaag gatggtgaca agaagaagaa    1020
gaagaagatt aaggaaaagt acatcgatca agaagagctc aacaaaacaa agcccatctg    1080
gaccagaaat cccgacgata ttactaatga ggagtacgga gaattctata agagcttgac    1140
caatgactgg gaagatcact tggcagtgaa gcattttca gttgaaggac agttggaatt    1200
cagagccctt ctatttgtcc cacgacgtgc tccttttgat ctgtttgaaa cagaaagaa    1260 aaagaacaac atcaaattgt atgtacgcag agttttcatc atggataact gtgaggagct    1320
aatccctgaa tatctgaact tcattagagg ggtggtagac tcggaggatc tccctctaaa    1380
catatcccgt gagatgttgc aacaaagcaa aattttgaaa gttatcagga agaatttggt    1440
caaaaaatgc ttagaactct ttactgaact ggcggaagat aaagagaact acaagaaatt    1500
ctatgagcag ttctctaaaa acataaagct tggaatacac gaagactctc aaaatcggaa    1560
gaagctttca gagctgttaa ggtactacac atctgcctct ggtgatgaga tggtttctct    1620
caaggactac tgcaccagaa tgaaggagaa ccagaaacat atctattata tcacaggtga    1680
gaccaaggac caggtagcta actcagcctt tgtgaacgt cttcggaaac atggcttaga    1740
agtgatctat atgattgagc ccattgatga gtactgtgtc caacagctga aggaatttga    1800
ggggaagact ttagtgtcag tcaccaaaga aggcctggaa cttccagagg atgaagaaga    1860 gaaaagaag caggaagaga aaaaacaaa gtttgagaac ctctgcaaaa tcatgaaaga    1920
catattggag aaaaaagttg aaaaggtggt tgtgtcaaac cgattggtga catctccatg    1980
ctgtattgtc acaagcacat atggctggac agcaaacatg gagagaatca tgaaagctca    2040
agccctaaga gacaactcaa caatgggtta catggcagca agaaacacc tggagataaa    2100 ccctgaccat tccattattg agaccttaag gcaaaaggca gaggctgata agaacgacaa    2160
gtctgtgaag gatctggtca tcttgcttta tgaaactgcg ctcctgtctt ctggcttcag    2220
tctggaagat ccccagacac atgctaacag gatctacagg atgatcaaac ttggtctggg    2280
tattgatgaa gatgacccta ctgctgatga taccagtgct gctgtaactg aagaaatgcc    2340 acccccttgaa ggagatgacg acacatcacg catggaagaa gtagactaat ctctggctga    2400
gggatgactt acctgttcag tactctacaa ttcctctgat aatatatttt caaggatgtt    2460
tttctttatt tttgttaata ttaaaaagtc tgtatggcat gacaactact ttaaggggaa    2520
gataagattt ctgtctacta agtgatgctg tgataccta ggcactaaag cagagctagt    2580
aatgcttttt gagtttcatg ttggtttatt ttcacagatt ggggtaacgt gcactgtaag    2640
acgtatgtaa catgatgtta actttgtggt ctaaagtgtt tagctgtcaa gccggatgcc    2700
taagtagacc aaatcttgtt attgaagtgt tctgagctgt atcttgatgt ttagaaaagt    2760
attcgttaca tcttgtagga tctactttt gaacttttca ttccctgtag ttgacaattc    2820
tgcatgtact agtcctctag aaataggtta aactgaagca acttgatgga aggatctctc    2880
cacagggctt gttttccaaa gaaagtatt gtttggagga gcaaagttaa aagcctacct    2940
aagcatatcg taaagctgtt caaaaataac tcagacccag tcttgtggat ggaaatgtag    3000
tgctcgagtc acattctgct taaagttgta acaaatacag atgagttaaa agatatttgtg    3060
```

```
tgacagtgtc ttatttaggg ggaaagggga gtatctggat gacagttagt gccaaaatgt    3120
aaaacatgag gcgctagcag gagatggtta aacactagct gctccaaggg ttgacatggt    3180
cttcccagca tgtactcagc aggtgtgggg tggagcacac gtaggcacag aaaacaggaa    3240
tgcagacaac atgcatcccc tgcgtccatg agttacatgt gttctcttag tgtccacgtt    3300
gttttgatgt tattcatgga ataccttctg tgttaaatac agtcacttaa ttccttggcc    3360
ttaaaa                                                               3366

<210> SEQ ID NO 16
<211> LENGTH: 2703
<212> TYPE: DNA
<213> ORGANISM: Homo sapiens

<400> SEQUENCE: 16
tttttcggac catgacgtca aggtgggctg gtggcggcag gtgcggggtt gacaatcata      60
ctcctttaag gcggagggat ctacaggagg gcggctgtac tgtgcttcgc cttatatagg     120
gcgacttggg gcacgcagta gctctctcga gtcactccgg cgcagtgttg ggactgtctg     180
ggtatcggaa agcaagccta cgttgctcac tattacgtat aatcctttc ttttcaagat      240 gcctgaggaa gtgcaccatg agaggagga ggtggagact tttgcctttc aggcagaaat      300
tgcccaactc atgtccctca tcatcaatac cttctattcc aacaaggaga ttttccttcg     360
ggagttgatc tctaatgctt ctgatgcctt ggacaagatt cgctatgaga gcctgacaga     420
cccttcgaag ttggacagtg gtaaagagct gaaaattgac atcatcccca cccctcagga     480
acgtaccctg actttggtag acacaggcat tggcatgacc aaagctgatc tcataaataa     540
tttgggaacc attgccaagt ctggtactaa agcattcatg gaggctcttc aggctggtgc     600
agacatctcc atgattgggc agtttggtgt tggcttttat tctgcctact tggtggcaga     660
gaaagtggtt gtgatcacaa agcacaacga tgatgaacag tatgcttggg agtcttctgc     720
tggaggttcc ttcactgtgc gtgctgacca tggtgagccc attggcaggg gtaccaaagt     780
gatcctccat cttaaagaag atcagacaga gtacctagaa gagaggcggg tcaaagaagt     840
agtgaagaag cattctcagt tcataggcta tcccatcacc ctttatttgg agaaggaacg     900
agagaaggaa attagtgatg atgaggcaga ggaagagaaa ggtgagaaag aagaggaaga     960
taaagatgat gaagaaaaac ccaagatcga agatgtgggt tcagatgagg aggatgacag    1020
cggtaaggat aagaagaaga aaactaagaa gatcaaagag aaatacattg atcaggaaga    1080
actaaacaag accaagccta tttggaccag aaaccctgat gacatcaccc aagaggagta    1140
tggagaattc tacaagagcc tcactaatga ctgggaagac cacttggcag tcaagcactt    1200
ttctgtagaa ggtcagttgg aattcagggc attgctattt attcctcgtc gggctccctt    1260 tgacctttt gagaacaaga gaaaaagaa caacatcaaa ctctatgtcc gccgtgtgtt    1320
catcatggac agctgtgatg agttgatacc agagtatctc aatttatcc gtggtgtggt    1380 tgactctgag gatctgcccc tgaacatctc ccgagaaatg ctccagcaga gcaaaatctt    1440
gaaagtcatt cgcaaaaaca ttgttaagaa gtgccttgag ctcttctctg agctggcaga    1500
agacaaggag aattacaaga aattctatga ggcattctct aaaaatctca gcttggaat    1560 ccacgaagac tccactaacc gccgccgcct gtctgagctg ctgcgctatc atacctccca    1620
gtctggagat gagatgacat ctctgtcaga gtatgtttct cgcatgaagg agacacagaa    1680
gtccatctat tacatcactg gtgagagcaa agagcaggtg gccaactcag cttttgtgga    1740
```

```
gcgagtgcgg aaacgggggct tcgaggtggt atatatgacc gagcccattg acgagtactg    1800
tgtgcagcag ctcaaggaat ttgatgggaa gagcctggtc tcagttacca aggagggtct    1860
ggagctgcct gaggatgagg aggagaagaa gaagatggaa gagagcaagg caaagtttga    1920
gaacctctgc aagctcatga agaaatcttt agataagaag gttgagaagg tgacaatctc    1980
caatagactt gtgtcttcac cttgctgcat tgtgaccagc acctacggct ggacagccaa    2040
tatggagcgg atcatgaaag cccaggcact tcgggacaac tccaccatgg gctatatgat    2100
ggccaaaaag cacctggaga tcaaccctga ccacccatt gtggagacgc tgcggcagaa    2160
ggctgaggcc gacaagaatg ataaggcagt taaggacctg gtggtgctgc tgtttgaaac    2220
cgccctgcta tcttctggct tttcccttga ggatcccag acccactcca accgcatcta    2280
tcgcatgatc aagctaggtc taggtattga tgaagatgaa gtggcagcag aggaacccaa    2340
tgctgcagtt cctgatgaga tccccctct cgagggcgat gaggatgcgt ctcgcatgga    2400
agaagtcgat taggttagga gttcatagtt ggaaaacttg tgcccttgta tagtgtcccc    2460
atgggctccc actgcagcct cgagtgcccc tgtcccacct ggctccccct gctggtgtct    2520
agtgtttttt tccctctcct gtccttgtgt tgaaggcagt aaactaaggg tgtcaagccc    2580
cattccctct ctactcttga cagcaggatt ggatgttgtg tattgtggtt tattttattt    2640
tcttcatttt gttctgaaat taaagtatgc aaaataaaga atatgccgtt tttatacagt    2700
tct                                                                  2703
```

<210> SEQ ID NO 17
<211> LENGTH: 2879
<212> TYPE: DNA
<213> ORGANISM: Homo sapiens

<400> SEQUENCE: 17

```
gattggtggg ttcatgtttc ccgtcccccg cccgcgggaa gtgggggtga aaagcggccc      60
gacctgcttg cggtgtagtg ggcggaccgc gcggctggag gtgtgaggat ccgaacccag     120
gggtgggggg tggaggcggc tcctgcgatc gaaggggact tgagactcac cggccgcacg     180
ccatgagggc cctgtgggtg ctgggcctct gctgcgtcct gctgaccttc gggtcggtca     240
gagctgacga tgaagttgat gtggatggta cagtagaaga ggatctgggt aaaagtagag     300
aaggatcaag gacggatgat gaagtagtac agagagagga agaagctatt cagttggatg     360
gattaaatgc atcacaaata agagaactta gagagaagtc ggaaaagttt gccttccaag     420
ccgaagttaa cagaatgatg aaacttatca tcaattcatt gtataaaaat aaagagattt     480
tcctgagaga actgatttca aatgcttctg atgctttaga taagataagg ctaatatcac     540
tgactgatga aaatgctctt tctggaaatg aggaactaac agtcaaaatt aagtgtgata     600
aggagaagaa cctgctgcat gtcacagaca ccggtgtagg aatgaccaga gaagagttgg     660
ttaaaaacct tggtaccata gccaaatctg ggacaagcga gttttttaaac aaaatgactg     720 aagcacagga agatggccag tcaacttctg aattgattgg ccagtttggt gtcggtttct     780
attccgcctt ccttgtagca gataaggtta ttgtcacttc aaaacacaac aacgataccc     840
agcacatctg ggagtctgac tccaatgaat tttctgtaat tgctgaccca agaggaaaca     900
ctctaggacg gggaacgaca attccccttg tcttaaaaga agaagcatct gattaccttg     960
aattggatac aattaaaaat ctcgtcaaaa aatattcaca gttcataaac tttcctattt    1020
atgtatggag cagcaagact gaaactgttg aggagcccat ggaggaagaa gaagcagcca    1080
aagaagagaa agaagaatct gatgatgaag ctgcagtaga ggaagaagaa gaagaaaaga    1140
```

```
aaccaaagac taaaaaagtt gaaaaaactg tctgggactg ggaacttatg aatgatatca    1200
aaccaatatg gcagagacca tcaaaagaag tagaagaaga tgaatacaaa gctttctaca    1260
aatcattttc aaaggaaagt gatgaccccca tggcttatat tcactttact gctgaagggg   1320
aagttacctt caaatcaatt ttatttgtac ccacatctgc tccacgtggt ctgtttgacg    1380
aatatggatc taaaaagagc gattacatta agctctatgt gcgccgtgta ttcatcacag    1440
acgacttcca tgatatgatg cctaaatacc tcaattttgt caagggtgtg gtggactcag    1500
atgatctccc cttgaatgtt tcccgcgaga ctcttcagca acataaactg cttaaggtga    1560
ttaggaagaa gcttgttcgt aaaacgctgg acatgatcaa aagagattgct gatgataaat    1620 acaatgatac tttttggaaa gaatttggta ccaacatcaa gcttggtgtg attgaagacc    1680
actcgaatcg aacacgtctt gctaaacttc ttaggttcca gtcttctcat catccaactg    1740
acattactag cctagaccag tatgtggaaa gaatgaagga aaaacaagac aaaatctact    1800
tcatggctgg gtccagcaga aaagaggctg aatcttctcc atttgttgag cgacttctga    1860
aaaagggcta tgaagttatt tacctcacag aacctgtgga tgaatactgt attcaggccc    1920
ttcccgaatt tgatgggaag aggttccaga atgttgccaa ggaaggagtg aagttcgatg    1980
aaagtgagaa aactaaggag agtcgtgaag cagttgagaa agaatttgag cctctgctga    2040
attggatgaa agataaagcc cttaaggaca agattgaaaa ggctgtggtg tctcagcgcc    2100
tgacagaatc tccgtgtgct tggtggcca gccagtacgg atggtctggc aacatggaga    2160
gaatcatgaa agcacaagcg taccaaacgg gcaaggacat ctctacaaat tactatgcga    2220
gtcagaagaa aacatttgaa attaatccca gacacccgct gatcagagac atgcttcgac    2280
gaattaagga agatgaagat gataaaacag ttttggatct tgctgtggtt ttgtttgaaa    2340
cagcaacgct tcggtcaggg tatctttttac cagacactaa agcatatgga gatagaatag    2400
aaagaatgct tcgcctcagt ttgaacattg accctgatgc aaaggtggaa gaagagcccg    2460
aagaagaacc tgaagagaca gcagaagaca caacagaaga cacagagcaa gacgaagatg    2520
aagaaatgga tgtgggaaca gatgaagaag aagaaacagc aaaggaatct acagctgaaa    2580
aagatgaatt gtaaattata ctctcaccat ttggatcctg tgtggagagg gaatgtgaaa    2640
tttacatcat ttcttttttgg gagagacttg ttttggatgc cccctaatcc ccttctcccc    2700
tgcactgtaa aatgtgggat tatgggtcac aggaaaaagt gggtttttta gttgaatttt    2760
ttttaacatt cctcatgaat gtaaatttgt actatttaac tgactattct tgatgtaaaa    2820
tcttgtcatg tgtataaaaa taaaaagat cccaaatact caaaaaaaaa aaaaaaaaa    2879
```

<210> SEQ ID NO 18
<211> LENGTH: 2445
<212> TYPE: DNA
<213> ORGANISM: Homo sapiens

<400> SEQUENCE: 18

```
ataaaagccc aggggcaagc ggtccggata acggctagcc tgaggagctg ctgcgacagt      60
ccactacctt tttcgagagt gactcccgtt gtcccaaggc ttcccagagc gaacctgtgc     120
ggctgcaggc accggcgcgt cgagtttccg gcgtccggaa ggaccgagct cttctcgcgg     180
atccagtgtt ccgtttccag cccccaatct cagagcggag ccgacagaga gcagggaacc     240
ggcatggcca aagccgcggc gatcggcatc gacctgggca ccaccactc ctgcgtgggg     300 gtgttccaac acggcaaggt ggagatcatc gccaacgacc agggcaaccg caccaccccc     360
```

```
agctacgtgg ccttcacgga caccgagcgg ctcatcgggg atgcggccaa gaaccaggtg    420
gcgctgaacc cgcagaacac cgtgtttgac gcgaagcggc tgattggccg caagttcggc    480
gacccggtgg tgcagtcgga catgaagcac tggcctttcc aggtgatcaa cgacggagac    540
aagcccaagg tgcaggtgag ctacaagggg gagaccaagg cattctaccc cgaggagatc    600
tcgtccatgg tgctgaccaa gatgaaggag atcgccgagg cgtacctggg ctacccggtg    660
accaacgcgg tgatcaccgt gccggcctac ttcaacgact cgcagcgcca ggccaccaag    720
gatgcgggtg tgatcgcggg gctcaacgtg ctgcggatca tcaacgagcc cacggccgcc    780
gccatcgcct acggcctgga cagaacgggc aaggggagc gcaacgtgct catctttgac    840
ctgggcgggg gcaccttcga cgtgtccatc ctgacgatcg acgacggcat cttcgaggtg    900
aaggccacgg ccggggacac ccacctgggt ggggaggact tgacaacag gctggtgaac    960
cacttcgtgg aggagttcaa gagaaaacac aagaaggaca tcagccagaa caagcgagcc   1020
gtgaggcggc tgcgcaccgc ctgcgagagg gccaagagga ccctgtcgtc cagcacccag   1080
gccagcctgg agatcgactc cctgtttgag ggcatcgact tctacacgtc catcaccagg   1140
gcgaggttcg aggagctgtg ctccgacctg ttccgaagca ccctggagcc cgtggagaag   1200
gctctgcgcg acgccaagct ggacaaggcc cagattcacg acctggtcct ggtcgggggc   1260
tccacccgca tccccaaggt gcagaagctg ctgcaggact tcttcaacgg gcgcgacctg   1320
aacaagagca tcaaccccga cgaggctgtg gcctacgggg cggcggtgca ggcggccatc   1380
ctgatggggg acaagtccga gaacgtgcag gacctgctgc tgctggacgt ggctcccctg   1440
tcgctggggc tggagacggc cggaggcgtg atgactgccc tgatcaagcg caactccacc   1500
atccccacca gcagacgca gatcttcacc acctactccg acaaccaacc cggggtgctg   1560
atccaggtgt acgagggcga gagggccatg acgaaagaca caatctgtt ggggcgcttc   1620
gagctgagcg gcatccctcc ggcccccagg ggcgtgcccc agatcgaggt gaccttcgac   1680
atcgatgcca acggcatcct gaacgtcacg gccacggaca gagcaccgg caaggccaac   1740
aagatcacca tcaccaacga caagggccgc ctgagcaagg aggagatcga gcgcatggtg   1800
caggaggcgg agaagtacaa agcggaggac gaggtgcagc gcgagaggt gtcagccaag   1860
aacgccctgg agtcctacgc cttcaacatg aagagcgccg tggaggatga ggggctcaag   1920
ggcaagatca gcgaggcgga caagaagaag gtgctggaca gtgtcaaga ggtcatctcg   1980
tggctggacg ccaacacctt ggccgagaag gacgagtttg agcacaagag gaaggagctg   2040
gagcaggtgt gtaaccccat catcagcgga ctgtaccagg gtgccggtgg tcccgggcct   2100
gggggcttcg gggctcaggg tcccaaggga gggtctgggt caggccccac cattgaggag   2160
gtagattagg ggccttttcca agattgctgt ttttgttttg gagcttcaag actttgcatt   2220
tcctagtatt tctgtttgtc agttctcaat ttcctgtgtt tgcaatgttg aaatttttg   2280
gtgaagtact gaacttgctt tttttccggt ttctacatgc agagatgaat ttatactgcc   2340
atcttacgac tatttcttct ttttaataca cttaactcag gccatttttt aagttggtta   2400
cttcaaagta aataaacttt aaaattcaaa aaaaaaaaa aaaaa                      2445
```

<210> SEQ ID NO 19
<211> LENGTH: 2551
<212> TYPE: DNA
<213> ORGANISM: Homo sapiens

<400> SEQUENCE: 19

```
ggaaaacggc cagcctgagg agctgctgcg agggtccgct tcgtctttcg agagtgactc      60
```

```
ccgcggtccc aaggctttcc agagcgaacc tgtgcggctg caggcaccgg cgtgttgagt    120
ttccggcgtt ccgaaggact gagctcttgt cgcggatccc gtccgccgtt ccagccccc     180 agtctcagag cggagcccac agagcagggc accggcatgg ccaaagccgc ggcgatcggc    240
atcgacctgg gcaccaccta ctcctgcgtg ggggtgttcc aacacggcaa ggtggagatc    300
atcgccaacg accagggcaa ccgcaccacc cccagctacg tggccttcac ggacaccgag    360
cggctcatcg gggatgcggc caagaaccag gtggcgctga acccgcagaa caccgtgttt    420
gacgcgaagc ggctgatcgg ccgcaagttc ggcgacccgg tggtgcagtc ggacatgaag    480
cactggcctt tccaggtgat caacgacgga gacaagccca aggtgcaggt gagctacaag    540
ggggagacca aggcattcta ccccgaggag atctcgtcca tggtgctgac caagatgaag    600
gagatcgccg aggcgtacct gggctacccg gtgaccaacg cggtgatcac cgtgccggcc    660
tacttcaacg actcgcagcg ccaggccacc aaggatgcgg gtgtgatcgc ggggctcaac    720
gtgctgcgga tcatcaacga gcccacggcc gccgccatcg cctacggcct ggacagaacg    780
ggcaaggggg agcgcaacgt gctcatcttt gacctgggcg ggggcacctt cgacgtgtcc    840
atcctgacga tcgacgacgg catcttcgag gtgaaggcca cggccgggga cacccacctg    900
ggtggggagg actttgacaa caggctggtg aaccacttcg tggaggagtt caagagaaaa    960
cacaagaagg acatcagcca gaacaagcga gccgtgaggc ggctgcgcac cgcctgcgag    1020
agggccaaga ggaccctgtc gtccagcacc caggccagcc tggagatcga ctccctgttt    1080
gagggcatcg acttctacac gtccatcacc agggcgaggt tcgaggagct gtgctccgac    1140
ctgttccgaa gcaccctgga gcccgtggag aaggctctgc gcgacgccaa gctggacaag    1200
gcccagattc acgacctggt cctggtcggg ggctccaccc gcatccccaa ggtgcagaag    1260
ctgctgcagg acttcttcaa cgggcgcgac ctgaacaaga gcatcaaccc cgacgaggct    1320
gtggcctacg gggcggcggt gcaggcggcc atcctgatgg gggacaagtc cgagaacgtg    1380
caggacctgc tgctgctgga cgtggctccc ctgtcgctgg ggctggagac ggccggaggc    1440
gtgatgactg ccctgatcaa cgcgcaactc accatcccca ccaagcagac gcagatcttc    1500
accacctact ccgacaacca acccggggtg ctgatccagg tgtacgaggg cgagagggcc    1560
atgacgaaag acaacaatct gttggggcgc ttcgagctga gcggcatccc tccggccccc    1620
aggggcgtgc cccagatcga ggtgaccttc gacatcgatg ccaacggcat cctgaacgtc    1680
acggccacgg acaagagcac cggcaaggcc aacaagatca ccatcaccaa cgacaagggc    1740
cgcctgagca aggaggagat cgagcgcatg gtgcaggagg cggagaagta caaagcggag    1800
gacgaggtgc agcgcgagag ggtgtcagcc aagaacgccc tggagtccta cgccttcaac    1860
atgaagagcg ccgtggagga tgaggggctc aagggcaaga tcagcgaggc ggacaagaag    1920
aaggttctgg acaagtgtca agaggtcatc tcgtggctgg acgccaacac cttggccgag    1980
aaggacgagt ttgagcacaa gaggaaggag ctggagcagg tgtgtaaccc catcatcagc    2040
ggactgtacc agggtgccgg tggtcccggg cctggcggct cggggctcag ggtcccaag     2100 ggagggtctg ggtcaggccc taccattgag gaggtggatt aggggccttt gttctttagt    2160
atgtttgtct ttgaggtgga ctgttgggac tcaaggactt tgctgctgtt ttcctatgtc    2220
atttctgctt cagctctttg ctgcttcact tctttgtaaa gttgtaacct gatggtaatt    2280
agctggcttc attattttttg tagtacaacc gatatgttca ttagaattct ttgcatttaa    2340
tgttgatact gtaagggtgt ttcgttccct ttaaatgaat caacactgcc accttctgta    2400
```

-continued

| | |
|---|---|
| cgagtttgtt tgttttttt tttttttttt tttttgctt ggcgaaaaca ctacaaaggc | 2460 |
| tgggaatgta tgttttata atttgtttat ttaaatatga aaataaaat gttaaacttt | 2520 |
| aaaaaaaaaa aaaaaaaaa aaaaaaaaaa a | 2551 |

<210> SEQ ID NO 20
<211> LENGTH: 3249
<212> TYPE: DNA
<213> ORGANISM: Homo sapiens

<400> SEQUENCE: 20

| | |
|---|---|
| caagcttagc ctggccggga aacgggaggc gtggaggccg ggagcagccc ccggggtcat | 60 |
| cgccctgcca ccgccgcccg attgctttag cttggaaatt ccggagctga agcggccagc | 120 |
| gagggaggat gaccctctcg gcccgggcac cctgtcagtc cggaaataac tgcagcattt | 180 |
| gttccggagg ggaaggcgcg aggtttccgg gaaagcagca ccgccccttg gcccccaggt | 240 |
| ggctagcgct ataaaggatc acgcgcccca gtcgacgctg agctcctctg ctactcagag | 300 |
| ttgcaacctc agcctcgcta tggctcccag cagccccgg cccgcgctgc ccgcactcct | 360 |
| ggtcctgctc ggggctctgt cccaggacc tggcaatgcc agacatctg tgtcccctc | 420 |
| aaaagtcatc ctgccccggg gaggctccgt gctggtgaca tgcagcacct cctgtgacca | 480 |
| gcccaagttg ttgggcatag agaccccgtt gcctaaaaag gagttgctcc tgcctgggaa | 540 |
| caaccggaag gtgtatgaac tgagcaatgt gcaagaagat agccaaccaa tgtgctattc | 600 |
| aaaactgccct gatgggcagt caacagctaa aaccttcctc accgtgtact ggactccaga | 660 |
| acgggtggaa ctggcacccc tcccctcttg gcagccagtg gcaagaacc ttaccctacg | 720 |
| ctgccaggtg gagggtgggg caccccgggc caacctcacc gtggtgctgc tccgtgggga | 780 |
| gaaggagctg aaacgggagc cagctgtggg ggagcccgct gaggtcacga ccacggtgct | 840 |
| ggtgaggaga gatcaccatg gagccaattt ctcgtgccgc actgaactgg acctgcggcc | 900 |
| ccaagggctg gagctgtttg agaacacctc ggccccctac cagctccaga cctttgtcct | 960 |
| gccagcgact cccccacaac ttgtcagccc ccgggtccta gaggtggaca cgcaggggac | 1020 |
| cgtggtctgt tccctggacg ggctgttccc agtctcggag gcccaggtcc acctggcact | 1080 |
| gggggaccag aggttgaacc ccacagtcac ctatggcaac gactccttct cggccaaggc | 1140 |
| ctcagtcagt gtgaccgcag aggacgaggg cacccagcgg ctgacgtgtg cagtaatact | 1200 |
| ggggaaccag agccaggaga cactgcagac agtgaccatc tacagctttc ggcgcccaa | 1260 |
| cgtgattctg acgaagccag aggtctcaga agggaccgag gtgacagtga agtgtgaggc | 1320 |
| ccaccctaga gccaaggtga cgctgaatgg ggttccagcc cagccactgg gcccgagggc | 1380 |
| ccagctcctg ctgaaggcca ccccagagga caacgggcgc agcttctcct gctctgcaac | 1440 |
| cctggaggtg gccggccagc ttatacacaa gaaccagacc cgggagcttc gtgtcctgta | 1500 |
| tggcccccga ctggacgaga gggattgtcc gggaaactgg acgtggccag aaaattccca | 1560 |
| gcagactcca atgtgccagg cttggggaa cccattgccc gagctcaagt gtctaaagga | 1620 |
| tggcactttc ccactgccca tcggggaatc agtgactgtc actcgagatc ttgagggcac | 1680 |
| ctacctctgt cggccagga gcactcaagg ggaggtcacc cgcaaggtga ccgtgaatgt | 1740 |
| gctctccccc cggtatgaga ttgtcatcat cactgtggta gcagccgcag tcataatggg | 1800 |
| cactgcaggc ctcagcacgt acctctataa ccgccagcgg aagatcaaga aatacagact | 1860 |
| acaacaggca caaaaaggga ccccccatgaa accgaacaca caagccacgc ctccctgaac | 1920 |
| ctatcccggg acagggcctc ttcctcggcc ttcccatatt ggtggcagtg gtgccacact | 1980 |

| | | |
|---|---|---|
| gaacagagtg gaagacatat gccatgcagc tacacctacc ggccctggga cgccggagga | 2040 | |
| cagggcattg tcctcagtca gatacaacag catttggggc catggtacct gcacacctaa | 2100 | |
| aacactaggc cacgcatctg atctgtagtc acatgactaa gccaagagga aggagcaaga | 2160 | |
| ctcaagacat gattgatgga tgttaaagtc tagcctgatg agaggggaag tggtggggga | 2220 | |
| gacatagccc caccatgagg acatacaact gggaaatact gaaacttgct gcctattggg | 2280 | |
| tatgctgagg ccccacagac ttacagaaga agtggccctc catagacatg tgtagcatca | 2340 | |
| aaacacaaag gcccacactt cctgacggat gccagcttgg gcactgctgt ctactgaccc | 2400 | |
| caacccttga tgatatgtat ttattcattt gttattttac cagctattta ttgagtgtct | 2460 | |
| tttatgtagg ctaaatgaac ataggtctct ggcctcacgg agctcccagt cctaatcaca | 2520 | |
| ttcaaggtca ccaggtacag ttgtacaggt tgtacactgc aggagagtgc ctggcaaaaa | 2580 | |
| gatcaaatgg ggctgggact tctcattggc caacctgcct ttccccagaa ggagtgattt | 2640 | |
| ttctatcggc acaaaagcac tatatggact ggtaatggtt acaggttcag agattaccca | 2700 | |
| gtgaggcctt attcctccct tcccccaaa actgacacct tgttagccca cctccccacc | 2760 | |
| cacatacatt tctgccagtg ttcacaatga cactcagcgg tcatgtctgg acatgagtgc | 2820 | |
| ccagggaata tgcccaagct atgccttgtc ctcttgtcct gtttgcattt cactgggagc | 2880 | |
| ttgcactatg cagctccagt ttcctgcagt gatcagggtc ctgcaagcag tggggaaggg | 2940 | |
| ggccaaggta ttggaggact ccctcccagc tttggaagcc tcatccgcgt gtgtgtgtgt | 3000 | |
| gtgtatgtgt agacaagctc tcgctctgtc acccaggctg gagtgcagtg gtgcaatcat | 3060 | |
| ggttcactgc agtcttgacc ttttgggctc aagtgatcct cccacctcag cctcctgagt | 3120 | |
| agctgggacc ataggctcac aacaccacac ctggcaaatt tgattttttt ttttttttcca | 3180 | |
| gagacggggt ctcgcaacat tgcccagact tcctttgtgt tagttaataa agctttctca | 3240 | |
| actgccaaa | 3249 | |

<210> SEQ ID NO 21
<211> LENGTH: 1240
<212> TYPE: DNA
<213> ORGANISM: Homo sapiens

<400> SEQUENCE: 21

| | | |
|---|---|---|
| cacattgttc tgatcatctg aagatcagct attagaagag aaagatcagt taagtccttt | 60 | |
| ggacctgatc agcttgatac aagaactact gatttcaact tctttggctt aattctctcg | 120 | |
| gaaacgatga aatatacaag ttatatcttg gcttttcagc tctgcatcgt tttgggttct | 180 | |
| cttggctgtt actgccagga cccatatgta aagaagcag aaaaccttaa gaaatatttt | 240 | |
| aatgcaggtc attcagatgt agcggataat ggaactcttt tcttaggcat tttgaagaat | 300 | |
| tggaaagagg agagtgacag aaaaataatg cagagccaaa ttgtctcctt ttacttcaaa | 360 | |
| cttttttaaaa actttaaaga tgaccagagc atccaaaaga gtgtggagac catcaaggaa | 420 | |
| gacatgaatg tcaagttttt caatagcaac aaaaagaaac gagatgactt cgaaaagctg | 480 | |
| actaattatt cggtaactga cttgaatgtc caacgcaaag caatacatga actcatccaa | 540 | |
| gtgatggctg aactgtcgcc agcagctaaa acagggaagc gaaaaggag tcagatgctg | 600 | |
| tttcgaggtc gaagagcatc ccagtaatgg ttgtcctgcc tgcaatattt gaattttaaa | 660 | |
| tctaaatcta tttattaata tttaacatta tttatgggg gaatatattt ttagactcat | 720 | |
| caatcaaata agtatttata atagcaactt ttgtgtaatg aaaatgaata tctattaata | 780 | |

| | |
|---|---|
| tatgtattat ttataattcc tatatcctgt gactgtctca cttaatcctt tgttttctga | 840 |
| ctaattaggc aaggctatgt gattacaagg ctttatctca ggggccaact aggcagccaa | 900 |
| cctaagcaag atcccatggg ttgtgtgttt atttcacttg atgatacaat gaacacttat | 960 |
| aagtgaagtg atactatcca gttactgccg gtttgaaaat atgcctgcaa tctgagccag | 1020 |
| tgctttaatg gcatgtcaga cagaacttga atgtgtcagg tgaccctgat gaaaacatag | 1080 |
| catctcagga gatttcatgc ctggtgcttc caaatattgt tgacaactgt gactgtaccc | 1140 |
| aaatggaaag taactcattt gttaaaatta tcaatatcta atatatatga ataaagtgta | 1200 |
| agttcacaac aaaaaaaaaa aaaaaaaaaa aaaaaaaaaa | 1240 |

<210> SEQ ID NO 22
<211> LENGTH: 1629
<212> TYPE: DNA
<213> ORGANISM: Homo sapiens

<400> SEQUENCE: 22

| | |
|---|---|
| acacatcagg ggcttgctct tgcaaaacca aaccacaaga cagacttgca aaagaaggca | 60 |
| tgcacagctc agcactgctc tgttgcctgg tcctcctgac tggggtgagg gccagcccag | 120 |
| gccagggcac ccagtctgag aacagctgca cccacttccc aggcaacctg cctaacatgc | 180 |
| ttcgagatct ccgagatgcc ttcagcagag tgaagacttt ctttcaaatg aaggatcagc | 240 |
| tggacaactt gttgttaaag gagtccttgc tggaggactt aagggttac ctgggttgcc | 300 |
| aagccttgtc tgagatgatc cagttttacc tggaggaggt gatgccccaa gctgagaacc | 360 |
| aagacccaga catcaaggcg catgtgaact ccctggggga gaacctgaag accctcaggc | 420 |
| tgaggctacg gcgctgtcat cgatttcttc cctgtgaaaa caagagcaag gccgtggagc | 480 |
| aggtgaagaa tgcctttaat aagctccaag agaaaggcat ctacaaagcc atgagtgagt | 540 |
| ttgacatctt catcaactac atagaagcct acatgacaat gaagatacga aactgagaca | 600 |
| tcagggtggc gactctatag actctaggac ataaattaga ggtctccaaa atcggatctg | 660 |
| gggctctggg atagctgacc cagccccttg agaaacctta ttgtacctct cttatagaat | 720 |
| atttattacc tctgatacct caaccccccat ttctatttat ttactgagct tctctgtgaa | 780 |
| cgatttagaa agaagcccaa tattataatt ttttcaata tttattattt tcacctgttt | 840 |
| ttaagctgtt tccatagggt gacacactat ggtatttgag tgttttaaga taaattataa | 900 |
| gttacataag ggaggaaaaa aaatgttctt tggggagcca acagaagctt ccattccaag | 960 |
| cctgaccacg ctttctagct gttgagctgt tttccctgac ctccctctaa tttatcttgt | 1020 |
| ctctgggctt ggggcttcct aactgctaca aatactctta ggaagagaaa ccagggagcc | 1080 |
| cctttgatga ttaattcacc ttccagtgtc tcggagggat tccctaacc tcattcccca | 1140 |
| accacttcat tcttgaaagc tgtggccagc ttgttattta taacaaccta aatttggttc | 1200 |
| taggccgggc gcggtggctc acgcctgtaa tcccagcact tgggaggct gaggcgggtg | 1260 |
| gatcacttga ggtcaggagt tcctaaccag cctggtcaac atggtgaaac cccgtctcta | 1320 |
| ctaaaaatac aaaaattagc cgggcatggt ggcgcgcacc tgtaatccca gctacttggg | 1380 |
| aggctgaggc aagagaattg cttgaaccca ggagatggaa gttgcagtga gctgatatca | 1440 |
| tgcccctgta ctccagcctg ggtgacagag caagactctg tctcaaaaaa taaaaataaa | 1500 |
| aataaatttg gttctaatag aactcagttt taactagaat ttattcaatt cctctgggaa | 1560 |
| tgttacattg tttgtctgtc ttcatagcag attttaattt tgaataaata aatgtatctt | 1620 |
| attcacatc | 1629 |

<210> SEQ ID NO 23
<211> LENGTH: 1832
<212> TYPE: DNA
<213> ORGANISM: Homo sapiens

<400> SEQUENCE: 23

| | | | | | |
|---|---|---|---|---|---|
| gagcggccag | gccagcctcg | gagccagcag | ggagctggga | gctggggaa | acgacgccag | 60 |
| gaaagctatc | gcgccagaga | gggcgacggg | ggctcgggaa | gcctgacagg | gcttttgcgc | 120 |
| acagctgccg | gctggctgct | acccgcccgc | gccagccccc | gagaacgcgc | gaccaggcac | 180 |
| ccagtccggt | caccgcagcg | gagagctcgc | cgctcgctgc | agcgaggccc | ggagcggccc | 240 |
| cgcagggacc | ctccccagac | cgcctgggcc | gcccggatgt | gcactaaaat | ggaacagccc | 300 |
| ttctaccacg | acgactcata | cacagctacg | ggatacggcc | gggcccctgg | tggcctctct | 360 |
| ctacacgact | acaaactcct | gaaaccgagc | ctggcggtca | acctggccga | cccctaccgg | 420 |
| agtctcaaag | cgcctggggc | tcgcggaccc | ggcccagagg | gcggcggtgg | cggcagctac | 480 |
| tttctggtc | agggctcgga | caccggcgcg | tctctcaagc | tcgcctcttc | ggagctggaa | 540 |
| cgcctgattg | tccccaacag | caacggcgtg | atcacgacga | cgcctacacc | ccgggacag | 600 |
| tactttacc | cccgcggggg | tggcagcggt | ggaggtgcag | ggggcgcagg | gggcggcgtc | 660 |
| accgaggagc | aggagggctt | cgccgacggc | tttgtcaaag | ccctggacga | tctgcacaag | 720 |
| atgaaccacg | tgacaccccc | caacgtgtcc | ctgggcgcta | ccggggggcc | cccggctggg | 780 |
| cccgggggcg | tctacgccgg | cccggagcca | cctcccgttt | acaccaacct | cagcagctac | 840 |
| tccccagcct | ctgcgtcctc | gggaggcgcc | ggggctgccg | tcgggaccgg | gagctcgtac | 900 |
| ccgacgacca | ccatcagcta | cctcccacac | gcgccgccct | tcgccggtgg | ccacccggcg | 960 |
| cagctgggct | tgggccgcgg | cgcctccacc | ttcaaggagg | aaccgcagac | cgtgccggag | 1020 |
| gcgcgcagcc | gggacgccac | gccgccggtg | tcccccatca | acatggaaga | ccaagagcgc | 1080 |
| atcaaagtgg | agcgcaagcg | gctgcggaac | cggctggcgg | ccaccaagtg | ccggaagcgg | 1140 |
| aagctggagc | gcatcgcgcg | cctggaggac | aaggtgaaga | cgctcaaggc | cgagaacgcg | 1200 |
| gggctgtcga | gtaccgccgg | cctcctccgg | gagcaggtgg | cccagctcaa | acagaaggtc | 1260 |
| atgacccacg | tcagcaacgg | ctgtcagctg | ctgcttgggg | tcaagggaca | cgccttctga | 1320 |
| acgtcccctg | ccccttttacg | gacaccccct | cgcttgacg | gctgggcaca | cgcctcccac | 1380 |
| tggggtccag | ggagcaggcg | gtgggcaccc | accctgggac | ctaggggcgc | cgcaaaccac | 1440 |
| actggactcc | ggccctccta | ccctgcgccc | agtccttcca | cctcgacgtt | tacaagcccc | 1500 |
| cccttccact | ttttttgta | tgtttttttt | ctgctggaaa | cagactcgat | tcatattgaa | 1560 |
| tataatatat | ttgtgtattt | aacagggagg | ggaagagggg | gcgatcgcgg | cggagctggc | 1620 |
| cccgccgcct | ggtactcaag | cccgcgggga | cattgggaag | gggacccccg | cccctgccc | 1680 |
| tcccctctct | gcaccgtact | gtggaaaaga | aacacgcact | tagtctctaa | agagtttatt | 1740 |
| ttaagacgtg | tttgtgtttg | tgtgtgtttg | ttctttttat | tgaatctatt | taagtaaaaa | 1800 |
| aaaaattggt | tctttaaaaa | aaaaaaaaaa | aa | | | 1832 |

<210> SEQ ID NO 24
<211> LENGTH: 4107
<212> TYPE: DNA
<213> ORGANISM: Homo sapiens

<400> SEQUENCE: 24

```
gcgcaacccct ccggaagctg ccgccccttt cccctttat gggaatactt tttttaaaaa    60
aaaagagttc gctggcgcca ccccgtagga ctggccgccc taaaaccgtg ataaaggagc   120
tgctcgccac ttctcacttc cgcttccttc cagtaaggag tcggggtctt ccccagtttt   180
ctcagccagg cggcggcggc gactggcaat gtttggcctc aaaagaaacg cggtaatcgg   240
actcaacctc tactgtgggg gggccggctt ggggccggc agcggcggcg ccacccgccc   300
gggagggcga cttttggcta cggagaagga ggcctcggcc cggcgagaga taggggagg   360 ggaggccggc gcggtgattg gcggaagcgc cggcgcaagc ccccgtcca ccctcacgcc   420 agactcccgg agggtcgcgc ggccgccgcc cattggcgcc gaggtccccg acgtcaccgc   480 gaccccccgcg aggctgcttt tcttcgcgcc caccgccgc gcggcgccgc ttgaggagat   540
ggaagccccg gccgctgacg ccatcatgtc gcccgaagag gagctggacg ggtacgagcc   600
ggagcctctc gggaagcggc cggctgtcct gccgctgctg gagttggtcg gggaatctgg   660
taataacacc agtacggacg ggtcactacc ctcgacgccg ccgccagcag aggaggagga   720
ggacgagttg taccggcagt cgctggagat tatctctcgg taccttcggg agcaggccac   780
cggcgccaag gacacaaagc caatgggcag gtctggggcc accagcagga aggcgctgga   840
gaccttacga cgggttgggg atggcgtgca gcgcaaccac gagacggcct tccaaggcat   900
gcttcggaaa ctggacatca aaaacgaaga cgatgtgaaa tcgttgtctc gagtgatgat   960
ccatgttttc agcgacggcg taacaaactg gggcaggatt gtgactctca tttcttttgg  1020
tgcctttgtg gctaaacact tgaagaccat aaaccaagaa agctgcatcg aaccattagc  1080
agaaagtatc acagacgttc tcgtaaggac aaaacgggac tggctagtta acaaagagg  1140 ctgggatggg tttgtggagt tcttccatgt agaggaccta aaggtggca tcaggaatgt  1200 gctgctggct tttgcaggtg ttgctggagt aggagctggt ttggcatatc taataagata  1260
gccttactgt aagtgcaata gttgacttt aaccaaccac caccaccacc aaaaccagtt  1320
tatgcagttg gactccaagc tgtaacttcc tagagttgca ccctagcaac ctagccagaa  1380
aagcaagtgg caagaggatt atggctaaca agaataaata catgggaaga gtgctcccca  1440
ttgattgaag agtcactgtc tgaaagaagc aaagttcagt tcagcaaca aacaaacttt  1500 gtttgggaag ctatggagga ggacttttag atttagtgaa gatggtaggg tggaaagact  1560
taatttcctt gttgagaaca ggaaagtggc cagtagccag gcaagtcata gaattgatta  1620
cccgccgaat tcattaattt actgtagtgt aagagaagc actaagaatg ccagtgacct  1680
gtgtaaaagt tacaagtaat agaactatga ctgtaagcct cagtactgta caagggaagc  1740
ttttcctctc tctaattagc ttccccagta tacttcttag aaagtccaag tgttcaggac  1800
ttttatacct gttatacttt ggcttggttt ccatgattct tactttatta gcctagttta  1860
tcaccaataa tacttgacgg aaggctcagt aattagttat gaatatggat atcctcaatt  1920
cttaagacag cttgtaaatg tatttgtaaa aattgtatat attttacag aaagtctatt  1980 tctttgaaac gaaggaagta tcgaatttac attagttttt ttcatacct tttgaacttt  2040 gcaacttccg taattaggaa cctgtttctt acagcttttc tatgctaaac tttgttctgt  2100
tcagttctag agtgtataca gaacgaattg atgtgtaact gtatgcagac tggttgtagt  2160
ggaacaaatc tgataactat gcaggtttaa attttcttat ctgatttggg taagtattcc  2220
ttagataggt ttttcttga aaacctggga ttgagaggtt gatgaatgga aattctttca  2280
cttcattata tgcaagtttt caataattag gtctaagtgg agttttaagg ttactgatga  2340
cttacaaata atgggctctg attgggcaat actcatttga gttccttcca tttgacctaa  2400
```

| | |
|---|---|
| tttaactggt gaaatttaaa gtgaattcat gggctcatct ttaaagcttt tactaaaaga | 2460 |
| ttttcagctg aatggaactc attagctgtg tgcatataaa aagatcacat caggtggatg | 2520 |
| gagagacatt tgatcccttg tttgcttaat aaattataaa atgatggctt ggaaaagcag | 2580 |
| gctagtctaa ccatggtgct attattaggc ttgcttgtta cacacacagg tctaagccta | 2640 |
| gtatgtcaat aaagcaaata cttactgttt tgtttctatt aatgattccc aaaccttgtt | 2700 |
| gcaagttttt gcattggcat cttttggattt cagtcttgat gtttgttcta tcagacttaa | 2760 |
| ccttttattt cctgtccttc cttgaaattg ctgattgttc tgctccctct acagatattt | 2820 |
| atatcaattc ctacagcttt ccctgccat ccctgaactc tttctagccc ttttagattt | 2880 |
| tggcactgtg aaacccctgc tggaaacctg agtgaccctc cctccccacc aagagtccac | 2940 |
| agacctttca tctttcacga acttgatcct gttagcaggt ggtaatacca tgggtgctgt | 3000 |
| gacactaaca gtcattgaga ggtgggagga agtcccttttt ccttggactg gtatctttttc | 3060 |
| aactattgtt ttatcctgtc tttggggggca atgtgtcaaa agtcccctca ggaattttca | 3120 |
| gaggaaagaa cattttatga ggctttctct aaagtttcct ttgtatagga gtatgctcac | 3180 |
| ttaaatttac agaagagggt gagctgtgtt aaacctcaga gttaaaagc tactgataaa | 3240 |
| ctgaagaaag tgtctatatt ggaactaggg tcatttgaaa gcttcagtct cggaacatga | 3300 |
| cctttagtct gtggactcca tttaaaaata ggtatgaata agatgactaa gaatgtaatg | 3360 |
| gggaagaact gccctgcctg cccatctcag agccataagg tcatctttgc tagagctatt | 3420 |
| tttacctatg tatttatcgt tcttgatcat aagccgctta tttatatcat gtatctctaa | 3480 |
| ggacctaaaa gcactttatg tagtttttaa ttaatcttaa gatctggtta cggtaactaa | 3540 |
| aaaagcctgt ctgccaaatc cagtggaaac aagtgcatag atgtgaattg gttttttaggg | 3600 |
| gccccacttc ccaattcatt aggtatgact gtggaaatac agacaaggat cttagttgat | 3660 |
| attttgggct tggggcagtg agggcttagg acaccccaag tggtttggga aaggaggagg | 3720 |
| ggagtggtgg gtttataggg ggaggaggag gcaggtggtc taagtgctga ctggctacgt | 3780 |
| agttcgggca aatcctccaa aagggaaagg gaggatttgc ttagaaggat ggcgctccca | 3840 |
| gtgactactt tttgacttct gtttgtctta cgcttctctc agggaaaaac atgcagtcct | 3900 |
| ctagtgtttc atgtacattc tgtgggggt gaacaccttg gttctggtta aacagctgta | 3960 |
| cttttgatag ctgtgccagg aagggttagg accaactaca aattaatgtt ggttgtcaaa | 4020 |
| tgtagtgtgt ttccctaact ttctgttttt cctgagaaaa aaaataaat cttttattca | 4080 |
| aatacaggga aaaaaaaaaa aaaaaaa | 4107 |

<210> SEQ ID NO 25
<211> LENGTH: 2081
<212> TYPE: DNA
<213> ORGANISM: Homo sapiens

<400> SEQUENCE: 25

| | |
|---|---|
| agcatgagtc agacagcctc tggctttctg gaagggcaag gactctatat atacagaggg | 60 |
| agcttcctag ctgggatatt ggagcagcaa gaggctggga agccatcact taccttgcac | 120 |
| tgagaaagaa gacaaaggcc agtatgcaca gctttcctcc actgctgctg ctgctgttct | 180 |
| ggggtgtggt gtctcacagc ttcccagcga ctctagaaac acaagagcaa gatgtggact | 240 |
| tagtccagaa atacctggaa aaatactaca acctgaagaa tgatgggagg caagttgaaa | 300 |
| agcggagaaa tagtggccca gtggttgaaa aattgaagca aatgcaggaa ttctttgggc | 360 |

-continued

```
tgaaagtgac tgggaaacca gatgctgaaa ccctgaaggt gatgaagcag cccagatgtg    420
gagtgcctga tgtggctcag tttgtcctca ctgaggggaa ccctcgctgg gagcaaacac    480
atctgaccta caggattgaa aattacacgc cagatttgcc aagagcagat gtggaccatg    540
ccattgagaa agccttccaa ctctggagta atgtcacacc tctgacattc accaaggtct    600
ctgagggtca agcagacatc atgatatctt ttgtcagggg agatcatcgg acaactctc     660 cttttgatgg acctggagga aatcttgctc atgcttttca accaggccca ggtattggag    720
gggatgctca tttttgatgaa gatgaaaggt ggaccaacaa tttcagagag tacaacttac    780
atcgtgttgc agctcatgaa ctcggccatt ctcttggact ctcccattct actgatatcg    840
gggctttgat gtaccctagc tacaccttca gtggtgatgt tcagctagct caggatgaca    900
ttgatggcat ccaagccata tatggacgtt cccaaaatcc tgtccagccc atcggcccac    960
aaaccccaaa agcgtgtgac agtaagctaa cctttgatgc tataactacg attcggggag   1020
aagtgatgtt cttaaagac agattctaca tgcgcacaaa tcccttctac ccggaagttg    1080
agctcaattt catttctgtt ttctggccac aactgccaaa tgggcttgaa gctgcttacg   1140
aatttgccga cagagatgaa gtccggtttt tcaaagggaa taagtactgg gctgttcagg   1200
gacagaatgt gctacacgga taccccaagg acatctacag ctccttttggc ttccctagaa   1260 ctgtgaagca tatcgatgct gctctttctg aggaaaacac tggaaaaacc tacttctttg   1320
ttgctaacaa atactggagg tatgatgaat ataaacgatc tatggatcca ggttatccca   1380
aaatgatagc acatgacttt cctggaattg ccacaaagt tgatgcagtt ttcatgaaag    1440 atggatttt ctatttcttt catggaacaa gacaatacaa atttgatcct aaaacgaaga    1500
gaattttgac tctccagaaa gctaatagct ggttcaactg caggaaaaat tgaacattac   1560
taatttgaat ggaaaacaca tggtgtgagt ccaaagaagg tgtttttcctg aagaactgtc   1620 tattttctca gtcatttttta acctctagag tcactgatac acagaatata atcttattta   1680
tacctcagtt tgcatatttt tttactattt agaatgtagc ccttttttgta ctgatataat   1740 ttagttccac aaatggtggg tacaaaagt caagtttgtg gcttatggat tcatataggc    1800
cagagttgca aagatctttt ccagagtatg caactctgac gttgatccca gagagcagct    1860
tcagtgacaa acatatcctt tcaagacaga agagacagg agacatgagt ctttgccgga    1920
ggaaaagcag ctcaagaaca catgtgcagt cactggtgtc accctggata ggcaagggat    1980
aactcttcta acacaaaata agtgttttat gtttggaata aagtcaacct tgtttctact    2040
gttttataca ctttcaaaaa aaaaaaaaaa aaaaaaaaa a                         2081
```

<210> SEQ ID NO 26
<211> LENGTH: 1906
<212> TYPE: DNA
<213> ORGANISM: Homo sapiens

<400> SEQUENCE: 26

```
aaagcaagga tgagtcaagc tgcgggtgat ccaaacaaac actgtcactc tttaaaagct     60
gcgctcccga ggttggacct acaaggaggc aggcaagaca gcaaggcata gagacaacat    120
agagctaagt aaagccagtg gaaatgaaga gtcttccaat cctactgttg ctgtgcgtgg    180
cagtttgctc agcctatcca ttggatggag ctgcaagggg tgaggacacc agcatgaacc    240
ttgttcagaa atatctagaa aactactacg acctcaaaaa agatgtgaaa cagttttgtta    300 ggagaaagga cagtggtcct gttgttaaaa aaatccgaga aatgcagaag ttccttggat    360
tggaggtgac ggggaagctg gactccgaca ctctggaggt gatgcgcaag cccaggtgtg    420
```

```
gagttcctga tgttggtcac ttcagaacct ttcctggcat cccgaagtgg aggaaaaccc      480
accttacata caggattgtg aattatacac cagatttgcc aaaagatgct gttgattctg      540
ctgttgagaa agctctgaaa gtctgggaag aggtgactcc actcacattc tccaggctgt      600
atgaaggaga ggctgatata atgatctctt ttgcagttag agaacatgga gacttttacc      660
cttttgatgg acctggaaat gttttggccc atgcctatgc ccctgggcca gggattaatg      720
gagatgccca ctttgatgat gatgaacaat ggacaaagga tacaacaggg accaatttat      780
ttctcgttgc tgctcatgaa attggccact ccctgggtct ctttcactca gccaacactg      840
aagctttgat gtacccactc tatcactcac tcacagacct gactcggttc cgcctgtctc      900
aagatgatat aaatggcatt cagtccctct atggacctcc ccctgactcc cctgagaccc      960
ccctggtacc cacggaacct gtccctccag aacctgggac gccagccaac tgtgatcctg     1020
ctttgtcctt tgatgctgtc agcactctga ggggagaaat cctgatcttt aaagacaggc     1080
acttttggcg caaatccctc aggaagcttg aacctgaatt gcatttgatc tcttcatttt     1140
ggccatctct tccttcaggc gtggatgccg catatgaagt tactagcaag gacctcgttt     1200 tcattttttaa aggaaatcaa ttctgggcta tcagaggaaa tgaggtacga gctggatacc     1260
caagaggcat ccacacccta ggtttccctc caaccgtgag gaaaatcgat gcagccattt     1320
ctgataagga aaagaacaaa acatatttct ttgtagagga caaatactgg agatttgatg     1380
agaagagaaa ttccatggag ccaggctttc ccaagcaaat agctgaagac tttccaggga     1440
ttgactcaaa gattgatgct gttttttgaag aatttgggtt cttttatttc tttactggat     1500
cttcacagtt ggagtttgac ccaaatgcaa agaaagtgac acacactttg aagagtaaca     1560
gctggcttaa ttgttgaaag agatatgtag aaggcacaat atgggcactt taaatgaagc     1620
taataattct tcacctaagt ctctgtgaat tgaaatgttc gttttctcct gcctgtgctg     1680
tgactcgagt cacactcaag ggaacttgag cgtgaatctg tatcttgccg gtcattttta     1740
tgttattaca gggcattcaa atgggctgct gcttagcttg caccttgtca catagagtga     1800
tctttcccaa gagaagggga agcactcgtg tgcaacagac aagtgactgt atctgtgtag     1860
actatttgct tatttaataa agacgatttg tcagttattt tatctt                    1906

<210> SEQ ID NO 27
<211> LENGTH: 2387
<212> TYPE: DNA
<213> ORGANISM: Homo sapiens

<400> SEQUENCE: 27
agacacctct gccctcacca tgagcctctg gcagcccctg gtcctggtgc tcctggtgct       60
gggctgctgc tttgctgccc ccagacagcg ccagtccacc cttgtgctct ccctggaga      120 cctgagaacc aatctcaccg acaggcagct ggcagaggaa tacctgtacc gctatggtta      180
cactcgggtg gcagagatgc gtggagagtc gaaatctctg gggcctgcgc tgctgcttct      240
ccagaagcaa ctgtccctgc ccgagaccgg tgagctggat agcgccacgc tgaaggccat      300 gcgaaccca cggtgcgggg tcccagacct gggcagattc caaacctttg agggcgacct      360
caagtggcac caccacaaca tcacctattg gatccaaaac tactcggaag acttgccgcg      420 gcggtgatt gacgacgcct tgcccgcgc cttcgcactg tggagcgcgg tgacgccgct      480
caccttcact cgcgtgtaca gccgggacg agacatcgtc atccagtttg tgtcgcgga      540 gcacggagac gggtatccct tcgacggga ggacgggctc ctggcacacg cctttcctcc      600
```

```
tggccccggc attcagggag acgcccattt cgacgatgac gagttgtggt ccctgggcaa      660
gggcgtcgtg gttccaactc ggtttggaaa cgcagatggc gcggcctgcc acttcccctt      720
catcttcgag ggccgctcct actctgcctg caccaccgac ggtcgctccg acggcttgcc      780
ctggtgcagt accacggcca actacgacac cgacgaccgg tttggcttct gccccagcga      840
gagactctac acccaggacg gcaatgctga tgggaaaccc tgccagtttc cattcatctt      900
ccaaggccaa tcctactccg cctgcaccac ggacggtcgc tccgacggct accgctggtg      960
cgccaccacc gccaactacg accgggacaa gctcttcggc ttctgcccga cccgagctga     1020
ctcgacggtg atggggggca actcggcggg ggagctgtgc gtcttcccct tcactttcct     1080
gggtaaggag tactcgacct gtaccagcga gggccgcgga gatgggcgcc tctggtgcgc     1140
taccacctcg aactttgaca cgacaagaa gtgggcttc tgcccggacc aaggatacag      1200
tttgttcctc gtggcggcgc atgagttcgg ccacgcgctg gcttagatc attcctcagt     1260 gccgaggcg ctcatgtacc ctatgtaccg cttcactgag gggccccct tgcataagga      1320 cgacgtgaat ggcatccggc acctctatgg tcctcgccct gaacctgagc cacggcctcc     1380
aaccaccacc acaccgcagc ccacggctcc cccgacggtc tgccccaccg accccccac      1440 tgtccacccc tcagagcgcc ccacagctgg ccccacaggt ccccctcag ctggccccac      1500 aggtcccccc actgctggcc cttctacggc cactactgtg cctttgagtc cggtggacga     1560
tgcctgcaac gtgaacatct tcgacgccat cgccgagatt gggaaccagc tgtatttgtt     1620
caaggatggg aagtactggc gattctctga gggcaggggg agccggccgc agggccctt      1680 ccttatcgcc gacaagtggc ccgcgctgcc ccgcaagctg gactcggtct ttgaggagcg     1740
gctctccaag aagctttct tcttctctgg gcgccaggtg tgggtgtaca caggcgcgtc     1800
ggtgctgggc ccgaggcgtc tggacaagct gggcctggga gccgacgtgg cccaggtgac     1860
cggggccctc cggagtggca ggggaagat gctgctgttc agcgggcggc gcctctggag     1920
gttcgacgtg aaggcgcaga tggtggatcc ccggagcgcc agcgaggtgg accggatgtt     1980
ccccggggtg cctttggaca cgcacgacgt cttccagtac cgagagaaag cctatttctg     2040
ccaggaccgc ttctactggc gcgtgagttc ccggagtgag ttgaaccagg tggaccaagt     2100
gggctacgtg acctatgaca tcctgcagtg ccctgaggac tagggctccc gtcctgcttt     2160
ggcagtgcca tgtaaatccc cactgggacc aaccctgggg aaggagccag tttgccggat     2220
acaaactggt attctgttct ggaggaaagg gaggagtgga ggtgggctgg ccctctctt      2280 ctcacctttg ttttttgttg gagtgtttct aataaacttg gattctctaa cctttaaaaa     2340
aaaaaaaaaa aaaaaaaaaa aaaaaaaaaa aaaaaaaaaa aaaaaa                   2387

<210> SEQ ID NO 28
<211> LENGTH: 1220
<212> TYPE: DNA
<213> ORGANISM: Homo sapiens

<400> SEQUENCE: 28
cgctccacct tcaagcagc cagcgcctgc ctgaatctgt tctgcccct ccccacccat        60 ttcaccacca ccatgacacc gggcacccag tctcctttct tcctgctgct gctcctcaca      120
gtgcttacag ttgttacggg ttctggtcat gcaagctcta ccccaggtgg agaaaaggag      180
acttcggcta cccagagaag ttcagtgccc agctctactg agaagaatgc tttgtctact      240 gggtctctt tcttttttcct gtcttttcac atttcaaacc tccagtttaa ttcctctctg      300
gaagatccca gcaccgacta ctaccaagag ctgcagagag acatttctga aatgttttg       360
```

```
cagatttata aacaagggggg ttttctgggc ctctccaata ttaagttcag gccaggatct      420
gtggtggtac aattgactct ggccttccga aaggtacca tcaatgtcca cgacgtggag        480
acacagttca atcagtataa aacggaagca gcctctcgat ataacctgac gatctcagac      540
gtcagcgtga gtgatgtgcc atttcctttc tctgcccagt ctggggctgg ggtgccaggc      600
tggggcatcg cgctgctggt gctggtctgt gttctggttg cgctggccat tgtctatctc      660
attgccttgg ctgtctgtca gtgccgccga aagaactacg ggcagctgga catctttcca      720
gcccgggata cctaccatcc tatgagcgag taccccacct accacaccca tgggcgctat      780
gtgcccccta gcagtaccga tcgtagcccc tatgagaagg tttctgcagg taatggtggc      840
agcagcctct cttacacaaa cccagcagtg gcagccactt ctgccaactt gtaggggcac      900
gtcgcccgct gagctgagtg gccagccagt gccattccac tccactcagg ttcttcaggg      960
ccagagcccc tgcaccctgt ttgggctggt gagctgggag ttcaggtggg ctgctcacag     1020
cctccttcag aggccccacc aatttctcgg acacttctca gtgtgtggaa gctcatgtgg     1080
gcccctgagg gctcatgcct gggaagtgtt gtggtggggg ctcccaggag gactggccca     1140
gagagccctg agatagcggg gatcctgaac tggactgaat aaaacgtggt ctcccactgc     1200
gccaaaaaaa aaaaaaaaa                                                   1220

<210> SEQ ID NO 29
<211> LENGTH: 4518
<212> TYPE: DNA
<213> ORGANISM: Homo sapiens

<400> SEQUENCE: 29
ggagtttatt cataacgcgc tctccaagta tacgtggcaa tgcgttgctg ggttatttta       60
atcattctag gcatcgtttt cctccttatg cctctatcat tcctccctat ctacactaac      120
atcccacgct ctgaacgcgc gcccattaat acccttcttt cctccactct ccctgggact      180
cttgatcaaa gcgcggccct ttccccagcc ttagcgaggc gccctgcagc ctggtacgcg      240
cgtggcgtgg cggtgggcgc gcagtgcgtt ctcggtgtgg agggcagctg ttccgcctgc      300 gatgattat actcacagga caaggatgcg gtttgtcaaa cagtactgct acggaggagc      360
agcagagaaa gggagagggt ttgagaggga gcaaaagaaa atggtaggcg cgcgtagtta      420
attcatgcgg ctctcttact ctgtttacat cctagagcta gagtgctcgg ctgccccggct     480 gagtctcctc cccaccttcc ccaccctccc caccctcccc ataagcgccc ctcccgggtt      540
cccaaagcag agggcgtggg ggaaaagaaa aaagatcctc tctcgctaat ctccgcccac      600 cggccctttta taatgcgagg gtctggacgg ctgaggaccc ccgagctgtg ctgctcgcgg     660
ccgccaccgc cgggcccggg ccgtccctgg ctccctcct gcctcgagaa gggcagggct      720
tctcagaggc ttggcgggaa aaagaacgga gggagggatc gcgctgagta taaaagccgg      780
ttttcggggc tttatctaac tcgctgtagt aattccagcg agaggcagag ggagcgagcg      840
ggcggccggc tagggtggaa gagccgggcg agcagagctg cgctgcgggc gtcctgggaa      900
gggagatccg gagcgaatag ggggcttcgc ctctggccca gccctcccgc tgatccccca      960
gccagcggtc cgcaacccct tgccgcatcc acgaaactttg cccatagcag cgggcgggca     1020
ctttgcactg gaacttacaa caccgagca aggacgcgac tctcccgacg cggggaggct       1080
attctgccca tttggggaca cttccccgcc gctgccagga cccgcttctc tgaaaggctc      1140
tccttgcagc tgcttagacg ctggattttt ttcgggtagt ggaaaaccag cagcctcccg      1200
```

```
cgacgatgcc cctcaacgtt agcttcacca acaggaacta tgacctcgac tacgactcgg    1260
tgcagccgta tttctactgc gacgaggagg agaacttcta ccagcagcag cagcagagcg    1320
agctgcagcc cccggcgccc agcgaggata tctggaagaa attcgagctg ctgcccaccc    1380 cgccctgtc ccctagccgc cgctccgggc tctgctcgcc ctcctacgtt gcggtcacac     1440
ccttctccct tcggggagac aacgacggcg gtggcgggag cttctccacg gccgaccagc    1500
tggagatggt gaccgagctg ctgggaggag acatggtgaa ccagagtttc atctgcgacc    1560
cggacgacga gaccttcatc aaaaacatca tcatccagga ctgtatgtgg agcggcttct    1620
cggccgccgc caagctcgtc tcagagaagc tggcctccta ccaggctgcg cgcaaagaca    1680
gcggcagccc gaacccgcc cgcggccaca gcgtctgctc cacctccagc ttgtacctgc     1740
aggatctgag cgccgccgcc tcagagtgca tcgacccctc ggtggtcttc ccctaccctc    1800
tcaacgacag cagctcgccc aagtcctgcg cctcgcaaga ctccagcgcc ttctctccgt    1860
cctcggattc tctgctctcc tcgacggagt cctccccgca gggcagcccc gagcccctgg    1920
tgctccatga ggagacaccg cccaccacca gcagcgactg tgaggaggaa caagaagatg    1980
aggaagaaat cgatgttgtt tctgtggaaa agaggcaggc tcctggcaaa aggtcagagt    2040
ctggatcacc ttctgctgga ggccacagca aacctcctca cagcccactg gtcctcaaga    2100
ggtgccacgt ctccacacat cagcacaact acgcagcgcc tccctccact cggaaggact    2160
atcctgctgc caagagggtc aagttggaca gtgtcagagt cctgagacag atcagcaaca    2220
accgaaaatg caccagcccc aggtcctcgg acaccgagga gaatgtcaag aggcgaacac    2280
acaacgtctt ggagcgccag aggaggaacg agctaaaacg gagctttttt gccctgcgtg    2340
accagatccc ggagttggaa acaatgaaa aggcccccaa ggtagttatc cttaaaaaag     2400
ccacagcata catcctgtcc gtccaagcag aggagcaaaa gctcatttct gaagaggact    2460
tgttgcggaa acgacgagaa cagttgaaac acaaacttga acagctacgg aactcttgtg    2520
cgtaaggaaa agtaaggaaa acgattcctt ctaacagaaa tgtcctgagc aatcaccta     2580 gaacttgttt caaatgcatg atcaaatgca acctcacaac cttggctgag tcttgagact    2640
gaaagattta gccataatgt aaactgcctc aaattggact ttgggcataa aagaactttt    2700
ttatgcttac catctttttt ttttctttaa cagatttgta tttaagaatt gttttaaaa     2760 aatttttaaga tttacacaat gtttctctgt aaatattgcc attaaatgta ataacttta    2820 ataaaacgtt tatagcagtt acacagaatt tcaatcctag tatatagtac ctagtattat    2880
aggtactata aaccctaatt tttttatttt aagtacatt tgcttttaa agttgatttt     2940 tttctattgt tttagaaaa ataaaataa ctggcaaata tatcattgag ccaaatctta    3000
agttgtgaat gttttgtttc gtttcttccc cctcccaacc accaccatcc ctgtttgttt    3060
tcatcaattg ccccttcaga gggtggtctt aagaaaggca agagttttcc tctgttgaaa    3120
tgggtctggg ggccttaagg tctttaagtt cttggaggtt ctaagatgct tcctggagac    3180
tatgataaca gccagagttg acagttagaa ggaatggcag aaggcaggtg agaaggtgag    3240
aggtaggcaa aggagataca agaggtcaaa ggtagcagtt aagtacacaa agaggcataa    3300
ggactgggga gttgggagga aggtgaggaa gaaactcctg ttactttagt taaccagtgc    3360
cagtcccctg ctcactccaa acccaggaat tctgcccagt tgatggggac acggtgggaa    3420
ccagcttctg ctgccttcac aaccaggcgc cagtcctgtc catgggttat ctcgcaaacc    3480
ccagaggatc tctgggagga atgctactat taaccctatt tcacaaacaa ggaaatagaa    3540
gagctcaaag aggttatgta acttatctgt agccacgcag ataatacaaa gcagcaatct    3600
```

```
ggacccattc tgttcaaaac acttaacccT tcgctatcat gccttggttc atctgggtct    3660
aatgtgctga gatcaagaag gtttaggacc taatggacag actcaagtca taacaatgct    3720
aagctctatt tgtgtcccaa gcactcctaa gcattttatc cctaactcta catcaaCCCC    3780
atgaaggaga tactgttgat ttccccatat tagaagtaga gagggaagct gaggcacaca    3840
aagactcatc cacatgccca agattcactg atagggaaaa gtggaagcga gatttgaacc    3900
caggctgttt actcctaacc tgtccaagcc acctctcaga cgacggtagg aatcagctgg    3960
ctgcttgtga gtacaggagt tacagtccag tgggttatgt ttttaagtc tcaacatcta    4020 agcctggtca ggcatcagtt ccccttttt tgtgattat tttgttttta ttttgttgtt    4080
cattgtttaa tttttccttt tacaatgaga aggtcaccat cttgactcct accttagcca    4140
tttgttgaat cagactcatg acggctcctg gaagaagcc agttcagatc ataaaataaa    4200
acatatttat tctttgtcat gggagtcatt attttagaaa ctacaaactc tccttgcttc    4260 catcctttt tacatactca tgacacatgc tcatcctgag tccttgaaaa ggtattttg     4320 aacatgtgta ttaattataa gcctctgaaa acctatggcc caaaccagaa atgatgttga    4380
ttatataggt aaatgaagga tgctattgct gttctaatta cctcattgtc tcagtctcaa    4440
agtaggtctt cagctccctg tactttggga ttttaatcta ccaccaccca taaatcaata    4500
aataattact ttctttga                                                  4518

<210> SEQ ID NO 30
<211> LENGTH: 4206
<212> TYPE: DNA
<213> ORGANISM: Homo sapiens

<400> SEQUENCE: 30
ataactttgt agcgagtcga aaactgaggc tccggccgca gagaactcag cctcattcct      60
gctttaaaat ctctcggcca cctttgatga ggggactggg cagttctaga cagtcccgaa     120
gttctcaagg cacaggtctc ttcctggttt gactgtcctt accccgggga ggcagtgcag     180
ccagctgcaa gccccacagt gaagaacatc tgagctcaaa tccagataag tgacataagt     240
gacctgcttt gtaaagccat agagatggcc tgtccttgga aatttctgtt caagaccaaa     300
ttccaccagt atgcaatgaa tggggaaaaa gacatcaaca acaatgtgga aaagccccc     360 tgtgccacct ccagtccagt gacacaggat gaccttcagt atcacaacct cagcaagcag     420
cagaatgagt ccccgcagcc cctcgtggag acgggaaaga agtctccaga atctctggtc     480
aagctggatg caaccccatt gtcctcccca cggcatgtga ggatcaaaaa ctggggcagc    540
gggatgactt tccaagacac acttcaccat aaggccaaag ggatttaac ttgcaggtcc     600 aaatcttgcc tggggtccat tatgactccc aaaagtttga ccagaggacc cagggacaag    660
cctacccctc cagatgagct tctacctcaa gctatcgaat ttgtcaacca atattacggc    720
tccttcaaag aggcaaaaat agaggaacat ctggccaggg tggaagcggt aacaaaggag    780
atagaaacaa caggaaccta ccaactgacg ggagatgagc tcatcttcgc caccaagcag    840
gcctggcgca atgccccacg ctgcattggg aggatccagt ggtccaacct gcaggtcttc    900
gatgcccgca gctgttccac tgcccgggaa atgtttgaac acatctgcag acacgtgcgt    960
tactccacca caatggcaa catcaggtcg gccatcaccg tgttccccca gcggagtgat   1020
ggcaagcacg acttccgggt gtggaatgct cagctcatcc gctatgctgg ctaccagatg   1080
ccagatggca gcatcagagg ggaccctgcc aacgtggaat tcactcagct gtgcatcgac   1140
```

```
ctgggctgga agcccaagta cggccgcttc gatgtggtcc ccctggtcct gcaggccaat    1200
ggccgtgacc ctgagctctt cgaaatccca cctgaccttg tgcttgaggt ggccatggaa    1260
catcccaaat acgagtggtt tcgggaactg gagctaaagt ggtacgccct gcctgcagtg    1320
gccaacatgc tgcttgaggt gggcggcctg gagttcccag ggtgccccct caatggctgg    1380
tacatgggca cagagatcgg agtccgggac ttctgtgacg tccagcgcta acatcctg     1440 gaggaagtgg gcaggagaat gggcctggaa acgcacaagc tggcctcgct ctggaaagac    1500
caggctgtcg ttgagatcaa cattgctgtg ctccatagtt ccagaagca gaatgtgacc    1560 atcatggacc accactcggc tgcagaatcc ttcatgaagt acatgcagaa tgaataccgg    1620
tcccgtgggg gctgcccggc agactggatt tggctggtcc ctcccatgtc tgggagcatc    1680
acccccgtgt tcaccagga gatgctgaac tacgtcctgt cccctttcta ctactatcag    1740
gtagaggcct ggaaaaccca tgtctggcag gacgagaagc ggagacccaa gagaagagag    1800
attccattga aagtcttggt caaagctgtg ctctttgcct gtatgctgat gcgcaagaca    1860
atggcgtccc gagtcagagt caccatcctc tttgcgacag agacaggaaa atcagaggcg    1920
ctggcctggg acctggggc cttattcagc tgtgccttca accccaaggt tgtctgcatg    1980
gataagtaca ggctgagctg cctggaggag aacggctgc tgttggtggt gaccagtacg    2040
tttggcaatg gagactgccc tggcaatgga gagaaactga gaaatcgct cttcatgctg    2100 aaagagctca caacaaatt caggtacgct gtgtttggcc tcggctccag catgtaccct    2160
cggttctgcg cctttgctca tgacattgat cagaagctgt cccacctggg ggcctctcag    2220 ctcacccga tgggagaagg ggatgagctc agtgggcagg aggacgcctt ccgcagctgg    2280
gccgtgcaaa ccttcaaggc agcctgtgag acgtttgatg tccgaggcaa acagcacatt    2340
cagatcccca gctctacac ctccaatgtg acctgggacc cgcaccacta caggctcgtg    2400
caggactcac agcctttgga cctcagcaaa gccctcagca gcatgcatgc caagaacgtg    2460
ttcaccatga ggctcaaatc tcggcagaat ctacaaagtc cgacatccag ccgtgccacc    2520
atcctggtgg aactctcctg tgaggatggc caaggcctga actacctgcc ggggagcac    2580 cttgggtttt gccaggcaa ccagccggcc tggtccaag gtatcctgga gcagtggtg    2640 gatggcccca cccccacca gacagtgcgc ctggaggccc tggatgagag tggcagctac    2700
tgggtcagtg acaagaggct gccccctgc tcactcagcc aggccctcac ctacttcctg    2760
gacatcacca cacccccaac ccagctgctg ctccaaaagc tggcccaggt ggccacagaa    2820
gagcctgaga cagaggct ggaggccctg tgccagccct cagagtacag caagtggaag    2880
ttcaccaaca gccccacatt cctggaggtg ctagaggagt tcccgtccct gcgggtgtct    2940
gctggcttcc tgctttccca gctccccatt ctgaagccca ggttctactc catcagctcc    3000 tccccgggatc acacgcccac agagatccac ctgactgtgg ccgtggtcac ctaccacacc    3060
cgagatggcc agggtcccct gcaccacggc gtctgcagca catggctcaa cagcctgaag    3120
ccccaagacc cagtgccctg ctttgtgcgg aatgccagcg gcttccacct ccccgaggat    3180
ccctcccatc cttgcatcct catcgggcct ggcacaggca tcgcgccctt ccgcagtttc    3240
tggcagcaac ggctccatga ctcccagcac aaggagtgc ggggaggccg catgaccttg    3300
gtgtttgggt gccgccgccc agatgaggac cacatctacc aggaggagat gctggagatg    3360
gcccagaagg gggtgctgca tgcggtgcac acagcctatt ccgcctgcc tgcaagccc    3420 aaggtctatg ttcaggacat cctgcggcag cagctggcca gcgaggtgct ccgtgtgctc    3480
cacaaggagc caggccacct ctatgtttgc ggggatgtgc gcatggcccg ggacgtggcc    3540
```

| | |
|---|---|
| cacaccctga agcagctggt ggctgccaag ctgaaattga atgaggagca ggtcgaggac | 3600 |
| tatttctttc agctcaagag ccagaagcgc tatcacgaag atatctttgg tgctgtattt | 3660 |
| ccttacgagg cgaagaagga cagggtggcg gtgcagccca gcagcctgga gatgtcagcg | 3720 |
| ctctgagggc ctacaggagg ggttaaagct gccggcacag aacttaagga tggagccagc | 3780 |
| tctgcattat ctgaggtcac agggcctggg gagatggagg aaagtgatat cccccagcct | 3840 |
| caagtcttat ttcctcaacg ttgctcccca tcaagccctt tacttgacct cctaacaagt | 3900 |
| agcaccctgg attgatcgga gcctcctctc tcaaactggg gcctccctgg tcccttggag | 3960 |
| acaaaatctt aaatgccagg cctggcaagt gggtgaaaga tggaacttgc tgctgagtgc | 4020 |
| accacttcaa gtgaccacca ggaggtgcta tcgcaccact gtgtatttaa ctgccttgtg | 4080 |
| tacagttatt tatgcctctg tatttaaaaa actaacaccc agtctgttcc ccatggccac | 4140 |
| ttgggtcttc cctgtatgat tccttgatgg agatatttac atgaattgca ttttacttta | 4200 |
| atcaca | 4206 |

<210> SEQ ID NO 31
<211> LENGTH: 13905
<212> TYPE: DNA
<213> ORGANISM: Homo sapiens

<400> SEQUENCE: 31

| | |
|---|---|
| gggaggggggg aggggagcca gagcgaggga gggtttatcg accggcgat tttggttaaa | 60 |
| atattcaaaa tggcggacgg aggagcagcg agtcaagatg agagttcagc cgcggcggca | 120 |
| gcagcagcag actcaagaat gaacaatccg tcagaaacca gtaaaccatc tatggagagt | 180 |
| ggagatggca acacaggcac acaaaccaat ggtctggact ttcagaagca gcctgtgcct | 240 |
| gtaggaggag caatctcaac agcccaggcg caggctttcc ttggacatct ccatcaggtc | 300 |
| caactcgctg gaacaagttt acaggctgct gctcagtctt taaatgtaca gtctaaatct | 360 |
| aatgaagaat cggggggattc gcagcagcca agccagcctt cccagcagcc ttcagtgcag | 420 |
| gcagccattc cccagaccca gcttatgcta gctggaggac agataactgg gcttactttg | 480 |
| acgcctgccc agcaacagtt actactccag caggcacagg cacaggcaca gctgctggct | 540 |
| gctgcagtgc agcagcactc cgccagccag cagcacagtg ctgctggagc caccatctcc | 600 |
| gcctctgctg ccacgcccat gacgcagatc cccctgtctc agcccataca gatcgcacag | 660 |
| gatcttcaac aactgcaaca gcttcaacag cagaatctca acctgcaaca gtttgtgttg | 720 |
| gtgcatccaa ccaccaattt gcagccagcg cagtttatca tctcacagac gccccagggc | 780 |
| cagcagggtc tcctgcaagc gcaaaatctt ctaacgcaac tacctcagca agccaagcc | 840 |
| aacctcctac agtcgcagcc aagcatcacc ctcacctccc agccagcaac cccaacacgc | 900 |
| acaatagcag caccccaat tcagacactt ccacagagcc agtcaacacc aaagcgaatt | 960 |
| gatactccca gcttggagga gcccagtgac cttgaggagc ttgagcagtt tgccaagacc | 1020 |
| ttcaaacaaa gacgaatcaa acttggattc actcagggtg atgttgggct cgctatgggg | 1080 |
| aaactatatg gaaatgactt cagccaaact accatctctc gatttgaagc cttgaacctc | 1140 |
| agctttaaga acatgtgcaa gttgaagcca cttttagaga agtggctaaa tgatgcagag | 1200 |
| aacctctcat ctgattcgtc cctctccagc ccaagtgccc tgaattctcc aggaattgag | 1260 |
| ggcttgagcc gtaggaggaa gaaacgcacc agcatagaga ccaacatccg tgtggcctta | 1320 |
| gagaagagtt tcttggagaa tcaaaagcct acctcggaag agatcactat gattgctgat | 1380 |

-continued

```
cagctcaata tggaaaaaga ggtgattcgt gtttggttct gtaaccgccg ccagaaagaa    1440
aaaagaatca acccaccaag cagtggtggg accagcagct cacctattaa agcaattttc    1500
cccagcccaa cttcactggt ggcgaccaca ccaagccttg tgactagcag tgcagcaact    1560
accctcacag tcagccctgt cctccctctg accagtgctg ctgtgacgaa tctttcagtt    1620
acaggcactt cagacaccac ctccaacaac acagcaaccg tgatttccac agcgcctcca    1680
gcttcctcag cagtcacgtc cccctctctg agtccctccc cttctgcctc agcctccacc    1740
tccgaggcat ccagtgccag tgagaccagc acaacacaga ccacctccac tcctttgtcc    1800
tcccctcttg ggaccagcca ggtgatggtg acagcatcag gtttgcaaac agcagcagct    1860
gctgcccttc aaggagctgc acagttgcca gcaaatgcca gtcttgctgc catggcagct    1920
gctgcaggac taaacccaag cctgatgcca ccctcacagt ttgcggctgg aggtgcctta    1980
ctcagtctga atccagggac cctgagcggt gctctcagcc cagctctaat gagcaacagt    2040
acactggcaa ctattcaagc tcttgcttct ggtggctctc ttccaataac atcacttgat    2100
gcaactggga acctggtatt tgccaatgcg ggaggagccc ccaacatcgt gactgccccc    2160
ctgttcctga accctcagaa cctctctctg ctcaccagca accctgttag cttggtctct    2220
gccgccgcag catctgcagg gaactctgca cctgtagcca gccttcacgc cacctccacc    2280
tctgctgagt ccatccagaa ctctctcttc acagtggcct ctgccagcgg ggctgcgtcc    2340
accaccacca ccgcctccaa ggcacagtga gctgggcaga gctgggctgc agaagccttt    2400
tttcactctg cagtgtgatt ggactgccag ccaggttaat aaactgaaaa atgtgattgg    2460
cttcctctcg ccgtgttgtg agggcaaagg agagaaggga gaaaaaaaaa aaaaaccac     2520 acacacccat acacacatac cagaaaaaga agaaaggat ggagacggaa catttgccta    2580
attttgtaat aaaacactgt cttttcagga ttgcttcatg gattggagaa ctttctaacc    2640
aaaaattaaa aaaaaaaaa aaaaagaaa caaaaaaatc aaaacaaac aaaaataagt      2700 gaaaggacta cttatcattt ccagcagtca tgatgacaag ttaaggtggg ttaccaattc    2760
caatatagga aggggatttc ttgtttgtct aaatttcttt ttttcttaaa aaaaaaaat    2820 cattttatg ggtctgttgt acaggccatt aagtcataac aaggtgttta taatcgtatc     2880
aattgtgttg ggggttcctt tcttaactgg tacaatttag gcaggcctgt attactgtat    2940
tattattgtt gttgttgtta ttgttttata tatatagttt ggacatgttt attatctctt    3000
gctcctggat cctatttcag tgagctccca cactgtgggg agggagggtt ttggggtaag    3060
gggagacttc tgttcttaac tgtgggaat gttcttgctg gtttccttat ccttgatgac     3120
tcttacagag gtgctagaaa attatttct tttgccactt atgcaagagg cttggtgcag     3180
aagctgaagg cagtgtgtgc aaacactccc attccacaca cgcccttcc cctcccaca      3240 tcaggtggtg cctttggagc acttttgtgt aggaaggaat tcctgctgaa ctgtagctct    3300 cactcaccc caaatcattg aatgaccctg aggcccagtt cctgtggtgc aacagtgctg     3360 cttctgcta ctttcaatgg aacagctgt acatgttgca gggcaggatt tggttccaa       3420 gagcaaagac tactgcagac acctgacttg gtggttctcc tgatttctta tctcctgaaa    3480
aatgctcctg ctgttggtgt gtttgtttgt tgttccatt ttgtggaagt ttttcatcca     3540
aactttaact aacttggcaa agaaaaaaaa ctgacttact gaaattggga aacttttccc    3600 ttctttatt ttctaaagga attctactag actattttcc attgataata tatacaaaag    3660
aggtgtgatg agaagggtat aaggttacca ccttttcctc tagagagcca cagacttcct    3720
ttccactgga tggtttataa attcctctaa ccctgagatt cttcttggtt ctctgactaa    3780
```

```
aggaggcact tattagccgg gctgggatct gtagaacctt tgaagaagga ctttgagcag   3840
gaactttgca cacaccttaa gtgtctcctt ggtttgttca tgatgctcct gctaggtagg   3900
tctaaatggc aatacacatc tctttattca atgtagaaag taattagctc tgtaattatt   3960
ttcagggtgt ttgtagacta tataaatgag cccattgaaa aggaagagtt tgtgaaagtg   4020
gatgaagagg aataagggta acttggagat taaattcctt tttttgtcag tgtactgttg   4080
ttatgccatc tgtaccaaaa aatttccaa aagactggat cactgcagtg cagctcatct    4140
aagttcccct tcttattgga gttaaaggtt cccatttggt ggctgtgggt gcttgcttaa   4200
atctctggtg gtcccaagac tgcactttt ctcccttcg agctggggat gtagagagaa     4260
cttacaggtg atttttattc tgattgcttt tgtttgtgtc cacaagggag cttggattct   4320
gtgtacttgt ctcttccca ttgtccagta aggcagtaaa tacagacaca atgtgtactt    4380
ttgtgtgtga ttcaagtggg agacagtctg ttaaaaggtc agaaacattt tagtccccctt  4440 taaaatattt cttttagttt atttctatcg tgttttattt cacagatatt taattaccac   4500
ccctaaattt cctcctctta cccttcacct tccctaaaat ccttccaaaa tcagtgaact   4560
gcaagcaggg aaactaacaa atgtccattc acccttttg tgtggtgtgt ttttttatgt    4620
tttgttttgt tttttaacta agcttgaacc aaagtcaatt tttagcaagc tgctgtacta   4680
atggactagt tgataacgtg cagttcagac acatcgagga gatagatgct actgacaatt   4740 tcttttcat ttgtctttat taatttata tgaaagttgc tgcttgtttt taatctttta     4800
tgttggtaaa ttgtgatatc ctctgggcag acattaactt gatgtttaac tagtttatta   4860
ggttggtgtg taaatagaat gacaatgtca attactaatt tctctcctct ccattcactt   4920
tttctctgtt gtagttaaat ttaatcttct atcctgactt gacatctcta cctttagtct   4980
gtggaaatga ttttagggct atcagtaatg ctgtagctgc ccataataat gagtccctcc   5040
cttgggagtg gtgaaactta gaaggaagga ttcaggagg gaaatgctgg tacccagtat    5100
actggattag aagttatagc attaatttct caaaattgct accaaggaa gtgtggagtc    5160 ccaagggact caagctcagt gaggtaagac aaagggcaag gaaaggctgt ttgggtggtt   5220 ttttttccc cacatatggt ttagaaaatg atccctttcc caaacaaaac tcaccaacag    5280
actttaatat tagaaaagat actaagcttt aaatgtcaat acagtggtct tttattccct   5340
gccctgtcta tattttctac tcaatttggg ataagggat tttatgtgaa gcacttgatg    5400
agggtagacc agcataaaaa atctgtttaa aagaagaaat aatctttagg aaaagataaa   5460
tctttagata aaaataaatt ttttctctt ttttactta tttaaaaata agttgtgaaa     5520
tgaaaggtac atttacacat gtacacacga aacactaata tagcttttg gtggttgttt    5580 agtttaaaat caactcccta tccatcatcc ctagatattc tacttatcgt attgcttcat   5640
gaacacctta gtcatttttt actttacgta tatatttttt tatcatctca agaaatgcat   5700
tttgaattga atgaactatc ttctaagcta agatactcaa atttaacttt tagccaccctt  5760 atatgggaga gcctggaaac taaaggggac cagggaccat ttgaccaaaa gaggtgtttg   5820
gtggagtttc tgcatttcaa agaagaaagg ccagataggt catcacaatt cattgtatta   5880 ttctttttt ttccccttaa tgtttatgca aattttattt tatatttctg aatttggtta    5940
gcacatacta agccaaagac tattctaaat gcatttatag tgaatactat gtatgcccat   6000
ggtaatgggc cctccctaag gagtggtgaa tgtaattgtg tgaatcctgc ttatcacaag   6060
tggtgcaatt tggtcataaa ctttatttat accctgtata catctgaata acagagcaga   6120
```

```
aagacctaaa aaagggcttc tcacaggaac aatattacta tgttgttcta agaaaaaata    6180
agttgagtgc tgtattagtt taagtgtttc taaagttcta taggcagcat tttagaatta    6240
agaattgtgt atatccatta actgatataa ttcacatgtc cttttatttg ttatcagaaa    6300
gatcaatact atcccaattt attcaacttg ttacccaaga aatggaacca aaggaatcca    6360
actttcattt tgtgtagaat catacctact tatacttaat gctagcactg taagaaataa    6420 gtctttttg tttaaaaaag ggaagataag attaaagatt cttagtgaga tcatcttgcc     6480
aatttgttgt acatctctca ttcattgttg ggggaaaaaa aagcacaact atacctcttt    6540
aatgttattt tcttccatta tccctcattt atttggaaag ataagggaaa ccttgtctgt    6600
attatccaga agcacagata tttgcttgac acaatattta aattcagccc aatctttaac    6660
attaaaaaat tttcttttta acttgctgga aaagttggat acattggcaa atatagggaa    6720
ttcatgtctt tttttttttt ttttttctgg tcttgctctg ttgcctaggc tagagtgcaa    6780
cggcatgatc tcggctcact gcaacctctg cctcccgggt tcaagcaatt ctcctgcttc    6840
agcctcccaa gtagctggga ttacaggcgc ccaccaccgc acccggctaa ttttttgtatt   6900 tttagtaggg acgggatttc tccgtgttgg ccaggctttt tgaactcctg accttaggtg    6960
atctgcctgc cttggcctcc caaagtgctg ggattacagg tatgagccac tgtgcccatc    7020
ctcatgtcaa tttttaaagt gataaatcct gatattatac attgcaatta gtgtagaata    7080
aacgcttggc ttatagaact ctctgttctt agtctaaagc tgttcccaaa ccaggtcatc    7140
ctcacgaaac attcttgacc aagaaaaaag ataaggtcat tgagataggg agacagagga    7200
aaagcctctt gctgttgttt cttcccaaga aaggagaagc cctgccaggg agaagtcagt    7260
agtattgctg actcactgta tcactgagtg tagggtgtgg tagcaaggag gaggcagggg    7320
attcacgctg acaggtggct ctggcctggc tcttgggggg ccttctgaag accagtctgc    7380
agtttgagga agggcccaa caattcattt ggagagcttg gccaaatact ttctcattaa    7440
atcagcacct aaacttgatg aacttaaagt ttgtttatta gagttgaaaa cattaaaaga    7500
tgactgatac taatgggaga aaaatactaa agacccaaaa tttaaaattt tccaaaatgg    7560
acaagaattg atgggttaat ttgctcataa ctgatatgag tttgctttta tgtgtgtgtg    7620
gaaagcattt aatgtgtgat gctgttcata gtcctggcta tttgatgtca ttttcagttt    7680
tacaacattt tgaggatgac actttataaa atggtaaatc tttctcagcg tttacaaact    7740
tggcttttga gaagggaaaa atcctctttg ctatttctgt aagaagaata actgagatca    7800
gctattatat aggtttgcat ggatggtgtc cacaatacaa atgtaaactt ggacaggaat    7860
aggataaata aattgctttc atcataaagg ccaatcatcc atttcttagt ccaaggagat    7920
taaatataaa taggacaccc ctgagatttc cagtaaggta tttgaaagga ttccactggg    7980
agggcaggga atatatttt tctcagagca tccagtttgt acccagtttt ctatatggtt     8040
tgtgaactgt agcttttaaa aaaaaatttt gtagttttct tctaacctta ttcattaagt    8100
agttccttgt tttggccctt ctactcttgg ccttagctaa aagcagtaaa tgtgagtgaa    8160
ttttatgttg attatgtcac ctggatctcc tttccttccc ttcttttct cattgaatgg     8220 tggtacctta atttgggtaa cagctagctt ctggcaccctt cataaaatac ctcagaatag   8280
cttagcattg ttgcaaaact ggttttaaac taaaaaccaa ataaataagt gaaaaatttt    8340
tataaatagt ggaaataatt ctagctgtag catttagttg aactaatgtt tattatgatc    8400
gataaacaag attgatgctg tatgtatttg ggatcctgtt tataggttac aatttatagg    8460
gttagggagg gttgggtggg ggaagaggag atgttgatta tgttagaagg aaaacattgc    8520
```

-continued

```
tcgtgtgtgt gtttgttttt tcttatatct gtcttgccaa aggaaacttg attttccctg    8580
tgattggctt tggcctctgt ggtctggtct gcagcagtgt gtggtggcat gcaggtaaca    8640
tatggggtgt ccagtaggtt cagggaccct gagggtgcat ttacatccct tcctatggtt    8700
gcccatgccc cccagaccct gccaacctct cctaatgatt cattacctct gtacatagca    8760
aaagcatagg caaaggatga atgcgtgaat gcctggatgt gcagttgaga aacagaggca    8820
gacatagaca tgcaccaatt aatttggagc caagaggtga gtgattgatg tatcttaaat    8880
ctaggaaagt taaagtgaaa caggttcttt gtgttgccct ctgtcaagtt actgaatgtt    8940
gtgctaataa cacaacactt taaaacctta cttactttc tcataccaag gctagttctt    9000
tctagaccaa aaacacaaac aggataaaaa gcaaaccaag aagttgaaag ctaacctgcc    9060
cacctcaccc ctgtgataca aagtgtgaac cttaaggatt agttggtggg attgaggaga    9120
gaattattct tggtgggaac atgaatgaga aatgatgctg gcttaggaaa aatcacaagc    9180
cctttctgcc catactctgg gacaaacttt cttggctccc tgagttcgga tatagactgt    9240
atctctagaa aggctatttt tttaaataaa tgatcccaca gaacttaagt gggatttggt    9300
ttagatacca aagacactgc taatgtcatt gcttatcctt aagttttcaa acaggcaga    9360 gggaatagga gcaaaaagcc aaaatttgga aaagctttac tttatctctt tccttccctt    9420
ttcccctttt cccagtcccc tgctttttga aggaagtctt cttggttatc ctggctttgg    9480
aaaagagatt tattttgttt tgctctgctg gctctttaaa gatggatagt tgctcaatct    9540
agcagtgatg ttcttggaat tgctgagaaa tttggggagg gcaaaagata ggggtagaat    9600

tttttcatta tttcccttta tctaatactt ttaaatagaa ccaacacagc ctatatgagt    9660
tcagacaata tttagatgtg gtatctccat ctgtctcctg taaaagataa gaattttcaa    9720
gaacaggatt acgtggaaaa ccaaaagatc ttcccttact ctcctataaa tgttttgttc    9780
caaatgtttt tatatatggg ctctagggag tcaggtagtt cattgtttcg gtgtactatt    9840
gataggacac agaagggag agagggtaaa gaaatgtatc actctctgaa tattgcatca    9900
aaaatgatta ggttgcagaa cttcatgaaa gctttactaa taatcttatt gttctgacat    9960
tatgtaaagg tggtattaat attgtatgac ttgtcaaagt gctagatagg tttataagta   10020
ggtaataggg atgttgaaga ttagagcact tgaaacagaa gttctgggaa aacaaggtgt   10080
gtgtaatgga acaccacttt gagcacagaa acaaggtcc cttggacctg gtagggaaga   10140 tgtgattat gattgtttct gtgtccctgt atctgcccac cctgcacagg gctccaccac   10200
ccagggccac cttctggttt aaacccagga cactgtcaaa aagttaagac cccaaaacta   10260
atttactgta aaaaacattg aggactgctg caaagttttc ccttgttttc tttgtgtact   10320

tgttcatcat tgtataagtt agccacagct tcacaagagc agcttaaggc ttctttcata   10380
aattggcagt ggcattgagt tctcaaacat tatatcccaa agtctgcagg cagacagctg   10440
gatacagcgc tgtgtataaa tgagacgtcc aaacacttga gtttcttaag attgggatct   10500
ctttcaaatg aaaaaggaca gagccaagta gagaaaagac tttgtgctcc cacccagcct   10560
taatgagtct catggtctaa agtatagga agaaatgaaa tgcactttca gaagctaaaa   10620

tgacagtgtc tgctacaaaa ggctgtagtt gtaggcagtc ggggatgcca tgtccttggt   10680

tccattcctg cgtgagtctg cagaaggcac acactttgta agagtagagt ggactagtgc   10740
cagcctgaat aggtttaaaa ctgcaaacag ttggagaaca tggaacaggt tggtgcagga   10800
agcctaagat tttgcaatca tattataaca ttggcttttg acaacataaa tgttgtatct   10860
```

```
tccctaaggt caggtcgggg aaagaaagac ttccagcttc ttacctctgc gtgcatgggc   10920
acgtgtgcat tgctcagtcc gcaggaggtc tcactccgca ggaaacgctc tcctcccgca   10980
taagtctgta cttccatccc ctcatctgtg gtagtagtga aggctaggtg agtaagcgtg   11040
ggctgttcta cccaccagaa gtccaggagc tgttgtatac ctcatttcta actcgtgacc   11100
gagtgacttg ctttaacttt ctcgaaatcc tacagagttg ccaagtctgc cctccctcct   11160
cagtcatgtt aaactctggc ctatagcatc atgggacctg tagcctaggg tgggacccccc   11220 taaagcctct gaatgtcgct gcttaaaagc tactgcaaac tgagggcaaa ttgcaatctt   11280
ctattccttt ttgttgcaag gggtcttcac aggtctctta acatctgctt tccctgccac   11340
cctgccttta ggggctggcc agctatccac acccctaacc caccctgtgt ttctgacagc   11400
tggccacacg tcaacttctg tacttgcctt ttccttggtg gggtagaggc caacccccttc   11460 tcctctgagg cctcagggtt ctgtttcttt tcaggacttt gggtagaagg gaagacacca   11520
aaggctcctt taagctgact gctgcataca catttcactt ttttttccttt gacatgacca   11580 aaaatatcca aatatttaag tttattatta ttattattat tatttgacaa tcttatatcc   11640
aatgggctct ctagaagctg catccccagc cctttcacct tttctttgaa tgtagttccc   11700
aaccttcaat tcccaccccct aatgctgaca aaaagcttag ccaggtcatg atactgctgc   11760
tataagccag gggagggtgg tttctttgtt ttgttttgtt ttgttttgtt tttcaaattt   11820
ccagccaaaa ccaaagattt cttaatgatt gtataaactc aaaacaaaca aaagaaccaa   11880
agaaaaggga agtcttcagc atcagtccag tctgtggtgt cctggcactt agaagagtga   11940
ggccagggaa ggtggggcgg gggggaccctc tgactggatc agaaagggca ggcaagctgc   12000
ttaccacctt ccagggtcca gcacaggtgc atgcccctag cttttggcccct cacaaacttg   12060 tgagcatgcc ctgaaacaaa ttggcatttc agattttcca aaacaaaagt caaaaaaccc   12120
catcaccacc atcatccacc ctacaccaac cagggtcact atggggactt agcacagggc   12180
ctagggaggt ggggagctgc tgctggactg gcccgaggac tccacagagt gggggacgtt   12240
gaagacactg gcgcacgatt ggctgctctg ctgggtgctt taacctctgg ggctgggcga   12300
atgcacgcca cggtgccctt ctgagccttt ttttctttttc ctgtactgga actgcttgga   12360
agtggctgtc ctgtttgtga gaaaacatgc agaaagatta tcaagctttt catttctctt   12420
tattgtagtt ttcttttcctt tttgcagcac cactgtgcaa ctatgcattg tacttcacaa   12480 cctttttgtgc taggtagatg cctgtgactt tttaacttgg ggggtggggg gattgcaaat   12540
gaaggaactt tttacatgga tcttttttaat ctcagttggt tgggggaggg gggtacttgg   12600
ttcttgggtc acacaagctc tatcccaaag caaaatccaa atgttaataa tattagcctg   12660
atgcagatac caaagataat ttctttcctg cagaaccta gactcgtgta ttaagtacga   12720
ttacccagca cttgcattag tctaacctca gtaattccaa agcttagatg tatatttttgg   12780 tatatttctg ggatattaaa aaaaaaatgt cgtttaactt cttgtttgtt tcagtgtaat   12840
gctcttaaag tcatagcatg aaaataattg aactgtccta ttcttagtag tttgaaataa   12900 tagtatttttt gtatgttttg ggtgtgtcta tgtatgtatt aacataacag ttttcactgc   12960
ctaggtgttc ataataaaaa agaaaatgaa aaaagttctg agtgtacata atattcaata   13020
ataatctccc accaggtgtc aatttagatt gcatattcct cattactgtt cccaactggg   13080 attttgttttt ctttttaaaga gacagtgatc gtgttttttct aaagatgttt tctttctctc   13140
tttcaatatc ttaactcact tttttttttct tccttttttg tcttaattat taattcaggg   13200
gtgtttgtcc actgttgtca aaggagggggc acaaggggaa ttggccccccg gcctcctaga   13260
```

```
acttttttgtt ttatgtactt taaaatgtga gtttgagttc ttctttgtgg aaacttaaga    13320
tgtggtgtaa atgattcttt ccaaaattgt ccagcagctt gaatgaggca gtgacaattc    13380
tgaggtggtt tattgggagt ccttctacat ttctcttaga taactctgca ctctgggtgg    13440
ctattgtgta gccttactgc cccagagtgc ctgttagcca aatatttccc ctctgatagg    13500
aatattttct aagaatcagc tgataacttg cgtgctggac cttgttatct gtgcccctgg    13560
gagacacacg ttttcttggt tttgaaaacc tgaaacacag gcaactttac attttgggga    13620
attagctgat gcctcctgaa gcctgaggag gtggcgggga atatgagcgg tgctgtctct    13680
ctcaaaagtg ccctttagat gattccccct cctaggctg cctgcagggg ctgtaggctt     13740
gggaaagatt gtgtaggtga cagtgaatca gaatgaagtg gtagattttg tgtagatgca    13800
tttgtctgct gtaattttt atatatat taaacttact gtaactgtac agttcatttc       13860
tgttgtaaaa catcattaaa ccatcttcca agtgttttca cattg                     13905

<210> SEQ ID NO 32
<211> LENGTH: 4507
<212> TYPE: DNA
<213> ORGANISM: Homo sapiens

<400> SEQUENCE: 32
gaccaattgt catacgactt gcagtgagcg tcaggagcac gtccaggaac tcctcagcag     60
cgcctccttc agctccacag ccagacgccc tcagacagca aagcctaccc ccgcgccgcg   120
ccctgcccgc cgctgcgatg ctcgcccgcg ccctgctgct gtgcgcggtc ctggcgctca   180
gccatacagc aaatccttgc tgttcccacc catgtcaaaa ccgaggtgta tgtatgagtg   240
tgggatttga ccagtataag tgcgattgta cccggacagg attctatgga gaaaactgct   300
caacaccgga atttttgaca agaataaaat tatttctgaa acccactcca aacacagtgc   360
actacatact tacccacttc aagggatttt ggaacgttgt gaataacatt cccttccttc   420
gaaatgcaat tatgagttat gtgttgacat ccagatcaca tttgattgac agtccaccaa   480
cttacaatgc tgactatggc tacaaaagct gggaagcctt ctctaacctc tcctattata   540
ctagagccct tcctcctgtg cctgatgatt gcccgactcc cttgggtgtc aaaggtaaaa   600
agcagcttcc tgattcaaat gagattgtgg aaaaattgct tctaagaaga agttcatcc    660 ctgatcccca gggctcaaac atgatgtttg cattctttgc ccagcacttc acgcatcagt   720
ttttcaagac agatcataag cgagggccag cttttcaccaa cgggctgggc catgggtgg   780 acttaaatca tatttacggt gaaactctgg ctagacagcg taaactgcgc ctttcaagg    840 atggaaaaat gaaatatcag ataattgatg gagagatgta tcctccaca gtcaaagata    900 ctcaggcaga gatgatctac cctcctcaag tccctgagca tctacggttt gctgtggggc   960
aggaggtctt tggtctggtg cctggtctga tgatgtatgc cacaatctgg ctgcgggaac   1020
acaacagagt atgcgatgtg cttaaacagg agcatcctga tggggtgat gagcagttgt    1080 tccagacaag caggctaata ctgataggag agactattaa gattgtgatt gaagattatg   1140
tgcaacactt gagtggctat cacttcaaac tgaaatttga cccagaacta cttttcaaca   1200
aacaattcca gtaccaaaat cgtattgctg ctgaatttaa caccctctat cactggcatc   1260
cccttctgcc tgacaccttt caaattcatg accagaaata caactatcaa cagtttatct   1320
acaacaactc tatattgctg gaacatggaa ttacccagtt tgttgaatca ttcaccaggc   1380
aaattgctgg cagggttgct ggtggtagga atgttccacc cgcagtacag aaagtatcac   1440
```

```
aggcttccat tgaccagagc aggcagatga ataccagtc ttttaatgag taccgcaaac    1500
gctttatgct gaagccctat gaatcatttg aagaacttac aggagaaaag gaaatgtctg    1560
cagagttgga agcactctat ggtgacatcg atgctgtgga gctgtatcct gcccttctgg    1620
tagaaaagcc tcggccagat gccatctttg gtgaaaccat ggtagaagtt ggagcaccat    1680
tctccttgaa aggacttatg ggtaatgtta tatgttctcc tgcctactgg aagccaagca    1740
cttttggtgg agaagtgggt tttcaaatca tcaacactgc ctcaattcag tctctcatct    1800
gcaataacgt gaagggctgt ccctttactt cattcagtgt tccagatcca gagctcatta    1860
aaacagtcac catcaatgca agttcttccc gctccggact agatgatatc aatcccacag    1920
tactactaaa agaacgttcg actgaactgt agaagtctaa tgatcatatt tatttattta    1980
tatgaaccat gtctattaat ttaattattt aataatattt atattaaact ccttatgtta    2040
cttaacatct tctgtaacag aagtcagtac tcctgttgcg gagaaaggag tcatacttgt    2100
gaagactttt atgtcactac tctaaagatt ttgctgttgc tgttaagttt ggaaaacagt    2160
ttttattctg ttttataaac cagagagaaa tgagttttga cgtcttttta cttgaatttc    2220
aacttatatt ataagaacga aagtaaagat gtttgaatac ttaaacactg tcacaagatg    2280
gcaaaatgct gaaagttttt acactgtcga tgtttccaat gcatcttcca tgatgcatta    2340
gaagtaacta atgtttgaaa ttttaaagta cttttggtta ttttctgtc atcaaacaaa    2400 aacaggtatc agtgcattat taaatgaata tttaaattag acattaccag taatttcatg    2460 tctactttt aaaatcagca atgaaacaat aatttgaaat ttctaaattc atagggtaga    2520
atcacctgta aaagcttgtt tgatttctta aagttattaa acttgtacat ataccaaaaa    2580
gaagctgtct tggatttaaa tctgtaaaat cagtagaaat tttactacaa ttgcttgtta    2640
aaatatttta taagtgatgt tccttttca ccaagagtat aaacctttt agtgtgactg    2700 ttaaaacttc cttttaaatc aaaatgccaa atttattaag gtggtggagc cactgcagtg    2760
ttatcttaaa ataagaatat tttgttgaga tattccagaa tttgtttata tggctggtaa    2820
catgtaaaat ctatatcagc aaaagggtct acctttaaaa taagcaataa caaagaagaa    2880
aaccaaatta ttgttcaaat ttaggtttaa acttttgaag caaactttt ttatccttg    2940 tgcactgcag gcctggtact cagattttgc tatgaggtta atgaagtacc aagctgtgct    3000
tgaataatga tatgttttct cagattttct gttgtacagt ttaatttagc agtccatatc    3060
acattgcaaa agtagcaatg acctcataaa atacctcttc aaaatgctta aattcatttc    3120
acacattaat tttatctcag tcttgaagcc aattcagtag gtgcattgga atcaagcctg    3180
gctacctgca tgctgttcct tttctttct tcttttagcc atttgctaa gagacacagt    3240 cttctcatca cttcgtttct cctattttgt tttactagtt ttaagatcag agttcacttt    3300
ctttggactc tgcctatatt ttcttacctg aacttttgca agttttcagg taaacctcag    3360
ctcaggactg ctatttagct cctcttaaga agattaaaag agaaaaaaa aggccctttt    3420 aaaaatagta tacacttatt ttaagtgaaa agcagagaat ttatttata gctaattta    3480 gctatctgta accaagatgg atgcaaagag gctagtgcct cagagagaac tgtacggggt    3540
ttgtgactgg aaaaagttac gttcccattc taattaatgc cctttcttat ttaaaaacaa    3600
aaccaaatga tatctaagta gttctcagca ataataataa tgacgataat acttctttc    3660 cacatctcat tgtcactgac atttaatggt actgtatatt acttaattta ttgaagatta    3720 ttatttgt cttattagga cactatggtt ataaactgtg tttaagccta caatcattga    3780 ttttttttg ttatgtcaca atcagtatat tttctttggg gttacctctc tgaatattat    3840
```

| | |
|---|---|
| gtaaacaatc caaagaaatg attgtattaa gatttgtgaa taaatttta gaaatctgat | 3900 |
| tggcatattg agatatttaa ggttgaatgt ttgtccttag gataggccta tgtgctagcc | 3960 |
| cacaaagaat attgtctcat tagcctgaat gtgccataag actgaccttt taaaatgttt | 4020 |
| tgagggatct gtggatgctt cgttaatttg ttcagccaca atttattgag aaatattct | 4080 |
| gtgtcaagca ctgtgggttt taatattttt aaatcaaacg ctgattacag ataatagtat | 4140 |
| ttatataaat aattgaaaaa aatttctttt tgggaagagg gagaaaatga aataaatatc | 4200 |
| attaaagata actcaggaga atcttcttta caattttacg tttagaatgt ttaaggttaa | 4260 |
| gaaagaaata gtcaatatgc ttgtataaaa cactgttcac tgttttttt aaaaaaaaa | 4320 |
| cttgatttgt tattaacatt gatctgctga caaaacctgg gaatttgggt tgtgtatgcg | 4380 |
| aatgtttcag tgcctcagac aaatgtgtat ttaacttatg taaagataa gtctggaaat | 4440 |
| aaatgtctgt ttatttttgt actatttaaa aattgacaga tcttttctga agaaaaaaaa | 4500 |
| aaaaaaa | 4507 |

<210> SEQ ID NO 33
<211> LENGTH: 579
<212> TYPE: DNA
<213> ORGANISM: Homo sapiens

<400> SEQUENCE: 33

| | |
|---|---|
| aggctcagta taaatagcag ccaccgctcc ctggcaggca gggacccgca gctcagctac | 60 |
| agcacagatc agcaccatga agcttctcac gggcctggtt ttctgctcct tggtcctggg | 120 |
| tgtcagcagc cgaagcttct tttcgttcct tggcgaggct tttgatgggg ctcgggacat | 180 |
| gtggagagcc tactctgaca tgagagaagc caattacatc ggctcagaca atacttcca | 240 |
| tgctcggggg aactatgatg ctgccaaaag gggacctggg ggtgcctggg ctgcagaagt | 300 |
| gatcagcgat gccagagaga atatccagag attctttggc catggtgcgg aggactcgct | 360 |
| ggctgatcag gctgccaatg aatggggcag gagtggcaaa gaccccaatc acttccgacc | 420 |
| tgctggcctg cctgagaaat actgagcttc ctcttcactc tgctctcagg agatctggct | 480 |
| gtgaggccct cagggcaggg atacaaagcg gggagagggt acacaatggg tatctaataa | 540 |
| atacttaaga ggtggaattt gtggaaaaaa aaaaaaaaa | 579 |

<210> SEQ ID NO 34
<211> LENGTH: 4326
<212> TYPE: DNA
<213> ORGANISM: Homo sapiens

<400> SEQUENCE: 34

| | |
|---|---|
| gctgagcgcg gagccgcccg gtgattggtg ggggcggaag ggggccgggc gccagcgctg | 60 |
| cctttctcc tgccgggtag tttcgctttc ctgcgcagag tctgcggagg ggctcggctg | 120 |
| caccgggggg atcgcgcctg gcagaccca gaccgagcag aggcgaccca gcgcgctcgg | 180 |
| gagaggctgc accgccgcgc cccgcctag cccttccgga tcctgcgcgc agaaaagttt | 240 |
| catttgctgt atgccatcct cgagagctgt ctaggttaac gttcgcactc tgtgtatata | 300 |
| acctcgacag tcttggcacc taacgtgctg tgcgtagctg ctcctttggt tgaatcccca | 360 |
| ggcccttgtt ggggcacaag gtggcaggat gtctcagtgg tacgaacttc agcagcttga | 420 |
| ctcaaaattc ctggagcagg ttcaccagct ttatgatgac agttttccca tggaaatcag | 480 |
| acagtacctg gcacagtggt tagaaaagca agactgggag cacgctgcca atgatgtttc | 540 |

```
atttgccacc atccgttttc atgacctcct gtcacagctg atgatcaat atagtcgctt    600
ttctttggag aataacttct tgctacagca taacataagg aaaagcaagc gtaatcttca    660
ggataatttt caggaagacc caatccagat gtctatgatc atttacagct gtctgaagga    720
agaaaggaaa attctggaaa acgcccagag atttaatcag gctcagtcgg ggaatattca    780
gagcacagtg atgttagaca aacagaaaga gcttgacagt aaagtcagaa atgtgaagga    840
caaggttatg tgtatagagc atgaaatcaa gagcctggaa gatttacaag atgaatatga    900
cttcaaatgc aaaaccttgc agaacagaga acacgagacc aatggtgtgg caaagagtga    960
tcagaaacaa gaacagctgt tactcaagaa gatgtattta atgcttgaca taagagaaaa   1020
ggaagtagtt cacaaaataa tagagttgct gaatgtcact gaacttaccc agaatgccct   1080
gattaatgat gaactagtgg agtggaagcg gagacagcag agcgcctgta ttgggggggcc   1140
gcccaatgct tgcttggatc agctgcagaa ctggttcact atagttgcgg agagtctgca   1200
gcaagttcgg cagcagctta aaagttgga ggaattggaa cagaaataca cctacgaaca   1260
tgaccctatc acaaaaaaca aacaagtgtt atgggaccgc accttcagtc ttttccagca   1320
gctcattcag agctcgtttg tggtggaaag acagccctgc atgccaacgc accctcagag   1380
gccgctggtc ttgaagacag gggtccagtt cactgtgaag ttgagactgt tggtgaaatt   1440
gcaagagctg aattataatt tgaaagtcaa agtcttattt gataaagatg tgaatgagag   1500
aaaatacagta aaaggattta ggaagttcaa cattttgggc acgcacacaa aagtgatgaa   1560
catggaggag tccaccaatg gcagtctggc ggctgaattt cggcacctgc aattgaaaga   1620
acagaaaaat gctggcacca gaacgaatga gggtcctctc atcgttactg aagagcttca   1680
ctcccttagt tttgaaaccc aattgtgcca gcctggtttg gtaattgacc tcgagacgac   1740
ctctctgccc gttgtggtga tctccaacgt cagccagctc ccgagcggtt gggcctccat   1800
cctttggtac aacatgctgg tggcggaacc caggaatctg tccttcttcc tgactccacc   1860
atgtgcacga tgggctcagc tttcagaagt gctgagttgg cagttttctt ctgtcaccaa   1920
aagaggtctc aatgtggacc agctgaacat gttgggagag aagcttcttg gtcctaacgc   1980
cagccccgat ggtctcattc cgtggacgag gttttgtaag gaaaatataa atgataaaaa   2040
ttttccttc tggctttgga ttgaaagcat cctagaactc attaaaaaac acctgctccc   2100
tctctggaat gatgggtgca tcatgggctt catcagcaag gagcgagagc gtgccctgtt   2160
gaaggaccag cagccgggga ccttcctgct gcggttcagt gagagctccc gggaaggggc   2220
catcacattc acatgggtgg agcggtccca aacggaggc gaacctgact tccatgcggt   2280
tgaaccctac acgaagaaag aactttctgc tgttactttc cctgacatca ttcgcaatta   2340
caaagtcatg gctgctgaga atattcctga gaatcccctg aagtatctgt atccaaatat   2400
tgacaaagac catgcctttg aaagtattca ctccaggcca aaggaagcac cagagccaat   2460
ggaacttgat ggccctaaag aactggata tatcaagact gagttgattt ctgtgtctga   2520
agttcacccct tctagacttc agaccacaga caacctgctc cccatgtctc ctgaggagtt   2580
tgacgaggtg tctcggatag tgggctctgt agaattcgac agtatgatga acacagtata   2640
gagcatgaat ttttttcatc ttctctggcg acagttttcc ttctcatctg tgattccctc   2700
ctgctactct gttccttcac atcctgtgtt tctagggaaa tgaaagaaag gccagcaaat   2760
tcgctgcaac ctgttgatag caagtgaatt tttctctaac tcagaaacat cagttactct   2820
gaagggcatc atgcatctta ctgaaggtaa aattgaaagg cattctctga agagtgggtt   2880
tcacaagtga aaaacatcca gatacaccca agtatcagg acgagaatga gggtcctttg   2940
```

```
ggaaaggaga agttaagcaa catctagcaa atgttatgca taaagtcagt gcccaactgt   3000
tataggttgt tggataaatc agtggttatt tagggaactg cttgacgtag gaacggtaaa   3060
tttctgtggg agaattctta catgttttct ttgctttaag tgtaactggc agttttccat   3120
tggtttacct gtgaaatagt tcaaagccaa gtttatatac aattatatca gtcctctttc   3180
aaaggtagcc atcatggatc tggtagggggg aaaatgtgta ttttattaca tctttcacat   3240
tggctattta aagacaaaga caaattctgt ttcttgagaa gagaatatta gctttactgt   3300
ttgttatggc ttaatgacac tagctaatat caatagaagg atgtacattt ccaaattcac   3360
aagttgtgtt tgatatccaa agctgaatac attctgcttt catcttggtc acatacaatt   3420 attttttacag ttctcccaag ggagttaggc tattcacaac cactcattca aaagttgaaa   3480
ttaaccatag atgtagataa actcagaaat ttaattcatg tttcttaaat gggctacttt   3540 gtccttttttg ttattagggt ggtatttagt ctattagcca caaaattggg aaaggagtag   3600
aaaaagcagt aactgacaac ttgaataata caccagagat aatatgagaa tcagatcatt   3660
tcaaaactca tttcctatgt aactgcattg agaactgcat atgtttcgct gatatatgtg   3720 ttttttcacat ttgcgaatgg ttccattctc tctcctgtac ttttttccaga cactttttttg   3780 agtggatgat gtttcgtgaa gtatactgta ttttttacctt tttccttcct tatcactgac   3840
acaaaaagta gattaagaga tgggtttgac aaggttcttc ccttttacat actgctgtct   3900
atgtggctgt atcttgtttt tccactactg ctaccacaac tatattatca tgcaaatgct   3960
gtattcttct ttggtggaga taaagatttc ttgagttttg ttttaaaatt aaagctaaag   4020
tatctgtatt gcattaaata taatatgcac acagtgcttt ccgtggcact gcatacaatc   4080
tgaggcctcc tctctcagtt tttatataga tggcgagaac ctaagtttca gttgatttta   4140
caattgaaat gactaaaaaa caaagaagac aacattaaaa caatattgtt tctaattgct   4200
gaggtttagc tgtcagttct ttttgcccctt tgggaattcg gcatggtttc attttactgc   4260
actagccaag agactttact tttaagaagt attaaaattc taaaattcaa aaaaaaaaaa   4320
aaaaaa                                                               4326
```

<210> SEQ ID NO 35
<211> LENGTH: 931
<212> TYPE: DNA
<213> ORGANISM: Homo sapiens

<400> SEQUENCE: 35

```
tttcgtcggc cgccccttg gcttctgcac tgatggtggg tggatgagta atgcatccag     60
gaagcctgga ggcctgtggt ttccgcaccc gctgccaccc ccgcccctag cgtggacatt    120
tatcctctag cgctcaggcc ctgccgccat cgccgcagat ccagcgccca gagagacacc    180
agagaaccca ccatggcccc ctttgagccc ctggcttctg gcatcctgtt gttgctgtgg    240
ctgatagccc ccagcagggc ctgcacctgt gtcccacccc acccacagac ggccttctgc    300
aattccgacc tcgtcatcag ggccaagttc gtggggacac cagaagtcaa ccagaccacc    360
ttataccagc gttatgagat caagatgacc aagatgtata aagggttcca agccttaggg    420
gatgccgctg acatccggtt cgtctacacc cccgccatgg agagtgtctg cggatacttc    480
cacaggtccc acaaccgcag cgaggagttt ctcattgctg gaaaactgca ggatggactc    540
ttgcacatca ctacctgcag ttttgtggct ccctggaaca gcctgagctt agctcagcgc    600
cggggcttca ccaagaccta cactgttggc tgtgaggaat gcacagtgtt tccctgttta    660
```

```
tccatcccct gcaaactgca gagtggcact cattgcttgt ggacggacca gctcctccaa      720
ggctctgaaa agggcttcca gtcccgtcac cttgcctgcc tgcctcggga gccagggctg      780
tgcacctggc agtccctgcg gtcccagata gcctgaatcc tgcccggagt ggaagctgaa      840
gcctgcacag tgtccaccct gttcccactc ccatctttct tccggacaat gaaataaaga      900
gttaccaccc agcagaaaaa aaaaaaaaaa a                                     931

<210> SEQ ID NO 36
<211> LENGTH: 3682
<212> TYPE: DNA
<213> ORGANISM: Homo sapiens

<400> SEQUENCE: 36
gcgagcgcag cggagcctgg agagaaggcg ctgggctgcg agggcgcgag ggcgcgaggg       60 caggggcaa ccggaccccg cccgcaccca tggcgcccgt cgccgtctgg gccgcgctgg      120
ccgtcggact ggagctctgg gctgcggcgc acgccttgcc cgcccaggtg gcatttacac      180
cctacgcccc ggagcccggg agcacatgcc ggctcagaga atactatgac cagacagctc      240
agatgtgctg cagcaaatgc tcgccgggcc aacatgcaaa agtcttctgt accaagacct      300
cggacaccgt gtgtgactcc tgtgaggaca gcacatacac ccagctctgg aactgggttc      360
ccgagtgctt gagctgtggc tcccgctgta gctctgacca ggtggaaact caagcctgca      420
ctcgggaaca gaaccgcatc tgcacctgca ggcccggctg gtactgcgcg ctgagcaagc      480
aggaggggtg ccggctgtgc gcgccgctgc gcaagtgccg cccgggcttc ggcgtggcca      540
gaccaggaac tgaaacatca gacgtggtgt gcaagccctg tgccccgggg acgttctcca      600
acacgacttc atccacggat atttgcaggc ccaccagat ctgtaacgtg gtggccatcc       660
ctgggaatgc aagcatggat gcagtctgca cgtccacgtc ccccacccgg agtatggccc      720
caggggcagt acacttaccc cagccagtgt ccacacgatc ccaacacacg cagccaactc      780
cagaacccag cactgctcca agcacctcct tcctgctccc aatgggcccc agcccccag      840 ctgaagggag cactggcgac ttcgctcttc cagttggact gattgtgggt gtgacagcct      900
tgggtctact aataatagga gtggtgaact gtgtcatcat gacccaggtg aaaaagaagc      960
ccttgtgcct gcagagagaa gccaaggtgc ctcacttgcc tgccgataag gcccggggta     1020
cacagggccc cgagcagcag cacctgctga tcacagcgcc gagctccagc agcagctccc     1080
tggagagctc ggccagtgcg ttggacagaa gggcgcccac tcggaaccag ccacaggcac     1140
caggcgtgga ggccagtggg gccggggagg cccgggccag caccgggagc tcagattctt     1200
cccctggtgg ccatgggacc caggtcaatg tcacctgcat cgtgaacgtc tgtagcagct     1260
ctgaccacag ctcacagtgc tcctcccaag ccagctccac aatgggagac acagattcca     1320
gcccctcgga gtccccgaag gacgagcagg tcccttctc aaggaggaa tgtgcctttc       1380 ggtcacagct ggagacgcca gagccctgc tggggagcac cgaagagaag cccctgcccc     1440
ttggagtgcc tgatgctggg atgaagccca gttaaccagg ccggtgtggg ctgtgtcgta     1500
gccaaggtgg gctgagccct ggcaggatga ccctgcgaag gggccctggt ccttccaggc     1560
ccccaccact aggactctga ggctctttct gggccaagtt cctctagtgc cctccacagc     1620
cgcagcctcc ctctgacctg caggccaaga gcagaggcag cgagttgtgg aaagcctctg     1680
ctgccatggc gtgtccctct cggaaggctg gctgggcatg gacgttcggg gcatgctggg     1740
gcaagtccct gactctctgt gacctgcccc gccagctgc acctgccagc ctggcttctg      1800
gagcccttgg gttttttgtt tgtttgtttg tttgtttgtt tgtttctccc cctgggctct     1860
```

```
gccccagctc tggcttccag aaaacccag catcctttc tgcagagggg ctttctggag    1920
aggagggatg ctgcctgagt cacccatgaa gacaggacag tgcttcagcc tgaggctgag    1980
actgcgggat ggtcctgggg ctctgtgcag ggaggaggtg gcagccctgt agggaacggg    2040
gtccttcaag ttagctcagg aggcttggaa agcatcacct caggccaggt gcagtggctc    2100
acgcctatga tcccagcact ttgggaggct gaggcgggtg gatcacctga ggttaggagt    2160
tcgagaccag cctggccaac atggtaaaac cccatctcta ctaaaaatac agaaattagc    2220
cgggcgtggt ggcgggcacc tatagtccca gctactcaga agcctgaggc tgggaaatcg    2280
tttgaacccg ggaagcggag gttgcaggga gccgagatca cgccactgca ctccagcctg    2340
ggcgacagag cgagagtctg tctcaaaaga aaaaaaaaag caccgcctcc aaatgccaac    2400
ttgtcctttt gtaccatggt gtgaaagtca gatgcccaga gggcccaggc aggccaccat    2460
attcagtgct gtggcctggg caagataacg cacttctaac tagaaatctg ccaattttt    2520 aaaaaagtaa gtaccactca ggccaacaag ccaacgacaa agccaaactc tgccagccac    2580
atccaacccc ccacctgcca tttgcaccct ccgccttcac tccggtgtgc ctgcagcccc    2640
gcgcctcctt ccttgctgtc ctaggccaca ccatctcctt tcagggaatt tcaggaacta    2700
gagatgactg agtcctcgta gccatctctc tactcctacc tcagcctaga ccctcctcct    2760
cccccagagg ggtgggttcc tcttccccac tccccacctt caattcctgg gccccaaacg    2820
ggctgccctg ccactttggt acatggccag tgtgatccca agtgccagtc ttgtgtctgc    2880
gtctgtgttg cgtgtcgtgg gtgtgtgtag ccaaggtcgg taagttgaat ggcctgcctt    2940
gaagccactg aagctgggat tcctccccat tagagtcagc cttcccctc ccagggccag    3000 ggccctgcag aggggaaacc agtgtagcct tgcccggatt ctgggaggaa gcaggttgag    3060
gggctcctgg aaaggctcag tctcaggagc atggggataa aggagaaggc atgaaattgt    3120
ctagcagagc aggggcaggg tgataaattg ttgataaatt ccactggact tgagcttggc    3180
agctgaacta ttggagggtg ggagagccca gccattacca tggagacaag aagggttttc    3240
caccctggaa tcaagatgtc agactggctg gctgcagtga cgtgcacctg tactcaggag    3300
gctgagggga ggatcactgg agcccaggag tttgaggctg cagcgagcta tgatcgcgcc    3360
actacactcc agcctgagca acagagtgag accctgtctc ttaaagaaaa aaaagtcag    3420 actgctggga ctggccaggt ttctgcccac attggaccca catgaggaca tgatggagcg    3480
cacctgcccc ctggtggaca gtcctgggag aacctcaggc ttccttggca tcacagggca    3540
gagccgggaa gcgatgaatt tggagactct gtggggcctt ggttcccttg tgtgtgtgtg    3600
ttgatcccaa gacaatgaaa gtttgcactg tatgctggac ggcattcctg cttatcaata    3660
aacctgtttg ttttaaaaaa aa                                            3682

<210> SEQ ID NO 37
<211> LENGTH: 1669
<212> TYPE: DNA
<213> ORGANISM: Homo sapiens

<400> SEQUENCE: 37
gaggtataag agcctccaag tctgcagctc tcgcccaact cccagacacc tcgcgggctc      60
tgcagcaccg gcaccgtttc caggaggcct ggcggggtgt gcgtccagcc gttgggcgct     120 ttcttttgg acctcgggc catccacacc gtccctccc cctccgcct ccctccccgc     180 ctcccccgcg cgccctcccc gcggaggtcc ctcccgtccg tcctcctgct ctctcctccg     240
```

```
cgggccgcat cgcccgggcc ggcgccgcgc gcggggggaag ctggcgggct gaggcgcccc    300
gctcttctcc tctgcccgg gcccgcgagg ccacgcgtcg ccgctcgaga gatgatgcag     360
gacgtgtcca gctcgccagt ctcgccggcc gacgacagcc tgagcaacag cgaggaagag   420
ccagaccggc agcagccgcc gagcggcaag cgcggggggac gcaagcggcg cagcagcagg   480
cgcagcgcgg gcggcggcgc ggggcccggc ggagccgcgg gtgggggcgt cggaggcggc   540
gacgagccgg gcagcccggc ccagggcaag cgcggcaaga agtctgcggg ctgtggcggc   600
ggcggcggcg cgggcggcgg cggcggcagc agcagcggcg gcgggagtcc gcagtcttac   660
gaggagctgc agacgcagcg ggtcatggcc aacgtgcggg agcgccagcg cacccagtcg   720
ctgaacgagg cgttcgccgc gctgcggaag atcatcccca cgctgccctc ggacaagctg   780
agcaagattc agaccctcaa gctggcggcc aggtacatcg acttcctcta ccaggtcctc   840
cagagcgacg agctggactc caagatggca agctgcagct atgtggctca cgagcggctc   900
agctacgcct tctcggtctg gaggatggag ggggcctggt ccatgtccgc gtcccactag   960
caggcggagc ccccacccc ctcagcaggg ccggagacct agatgtcatt gtttccagag   1020
aaggagaaaa tggacagtct agagactctg gagctggata actaaaaata aaaatatatg   1080
ccaaagattt tcttggaaat tagaagagca aaatccaaat tcaaagaaac agggcgtggg   1140
gcgcactttt aaaagagaaa gcgagacagg cccgtggaca gtgattccca gacgggcagc   1200
ggcaccatcc tcacacctct gcattctgat agaagtctga acagttgttt gtgtttttt    1260
ttttttttt tttgacgaag aatgttttta ttttttatttt tttcatgcat gcattctcaa   1320
gaggtcgtgc caatcagcca ctgaaaggaa aggcatcact atggactttc tctattttaa   1380
aatggtaaca atcagaggaa ctataagaac acctttagaa ataaaaatac tgggatcaaa   1440
ctggcctgca aaaccatagt cagttaattc ttttttcat ccttcctctg aggggaaaaa    1500
caaaaaaaaa cttaaaatac aaaaaacaac attctattta tttattgagg acccatggta   1560
aaatgcaaat agatccggtg tctaaatgca ttcatatttt tatgattgtt ttgtaaatat   1620
ctttgtatat ttttctgcaa taaataaata taaaaatttt agagaaaaa                1669
```

<210> SEQ ID NO 38
<211> LENGTH: 2195
<212> TYPE: DNA
<213> ORGANISM: Homo sapiens

<400> SEQUENCE: 38

```
aagaaaaacc ttcccggtgc aatcgtgatc tgggaggccc acgtatggcg cctctccaaa     60
ggctgcagaa gtttcttgct aacaaaaagt ccgcacattc gagcaaagac aggctttagc    120
gagttattaa aaacttaggg gcgctcttgt ccccacagg gcccgaccgc acacagcaag    180
gcgatggccc agctgtaagt tggtagcact gagaactagc agcgcgcgcg gagcccgctg    240
agacttgaat caatctggtc taacggtttc ccctaaaccg ctaggagccc tcaatcggcg   300
ggacagcagg gcgcgtcctc tgccactctc gctccgaggt ccccgcgcca gagacgcagc   360
cgcgctccca ccacccacac ccaccgcgcc ctcgttcgcc tcttctccgg gagccagtcc   420
gcgccaccgc cgccgcccag gccatcgcca ccctccgcag ccatgtccac caggtccgtg   480
tcctcgtcct cctaccgcag gatgttcggc ggcccgggca ccgcgagccg gccgagctcc   540
agccggagct acgtgactac gtccaccccgc acctacagcc tgggcagcgc gctgcgcccc  600
agcaccagcc gcagcctcta cgcctcgtcc ccggcgggc tgtatgccac gcgctcctct   660
gccgtgcgcc tgcggagcag cgtgcccggg gtgcggctcc tgcaggactc ggtggacttc  720
```

-continued

| | |
|---|---|
| tcgctggccg acgccatcaa caccgagttc aagaacaccc gcaccaacga gaaggtggag | 780 |
| ctgcaggagc tgaatgaccg cttcgccaac tacatcgaca aggtgcgctt cctggagcag | 840 |
| cagaataaga tcctgctggc cgagctcgag cagctcaagg gccaaggcaa gtcgcgcctg | 900 |
| ggggacctct acgaggagga gatgcggcag ctgcgccggc aggtggacca gctaaccaac | 960 |
| gacaaagccc gcgtcgaggt ggagcgcgac aacctggccg aggacatcat gcgcctccgg | 1020 |
| gagaaattgc aggaggagat gcttcagaga gaggaagccg aaaacaccct gcaatctttc | 1080 |
| agacaggatg ttgacaatgc gtctctggca cgtcttgacc ttgaacgcaa agtggaatct | 1140 |
| ttgcaagaag agattgcctt tttgaagaaa ctccacgaag aggaaatcca ggagctgcag | 1200 |
| gctcagattc aggaacagca tgtccaaatc gatgtggatg tttccaagcc tgacctcacg | 1260 |
| gctgccctgc gtgacgtacg tcagcaatat gaaagtgtgg ctgccaagaa cctgcaggag | 1320 |
| gcagaagaat ggtacaaatc caagtttgct gacctctctg aggctgccaa ccggaacaat | 1380 |
| gacgccctgc gccaggcaaa gcaggagtcc actgagtacc ggagacaggt gcagtccctc | 1440 |
| acctgtgaag tggatgccct taaggaacc aatgagtccc tggaacgcca gatgcgtgaa | 1500 |
| atggaagaga ctttgccgt tgaagctgct aactaccaag acactattgg ccgcctgcag | 1560 |
| gatgagattc agaatatgaa ggaggaaatg gctcgtcacc ttcgtgaata ccaagacctg | 1620 |
| ctcaatgtta agatggccct tgacattgag attgccacct acaggaagct gctggaaggc | 1680 |
| gaggagagca ggatttctct gcctcttcca aacttttcct ccctgaacct gagggaaact | 1740 |
| aatctggatt cactccctct ggttgatacc cactcaaaaa ggacacttct gattaagacg | 1800 |
| gttgaaacta gagatggaca ggttatcaac gaaacttctc agcatcacga tgaccttgaa | 1860 |
| taaaaattgc acacactcag tgcagcaata tattaccagc aagaataaaa aagaaatcca | 1920 |
| tatcttaaag aaacagcttt caagtgcctt tctgcagttt tcaggagcg caagatagat | 1980 |
| ttggaatagg aataagctct agttcttaac aaccgacact cctacaagat ttagaaaaaa | 2040 |
| gtttacaaca taatctagtt tacagaaaaa tcttgtgcta gaatactttt taaaaggtat | 2100 |
| tttgaatacc attaaaactg cttttttttt tccagcaagt atccaaccaa cttggttctg | 2160 |
| cttcaataaa tctttggaaa aactctttta aaaaa | 2195 |

<210> SEQ ID NO 39
<211> LENGTH: 5998
<212> TYPE: DNA
<213> ORGANISM: Homo sapiens

<400> SEQUENCE: 39

| | |
|---|---|
| ggggggaag gggagggag gggaggagg tgactcgagc atttagacac aagcgagagg | 60 |
| atcatggcgc atggccccag gtgtaagcgc agaaagcagg cgaacccgcg gcgcaataac | 120 |
| gttacaaatt ataatactgt ggtagaaaca aattcagatt cagatgatga agacaaactg | 180 |
| catattgtgg aagaagaaag tgttacagat gcagctgact gtgaaggtgt accagaggat | 240 |
| gacctgccaa cagaccagac agtgttacca gggaggagca gtgaaagaga agggaatgct | 300 |
| aagaactgct gggaggatga cagaaaggaa gggcaagaaa tcctggggcc tgaagctcag | 360 |
| gcagatgaag caggatgtac agtaaaagat gatgaatgca gtcagatgc agaaaatgag | 420 |
| caaaaccatg atcctaatgt tgaagagttt ctacaacaac aagacactgc tgtcattttt | 480 |
| cctgaggcac ctgaagagga ccagaggcag ggcacaccag aagccagtgg tcatgatgaa | 540 |
| aatggaacac cagatgcatt tcacaattta ctcacctgtc catattgtga tagaggctat | 600 |

| | | |
|---|---|---|
| aaacgcttta cctctctgaa agaacacatt aaatatcgtc atgaaaagaa tgaagataac | 660 |
| tttagttgct ccctgtgcag ttacaccttt gcatacagaa cccaacttga acgtcacatg | 720 |
| acatcacata aatcaggaag agatcaaaga catgtgacgc agtctgggtg taatcgtaaa | 780 |
| ttcaaatgca ctgagtgtgg aaaagctttc aaatacaaac atcacctaaa agagcactta | 840 |
| agaattcaca gtggagagaa gccatatgaa tgcccaaact gcaagaaacg ctttcccat | 900 |
| tctggctcct atagctcaca cataagcagt aagaaatgta tcagcttgat acctgtgaat | 960 |
| gggcgaccaa gaacaggact caagacatct cagtgttctt caccgtctct ttcagcatca | 1020 |
| ccaggcagtc ccacacgacc acagatacgg caaaagatag agaataaacc ccttcaagaa | 1080 |
| caactttctg ttaaccaaat taaaactgaa cctgtggatt atgaattcaa acccatagtg | 1140 |
| gttgcttcag gaatcaactg ttcaaccct ttacaaaatg gggttttcac tggtggtggc | 1200 |
| ccattacagg caaccagttc tcctcagggc atggtgcaag ctgttgttct gccaacagtt | 1260 |
| ggtttggtgt ctcccataag tatcaattta agtgatattc agaatgtact taaagtggcg | 1320 |
| gtagatggta atgtaataag gcaagtgttg gagaataatc aagccaatct tgcatccaaa | 1380 |
| gaacaagaaa caatcaatgc ttcacccata caacaaggtg gccattctgt tatttcagcc | 1440 |
| atcagtcttc ctttggttga tcaagatgga acaaccaaaa ttatcatcaa ctacagtctt | 1500 |
| gagcagccta gccaacttca gttgttcct caaaatttaa aaaagaaaa tccagtcgct | 1560 |
| acaaacagtt gtaaaagtga aaagttacca gaagatctta ctgttaagtc tgagaaggac | 1620 |
| aaaagctttg aagggggggt gaatgatagc acttgtcttc tgtgtgatga ttgtccagga | 1680 |
| gatattaatg cacttccaga attaaagcac tatgacctaa agcagcctac tcagcctcct | 1740 |
| ccactccctg cagcagaagc tgagaagcct gagtcctctg tttcatcagc tactggagat | 1800 |
| ggcaatttgt ctcctagtca gccacctta aagaacctct tgtctctcct aaaagcatat | 1860 |
| tatgctttga atgcacaacc aagtgcagaa gagctctcaa aaattgctga ttcagtaaac | 1920 |
| ctaccactgg atgtagtaaa aaagtggttt gaaaagatgc aagctggaca gatttcagtg | 1980 |
| cagtcttctg aaccatcttc tcctgaacca ggcaaagtaa atatccctgc caagaacaat | 2040 |
| gatcagcctc aatctgcaaa tgcaaatgaa ccccaggaca gcacagtaaa tctacaaagt | 2100 |
| ccttttgaaga tgactaactc cccagtttta ccagtgggat caaccaccaa tggttccaga | 2160 |
| agtagtacac catccccatc acctctaaac ctttcctcat ccagaaatac acagggttac | 2220 |
| ttgtacacag ctgagggtgc acaagaagag ccacaagtag aacctcttga tctttcacta | 2280 |
| ccaaagcaac agggagaatt attagaaagg tcaactatca ctagtgttta ccagaacagt | 2340 |
| gtttattctg tccaggaaga acccttgaac ttgtcttgcg caaaaaagga gccacaaaag | 2400 |
| gacagttgtg ttacagactc agaaccagtt gtaaatgtaa tcccaccaag tgccaaccccc | 2460 |
| ataaatatcg ctatacctac agtcactgcc cagttaccca caatcgtggc cattgctgac | 2520 |
| cagaacagtg ttccatgctt aagagcgcta gctgccaata gcaaacgat tctgattccc | 2580 |
| caggtggcat acacctactc aactacggtc agccctgcag tccaagaacc acccttgaaa | 2640 |
| gtgatccagc caaatggaaa tcaggatgaa agacaagata ctagctcaga aggagtatca | 2700 |
| aatgtagagg atcagaatga ctctgattct acaccgccca aaaagaaaat gcggaagaca | 2760 |
| gaaaatggaa tgtatgcttg tgatttgtgt gacaagatat tccaaagag tagttcatta | 2820 |
| ttgagacata aatatgaaca cacaggtaaa agacctcatg agtgtggaat ctgtaaaaag | 2880 |
| gcatttaaac acaaacatca tttgattgaa cacatgcgat tacattctgg agaaaagccc | 2940 |
| tatcaatgtg acaaatgtgg aaagcgcttc tcacactctg ggtcttattc tcaacacatg | 3000 |

```
aatcatcgct actcctactg taagagagaa gcggaagaac gtgacagcac agagcaggaa    3060
gaggcagggc ctgaaatcct ctcgaatgag cacgtgggtg ccagggcgtc tccctcacag    3120
ggcgactcgg acgagagaga gagtttgaca agggaagagg atgaagacag tgaaaaagag    3180
gaagaggagg aggataaaga gatggaagaa ttgcaggaag aaaaagaatg tgaaaaacca    3240
caagggdatg aggaagagga ggaggaggag gaagaagtgg aagaagaaga ggtagaagag    3300
gcagagaatg agggagaaga agcaaaaact gaaggtctga tgaaggatga cagggctgaa    3360
agtcaagcaa gcagcttagg acaaaaagta ggcgagagta gtgagcaagt gtctgaagaa    3420
aagacaaatg aagcctaatc gttttttctag aaggaaaata aattctaatt gataatgaat    3480
ttcgttcaat attatccttg cttttcatgg aaacacagta acctgtatgc tgtgattcct    3540
gttcactact gtgtaaagta aaactaaaa aaatacaaaa tacaaaacac acacacac    3600 acacacacac acacacacac acacacaaaa taaatccggg tgtgcctgaa cctcagacct    3660
agtaattttt catgcagttt tcaaagttag aacaagttt gtaacatgca gcagattaga    3720
aaaccttaat gactcagaga gcaacaatac aagaggttaa aggaagctga ttaattagat    3780
atgcatctgg cattgtttta tcttatcagt attatcactc ttatgttggt ttattcttaa    3840
gctgtacaat tgggagaaat tttataattt tttattggta aacatatgct aaatccgctt    3900
cagtatttta ttatgttttt taaaatgtga gaacttctgc actacaaaat tcccttcaca    3960
gagaagtata atgtagttcc aacccgtgct aactaccttt tataaattca gtctagaagg    4020
tagtaatttc taatatttag atgtcttagt agagcgtatt atcatttaaa gtgtattgtt    4080
agccttaaga aagcagctga tagaagaact gaagtttctt actcacgtgg tttaaaatgg    4140
agttcaaaag attgccattg agttctgatt gcagggacta acaatgttaa tctgataagg    4200
acagcaaaat catcagaatc agtgtttgtg attgtgtttg aatatgtggt aacatatgaa    4260
ggatatgaca tgaagctttg tatctccttt ggccttaagc aagacctgtg tgctgtaagt    4320 gccattctc agtattttca aggctctaac ccgccttcat ccaatgtgtg gcctacaata    4380
actagcattt gttgatttgt ctcttgtatc aaaattccca aataaaactt aaaaccactg    4440
actctgtcag agaaactgaa acactgggac atttcatcct tcaattcctc ggtattgatt    4500
ttatgttgat tgattttcag aatttctcta cagaaacgaa agggaaattt tctaatctgc    4560
tttatccatg tacttgcatt tcagacatgg acatgctatt gttatttggc tcataactgt    4620
ttccaaatgt tagttattat ggacccaatt tattaacaac attagctgat tttttacctat   4680 cagtattatt ttatttcttt tagttttatag atctgtgcaa cattttttgta ctgtatgtct   4740 tcaaacctgg cagtattaat acccttctta ctgacatatg tacttttagt tttagaaaac    4800
ttttatattt atgtgtctta ttttttatatt tcttttattta ttacacagtg tagtgtataa   4860
tactgtagtt tgtattaata caataatata tttttagtatg aaaatttgga aagttgataa   4920
gatttaaagt agagatgcaa ttggttctcc tgcattgaga tttgatttaa cagtgttatg    4980
ttaacattta tacttgcctt ggactgtaga acagaactta aatgggaatg tattagtttt    5040
acaactacaa tcaagtcatt ttacctttac ccagttttta atataaaact taaattttga    5100
aattcactgt gtgactaata gcatgatgct ctgcagtttt attaagaaat cagcctaacc    5160
atacaactct catttcctta gtaagccaaa ttaggattaa cttctataaa cagtgttggg    5220
aacaatgttt aacattttgt gccaattttgt tcctgtattc atgtatgtaa gttacagatc    5280
tgactcttca ttttttaagtt ccttgttaca tcatggtcat tttctagttt tttaccagac    5340
```

-continued

```
tcccatctca caataaaatg catcaacaag cctgaactgc tgtcattctt ttcatcatta    5400
tcagtatttt ctttggaaaa ctgtgaaatg gggtacattg tcatcctgca tttgattcat    5460
cttgagctga atttgggtaa cactaaatgt tttagacatt ctccactaaa ttatggattt    5520
tcttgtggct aaatgtttct ggagaggtca gagttgacaa aacctcttca caggttgctc    5580
cttcttcctg aaatccttaa tcctccgcat ttcatgcttc aggtcatttc agggaagcct    5640
gggtttagat gcctttctga ctctcagctc ctgcacttct gtcatcatac ctctgatact    5700
attatttata ttccttcccc actaggaaca ggaaccacat ttgtcatagt cactctcaca    5760
ttcctcactg cctaacaggg tgcctggcat aagttgggac aacagatatt tgttgaataa    5820
aaatataatt tgcatgttta tggagctcag ctatgttctc actttttttg cttctaattc    5880
cagaatatat gttaaatgat ctaataattt gattattttc ttataagtct tattaaacac    5940
tagtcataat agacacaata aattatgcct tcttttcta ttgccttaaa aaaaaaaa     5998
```